US012673084B2

(12) United States Patent
Blainey et al.

(10) Patent No.: US 12,673,084 B2
(45) Date of Patent: Jul. 7, 2026

(54) COMPOSITIONS AND METHODS FOR COMBINATORIAL DRUG DISCOVERY IN NANOLITER DROPLETS

(71) Applicants: The Broad Institute, Inc., Cambridge, MA (US); Massachusetts Institute of Technology, Cambridge, MA (US)

(72) Inventors: Paul Blainey, Cambridge, MA (US); Anthony Kulesa, Cambridge, MA (US); Jared Kehe, Cambridge, MA (US)

(73) Assignees: The Broad Institute, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 200 days.

(21) Appl. No.: 18/068,387

(22) Filed: Dec. 19, 2022

(65) Prior Publication Data

US 2023/0346879 A1 Nov. 2, 2023

Related U.S. Application Data

(62) Division of application No. 16/754,668, filed as application No. PCT/US2018/054916 on Oct. 9, 2018, now Pat. No. 11,564,970.

(60) Provisional application No. 62/578,140, filed on Oct. 27, 2017, provisional application No. 62/570,585, filed on Oct. 10, 2017, provisional application No. 62/570,014, filed on Oct. 9, 2017.

(51) Int. Cl.

| | |
|---|---|
| *A61K 38/08* | (2019.01) |
| *A61K 31/14* | (2006.01) |
| *A61K 31/165* | (2006.01) |
| *A61K 31/4164* | (2006.01) |
| *A61K 31/42* | (2006.01) |
| *A61K 31/43* | (2006.01) |
| *A61K 31/4704* | (2006.01) |
| *A61K 31/506* | (2006.01) |
| *A61K 31/65* | (2006.01) |
| *A61K 31/7048* | (2006.01) |
| *A61K 38/12* | (2006.01) |
| *A61K 38/14* | (2006.01) |
| *A61K 45/06* | (2006.01) |
| *A61P 31/04* | (2006.01) |
| *C07K 7/14* | (2006.01) |
| *C07K 7/64* | (2006.01) |

(52) U.S. Cl.

CPC .............. *A61K 38/12* (2013.01); *A61K 31/14* (2013.01); *A61K 31/165* (2013.01); *A61K 31/4164* (2013.01); *A61K 31/4704* (2013.01); *A61K 31/506* (2013.01); *A61K 31/7048* (2013.01); *A61P 31/04* (2018.01)

(58) Field of Classification Search

CPC ........ A61K 38/08; A61K 38/12; A61K 38/14; A61K 45/06; A61K 31/14; A61K 31/65; A61K 2300/00; A61K 31/132; A61K 31/165; A61K 31/166; A61K 31/4164; A61K 31/42; A61K 31/43; A61K 31/4704; A61K 31/496; A61K 31/505; A61K 31/506; A61K 31/665; A61K 31/7048; C07K 7/14; C07K 7/64; A61P 31/04

See application file for complete search history.

(56) References Cited

U.S. PATENT DOCUMENTS

| | | | | |
|---|---|---|---|---|
| 5,023,085 | A | 6/1991 | Francoeur et al. | |
| 5,834,430 | A * | 11/1998 | Porro | C07K 7/06 530/319 |
| 5,989,832 | A * | 11/1999 | Trias | A61K 38/05 514/23 |
| 7,968,085 | B2 | 6/2011 | Hersel et al. | |
| 11,564,970 | B2 | 1/2023 | Blainey et al. | |
| 2004/0198743 | A1 | 10/2004 | Hey et al. | |
| 2005/0004155 | A1 * | 1/2005 | Boyd | A61K 9/02 514/282 |
| 2005/0261242 | A1 | 11/2005 | Soldato | |
| 2010/0221245 | A1 | 9/2010 | Kunin | |
| 2010/0226943 | A1 | 9/2010 | Brennan et al. | |
| 2011/0244486 | A1 | 10/2011 | Perego et al. | |
| 2012/0141467 | A1 | 6/2012 | Schneider | |
| 2013/0046005 | A1 | 2/2013 | Sturgill et al. | |
| 2015/0335613 | A1 | 11/2015 | Paez-Pereda et al. | |

FOREIGN PATENT DOCUMENTS

| | | | |
|---|---|---|---|
| CN | 107158020 | A | 9/2017 |
| WO | 2008074856 | A1 | 6/2008 |
| WO | 2016149661 | A1 | 9/2016 |

OTHER PUBLICATIONS

Colao et al., "Pasireotide Versus Octreotide in Acromegaly: A Head-to-Head Superiority Study," J. Clin. Endocrinol. Metab., Mar. 2014, 99(3): 791-799. (Year: 2014).*

Verne et al., :Effect of Octreotide and Erythromycin on Idiopathic and Scleroderma-Associated Intestinal Pseudoobstruction, Digestive Diseases and Sciences, 1995, 40(9): 1892-1901. (Year: 1995).*

Herrick A L: "Advances in Palliative Care for the Patient With Scleroderma", Current Opinion in Rheumatology, Current Science, London, GB, vol. 8, No. 6, Nov. 1, 1996.

Cazzola Mario et al: "Use of indacaterol for the treatment of COPD: a pharmacokinetic evaluation", Expert Opinion on Drug Metabolism & Toxicology, vol. 10, No. 1, Jan. 1, 2014.

Anonymous: "Highlights of Prescribing Information Advair Diskus", Jan. 1, 2008.

(Continued)

*Primary Examiner* — Julie Ha

(74) *Attorney, Agent, or Firm* — Greenberg Traurig, LLP; Melissa Hunter-Ensor; Nathan Hsu

(57) ABSTRACT

Compounds and methods for combinatorial drug discovery in nanoliter droplets are described herein. More particularly, novel synergistic agents that increase efficacy of antibiotic agents to treat bacterial infections are described.

6 Claims, 159 Drawing Sheets

(56) References Cited

OTHER PUBLICATIONS

Siriyong Thanyaluck et al: "Holarrhena antidysenterica Extract and Its Steroidal Alkaloid, Conessine, as Resistance-Modifying Agents Against Extensively Drug-Resistant Acinetobacter baumannii", Microbial Drug Resistance, vol. 22, No. 4, Jun. 1, 2016.
Thanyaluck Siriyong et al: "Conessine as a novel inhibitor of multidrug efflux pump systems in Pseudomonas Aeruginosa", BMC Complementary and Alternative Medicine, Biomed Central Ltd, London, UK, vol. 17, No. 1, Aug. 14, 2017.
Andersen J A: "Benurestat, a urease inhibitor for the therapy of infected ureolysis", Investigative Urology, XX, XX, vol. 12, No. 5, Jan. 1, 1975.
Musher D. M. et al: "Interaction Between Acetohydroxamic Acid and 12 Antibiotics Against 14 Gram-Negative Pathogenic Bacteria", Antimicrobial Agents and Chemotherapy, vol. 5, No. 2, Feb. 1, 1974.
Lange Roland et al: "The Targets of Currently Used Antibacterial Agents: Lessons for Drug Discovery", Current Pharmaceutical Design, vol. 13, No. 30, Oct. 1, 2007.
Examination Report in corresponding EP application No. 18866041.9 dated Feb. 21, 2025.
International Search Report dated Dec. 17, 2018 for related Application No. PCT/US18/54916.
Athanasakis et al., Octreotide enhances the accelerating effect of erythromycin on gastric emptying in healthy subjects, Aliment Pharmacology and Therapeutics, vol. 16, 2002 [retrieved on Nov. 29, 2018].
Ahmed et al., "Current concepts in combination antibiotic therapy for critically ill patients," Indian Journal of Critical Care Medicine, May 2014, 18(5): 310-314. (Year: 2014).
Borisy et al., "Systematic discovery of multicomponent therapeutics," PNAS, 2003, vol. 100, No. 13, pp. 7977-7982.
Buck et al., "Rapamycin synergizes with the epidermal growth factor receptor inhibitor erlotinib in non-small-cell lung, pancreatic, colon, and breast tumors," Mol Cancer Ther, 2006, vol. 5, No. 11, pp. 2676-2684.
Cadee et al., "Release of recombinant human interleukin-2 from dextran-based hydrogels," Journal of Controlled Release, 2002, vol. 78, pp. 1-13.
Hennink et al., "Novel crosslinking methods to design hydrogels," Advanced Drug Delivery Reviews, vol. 54, pp. 13-36, Year 2002.
Hoffman "Hydrogels for biomedical applications," Advanced Drug Delivery Reviews, 2002, vol. 54, pp. 3-12.
Magazanik et al., "Block of open channels of recombinant AMPA receptors and native AMPA/kainate receptors by adamantane derivatives," Journal of Physiology, 1997, pp. 655-663.
Surini et al., "Release phenomena of insulin from an implantable device composed of a polyion complex of chitosan and sodium hyaluronate," Journal of Controlled Release, 2003, vol. 90, pp. 291-301.
Written Opinion mailed Dec. 17, 2018, in corresponding International PCT Patent Application No. PCT/US2018/054916 (8 pages).
Extended European Search Report dated Jun. 11, 2021, in corresponding European Patent Application No. 18866041.9 (25 pages).
Office Action dated Feb. 18, 2026, in corresponding European Patent Application No. 18866041.9 (8 pages).

* cited by examiner

Chip (FIC ≤ 0.3125)

| Ampication (ug/mL) | 0 | 4 | 8 | 16 | 32 | 64 | 128 | 256 Subtacts |
|---|---|---|---|---|---|---|---|---|
| 512 | 0.258 | 0.135 | 0.101 | 0.060 | 0.050 | 0.034 | 0.025 | 0.010 |
| 256 | 0.510 | 0.251 | 0.179 | 0.120 | 0.070 | 0.059 | 0.033 | 0.019 |
| 128 | 0.928 | 0.515 | 0.384 | 0.234 | 0.153 | 0.102 | 0.057 | 0.043 |
| 64 | 1.052 | 0.501 | 0.725 | 0.510 | 0.378 | 0.236 | 0.153 | 0.074 |
| 32 | 1.000 | 1.004 | 0.385 | 0.872 | 0.754 | 0.008 | 0.401 | 0.199 |
| 16 | 1.053 | 1.011 | 1.008 | 0.563 | 0.563 | 0.843 | 0.662 | 0.374 |
| 8 | 1.000 | 1.010 | 1.000 | 0.967 | 1.030 | 0.945 | 0.759 | 0.534 |
| 0 | 1 | 1.010 | 1.007 | 0.994 | 1.000 | 1.006 | 0.922 | 0.675 |

Plate (FIC ≤ 0.5)

| m (ug/mL) | 0 | 4 | 8 | 16 | 32 | 64 | 128 | 256 |
|---|---|---|---|---|---|---|---|---|
| | 0.006 | 0.382 | 0.280 | 0.181 | 0.111 | 0.061 | 0.059 | 0.022 |
| | 0.827 | 0.533 | 0.427 | 0.300 | 0.166 | 0.112 | 0.062 | 0.058 |
| | 0.934 | 0.747 | 0.606 | 0.507 | 0.388 | 0.265 | 0.127 | 0.100 |
| | 1 | 0.848 | 0.754 | 0.723 | 0.585 | 0.490 | 0.332 | 0.186 |
| | 0.990 | 0.956 | 0.869 | 0.870 | 0.815 | 0.721 | 0.511 | 0.332 |
| | 0.952 | 0.919 | 0.925 | 0.863 | 0.846 | 0.772 | 0.754 | 0.455 |
| | 0.877 | 0.889 | 0.642 | 0.647 | 0.851 | 0.793 | 0.740 | 0.560 |
| | 0.806 | 0.655 | 0.829 | 0.801 | 0.743 | 0.762 | 0.712 | 0.634 |

FIG. 2E

| | $Log_{10}$ $IC_{50}$ RMS Difference | | | $R^2$ between replicates | |
|---|---|---|---|---|---|
| | Chip vs. Plate | Chip vs. Chip | Chip vs. Plate | Chip vs. Chip | Plate vs. Plate |
| *P. aeruginosa* | 0.233 | 0.052 | 0.051 | 0.988 | 0.963 |
| *S. aureus* | 0.117 | 0.080 | 0.130 | 0.965 | 0.890 |
| *E. coli* | 0.212 | 0.047 | 0.156 | 0.976 | 0.933 |

FIG. 2J

| | Chips | Compounds | Combinations |
|---|---|---|---|
| Starting | 126 | 3,336 | 100,080 |
| Run failure | 1 (0.794%) | 28 (0.839%) | 840 (0.839%) |
| Quality filtered | 16 (12.7%) | 412 (12.4%) | 12,360 (12.4%) |
| No droplets | | 49 (1.47%) | 1470 (1.47%) |
| Dropout (< 5 wells) | | | 3255 (3.25%) |
| Final Total | 109 (86.5%) | 2,847 (85.3%) | 82,155 (82.1%) |

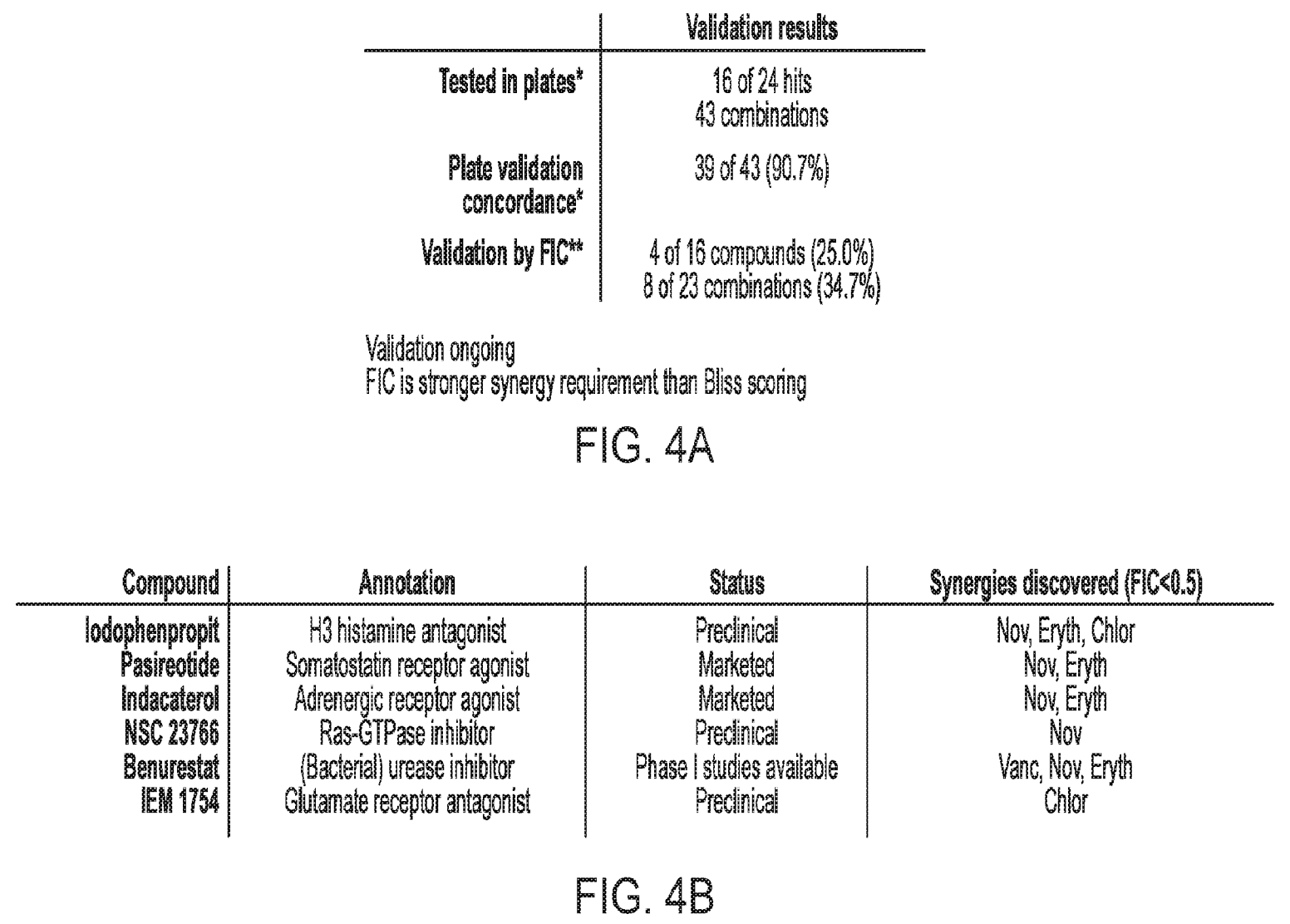

| | Validation results |
|---|---|
| Tested in plates* | 16 of 24 hits<br>43 combinations |
| Plate validation concordance* | 39 of 43 (90.7%) |
| Validation by FIC** | 4 of 16 compounds (25.0%)<br>8 of 23 combinations (34.7%) |

Validation ongoing
FIC is stronger synergy requirement than Bliss scoring

FIG. 4A

| Compound | Annotation | Status | Synergies discovered (FIC<0.5) |
|---|---|---|---|
| **Iodophenpropit** | H3 histamine antagonist | Preclinical | Nov, Eryth, Chlor |
| **Pasireotide** | Somatostatin receptor agonist | Marketed | Nov, Eryth |
| **Indacaterol** | Adrenergic receptor agonist | Marketed | Nov, Eryth |
| **NSC 23766** | Ras-GTPase inhibitor | Preclinical | Nov |
| **Benurestat** | (Bacterial) urease inhibitor | Phase I studies available | Vanc, Nov, Eryth |
| **IEM 1754** | Glutamate receptor antagonist | Preclinical | Chlor |

FIG. 4B

Iodophenpropit
$H_3$ histamine antagonist
Preclinical

Validated synergies

| Antibiotic | FIC |
|---|---|
| Novobiocin | 0.3125 |
| Erythromycin | 0.5 |
| Chloramphenicol | 0.375 |

| Compound | Target | Status | Synergies (FIC≤0.5) |
|---|---|---|---|
| **Iodophenpropit** | H3 histamine receptor | Preclinical | Nov, Eryth, Chlor |
| **Pasireotide** | Somatostatin receptor | Marketed | Nov, Eryth |
| **Indacaterol** | Adrenergic receptor | Marketed | Nov, Eryth |
| **NSC 23766** | Ras-GTPase | Preclinical | Nov |
| **Benurestat** | (Bacterial) urease | Phase I | Vanc, Nov, Eryth, Chlor |
| **IEM 1754** | Glutamate receptor | Preclinical | |

NSC 23766

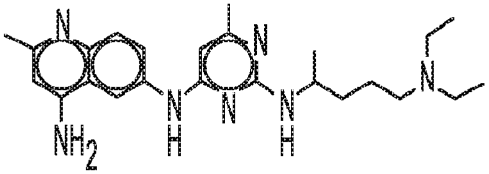

Indacaterol

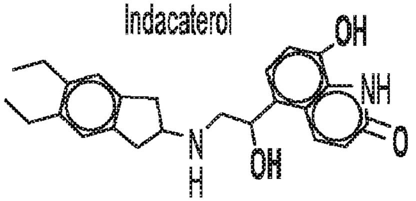

Pasireotide

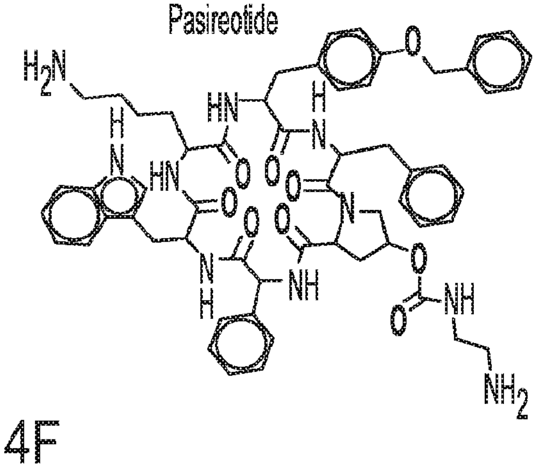

FIG. 4F

<table>
<tr><th colspan="25">Compounds are stocked in 384 well plates</th></tr>
<tr><th></th><th>1</th><th>2</th><th>3</th><th>4</th><th>5</th><th>6</th><th>7</th><th>8</th><th>9</th><th>10</th><th>11</th><th>12</th><th>13</th><th>14</th><th>15</th><th>16</th><th>17</th><th>18</th><th>19</th><th>20</th><th>21</th><th>22</th><th>23</th><th>24</th></tr>
<tr><td>A</td><td rowspan="16" colspan="2">Blank</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td rowspan="16" colspan="2">Blank</td></tr>
<tr><td>B</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td></tr>
<tr><td>C</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td></tr>
<tr><td>D</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td></tr>
<tr><td>E</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td></tr>
<tr><td>F</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td></tr>
<tr><td>G</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td></tr>
<tr><td>H</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td></tr>
<tr><td>I</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td></tr>
<tr><td>J</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td></tr>
<tr><td>K</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td></tr>
<tr><td>L</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td></tr>
<tr><td>M</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td></tr>
<tr><td>N</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td></tr>
<tr><td>O</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td><td>Q1</td><td>Q2</td></tr>
<tr><td>P</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td><td>Q3</td><td>Q4</td></tr>
</table>

FIG. 5A

Step 1: Echo compounds in each of 4 quadrants into 96-well plate ARPs

| | 1 | 2 | 3 | 4 | 5 | 6 | 7 | 8 | 9 | 10 | 11 | 12 |
|---|---|---|---|---|---|---|---|---|---|---|---|---|
| A | | Q1 | Q1 | Q1 | Q1 | Q1 | Q1 | Q1 | Q1 | Q1 | Q1 | |
| B | | Q1 | Q1 | Q1 | Q1 | Q1 | Q1 | Q1 | Q1 | Q1 | Q1 | |
| C | | Q1 | Q1 | Q1 | Q1 | Q1 | Q1 | Q1 | Q1 | Q1 | Q1 | |
| D | | Q1 | Q1 | Q1 | Q1 | Q1 | Q1 | Q1 | Q1 | Q1 | Q1 | |
| E | | Q1 | Q1 | Q1 | Q1 | Q1 | Q1 | Q1 | Q1 | Q1 | Q1 | |
| F | | Q1 | Q1 | Q1 | Q1 | Q1 | Q1 | Q1 | Q1 | Q1 | Q1 | |
| G | | Q1 | Q1 | Q1 | Q1 | Q1 | Q1 | Q1 | Q1 | Q1 | Q1 | |
| H | | Q1 | Q1 | Q1 | Q1 | Q1 | Q1 | Q1 | Q1 | Q1 | Q1 | |

| | 1 | 2 | 3 | 4 | 5 | 6 | 7 | 8 | 9 | 10 | 11 | 12 |
|---|---|---|---|---|---|---|---|---|---|---|---|---|
| A | | Q2 | Q2 | Q2 | Q2 | Q2 | Q2 | Q2 | Q2 | Q2 | Q2 | |
| B | | Q2 | Q2 | Q2 | Q2 | Q2 | Q2 | Q2 | Q2 | Q2 | Q2 | |
| C | | Q2 | Q2 | Q2 | Q2 | Q2 | Q2 | Q2 | Q2 | Q2 | Q2 | |
| D | | Q2 | Q2 | Q2 | Q2 | Q2 | Q2 | Q2 | Q2 | Q2 | Q2 | |
| E | | Q2 | Q2 | Q2 | Q2 | Q2 | Q2 | Q2 | Q2 | Q2 | Q2 | |
| F | | Q2 | Q2 | Q2 | Q2 | Q2 | Q2 | Q2 | Q2 | Q2 | Q2 | |
| G | | Q2 | Q2 | Q2 | Q2 | Q2 | Q2 | Q2 | Q2 | Q2 | Q2 | |
| H | | Q2 | Q2 | Q2 | Q2 | Q2 | Q2 | Q2 | Q2 | Q2 | Q2 | |

| | 1 | 2 | 3 | 4 | 5 | 6 | 7 | 8 | 9 | 10 | 11 | 12 |
|---|---|---|---|---|---|---|---|---|---|---|---|---|
| A | | Q3 | Q3 | Q3 | Q3 | Q3 | Q3 | Q3 | Q3 | Q3 | Q3 | |
| B | | Q3 | Q3 | Q3 | Q3 | Q3 | Q3 | Q3 | Q3 | Q3 | Q3 | |
| C | | Q3 | Q3 | Q3 | Q3 | Q3 | Q3 | Q3 | Q3 | Q3 | Q3 | |
| D | | Q3 | Q3 | Q3 | Q3 | Q3 | Q3 | Q3 | Q3 | Q3 | Q3 | |
| E | | Q3 | Q3 | Q3 | Q3 | Q3 | Q3 | Q3 | Q3 | Q3 | Q3 | |
| F | | Q3 | Q3 | Q3 | Q3 | Q3 | Q3 | Q3 | Q3 | Q3 | Q3 | |
| G | | Q3 | Q3 | Q3 | Q3 | Q3 | Q3 | Q3 | Q3 | Q3 | Q3 | |
| H | | Q3 | Q3 | Q3 | Q3 | Q3 | Q3 | Q3 | Q3 | Q3 | Q3 | |

| | 1 | 2 | 3 | 4 | 5 | 6 | 7 | 8 | 9 | 10 | 11 | 12 |
|---|---|---|---|---|---|---|---|---|---|---|---|---|
| A | | Q4 | Q4 | Q4 | Q4 | Q4 | Q4 | Q4 | Q4 | Q4 | Q4 | |
| B | | Q4 | Q4 | Q4 | Q4 | Q4 | Q4 | Q4 | Q4 | Q4 | Q4 | |
| C | | Q4 | Q4 | Q4 | Q4 | Q4 | Q4 | Q4 | Q4 | Q4 | Q4 | |
| D | | Q4 | Q4 | Q4 | Q4 | Q4 | Q4 | Q4 | Q4 | Q4 | Q4 | |
| E | | Q4 | Q4 | Q4 | Q4 | Q4 | Q4 | Q4 | Q4 | Q4 | Q4 | |
| F | | Q4 | Q4 | Q4 | Q4 | Q4 | Q4 | Q4 | Q4 | Q4 | Q4 | |
| G | | Q4 | Q4 | Q4 | Q4 | Q4 | Q4 | Q4 | Q4 | Q4 | Q4 | |
| H | | Q4 | Q4 | Q4 | Q4 | Q4 | Q4 | Q4 | Q4 | Q4 | Q4 | |

FIG. 5B

Step 2: Add second plate of controls and dye

| | 1 | 2 | 3 | 4 | 5 | 6 | 7 | 8 | 9 | 10 | 11 | 12 |
|---|---|---|---|---|---|---|---|---|---|---|---|---|
| A | Eryth | A2 | A3 | A4 | A5 | A6 | A7 | A8 | A9 | A10 | A11 | Eryth |
| B | Neg | B2 | B3 | B4 | B5 | B6 | B7 | B8 | B9 | B10 | B11 | Neg |
| C | Bugs 1 | C2 | C3 | C4 | C5 | C6 | C7 | C8 | C9 | C10 | C11 | Bugs 1 |
| D | Bugs 2 | D2 | D3 | D4 | D5 | D6 | D7 | D8 | D9 | D10 | D11 | Bugs 2 |
| E | Sulb | E2 | E3 | E4 | E5 | E6 | E7 | E8 | E9 | E10 | E11 | Sulb |
| F | Neg | F2 | F3 | F4 | F5 | F6 | F7 | F8 | F9 | F10 | F11 | Neg |
| G | Bugs 1 | G2 | G3 | G4 | G5 | G6 | G7 | G8 | G9 | G10 | G11 | Bugs 1 |
| H | Bugs 2 | H2 | H3 | H4 | H5 | H6 | H7 | H8 | H9 | H10 | H11 | Bugs 2 |

| Legend | |
|---|---|
| Eryth | Erythomycin, final conc 20 uM |
| Sulb | Sulbactam, final conc 20 uM |
| Neg | Nothing |
| Bugs 1 | Nothing |
| Bugs 2 | Nothing |

FIG. 5C

| | | | | | | | | | | | |
|---|---|---|---|---|---|---|---|---|---|---|---|
| **Construction of source plate** | | | | | | | | | | | |
| Goal is to construct the following source plate | | | | | | | | | | | |
| 384 Plate | 13 | | | Plate = Abbgene 384 well PCR plate (well volume = 40 uL ) | | | | | | | |
| Reps | 2 | | | | | | | | | | |
| Volume | 0.5 | uL | | | | | | | | | |
| Dead | 5 | uL | | | | | | | | | |
| **Total Volume** | 18 | uL | | | | | | | | | |
| | | | | | | | | | | | |
| Therefore, prepare a 96 well plate to be split across the 4 wells | | | | | | | | | | | |
| **Volume** | 79.2 | uL | | | | | | | | | |
| | | | | | | | | | | | |
| | | | | | | | | | | | |
| **1) CONTROLS** | | | | | | | | | | | |
| **Stocks** | | | | | / 10 mg | | | **Solubility** | | | |
| ~~Sulbactam~~ | ~~100~~ | ~~mM~~ | 23.5 | mg/ml | 426 uL | DMSO | | Sulbactam | 200 mM (DMS | | |
| ~~Erythromycin~~ | ~~100~~ | ~~mM~~ | 73.5 | mg/ml | 136 uL DMSO | | | Erythromycin | 200 mM (DMS | | |
| | | | | | | | | | | | |
| Sulbactam | 40 | mM | https:// | (was already 40 mM DMSO stock here) | | | | | | | |
| Erythromycin | 40 | mM | 29.4 | mg/ml | | | | | | | |
| | | | | | | | | | | | |
| **Concentration** | | | | | | | | | | | |
| Volume | 0.5 | uL | | | | | | | | | |
| Drop Vol | 25 | uL | | | | | | | | | |
| Merging Dil | 2 | | | | | | | | | | |
| Final dilution | 100 | | | | | | | | | | |
| Final Conc | 20 | uM | | | | | | | | | |
| | | | | | | | | | | | |
| **Conc in Plate** | **2** | **mM** | | | | | | | | | |
| **Dilution** | **20** | **fold** | | | | | | | | | |
| 1) Construct 100 mM DMSO stocks of Sulbactam and Erythromycin | | | | | | | | | | | |
| 2) Add 1 uL per 20 uL of dye plate in corresponding well | | | | | | | | | | | |

FIG. 5D

C) Use the Bravo to split 20 uL across 384-well plate

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| A | Eryth | Eryth | | | | | | | | | | | | | | | | | | | | | | |
| B | Eryth | Eryth | | | | | | | | | | | | | | | | | | | | | | |
| C | Neg | Neg | | | | | | | | | | | | | | | | | | | | | | |
| D | Neg | Neg | | | | | | | | | | | | | | | | | | | | | | |
| E | Bugs 1 | Bugs 1 | | | | | | | | | | | | | | | | | | | | | | |
| F | Bugs 1 | Bugs 1 | | | | | | | | | | | | | | | | | | | | | | |
| G | Bugs 2 | Bugs 2 | | | | | | | | | | | | | | | | | | | | | | |
| H | Bugs 2 | Bugs 2 | | | | | | | | | | | | | | | | | | | | | | |
| I | Eryth | Eryth | | | | | | | | | | | | | | | | | | | | | Blank | |
| J | Eryth | Eryth | | | | | | | | | | | | | | | | | | | | | | |
| K | Neg | Neg | | | | | | | | | | | | | | | | | | | | | | |
| L | Neg | Neg | | | | | | | | | | | | | | | | | | | | | | |

FIG.5E
CONTINUED

Master Plate

| | 1 | 2 | 3 | 4 | 5 | 6 | 7 | 8 |
|---|---|---|---|---|---|---|---|---|
| A | [0,50,0] | [1,0,49] | [1,4,45] | [1,8,40] | [2,13,36] | [2,17,31] | [2,21,27] | [3,25,22] |
| B | [3,29,18] | [3,33,13] | [4,38,9] | [4,42,4] | [5,0,45] | [6,4,40] | [6,8,36] | [6,13,31] |
| C | [7,17,27] | [7,21,22] | [7,25,18] | [8,29,13] | [8,33,9] | [8,38,4] | [10,0,40] | [10,4,36] |
| D | [10,8,31] | [11,13,27] | [11,17,22] | [11,21,18] | [12,25,13] | [12,29,9] | [12,33,4] | [14,0,36] |
| E | [15,4,31] | [15,8,27] | [15,13,22] | [16,17,18] | [16,21,13] | [16,25,9] | [17,29,4] | [19,0,31] |
| F | [19,4,27] | [20,8,22] | [20,13,18] | [20,17,13] | [21,21,9] | [21,25,4] | [24,0,26] | [24,4,22] |
| G | [24,8,17] | [25,13,13] | [25,17,9] | [25,21,4] | [28,0,22] | [28,4,17] | [29,8,13] | [29,13,8] |
| H | [29,17,4] | [33,0,17] | [33,4,13] | [33,8,8] | [34,13,4] | [37,0,13] | [38,4,8] | [38,8,4] |

Antibiotics Barcodes
Adjuvants Barcodes

FIG. 6A

Adjuvants Plate

| | 1 | 2 | 3 | 4 | 5 | 6 | 7 | 8 | 9 | 10 | 11 | 12 |
|---|---|---|---|---|---|---|---|---|---|---|---|---|
| A | [15,4,31] | [15,8,27] | [15,13,22] | [16,17,18] | [16,21,13] | [16,25,9] | [17,29,4] | [19,0,31] | [19,0,31] | [24,4,22] | [29,13,8] | [38,8,4] |
| B | [19,4,27] | [20,8,22] | [20,13,18] | [20,17,13] | [21,21,9] | [21,25,4] | [24,0,26] | [24,4,22] | [17,29,4] | [24,0,26] | [29,8,13] | [38,4,8] |
| C | [24,8,17] | [25,13,13] | [25,17,9] | [25,21,4] | [28,0,22] | [28,4,17] | [29,8,13] | [29,13,8] | [16,25,9] | [21,25,4] | [28,4,17] | [37,0,13] |
| D | [29,17,4] | [33,0,17] | [33,4,13] | [33,8,8] | [34,13,4] | [37,0,13] | [38,4,8] | [38,8,4] | [16,21,13] | [21,21,9] | [28,0,22] | [34,13,4] |
| E | [15,4,31] | [15,8,27] | [15,13,22] | [16,17,18] | [16,21,13] | [16,25,9] | [17,29,4] | [19,0,31] | [16,17,18] | [20,17,13] | [25,21,4] | [33,8,8] |
| F | [19,4,27] | [20,8,22] | [20,13,18] | [20,17,13] | [21,21,9] | [21,25,4] | [24,0,26] | [24,4,22] | [15,13,22] | [20,13,18] | [25,17,9] | [33,4,13] |
| G | [24,8,17] | [25,13,13] | [25,17,9] | [25,21,4] | [28,0,22] | [28,4,17] | [29,8,13] | [29,13,8] | [15,8,27] | [20,8,22] | [25,13,13] | [33,0,17] |
| H | [29,17,4] | [33,0,17] | [33,4,13] | [33,8,8] | [34,13,4] | [37,0,13] | [38,4,8] | [38,8,4] | [15,4,31] | [19,4,27] | [24,8,17] | [29,17,4] |

FIG. 6B

| | | | | |
|---|---|---|---|---|
| SOURCE PLATE | | | | |
| Volume (uL) | 0.5 | | | |
| Concentration (mM) | 10 | | Concentration (uM) | 10000 |
| | | | % DMSO (v/v) | 100 |
| ADDITIONS TO SOURCE | | | | |
| Media (uL) | 0 | Media | Concentration (uM) | 200 |
| Dye (uL) | 0.5 | DMSO | % DMSO (v/v) | 4 |
| Volume bugs (uL) | 24 | Media | | |
| | | | | |
| Total volume for droplets | 25 | | Final concentration (uM | 100 |
| | | | Final % DMSO (v/v) | 2 |

FIG. 8

| | | | | | | | | |
|---|---|---|---|---|---|---|---|---|
| **Make Stocks at 100x (5 mM)** | | | | | | | | |
| | | | | | | | | |
| **Stocks** | | | | | | | | |
| Alexa 555 | 5 | mg | 1250 | g/mol | 0.004 | mmol | | |
| Alexa 594 | 5 | mg | 820 | g/mol | 0.006 | mmol | | |
| Alexa 647 | 5 | mg | 1250 | g/mol | 0.004 | mmol | | |
| | | | | | | | | |
| **A) Make 5 mM stocks in DMSO** | | | | | | | | |
| Alexa 555 | 0.8 | mL | (5 mM stock) | | * soluble in 1-10 mg/ml in DMSO, DMF, or acquous buffer (PBS) | | | |
| Alexa 594 | 1.22 | mL | (5 mM stock) | | * soluble in 1-10 mg/ml in DMSO, DMF, or acquous buffer (PBS) | | | |
| Alexa 647 | 0.8 | mL | (5 mM stock) | | * soluble in 1-10 mg/ml in DMSO, DMF, or acquous buffer (PBS) | | | |
| | | | | | | | | |
| **B) Make 1:100 dlutions and measure on Nanodrop, then normalize concentrations** | | | | | | | | |
| | 1/400 | | Real Conc | | Final conc | Final volume | | |
| Alexa 555 | 23.5 | uM | 9.4 | mM | 5.6 mM | 0.8 | mL | |
| Alexa 594 | 26.7 | uM | 10.68 | mM | 6.9 mM | 1.22 | mL | |
| Alexa 647 | 25 | uM | 10 | mM | 4.1 mM | 0.8 | mL | |
| | | | | | | | | |

FIG. 9A

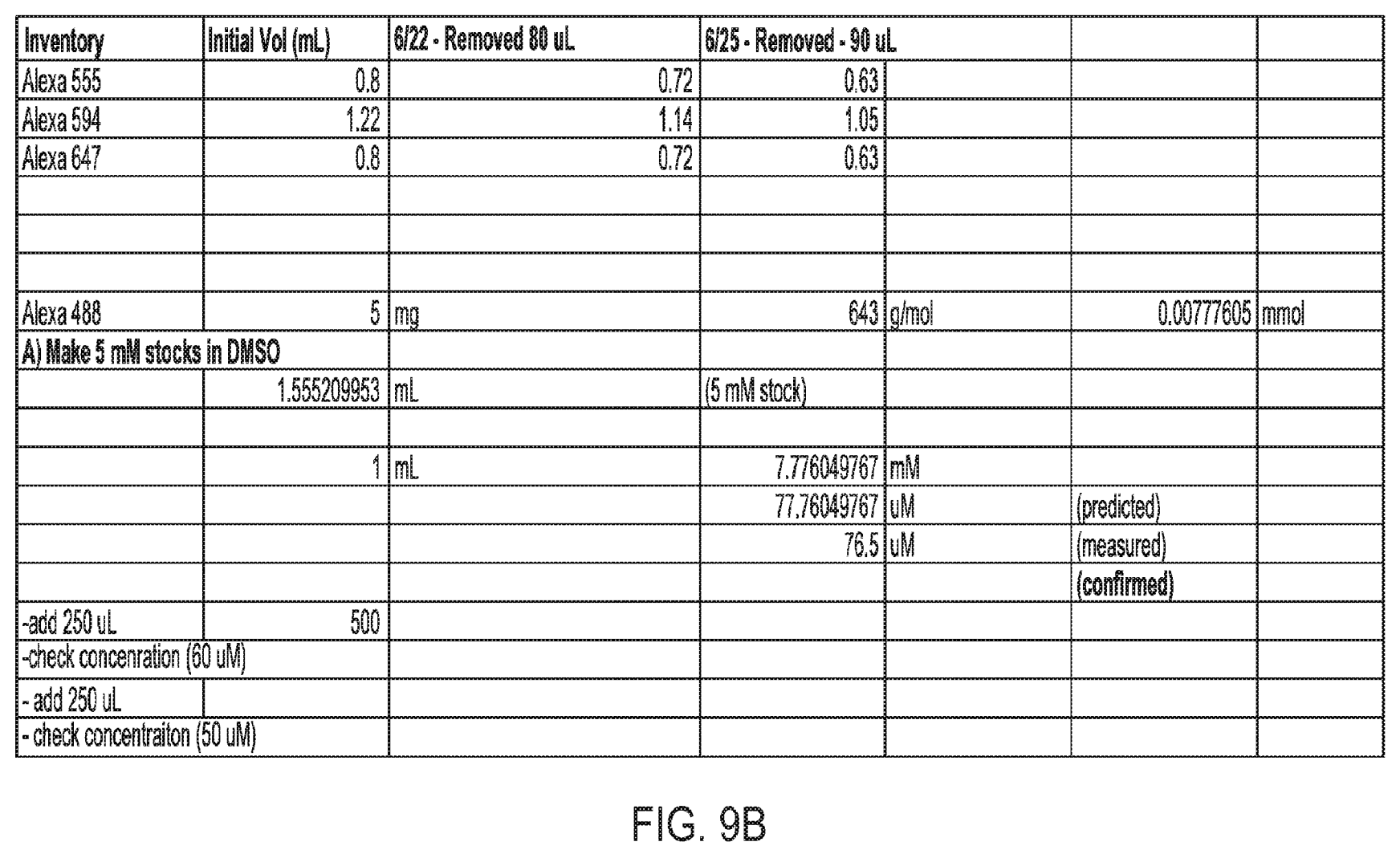

| Inventory | Initial Vol (mL) | 6/22 - Removed 80 uL | 6/25 - Removed - 90 uL | | | |
|---|---|---|---|---|---|---|
| Alexa 555 | 0.8 | 0.72 | 0.63 | | | |
| Alexa 594 | 1.22 | 1.14 | 1.05 | | | |
| Alexa 647 | 0.8 | 0.72 | 0.63 | | | |
| | | | | | | |
| | | | | | | |
| | | | | | | |
| Alexa 488 | 5 | mg | 643 | g/mol | 0.00777605 | mmol |
| A) Make 5 mM stocks in DMSO | | | | | | |
| | 1.555209953 | mL | (5 mM stock) | | | |
| | | | | | | |
| | 1 | mL | 7.776049767 | mM | | |
| | | | 77.76049767 | uM | (predicted) | |
| | | | 76.5 | uM | (measured) | |
| | | | | | (confirmed) | |
| -add 250 uL | 500 | | | | | |
| -check concenration (60 uM) | | | | | | |
| - add 250 uL | | | | | | |
| - check concentraiton (50 uM) | | | | | | |

FIG. 9B

| MAKE ANTIBIOTIC STOCKS | | | | | | | | | | |
|---|---|---|---|---|---|---|---|---|---|---|
| Antibiotic | Concentration (mg/ml) | Solvent | Aliquots | Volume (aliquot) | Total (mL) | Mass (mg) | Tube max (mL) | Max mass (mg) | Min (mg) | Max (mg) |
| Vancomycin | 10 | Water | 8 | 200 | 1.6 | 16 | 2 | 20 | 16 | 20 |
| Cycloserine | 10 | Water | 8 | 200 | 1.6 | 16 | 2 | 20 | 16 | 20 |
| Fosfomycin | 10 | Water | 8 | 200 | 1.6 | 16 | 2 | 20 | 16 | 20 |
| Novobiocin | 10 | Water | 8 | 200 | 1.6 | 16 | 2 | 20 | 16 | 20 |
| Erythromycin | 10 | EtOH | 8 | 200 | 1.6 | 16 | 2 | 20 | 16 | 20 |
| Tetracycline | 10 | Water | 8 | 200 | 1.6 | 16 | 2 | 20 | 16 | 20 |
| Ampicillin | 10 | Water | 8 | 200 | 1.6 | 16 | 2 | 20 | 16 | 20 |
| Trimethoprim | 10 | DMSO | 8 | 200 | 1.6 | 16 | 2 | 20 | 16 | 20 |
| Chloramphenicol | 10 | EtOH | 8 | 200 | 1.6 | 16 | 2 | 20 | 16 | 20 |
| Norfloxacin | 10 | Water + 1% Acetic Acid | 8 | 200 | 1.6 | 16 | 2 | 20 | 16 | 20 |
| 1) Weight out 16-20 mg of antibiotic and dilute to 10 mg/ml in corresponding solvent | | | | | | | | | | |
| 2) Label 8 tubes of for antibiotics with stickers | | | | | | | | | | |

FIG. 10A

| MAKE CURVES | | | | | | | | | | |
|---|---|---|---|---|---|---|---|---|---|---|
| E. coli | | | | | | | | | | |
| | Vancomycin 1 | Cycloserine 2 | Fosfomycin 3 | Novobiocin 4 | Erythromycin 5 | Tetracycline 6 | Ampicillin 7 | Trimethoprim 8 | Chloramphenicol 9 | Norfloxacin 10 |
| A | 128 | 16 | 2 | 128 | 64 | 0.5 | 4 | 0.3125 | 4 | 0.0625 |
| B | 64 | 8 | 1 | 64 | 32 | 0.25 | 2 | 0.15625 | 2 | 0.03125 |
| C | 32 | 4 | 0.5 | 32 | 16 | 0.125 | 1 | 0.078125 | 1 | 0.015625 |
| | | | | | | | | | | |
| | | | | | | | | | | |
| Final volume for droplets | 25 | ul | | | | | | | | |
| Volume of antibiotics | 1 | ul | | | | | | | | |
| Fold dilution (bugs addition) | 25 | fold | | | | | | | | |
| Number of replicates | 120 | | | | | | | | | |
| Dead volume | 5 | uL | | | | | | | | |
| Error tolerance | 0.2 | (fractional) | | | | | | | | |
| | | | | | | | | | | |
| Total volume | 150 | uL | | | | | | | | |
| Top row = 2x volume | 300 | uL | | | | | | | | |
| | | | | | | | | | | |

FIG. 10B

| Antibiotic | Vancomycin | Cycloserine | Fosfomycin | Novobiocin | Erythromycin | Tetracycline | Ampicillin | Trimethoprim | Chloramphenicol | Norfloxacin |
|---|---|---|---|---|---|---|---|---|---|---|
| TARGET | 128 | 16 | 2 | 128 | 64 | 0.5 | 4 | 0.3125 | 4 | 0.0625 |
| 2X (PRE-DROPLET-MERGE) | 256 | 32 | 4 | 256 | 128 | 1 | 8 | 0.625 | 8 | 0.125 |
| Pre - Bugs addition | 6400 | 800 | 100 | 6400 | 3200 | 25 | 200 | 15.625 | 200 | 3.125 |
| | | | | | | | | | | |
| | 1 | 2 | 3 | 4 | 5 | 6 | 7 | 8 | 9 | 10 |
| Antibiotic | Vancomycin | Cycloserine | Fosfomycin | Novobiocin | Erythromycin | Tetracycline | Ampicillin | Trimethoprim | Chloramphenicol | Norfloxacin |
| Concentration (ug/ml) | 6400 | 800 | 100 | 6400 | 3200 | 25 | 200 | 15.625 | 200 | 3.125 |

| | | | | | | | | | | |
|---|---|---|---|---|---|---|---|---|---|---|
| | Antibiotic panel for potentiation screen | | | | | | | | | |
| | All concentrations are reported as (ug/mL, final concentration) in cation-adjusted Mueller Hinton Broth, 2% DMSO. | | | | | | | | | |
| | | | | | | | | | | |
| | Vancomycin | Cycloserine | Fosfomycin | Novobiocin | Erythromycin | Tetracycline | Ampicillin | Trimethoprim | Chloramphenicol | Norfloxacin |
| A | 128 | 16 | 2 | 128 | 64 | 0.5 | 4 | 0.3125 | 4 | 0.0625 |
| B | 64 | 8 | 1 | 64 | 32 | 0.25 | 2 | 0.15625 | 2 | 0.03125 |
| C | 32 | 4 | 0.5 | 32 | 16 | 0.125 | 1 | 0.078125 | 1 | 0.015625 |

FIG. 10C

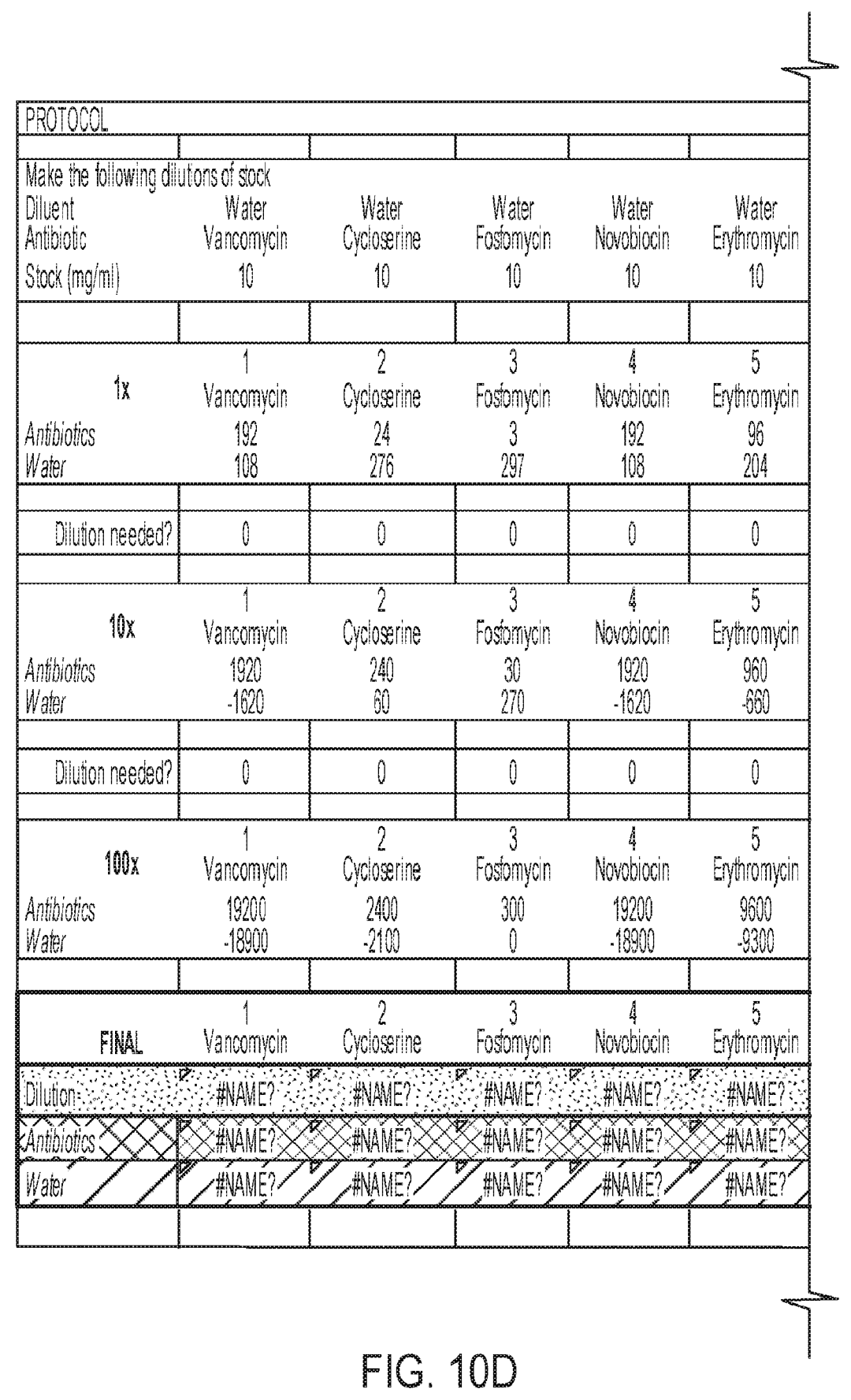

| PROTOCOL | | | | | |
|---|---|---|---|---|---|
| | | | | | |
| Make the following dilutions of stock | | | | | |
| Diluent | Water | Water | Water | Water | Water |
| Antibiotic | Vancomycin | Cycloserine | Fosfomycin | Novobiocin | Erythromycin |
| Stock (mg/ml) | 10 | 10 | 10 | 10 | 10 |
| | | | | | |
| | 1 | 2 | 3 | 4 | 5 |
| **1x** | Vancomycin | Cycloserine | Fosfomycin | Novobiocin | Erythromycin |
| *Antibiotics* | 192 | 24 | 3 | 192 | 96 |
| *Water* | 108 | 276 | 297 | 108 | 204 |
| | | | | | |
| Dilution needed? | 0 | 0 | 0 | 0 | 0 |
| | | | | | |
| | 1 | 2 | 3 | 4 | 5 |
| **10x** | Vancomycin | Cycloserine | Fosfomycin | Novobiocin | Erythromycin |
| *Antibiotics* | 1920 | 240 | 30 | 1920 | 960 |
| *Water* | -1620 | 60 | 270 | -1620 | -660 |
| | | | | | |
| Dilution needed? | 0 | 0 | 0 | 0 | 0 |
| | | | | | |
| | 1 | 2 | 3 | 4 | 5 |
| **100x** | Vancomycin | Cycloserine | Fosfomycin | Novobiocin | Erythromycin |
| *Antibiotics* | 19200 | 2400 | 300 | 19200 | 9600 |
| *Water* | -18900 | -2100 | 0 | -18900 | -9300 |
| | | | | | |
| | 1 | 2 | 3 | 4 | 5 |
| **FINAL** | Vancomycin | Cycloserine | Fosfomycin | Novobiocin | Erythromycin |
| Dilution | #NAME? | #NAME? | #NAME? | #NAME? | #NAME? |
| *Antibiotics* | #NAME? | #NAME? | #NAME? | #NAME? | #NAME? |
| *Water* | #NAME? | #NAME? | #NAME? | #NAME? | #NAME? |
| | | | | | |

FIG. 10D

| | | | | |
|---|---|---|---|---|
| | | | | |
| Water<br>Tetracycline<br>10 | Water<br>Ampicillin<br>10 | Water<br>Trimethoprim<br>10 | Water<br>Chloramphenicol<br>10 | Water<br>Norfloxacin<br>10 |
| | | | | |
| 6<br>Tetracycline<br>0.75<br>299.25 | 7<br>Ampicillin<br>6<br>294 | 8<br>Trimethoprim<br>0.46875<br>299.53125 | 9<br>Chloramphenicol<br>6<br>294 | 10<br>Norfloxacin<br>0.09375<br>299.90625 |
| | | | | |
| 1 | 0 | 1 | 0 | 1 |
| | | | | |
| 6<br>Tetracycline<br>7.5<br>292.5 | 7<br>Ampicillin<br>60<br>240 | 8<br>Trimethoprim<br>4.6875<br>295.3125 | 9<br>Chloramphenicol<br>60<br>240 | 10<br>Norfloxacin<br>0.9375<br>299.0625 |
| | | | | |
| 0 | 0 | 0 | 0 | 1 |
| | | | | |
| 6<br>Tetracycline<br>75<br>225 | 7<br>Ampicillin<br>600<br>-300 | 8<br>Trimethoprim<br>46.875<br>253.125 | 9<br>Chloramphenicol<br>600<br>-300 | 10<br>Norfloxacin<br>9.375<br>290.625 |
| | | | | |
| 6<br>Tetracycline | 7<br>Ampicillin | 8<br>Trimethoprim | 9<br>Chloramphenicol | 10<br>Norfloxacin |
| #NAME? | #NAME? | #NAME? | #NAME? | #NAME? |
| #NAME? | #NAME? | #NAME? | #NAME? | #NAME? |
| #NAME? | #NAME? | #NAME? | #NAME? | #NAME? |
| | | | | |

FIG. 10D
CONTINUED

Map to Plate

*Original*

| | 1 | 2 | 3 | 4 | 5 | 6 | 7 | 8 | 9 | 10 |
|---|---|---|---|---|---|---|---|---|---|---|
| A | Vanc 128 | Cyc 16 | Fos 2 | Nov 128 | Eryth 64 | Tet 0.5 | Amp 4 | Trim 0.3125 | Chlor 4 | Nor 0.0625 |
| B | Vanc 64 | Cyc 8 | Fos 1 | Nov 64 | Eryth 32 | Tet 0.25 | Amp 2 | Trim 0.15625 | Chlor 2 | Nor 0.03125 |
| C | Vanc 32 | Cyc 4 | Fos 0.5 | Nov 32 | Eryth 16 | Tet 0.125 | Amp 1 | Trim 0.078125 | Chlor 1 | Nor 0.015625 |

*Remap*

| | 1 | 2 | 3 | 4 | 5 | 6 | 7 | 8 | 9 | 10 |
|---|---|---|---|---|---|---|---|---|---|---|
| | Vanc 128 | Cyc 16 | Fos 2 | Nov 128 | Eryth 64 | Tet 0.5 | Amp 4 | Trim 0.3125 | Chlor 4 | Nor 0.0625 |
| A | Vanc 64 | Cyc 8 | Fos 1 | Nov 64 | Eryth 32 | Tet 0.25 | Amp 2 | Trim 0.15625 | Chlor 2 | Nor 0.03125 |
| B | Vanc 32 | Cyc 4 | Fos 0.5 | Nov 32 | Eryth 16 | Tet 0.125 | Amp 1 | Trim 0.078125 | Chlor 1 | Nor 0.015625 |
| C | Chlor 4 | Chlor 2 | Chlor 1 | Nor 0.0625 | Nor 0.03125 | Nor 0.015625 | NB 1 | NB 2 | | |

FIG. 10E

| | | | | | | |
|---|---|---|---|---|---|---|
| **Assemble plates** | | | | | | |
| | | | **Total (well)** | | **Total (overall)** | |
| **Total plates** | 30 | | | | | |
| **Total well volume** | 25 | ul | 750 | uL | | |
| **Wells** | 32 | | | | | |
| | | | | | | |
| **Dye volume** | 1 | ul | 30 | uL | | |
| **Abx volume** | 1 | ul | 30 | uL | | |
| **Media volume** | 23 | ul | 690 | uL | 22.08 | ml |
| | | | | | | |
| **Deep well volume** | 0.8 | mL | | | | |
| | | | | | | |
| 1) Make 4 0.8 mL Deep well Plates using the above volumes | | | | | | |
| 2) Use Bravo (175 uL tips) to split 25 uL across 5 plates x 5 runs per deep well plate (30 plates total per deep well) | | | | | | |
| 3) Use the clear stick film, and put in box (label batch) | | | | | | |
| 4) Put box in chest freezer | | | | | | |
| *** Antibiotic curves were measured in Ab_curves (left 1 day at 4C) | | | | | | |

FIG. 10F

| CLOCK | N | MICROSCOPE | 1 | 2 | 3 | POOLING |
|---|---|---|---|---|---|---|
| 6:15 AM | Dilute culture (Set 1) | | | | | |
| 6:18 AM | | | | | | |
| 6:21 AM | | | | | | |
| | | | | | | |
| 8:00 AM | Clean all loaders, check supplies (pipettes, oil, etc.) | | | | | |
| 8:03 AM | | | | | | |
| 8:06 AM | | | | | | |
| 8:09 AM | | | | | | |
| 8:12 AM | | | | | | |
| | | | | | | |
| 8:15 AM | Prep for day | | | | | |
| 8:18 AM | | | | | | |
| 8:21 AM | | | | | | |
| 8:24 AM | Start culture 2 | | | | | |
| 8:27 AM | | | Thaw plates | | | |
| 8:30 AM | Pellet and resuspend culture | | Setup Janus | | | |
| 8:33 AM | | | Make Droplets (Antibiotic) | | | |
| 8:36 AM | | | | | | |
| 8:39 AM | | | | | | |
| 8:42 AM | | | | | | |
| 8:45 AM | | | Add bugs | | | |

FIG. 11A

| CLOCK | PERSON 1 | PERSON 2 | N | | CLOCK |
|---|---|---|---|---|---|
| 6:15 AM | Dilute culture (Set 1) | | | | 6:15 AM |
| 6:18 AM | | | | | 6:18 AM |
| 6:21 AM | | | | | 6:21 AM |
| | | | | | |
| 8:00 AM | Clean all loaders, check supplies (pipettes, oil) | | | | 8:00 AM |
| 8:03 AM | | | | | 8:03 AM |
| 8:06 AM | | | | | 8:06 AM |
| 8:09 AM | | | | | 8:09 AM |
| 8:12 AM | | | | | 8:12 AM |
| | | | | | |
| 8:15 AM | Prep for day | | | | 8:15 AM |
| 8:18 AM | | | | | 8:18 AM |
| 8:21 AM | | | | | 8:21 AM |
| 8:24 AM | Start culture 2 | | | | 8:24 AM |
| 8:27 AM | | Thaw plates | | | 8:27 AM |
| 8:30 AM | Pellet and resuspend culture | Setup Janus | | | 8:30 AM |
| 8:33 AM | | Make Droplets (Antibiotic) Add bugs | | | 8:33 AM |
| 8:36 AM | | | | | 8:36 AM |
| 8:39 AM | | | | | 8:39 AM |
| 8:42 AM | | | | | 8:42 AM |
| 8:45 AM | | | | | 8:45 AM |

FIG. 11A CONTINUED

Times: 10:39 AM, 10:42 AM, 10:45 AM, 10:48 AM, 10:51 AM, 10:54 AM, 10:57 AM, 11:00 AM, 11:03 AM, 11:06 AM, 11:09 AM, 11:12 AM, 11:15 AM, 11:18 AM, 11:21 AM, 11:24 AM, 11:27 AM, 11:30 AM, 11:33 AM, 11:36 AM, 11:39 AM Task labels:
- Pellet and resuspend culture
- Thaw plates
- Setup Janus
- Make Droplets (Antibiotic) Add bugs
- Make Droplets (Set 1)
- Run Chip 3
- Merge Chip 3
- Pool Droplets (Set 1)
- Start culture 3
- Load Chip 1
- Setup scope (Chip 1)

11:42 AM 11:45 AM 11:48 AM 11:51 AM 11:54 AM 11:57 AM 12:00 PM 12:03 PM 12:06 PM 12:09 PM 12:12 PM 12:15 PM 12:18 PM 12:21 PM 12:24 PM 12:27 PM 12:30 PM 12:33 PM 12:36 PM 12:39 PM 12:42 PM

Add bugs
Make Droplets (Set 2)
Pool Droplets (Set 2)
Run Chip 1
Setup scope (Chip 2)
Setup scope (Chip 2)
Add bugs
Make Droplets (Set 3)
Pool Droplets (Set 3)

Set up Chip 2
Load Chip 2
Merge Chip 1
Set up Chip 3

11:42 AM 11:45 AM 11:48 AM 11:51 AM 11:54 AM 11:57 AM 12:00 PM 12:03 PM 12:06 PM 12:09 PM 12:12 PM 12:15 PM 12:18 PM 12:21 PM 12:24 PM 12:27 PM 12:30 PM 12:33 PM 12:36 PM 12:39 PM 12:42 PM

Pool Droplets (Set 2)
Add bugs
Make Droplets (Set 3)
Pool Droplets (Set 3)

Add bugs
Make Droplets (Set 2)

Run Chip 1
Setup scope (Chip 2)

Set up Chip 2
Load Chip 2
Merge Chip 1
Set up Chip 3

11:42 AM 11:45 AM 11:48 AM 11:51 AM 11:54 AM 11:57 AM 12:00 PM 12:03 PM 12:06 PM 12:09 PM 12:12 PM 12:15 PM 12:18 PM 12:21 PM 12:24 PM 12:27 PM 12:30 PM 12:33 PM 12:36 PM 12:39 PM 12:42 PM

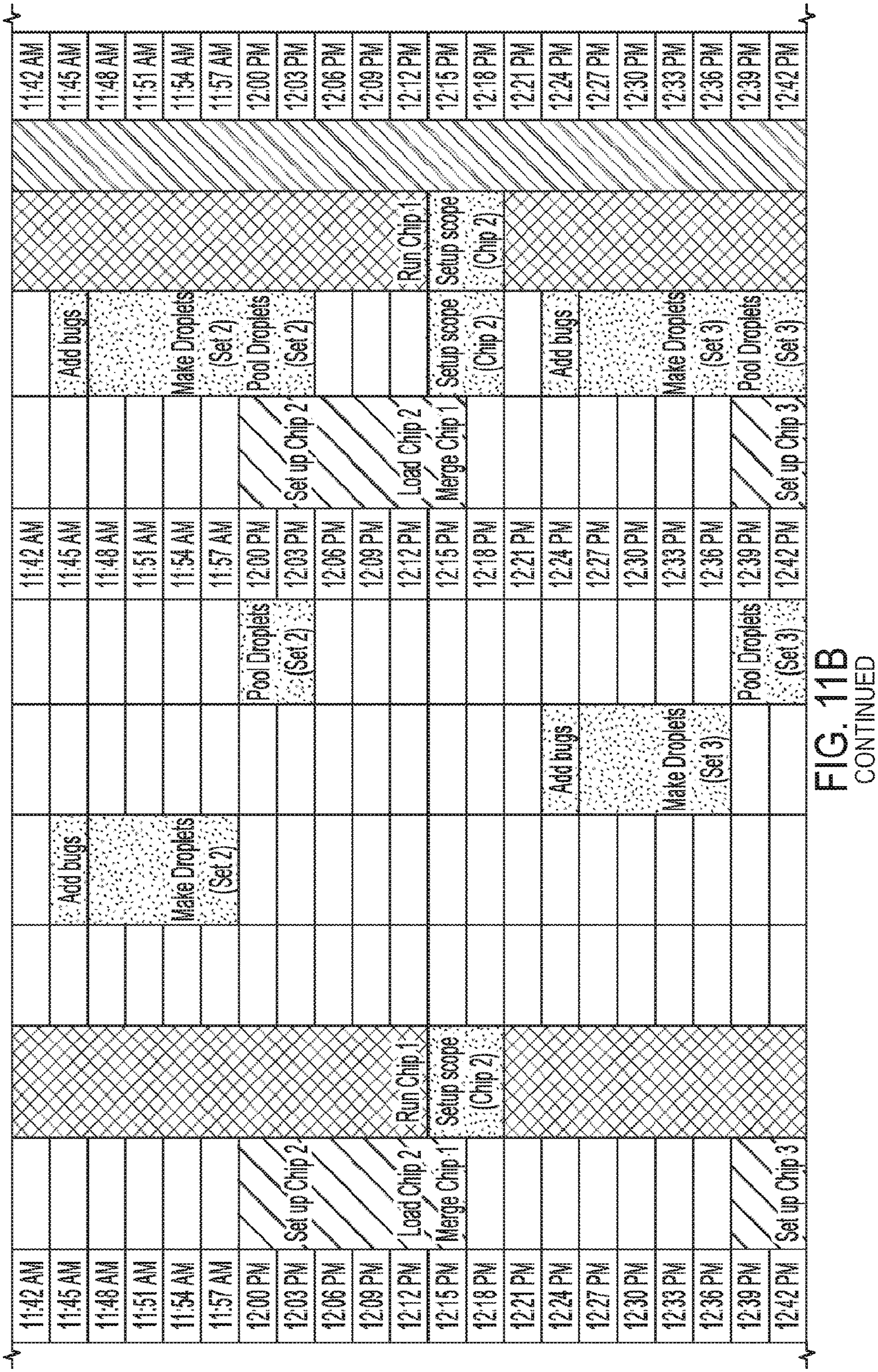

FIG. 11B
CONTINUED

| Time | Column A | Column B | Time | Column C | Column D | Column E | Column F | Column G | Time | Column H | Column I |
|------|----------|----------|------|----------|----------|----------|----------|----------|------|----------|----------|
| 2:57 PM | Load Chip 1 | Run Chip 1 | 2:57 PM | | | | Add bugs | | 2:57 PM | Load Chip 1 | Run Chip 1 |
| 3:00 PM | Merge Chip 1 | Setup scope (Chip 2) | 3:00 PM | | | | | | 3:00 PM | Merge Chip 1 | Setup scope (Chip 2) |
| 3:03 PM | | | 3:03 PM | | | | | | 3:03 PM | | |
| 3:06 PM | | | 3:06 PM | | | | | | 3:06 PM | | |
| 3:09 PM | | | 3:09 PM | | | | Make Droplets (Set 3) | | 3:09 PM | | |
| 3:12 PM | | | 3:12 PM | | | | | | 3:12 PM | | |
| 3:15 PM | | | 3:15 PM | | | | | | 3:15 PM | | |
| 3:18 PM | | | 3:18 PM | | | | | | 3:18 PM | | |
| 3:21 PM | | | 3:21 PM | | | | | | 3:21 PM | | |
| 3:24 PM | Set up Chip 3 | | 3:24 PM | | | Pool Droplets (Set 3) | | | 3:24 PM | Set up Chip 3 | |
| 3:27 PM | | | 3:27 PM | | | | | | 3:27 PM | | |
| 3:30 PM | Load Chip 3 | | 3:30 PM | | | | | | 3:30 PM | Load Chip 3 | |
| 3:33 PM | | | 3:33 PM | | | | | | 3:33 PM | | |
| 3:36 PM | Merge Chip 2 | Run Chip 2 | 3:36 PM | | | | | | 3:36 PM | Merge Chip 2 | Run Chip 2 |
| 3:39 PM | | Setup scope (Chip 3) | 3:39 PM | | | | | | 3:39 PM | | Setup scope (Chip 3) |
| 3:42 PM | | | 3:42 PM | | | | | | 3:42 PM | | |
| 3:45 PM | | | 3:45 PM | | | | | | 3:45 PM | | |
| 3:48 PM | | | 3:48 PM | | | | | | 3:48 PM | | |

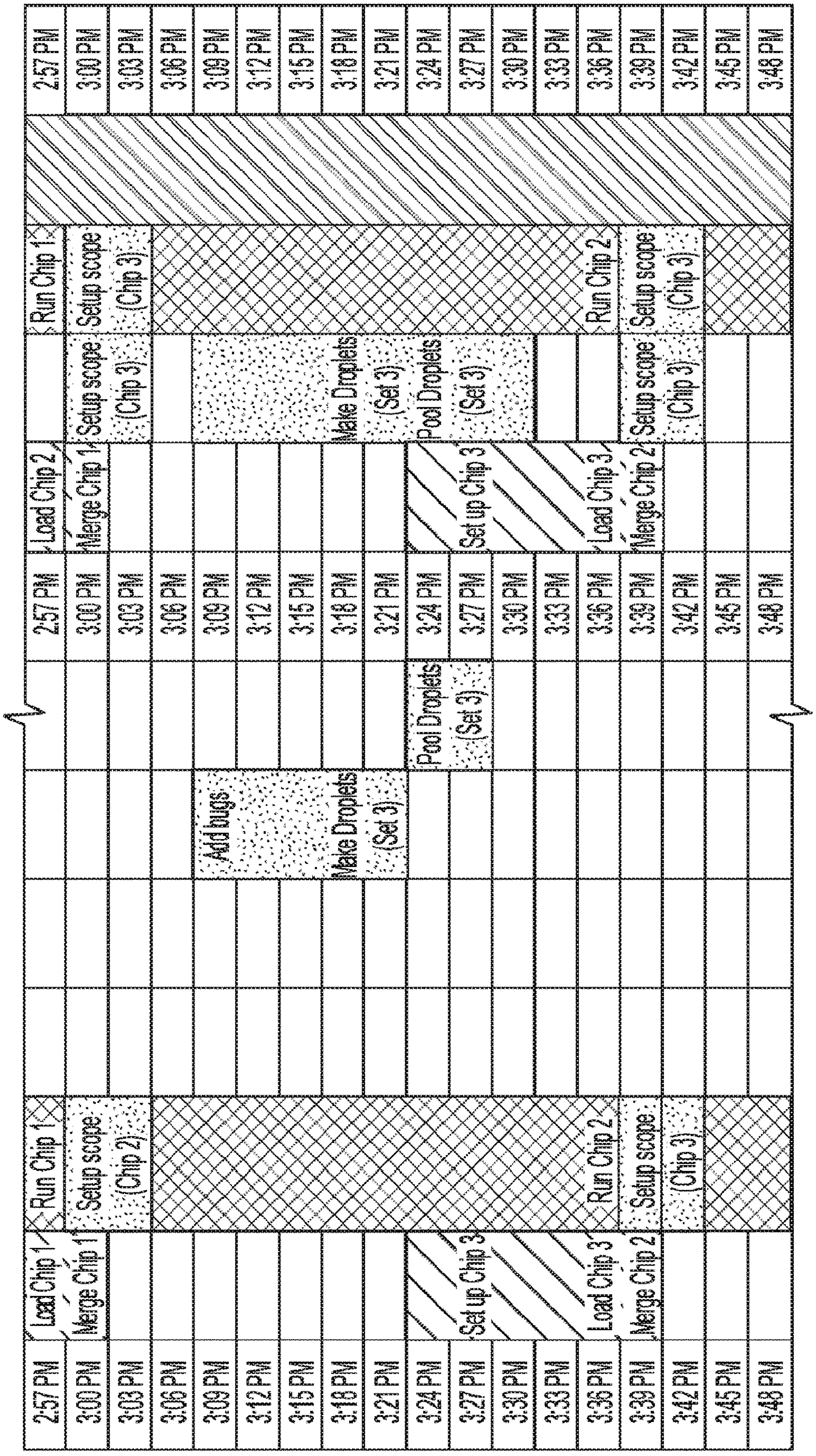

FIG. 11C
CONTINUED

Shift 3

3:51 PM
3:54 PM
3:57 PM
4:00 PM
4:03 PM
4:06 PM
4:09 PM
4:12 PM
4:15 PM
4:18 PM
4:21 PM
4:24 PM

Run Chip 3

Merge Chip 3

3:51 PM
3:54 PM
3:57 PM
4:00 PM
4:03 PM
4:06 PM
4:09 PM
4:12 PM
4:15 PM
4:18 PM
4:21 PM
4:24 PM
12:00 AM

Run Chip 3

Merge Chip 3

3:51 PM
3:54 PM
3:57 PM
4:00 PM
4:03 PM
4:06 PM
4:09 PM
4:12 PM
4:15 PM
4:18 PM
4:21 PM
4:24 PM

CONTINUED

| ID | Chip | Label | Structure | Net | Vanc | Cyc |
|---|---|---|---|---|---|---|
| 0 | Plate: BR88914Block: B3Eryth: 0.552757912805Sulb: 0.791452168321 | B9 | *5,6-Dihydro-5-aza-2'-deoxycytidine* | 0.01 | 0.09 | 0.31 |
| 1 | Plate: BR88914Block: B3Eryth: 0.552757912805Sulb: 0.791452168321 | G10 | *Iodophenpropit dihydrobromide* | 0.33 | -0.1 | 0.09 |
| 2 | Plate: BR88916Block: B2Sulb: 0.606583634662 | G2 | *Pasireotide (ditrifluoroacetate)* | 0.22 | 0.09 | 0.36 |
| 3 | Plate: BR88919Block: B3Eryth: 0.352404148517Sulb: 1.21522556775 | E9 | *NVP-BSK805 2HCl* | 0.18 | 0 | 0.47 |
| 4 | Plate: BR88923Block: B2Sulb: 0.0922699886818 | H4 | *DICHLOROPHEN* | 0.51 | 0.74 | 1.25 |
| 5 | Plate: BR88925Block: B3Eryth: 0.701507307538Sulb: 0.938863511725 | A9 | *NSC 23766* | 0.14 | -0.7 | 0.01 |
| 6 | Plate: BR88930Block: B2Sulb: 0.779245883318 | F7 | *SNS-032 (BMS-387032)* | 0.18 | -0.2 | 0 |
| 7 | Plate: BR88930Block: B3Eryth: 0.289772902424Sulb: 1.15710615965 | F9 | *Riboflavin (Vitamin B2)* | 0.06 | 0.21 | 0.18 |
| 8 | Plate: BR88973Block: B3Eryth: 0.79209429415Sulb: 0.847704544035 | D9 | *Ciglitazone* | 0.49 | 0.8 | 0.3 |
| 9 | Plate: BR88984Block: B2Sulb: 0.185720504599 | G3 | *20-Hydroxyecdysone* | 0.04 | 1.09 | 0.26 |
| 10 | Plate: BR88984Block: B3Eryth: -0.500922931795Sulb: -0.134836392492 | G11 | *Cephalomannine* | -0.1 | 0.23 | 0 |
| 11 | Plate: BR88986Block: B1Eryth: 0.460040217986 | D2 | *SOTALOL HYDROCHLORIDE* | 0.16 | 0.86 | 0.19 |
| 12 | Plate: BR88986Block: B2Sulb: 1.00627835803 | E3 | *NICERGOLINE* | 0.38 | 0.77 | 0 |
| 13 | Plate: BR88986Block: B3Eryth: 0.167514321456Sulb: 1.14743721345 | C10 | *D-LACTITOL MONOHYDRATE* | 0.42 | 0.98 | 0.13 |
| 14 | Plate: BR89003Block: B3Eryth: 0.51768987887Sulb: 0.943139850296 | G10 | *PENTETIC ACID* | 0.5 | 0.77 | 0.12 |
| 15 | Plate: BR89009Block: B3Eryth: -0.0645830745771Sulb: 0.258012697852 | G11 | *Ponatinib (AP24534)* | 0.06 | 0.35 | 0.58 |
| 16 | Plate: BR89009Block: B3Eryth: -0.0645830745771Sulb: 0.258012697852 | G9 | *AT7867* | 0.27 | -0.2 | 0.29 |
| 17 | Plate: BR89013Block: B1Eryth: 0.3815278056665 | C5 | *Indacaterol Maleate* | 0.19 | 0.36 | 0.06 |
| 18 | Plate: BR89018Block: B1Eryth: 0.376834525321 | B5 | *Flucloxacillin sodium* | 0.09 | 0.01 | 0 |

FIG. 12A

| | | | | | | |
|---|---|---|---|---|---|---|
| 19 | Plate: BR89018Block: B1Eryth: 0.376834525321 | C4 | *Pivmecillinam hydrochloride* | 0.36 | 0.12 | 0.66 |
| 20 | Plate: BR89018Block: B3Eryth: 0.0405261448726Sulb: 0.0613600236718 | F11 | *Tenovin-6* | 0.03 | 0.05 | 0.08 |
| 21 | Plate: BR89020Block: B3Eryth: 0.527951819872Sulb: 0.993947289986 | A10 | *GW 9662* | 0.45 | 0.74 | 0.03 |
| 22 | Plate: BR89020Block: B3Eryth: 0.527951819872Sulb: 0.993947289986 | D11 | *Taltobulin (trifluoroacetate)* | 0.49 | 0.71 | 0.03 |
| 23 | Plate: BR89024Block: B2Sulb: 0.926542923672 | F3 | *Oxacillin sodium monohydrate* | 0.12 | 0.2 | 0.34 |
| 24 | Plate: BR89047Block: B3Eryth: 0.67171808179Sulb: 1.38228858605 | D9 | *Acarbose* | 0.17 | 0.8 | 0.76 |
| 25 | Plate: BR89051Block: B3Eryth: 0.531751964308Sulb: 1.10652292514 | C10 | *PRT062607 (P505-15, BIIB057) HCl* | 0.2 | 0 | 0.7 |
| 26 | Plate: BR88912Block: B1Eryth: 0.421761329819 | B8 | *Panobinostat (LBH589)* | 0.04 | 0.14 | 0.38 |
| 27 | Plate: BR88921Block: B1Eryth: -0.00601100214676 | A4 | *P1,P4-Di(adenosine-5')tetraphosphate ammonium* | 0.01 | 0.15 | 0.15 |
| 28 | Plate: BR88930Block: B1Eryth: 0.586600956812 | D7 | *BORNYL ACETATE* | 0 | 0.15 | 0.32 |
| 29 | Plate: BR88951Block: B2Sulb: 1.3888417617 | H7 | *ASPIRIN* | 0 | 0 | 0.13 |
| 30 | Plate: BR88988Block: B3Eryth: 0.648603000401Sulb: 0.937638911073 | G10 | *PENICILLIN G POTASSIUM* | 0.59 | 0.67 | 0.7 |
| 31 | Plate: BR88992Block: B2Sulb: 0.985637785972 | H3 | *2-Deoxy-2-fluoro-D-glucose* | 0.13 | 0.33 | -0.1 |
| 32 | Plate: BR88995Block: B1Eryth: 0.305760611571 | A6 | *IPAG* | 0 | 0.36 | 0.78 |
| 33 | Plate: BR89013Block: B2Sulb: 0.786950293262 | G7 | *HEXACHLOROPHENE* | 0 | 0 | 0.55 |
| 34 | Plate: BR89020Block: B1Eryth: 0.0229772036644 | B6 | *SDZ 21009* | -0.1 | 0.27 | 0.64 |
| 35 | Plate: BR89020Block: B1Eryth: 0.0229772036644 | D4 | *Enisamium iodide* | 0 | 0.08 | 0.42 |
| 36 | Plate: BR89024Block: B1Eryth: 0.559955406578 | D7 | *D-Glucose 6-Phosphate Barium Salt Heptahydrate* | 0.02 | 0 | 0 |

FIG. 12A
CONTINUED

| Fos | Nov | Eryth | Tet | Amp | Trim | Chlor | Nor | LogD | FULLNAME | VENDORCATALOGID |
|---|---|---|---|---|---|---|---|---|---|---|
| -0.1 | -0.1 | 0.09 | 0.04 | 0.73 | -0.4 | 0.07 | -0.2 | -1.668 | Berry and Associates | PY 7106 |
| -0.2 | 0.75 | 0.68 | 0 | -0.1 | 0.54 | 0.91 | 0.21 | 3.874 | Tocris Bioscience | 779 |
| 0.1 | 0.62 | 1.02 | 0.31 | 0.17 | 0.47 | 0.27 | -0.1 | 1.711 | Medchemexpress | HY-79135 |
| -0.4 | 0.4 | 0.26 | 0.33 | 0.71 | 0.35 | 0.49 | 0.25 | 1.83 | Selleck | S2686 |
| 0.76 | 0.64 | 1.15 | 0.79 | 1.04 | -0.2 | 0.7 | 1 | 4.391 | MicroSource Discovery Systems Inc. | 1500626 |
| -0.3 | 0.82 | 0.43 | 0.25 | -0.2 | 0.42 | 0.78 | 0.03 | 3.045 | Tocris Bioscience | 2161 |
| 0.09 | 0.33 | 1.16 | 0.21 | 0.05 | 0.08 | 0.69 | 0 | 1.067 | Selleck | S1145 |
| 0.32 | 0 | 0.12 | -0.1 | 0.71 | 0 | -0.2 | 0.03 | -0.271 | Selleck | S2540 |
| -0.2 | 0.36 | 0.08 | 0 | 0.21 | 0.13 | -0.1 | 0.3 | 4.571 | Tocris Bioscience | 1307 |
| 0.36 | 0.13 | -0.2 | 0.11 | 0 | 0 | 0 | 0.68 | 1.137 | Selleck | S2417 |
| 0 | 0.81 | 0.23 | 0.26 | 0.22 | 0.13 | 0.3 | 0.33 | 2.937 | Selleck | S2408 |
| 0.25 | 0.14 | 0.08 | 0.04 | 0.14 | 0.01 | -0.1 | 0.35 | -0.685 | MicroSource Discovery Systems Inc. | 1506043 |
| -0.1 | 0.14 | 0 | 0 | 0.15 | 0.01 | -0.2 | 0.34 | 1.902 | MicroSource Discovery Systems Inc. | 1501133 |
| -0.4 | 0.42 | 0 | -0.2 | -0.2 | 0.17 | -0.3 | 0.26 | -4.688 | MicroSource Discovery Systems Inc. | 1505436 |
| 0.06 | 0.36 | 0.68 | 0.34 | 0.02 | -0.2 | 0.26 | 0.11 | -12.469 | MicroSource Discovery Systems Inc. | 1506082 |
| -0.2 | 0.1 | 0 | 0.09 | 0.83 | 0 | 0.05 | 0.07 | 5.015 | Selleck | S1490 |
| 0.31 | 0.46 | 1.17 | 0.33 | 0.08 | 0.26 | 0.85 | 0.22 | 2.807 | Selleck | S1558 |
| -0.1 | 0.76 | 1.46 | 0.19 | 0 | 0.54 | 1.16 | 0 | 2.699 | Selleck | S3083 |

FIG.12B

| | | | | | | | | | | |
|---|---|---|---|---|---|---|---|---|---|---|
| 0.57 | 0 | 0.11 | -0.2 | 0.82 | 0.01 | 0 | 0.04 | 2.503 | Prestwick Chemical Inc. | Prestw-1011 |
| 0.49 | -0.1 | 0 | -0.3 | 0.72 | -0.1 | -0.6 | 0.01 | 2.676 | Prestwick Chemical Inc. | Prestw-1053 |
| 0.19 | 0.04 | 0 | 0.05 | 0.8 | -0.1 | 0 | 0 | 3.75 | Selleck | S4900 |
| -0.1 | 0.16 | 0 | -0.2 | 0.19 | 0 | -0.2 | 0.33 | 3.173 | Tocris Bioscience | 1508 |
| -0.4 | 0.19 | 0 | -0.1 | 0.14 | 0 | -0.3 | 0.29 | 2.891 | Medchemexpress | HY-15584A |
| 0.48 | 0.16 | 0.06 | 0.2 | 1.19 | 0.03 | 0.07 | 0.17 | 1.634 | Selleck | S2563 |
| 1.12 | 0.43 | 0.7 | 0.22 | 0.11 | 0.18 | 0.19 | 0.42 | -6.84 | Selleck | S1271 |
| 0.08 | 0.55 | 0.9 | 0.38 | 0.27 | 0.3 | 0.65 | 0.22 | 0.646 | Selleck | S8032 |
| 0.76 | 0.06 | 0.38 | 0.2 | 0.18 | 0.21 | 0.23 | 0.17 | 1.963 | Selleck | S1030 |
| 0.73 | 0.14 | 0.13 | 0.49 | 0.18 | 0.18 | 0.19 | 0 | -10.158 | Enzo Life Sciences | AC954 |
| 1.14 | 0.44 | 0.09 | 0.24 | 0.04 | 0.02 | 0 | -0.2 | 2.354 | MicroSource Discovery Systems Inc. | 1502510 |
| 1.55 | -0.1 | 0.12 | 0.14 | 0.28 | 0.37 | 0.11 | -0.2 | -0.245 | MicroSource Discovery Systems Inc. | 1500130 |
| 0.4 | -0.1 | 0.37 | 0.36 | 0.57 | 0.45 | 0.14 | 0.19 | -0.35 | MicroSource Discovery Systems Inc. | 1500465 |
| 0.77 | 0.03 | 0.4 | -0.1 | -0.2 | -0.2 | -0.2 | -0.2 | -1.574 | santa cruz biotechnology, inc. | sc-220725 |
| 0.22 | 0.16 | 0.3 | 0.18 | 0.64 | 0.16 | 0.21 | 0.48 | 3.855 | Tocris Bioscience | 544 |
| 0.96 | 0.26 | 0.24 | 0.29 | 0.41 | 0.04 | 0.29 | 0.31 | 7.305 | MicroSource Discovery Systems Inc. | 1500328 |
| 1.13 | 0.62 | 0.61 | 0.44 | -0.1 | 0 | 0.02 | 0 | 1.772 | Tocris Bioscience | 1516 |
| 1.02 | 0.63 | 0.38 | 0.25 | 0.19 | -0.2 | -0.1 | -0.3 | 2.226 | Vitas-M Laboratory Ltd. | STL194198 |
| 0.94 | -0.1 | 0.08 | 0.09 | -0.1 | -0.1 | -0.1 | 0 | -4.071 | TCI America | G0052 |

FIG.12B
CONTINUED

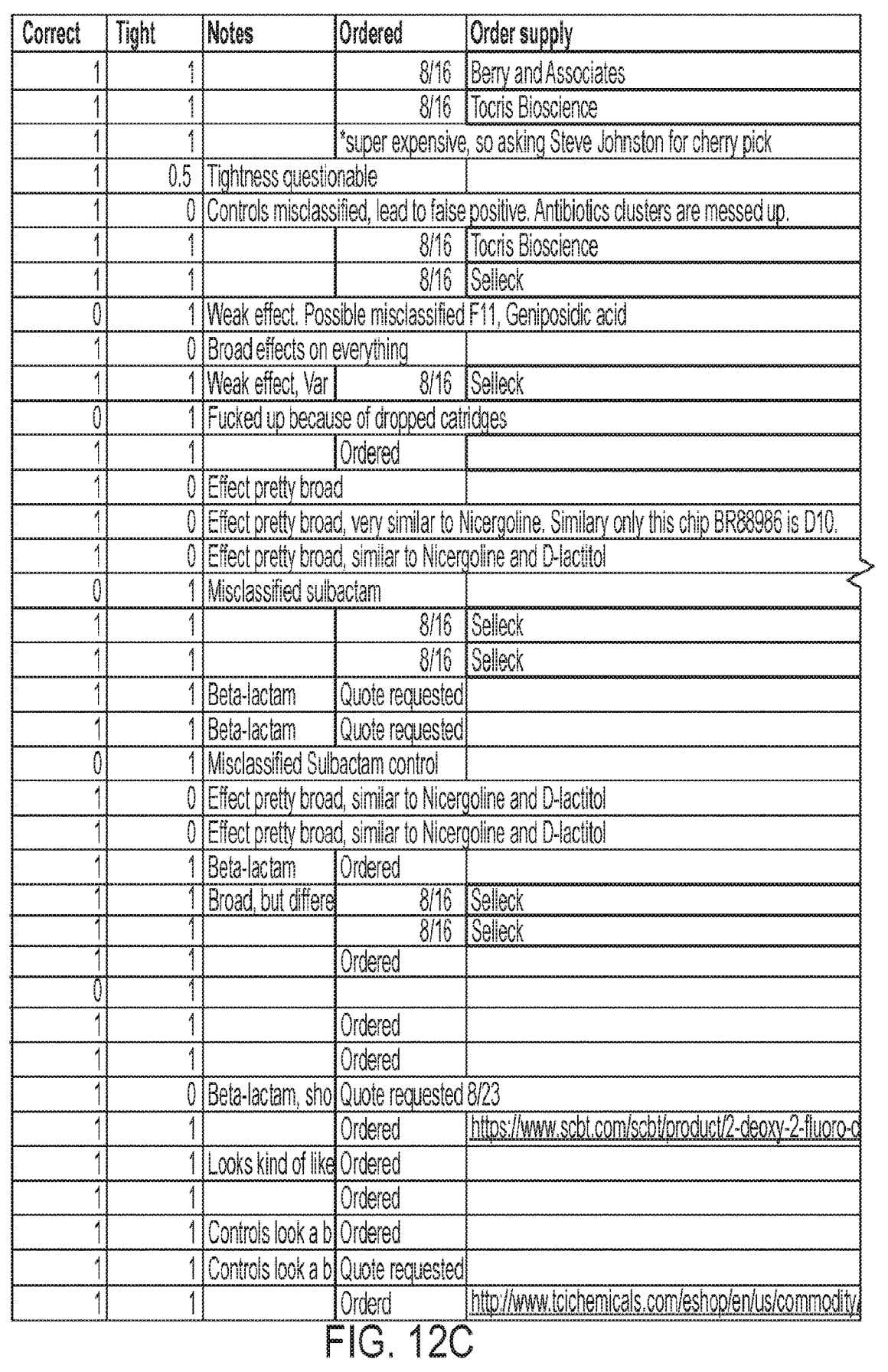

| Correct | Tight | Notes | Ordered | Order supply |
|---|---|---|---|---|
| 1 | 1 | | 8/16 | Berry and Associates |
| 1 | 1 | | 8/16 | Tocris Bioscience |
| 1 | 1 | | *super expensive, so asking Steve Johnston for cherry pick | |
| 1 | 0.5 | Tightness questionable | | |
| 1 | 0 | Controls misclassified, lead to false positive. Antibiotics clusters are messed up. | | |
| 1 | 1 | | 8/16 | Tocris Bioscience |
| 1 | 1 | | 8/16 | Selleck |
| 0 | 1 | Weak effect. Possible misclassified F11, Geniposidic acid | | |
| 1 | 0 | Broad effects on everything | | |
| 1 | 1 | Weak effect, Var | 8/16 | Selleck |
| 0 | 1 | Fucked up because of dropped catridges | | |
| 1 | 1 | | Ordered | |
| 1 | 0 | Effect pretty broad | | |
| 1 | 0 | Effect pretty broad, very similar to Nicergoline. Similary only this chip BR88986 is D10. | | |
| 1 | 0 | Effect pretty broad, similar to Nicergoline and D-lactitol | | |
| 0 | 1 | Misclassified sulbactam | | |
| 1 | 1 | | 8/16 | Selleck |
| 1 | 1 | | 8/16 | Selleck |
| 1 | 1 | Beta-lactam | Quote requested | |
| 1 | 1 | Beta-lactam | Quote requested | |
| 0 | 1 | Misclassified Sulbactam control | | |
| 1 | 0 | Effect pretty broad, similar to Nicergoline and D-lactitol | | |
| 1 | 0 | Effect pretty broad, similar to Nicergoline and D-lactitol | | |
| 1 | 1 | Beta-lactam | Ordered | |
| 1 | 1 | Broad, but differe | 8/16 | Selleck |
| 1 | 1 | | 8/16 | Selleck |
| 1 | 1 | | Ordered | |
| 0 | 1 | | | |
| 1 | 1 | | Ordered | |
| 1 | 1 | | Ordered | |
| 1 | 0 | Beta-lactam, sho | Quote requested 8/23 | |
| 1 | 1 | | Ordered | https://www.scbt.com/scbt/product/2-deoxy-2-fluoro-d |
| 1 | 1 | Looks kind of like | Ordered | |
| 1 | 1 | | Ordered | |
| 1 | 1 | Controls look a b | Ordered | |
| 1 | 1 | Controls look a b | Quote requested | |
| 1 | 1 | | Orderd | http://www.tcichemicals.com/eshop/en/us/commodity/ |

FIG. 12C

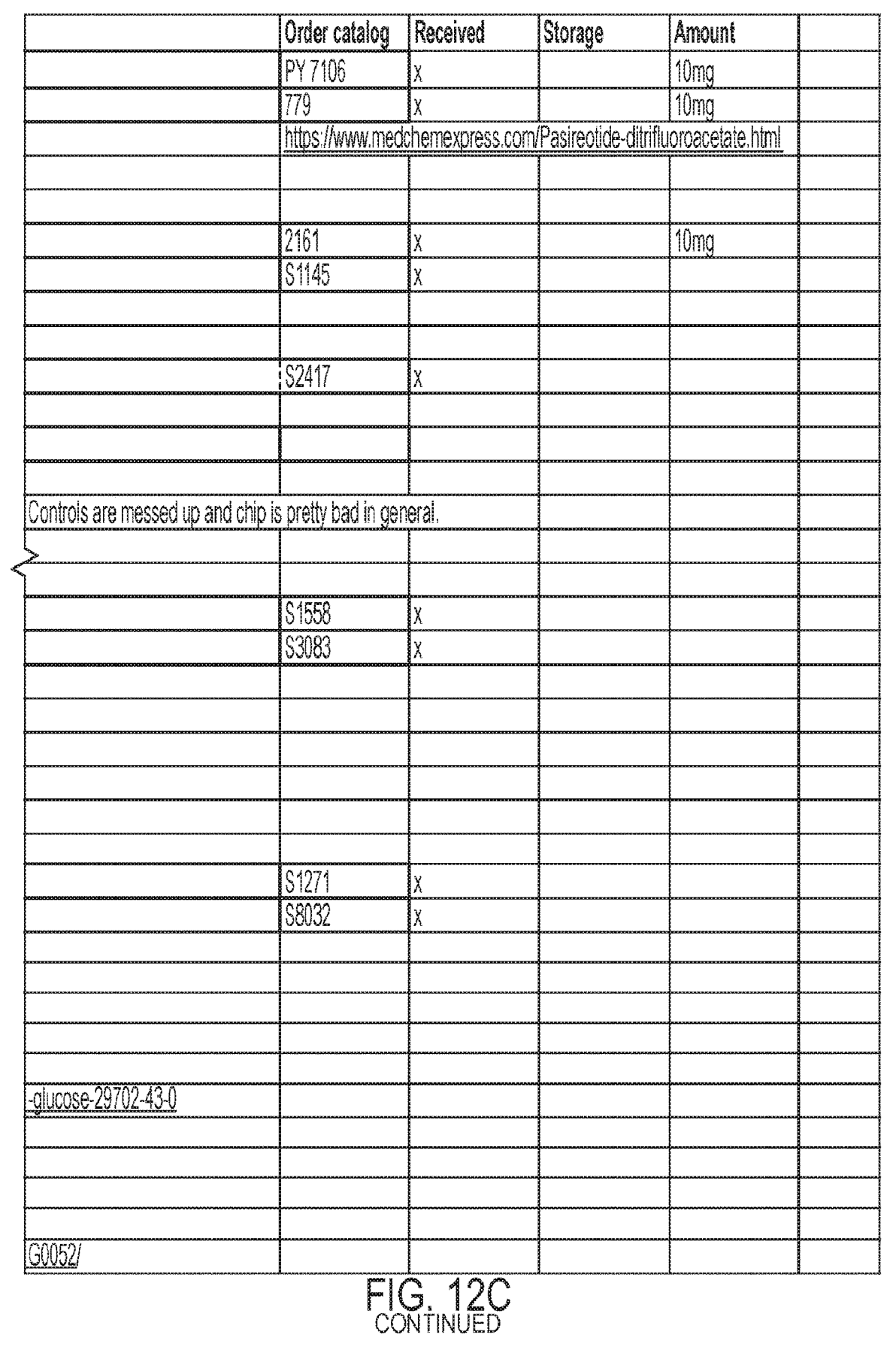

| | Order catalog | Received | Storage | Amount | |
|---|---|---|---|---|---|
| | PY 7106 | x | | 10mg | |
| | 779 | x | | 10mg | |
| | https://www.medchemexpress.com/Pasireotide-ditrifluoroacetate.html | | | | |
| | | | | | |
| | | | | | |
| | 2161 | x | | 10mg | |
| | S1145 | x | | | |
| | | | | | |
| | | | | | |
| | S2417 | x | | | |
| | | | | | |
| | | | | | |
| | | | | | |
| Controls are messed up and chip is pretty bad in general. | | | | | |
| | | | | | |
| | | | | | |
| | S1558 | x | | | |
| | S3083 | x | | | |
| | | | | | |
| | | | | | |
| | | | | | |
| | | | | | |
| | | | | | |
| | | | | | |
| | S1271 | x | | | |
| | S8032 | x | | | |
| | | | | | |
| | | | | | |
| | | | | | |
| | | | | | |
| | | | | | |
| -glucose-29702-43-0 | | | | | |
| | | | | | |
| | | | | | |
| | | | | | |
| | | | | | |
| G0052/ | | | | | |

FIG. 12C
CONTINUED

Parameters

| | |
|---|---|
| Antibiotic Stock | 100 ** MAKE NEW STOCKS AT 100 MG/ML IN DMSO |
| Dilution Factor | 100 * See Model Tab, expect 1 uL in total volume 100 uL culture in final checkerboard plate |
| Volume | 400 |
| Volume of top row | 800 |

Concentrations from initial screening run (From "Antibiotics Concentrations" tab: https://docs.google.com/spreadsheets/d/1MQ2Sx5lYcrqA_JUzSHUGtlC33o9kwZiee8pF-xndOT8/e

| | Vancomycin | Cycloserine | Fosfomycin | Novobiocin | Erythromycin | Tetracycline | Ampicillin | Trimethoprim | Chloramphenicol | Norfloxacin |
|---|---|---|---|---|---|---|---|---|---|---|
| 1 | 128 | 16 | 2 | 128 | 64 | 0.5 | 4 | 0.3125 | 4 | 0.0625 |
| 2 | 64 | 8 | 1 | 64 | 32 | 0.25 | 2 | 0.15625 | 2 | 0.03125 |
| 3 | 32 | 4 | 0.5 | 32 | 16 | 0.125 | 1 | 0.078125 | 1 | 0.015625 |

Concentrations for original bchip validation checkerboards (best comparison is to use these curves so we can compare directly to bchip experiments)

| | Vancomycin | Cycloserine | Fosfomycin | Novobiocin | Erythromycin | Tetracycline | Ampicillin | Trimethoprim | Chloramphenicol | Norfloxacin |
|---|---|---|---|---|---|---|---|---|---|---|
| 1 | 512 | 64 | 8 | 512 | 256 | 2 | 16 | 1.25 | 16 | 0.5 |
| 2 | 256 | 32 | 4 | 256 | 128 | 1 | 8 | 0.625 | 8 | 0.25 |
| 3 | 128 | 16 | 2 | 128 | 64 | 0.5 | 4 | 0.3125 | 4 | 0.125 |
| 4 | 64 | 8 | 1 | 64 | 32 | 0.25 | 2 | 0.15625 | 2 | 0.0625 |
| 5 | 32 | 4 | 0.5 | 32 | 16 | 0.125 | 1 | 0.078125 | 1 | 0.03125 |
| 6 | 16 | 2 | 0.25 | 16 | 8 | 0.0625 | 0.5 | 0.0390625 | 0.5 | 0.015625 |
| 7 | 8 | 1 | 0.125 | 8 | 4 | 0.03125 | 0.25 | 0.01953125 | 0.25 | 0.0078125 |
| 8 | 0 | 0 | 0 | 0 | 0 | 0 | 0 | 0 | 0 | 0 |

FIG. 13A

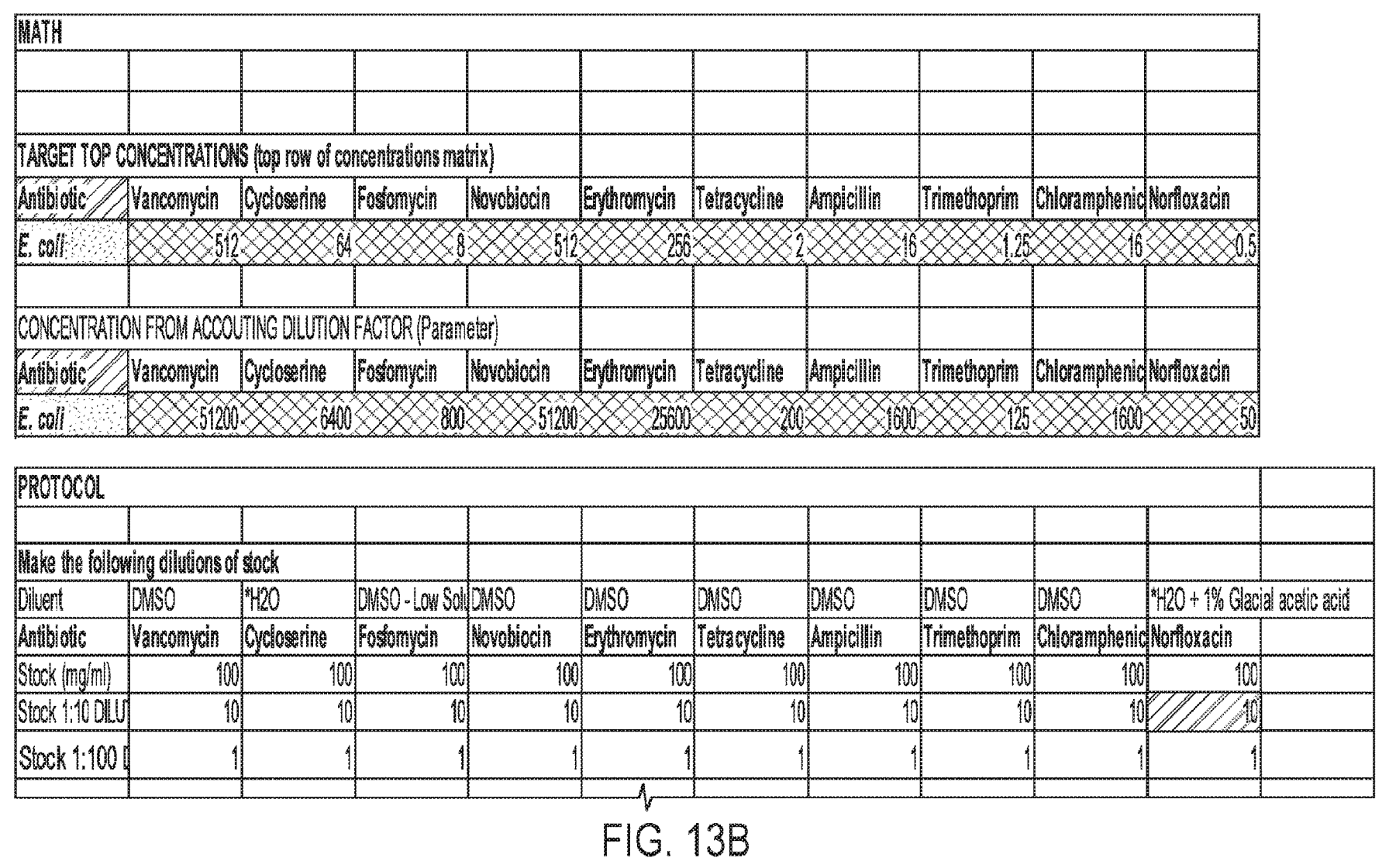

| MATH | | | | | | | | | | | |
|---|---|---|---|---|---|---|---|---|---|---|---|
| | | | | | | | | | | | |
| | | | | | | | | | | | |
| TARGET TOP CONCENTRATIONS (top row of concentrations matrix) | | | | | | | | | | | |
| Antibiotic | Vancomycin | Cycloserine | Fosfomycin | Novobiocin | Erythromycin | Tetracycline | Ampicillin | Trimethoprim | Chloramphenic | Norfloxacin | |
| *E. coli* | 512 | 64 | 8 | 512 | 256 | 2 | 16 | 1.25 | 16 | 0.5 | |
| | | | | | | | | | | | |
| CONCENTRATION FROM ACCOUTING DILUTION FACTOR (Parameter) | | | | | | | | | | | |
| Antibiotic | Vancomycin | Cycloserine | Fosfomycin | Novobiocin | Erythromycin | Tetracycline | Ampicillin | Trimethoprim | Chloramphenic | Norfloxacin | |
| *E. coli* | 51200 | 6400 | 800 | 51200 | 25600 | 200 | 1600 | 125 | 1600 | 50 | |

| PROTOCOL | | | | | | | | | | | |
|---|---|---|---|---|---|---|---|---|---|---|---|
| | | | | | | | | | | | |
| Make the following dilutions of stock | | | | | | | | | | | |
| Diluent | DMSO | *H2O | DMSO - Low Sol | DMSO | DMSO | DMSO | DMSO | DMSO | DMSO | *H2O + 1% Glacial acetic acid | |
| Antibiotic | Vancomycin | Cycloserine | Fosfomycin | Novobiocin | Erythromycin | Tetracycline | Ampicillin | Trimethoprim | Chloramphenic | Norfloxacin | |
| Stock (mg/ml) | 100 | 100 | 100 | 100 | 100 | 100 | 100 | 100 | 100 | 100 | |
| Stock 1:10 DILU | 10 | 10 | 10 | 10 | 10 | 10 | 10 | 10 | 10 | 10 | |
| Stock 1:100 D | 1 | 1 | 1 | 1 | 1 | 1 | 1 | 1 | 1 | 1 | |
| | | | | | | | | | | | |

FIG. 13B

| | | | | | | | | | | | |
|---|---|---|---|---|---|---|---|---|---|---|---|
| To create, add this volume of 100 mg/ml STOCK to a new STOCK PLATE | | | | | | | | | | | |
| | 1 | 2 | 3 | 4 | 5 | 6 | 7 | 8 | 9 | 10 | |
| | Vancomycin | Cycloserine | Fosfomycin | Novobiocin | Erythromycin | Tetracycline | Ampicillin | Trimethoprim | Chloramphenic | Norfloxacin | |
| | 409.6 | 51.2 | 6.4 | 409.6 | 204.8 | 1.6 | 12.8 | 1 | 12.8 | 0.4 | |
| *E. coli* | 409.6 | 51.2 | 6.4 | 409.6 | 204.8 | 1.6 | 12.8 | 1 | 12.8 | 4 | |
| | | | | | | | | | | | |
| add DMSO | 1 | 2 | 3 | 4 | 5 | 6 | 7 | 8 | 9 | 10 | |
| | Vancomycin | Cycloserine | Fosfomycin | Novobiocin | Erythromycin | Tetracycline | Ampicillin | Trimethoprim | Chloramphenic | Norfloxacin | |
| *E. coli* | 390.4 | 748.8 | 793.6 | 390.4 | 595.2 | 798.4 | 787.2 | 799 | 787.2 | 796 | |
| | | | | | | | | | | | |
| Finally, serially dilute down the rows, leaving bottom row as pure DMSO | | | | | | | | | | | |
| | | | | | | | | | | | |
| NOTES | | | | | | | | | | | |
| - Cyc 100 mg/ml is in H2O | | | | | | | | | | | |
| - Nor 100 mg/ml is in H2O + 1% Glacial Acetic Acid | | | | | | | | | | | |
| - Everything else is in DMSO | | | | | | | | | | | |
| - Fosfomycin 100 mg/ml did not dissolve, but I was able to pipette anyway into the undissolved solution of the top well, with Cyc and Nor I couldn't | | | | | | | | | | | |

FIG. 13B
CONTINUED

| SOURCE PLATES | | | | |
|---|---|---|---|---|
| | | | | |
| Plate Barcode | Full Barcode | Antibiotics | Volume: 35 uL | 3357065 |
| 77 | 335706577 | Vanc | | |
| 78 | 335706578 | Cyc | | |
| 79 | 335706579 | Fos | | |
| 80 | 335706580 | Nov | | |
| 81 | 335706581 | Eryth | | |
| 82 | 335706582 | Tet | | |
| 83 | 335706583 | Amp | | |
| 84 | 335706584 | Trim | | |
| 85 | 335706585 | Chlor | | |
| 86 | 335706586 | Nor | | |

FIG. 13C

| | Plate | Well | Compound Name | Pos Abx | Neg Abx | Status |
|---|---|---|---|---|---|---|
| Batch 1 | Plate: BR88930 | F7 | SNS-032 (BMS-387032) | Eryth, Nov | Nor | -20C |
| | Plate: BR88984 | G3 | 20-Hydroxyecdysone | Vanc | Amp | -20C |
| | Plate: BR89009 | G9 | AT7867 | Eryth, Chlor | Tet | -20C |
| | Plate: BR89013 | C5 | Indacaterol Maleate | Nov, Eryth, Chlor | Cyc | -20C |
| | Plate: BR89047 | D9 | Acarbose | Vanc, Eryth, Cyc | Trim | -20C |
| | Plate: BR89051 | C10 | PRT062607 (P505-15, BIIB057) HCl | Eryth, Cyc, Chlor | Nor | -20C |
| | Plate: BR88914 | B9 | 5,6-Dihydro-5-aza-2'-deoxycytidine | Amp | Tet | 4C |
| | Plate: BR88914 | G10 | Iodophenpropit dihydrobromide | Nov, Eryth, Chlor | Nor | 4C |
| | Plate: BR88925 | A9 | NSC 23766 | Nov, Chlor | Tet | 4C |
| | | | | | | |
| Batch 2 | Plate: BR88916 | G2 | Pasireotide (ditrifluoroacetate) | Nov, Eryth, Trim | Nor | -20C |
| | Plate: BR88919 | E9 | NVP-BSK805 2HCl | Amp | Tet | -20C |
| | Plate: BR89024 | F3 | Oxacillin sodium monohydrate | Amp | Tet | -20C |
| | Plate: BR88912 | B8 | Panobinostat (LBH589) | Fos | Vanc | -20C |
| | Plate: BR88995 | A6 | IPAG | Cyc | Tet | 4C |
| | Plate: BR89020 | B6 | SDZ 21009 | Fos | Vanc | 4C |
| | Plate: BR89024 | D7 | Glucose 6-Phosphate Barium Salt Heptahyd | Fos | Amp | 4C |
| | | | Sulbactam | Amp | Tet | -20C |

FIG. 14A

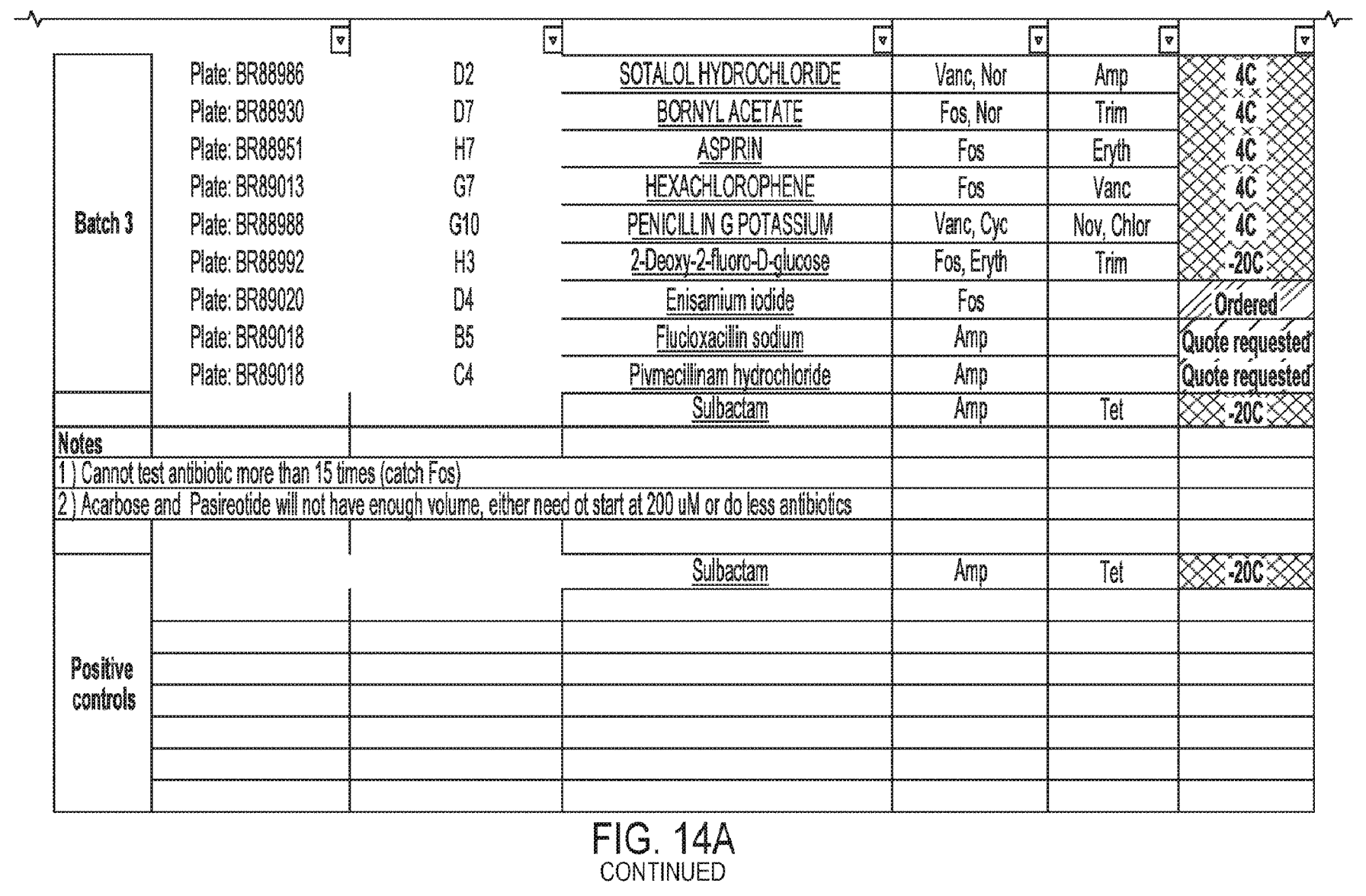

| | | | | | | |
|---|---|---|---|---|---|---|
| Batch 3 | Plate: BR88986 | D2 | SOTALOL HYDROCHLORIDE | Vanc, Nor | Amp | 4C |
| | Plate: BR88930 | D7 | BORNYL ACETATE | Fos, Nor | Trim | 4C |
| | Plate: BR88951 | H7 | ASPIRIN | Fos | Eryth | 4C |
| | Plate: BR89013 | G7 | HEXACHLOROPHENE | Fos | Vanc | 4C |
| | Plate: BR88988 | G10 | PENICILLIN G POTASSIUM | Vanc, Cyc | Nov, Chlor | 4C |
| | Plate: BR88992 | H3 | 2-Deoxy-2-fluoro-D-glucose | Fos, Eryth | Trim | -20C |
| | Plate: BR89020 | D4 | Enisamium iodide | Fos | | Ordered |
| | Plate: BR89018 | B5 | Flucloxacillin sodium | Amp | | Quote requested |
| | Plate: BR89018 | C4 | Pivmecillinam hydrochloride | Amp | | Quote requested |
| | | | Sulbactam | Amp | Tet | -20C |
| Notes | | | | | | |
| 1 ) Cannot test antibiotic more than 15 times (catch Fos) | | | | | | |
| 2 ) Acarbose and Pasireotide will not have enough volume, either need ot start at 200 uM or do less antibiotics | | | | | | |
| | | | | | | |
| Positive controls | | | Sulbactam | Amp | Tet | -20C |
| | | | | | | |
| | | | | | | |
| | | | | | | |
| | | | | | | |
| | | | | | | |
| | | | | | | |
| | | | | | | |

FIG. 14A CONTINUED

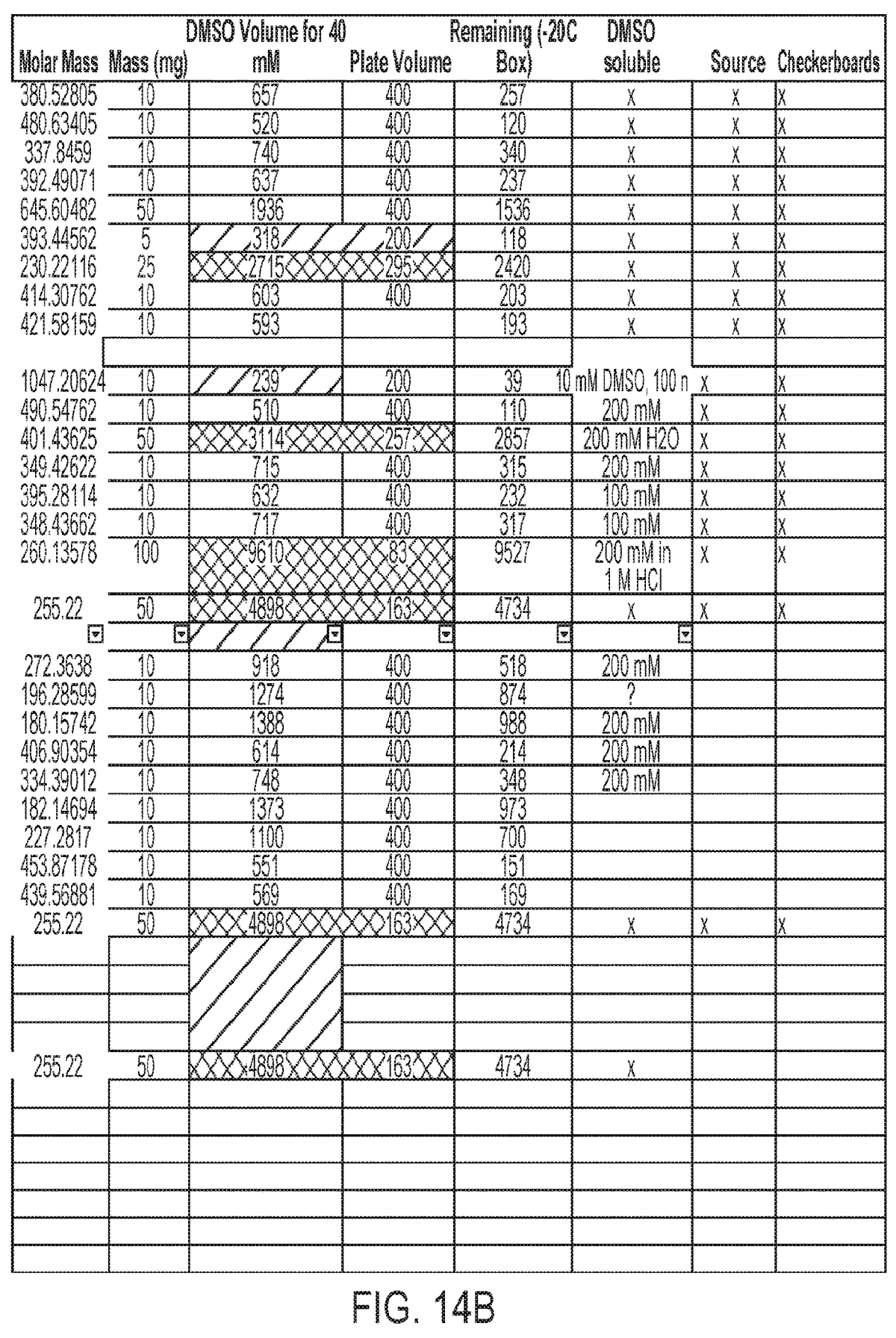

| Molar Mass | Mass (mg) | DMSO Volume for 40 mM | Plate Volume | Remaining (-20C Box) | DMSO soluble | Source | Checkerboards |
|---|---|---|---|---|---|---|---|
| 380.52805 | 10 | 657 | 400 | 257 | x | x | x |
| 480.63405 | 10 | 520 | 400 | 120 | x | x | x |
| 337.8459 | 10 | 740 | 400 | 340 | x | x | x |
| 392.49071 | 10 | 637 | 400 | 237 | x | x | x |
| 645.60482 | 50 | 1936 | 400 | 1536 | x | x | x |
| 393.44562 | 5 | 318 | 200 | 118 | x | x | x |
| 230.22116 | 25 | 2715 | 295 | 2420 | x | x | x |
| 414.30762 | 10 | 603 | 400 | 203 | x | x | x |
| 421.58159 | 10 | 593 | | 193 | x | x | x |
| | | | | | | | |
| 1047.20624 | 10 | 239 | 200 | 39 | 10 mM DMSO, 100 n | x | x |
| 490.54762 | 10 | 510 | 400 | 110 | 200 mM | x | x |
| 401.43625 | 50 | 3114 | 257 | 2857 | 200 mM H2O | x | x |
| 349.42622 | 10 | 715 | 400 | 315 | 200 mM | x | x |
| 395.28114 | 10 | 632 | 400 | 232 | 100 mM | x | x |
| 348.43662 | 10 | 717 | 400 | 317 | 100 mM | x | x |
| 260.13578 | 100 | 9610 | 83 | 9527 | 200 mM in 1 M HCl | x | x |
| 255.22 | 50 | 4898 | 163 | 4734 | x | x | x |
| | | | | | | | |
| 272.3638 | 10 | 918 | 400 | 518 | 200 mM | | |
| 196.28599 | 10 | 1274 | 400 | 874 | ? | | |
| 180.15742 | 10 | 1388 | 400 | 988 | 200 mM | | |
| 406.90354 | 10 | 614 | 400 | 214 | 200 mM | | |
| 334.39012 | 10 | 748 | 400 | 348 | 200 mM | | |
| 182.14694 | 10 | 1373 | 400 | 973 | | | |
| 227.2817 | 10 | 1100 | 400 | 700 | | | |
| 453.87178 | 10 | 551 | 400 | 151 | | | |
| 439.56881 | 10 | 569 | 400 | 169 | | | |
| 255.22 | 50 | 4898 | 163 | 4734 | x | x | x |
| | | | | | | | |
| 255.22 | 50 | 4898 | 163 | 4734 | x | | |

FIG. 14B

| | | | | | |
|---|---|---|---|---|---|
| 1) Prepare stock plate (800 uL Deep Well Plate) | | | | | |
| | | | | | |
| | | | | | |
| | | | | | |
| 1) Make 40 mM DMSO stocks according to information above | | | | | |
| 2) For GREEN cells, volume is greater than 2000 uL . Therefore, dilute in 2000, and then add the volume in the next column to STOCK plate, and normalize to 400 uL | | | | | |
| 3) For RED cells, volume is < 400 uL. Therefore add 200 uL to stock plate, and supplement with 200 uL DMSO to go to 400 uL | | | | | |
| 4) Serially dilute down the plate | | | | | |
| | | | | | |

FIG. 14C

| Plate map | | 1 | 2 | 3 | 4 | 5 | 6 | 7 | 8 | 9 | 10 | 11 | 12 |
|---|---|---|---|---|---|---|---|---|---|---|---|---|---|
| | | | 400 SOTALOL HYDROCHLORIDE | 400 BORNYL ACETATE | 400 ASPIRIN | 400 HEXACHLOROPHENE | 400 PENICILLIN G POTASSIUM | 163.3408 Sulbactam | | | | | |
| | A | | 40 | 40 | 40 | 40 | 40 | 40 | | | | | |
| | B | | 20 | 20 | 20 | 20 | 20 | 20 | | | | | |
| | C | | 10 | 10 | 10 | 10 | 10 | 10 | | | | | |
| | D | | 5 | 5 | 5 | 5 | 5 | 5 | | | | | |
| | E | | 2.5 | 2.5 | 2.5 | 2.5 | 2.5 | 2.5 | | | | | |
| | F | | 1.25 | 1.25 | 1.25 | 1.25 | 1.25 | 1.25 | | | | | |
| | G | | 0.625 | 0.625 | 0.625 | 0.625 | 0.625 | 0.625 | | | | | |
| | H | | 0 | 0 | 0 | 0 | 0 | 0 | | | | | |

FIG. 14D

| Abx counts | |
|---|---|
| Vanc | 7 |
| Cyc | 5 |
| Fos | 8 |
| Nov | 6 |
| Eryth | 9 |
| Eryth | 8 |
| Amp | 10 |
| Trim | 4 |
| Chlor | 6 |
| Nov | 6 |
| | |

FIG. 14E

| Source plates | | | |
| --- | --- | --- | --- |
| Plate Barcode | Full Barcode | Antibiotics | |
| 87 | 335706587 | SNS-032 (BMS-387032) | 3357065 |
| 88 | 335706588 | 20-Hydroxyecdysone | |
| 89 | 335706589 | AT7867 | |
| 90 | 335706590 | Indacaterol Maleate | |
| 91 | 335706591 | Acarbose | |
| 92 | 335706592 | PRT062607 (P505-15, BIIB057) HCl | |
| 93 | 335706593 | 5,6-Dihydro-5-aza-2'-deoxycytidine | |
| 94 | 335706594 | Iodophenpropit dihydrobromide | |
| 95 | 335706595 | NSC 23766 | |
| 96 | 335706596 | Sulbactam | |

FIG. 14F

| Notes: | | | | | |
|---|---|---|---|---|---|
| Pipette Limit | 5 uL | | | | |
| Expected plate volume (96) | 100 uL | | | | |
| Top concentration to test | 400 uM | | | | |
| | | | | | |
| Adjuvant (Transfer 1) | | | | | |
| From source | | | | | |
| Adjuvant Volume (uL) | 1 | < 5 uL | | | |
| Concentration (mM) | 40 | 100x | Concentration (uM) | 40000 | |
| | | | %DMSO (v/v) | 100 | |
| Other additions | | | | | |
| Antibiotic (uL) | 1 | (I10) | Concentration (uM) | 400 | |
| Dye (uL) | 0 | | % DMSO (v/v) | 1 | |
| Volume bugs (uL) | 98 | | | | |
| | | | | | |
| Total volume | 100 | 100 uL | Final concentration (uM) | 400 | 400 uM |
| | | | Final % DMSO (v/v) | 2 | |
| | | | | | |
| Adjuvant stock | | | | | |
| Stock -> Source | 9 | x | | | |
| Stock -> Source Dead Volume | 50 | uL | | | |
| | | | | | |
| Stock -> Checkerboard | 4 | x | # of abx x each adj | | |
| Stock -> Checkerboard Dead Vol. | 5 | uL | | | |
| | | | | | |
| Number of replicate checkerboard | 2 | x | | | |
| | | | | | |
| | | | | | |
| Source Plate volume (uL) | 13 | uL | | | |
| Total stock volume (uL) | 167 | uL | | | |
| | | | | | |
| 2X for 2-fold dilution curve | 334 | uL | | | |
| Round up | 400 | uL | | | |
| | | | | | |
| Volume of stock to make | 400 | uL | | | |

FIG. 15A

| | | |
|---|---|---|
| Antibiotic (transfer 2) | | |
| SOURCE PLATE | | |
| Volume (uL) | 1 | <5 uL |
| Conc. factor | 100 | x |
| | | |
| ADDITIONS TO SOURCE | | |
| Antibiotic (uL) | 1 | (b10) |
| Dye (uL) | 0 | (b15) |
| Volume bugs (uL) | 98 | (b16) |
| | | |
| Total volume | 100 | 100 uL |
| | | |
| | | |
| Adjuvant stock | | |
| Stock -> Source | 9 | x |
| Stock -> Source Dead Volume | 40 | uL |
| | | |
| Source -> Checkerboard | 15 | x |
| Source -> Checkerboard Dead Vol. | 10 | uL |
| | | |
| Number of replicate checkerboard | 2 | x |
| | | |
| | | |
| Source Plate volume (uL) | 40 | uL |
| Total stock volume (uL) | 400 | uL |
| | | |
| 2X for 2-fold dilution curve | 800 | uL |
| Round up | 800 | uL |
| | | |
| Volume of stock to make | 800 | uL |

FIG. 15B

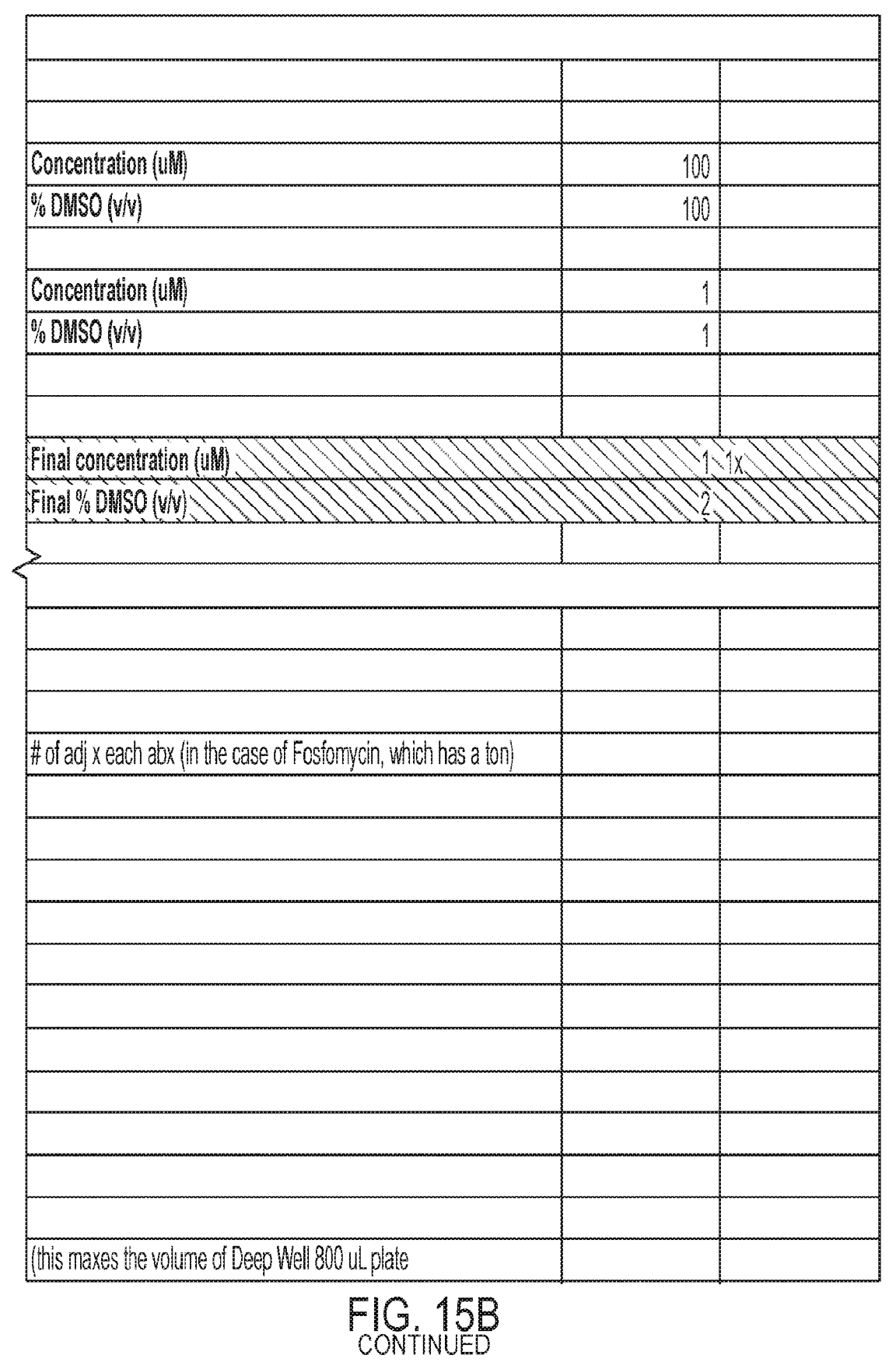

| | | |
|---|---|---|
| | | |
| | | |
| | | |
| Concentration (uM) | 100 | |
| % DMSO (v/v) | 100 | |
| | | |
| Concentration (uM) | 1 | |
| % DMSO (v/v) | 1 | |
| | | |
| | | |
| Final concentration (uM) | 1 | 1x |
| Final % DMSO (v/v) | 2 | |
| | | |
| | | |
| | | |
| | | |
| | | |
| # of adj x each abx (in the case of Fosfomycin, which has a ton) | | |
| | | |
| | | |
| | | |
| | | |
| | | |
| | | |
| | | |
| | | |
| | | |
| | | |
| | | |
| | | |
| (this maxes the volume of Deep Well 800 uL plate | | |

FIG. 15B
CONTINUED

1) STOCK PLATES

Plate: 800 uL Deep well plate

Protocol

1) Add 400 uL of compound in DMSO to top row

2) Add 200 uL of DMSO to remaining rows

3) Serially dilute 200 uL to row B-G , leaving G

STOCK - ADJ (small scale)

| | IEM | Dolasetron | 3 | 4 | 5 | 6 | 7 | 8 | 9 | 10 | 11 | 12 |
|---|---|---|---|---|---|---|---|---|---|---|---|---|
| A | Cmp 400 uM | Cmp 400 uM | | | | | | | | | | |
| B | Cmp 200 uM | Cmp 200 uM | | | | | | | | | | |
| C | Cmp 100 uM | Cmp 100 uM | | | | | | | | | | |
| D | Cmp 50 uM | Cmp 50 uM | | | | | | | | | | |
| E | Cmp 25 uM | Cmp 25 uM | | | | | | | | | | |
| F | Cmp 12.5 uM | Cmp 12.5 uM | | | | | | | | | | |
| G | Cmpd 6.25 uM | Cmpd 6.25 uM | | | | | | | | | | |
| H | DMSO | DMSO | DMSO | DMSO | DMSO | DMSO | DMSO | DMSO | DMSO | DMSO | DMSO | DMSO |

STOCK - ABX

| | 5 | AB 1 | AB 2 | 5 | 5 | 6 | 7 | 8 | 9 | 10 | 11 | 12 |
|---|---|---|---|---|---|---|---|---|---|---|---|---|
| A | | AB 50 | AB 50 | | | | | | | | | |
| B | | AB 25 | AB 25 | | | | | | | | | |
| C | | AB 12.5 | AB 12.5 | | | | | | | | | |
| D | | AB 6.25 | AB 6.25 | | | | | | | | | |
| E | | AB 3.125 | AB 3.125 | | | | | | | | | |
| F | | AB 1.5 | AB 1.5 | | | | | | | | | |
| G | | AB 0.7 | AB 0.7 | | | | | | | | | |
| H | | DMSO | DMSO | DMSO | DMSO | DMSO | DMSO | DMSO | DMSO | DMSO | DMSO | DMSO |

FIG. 16A

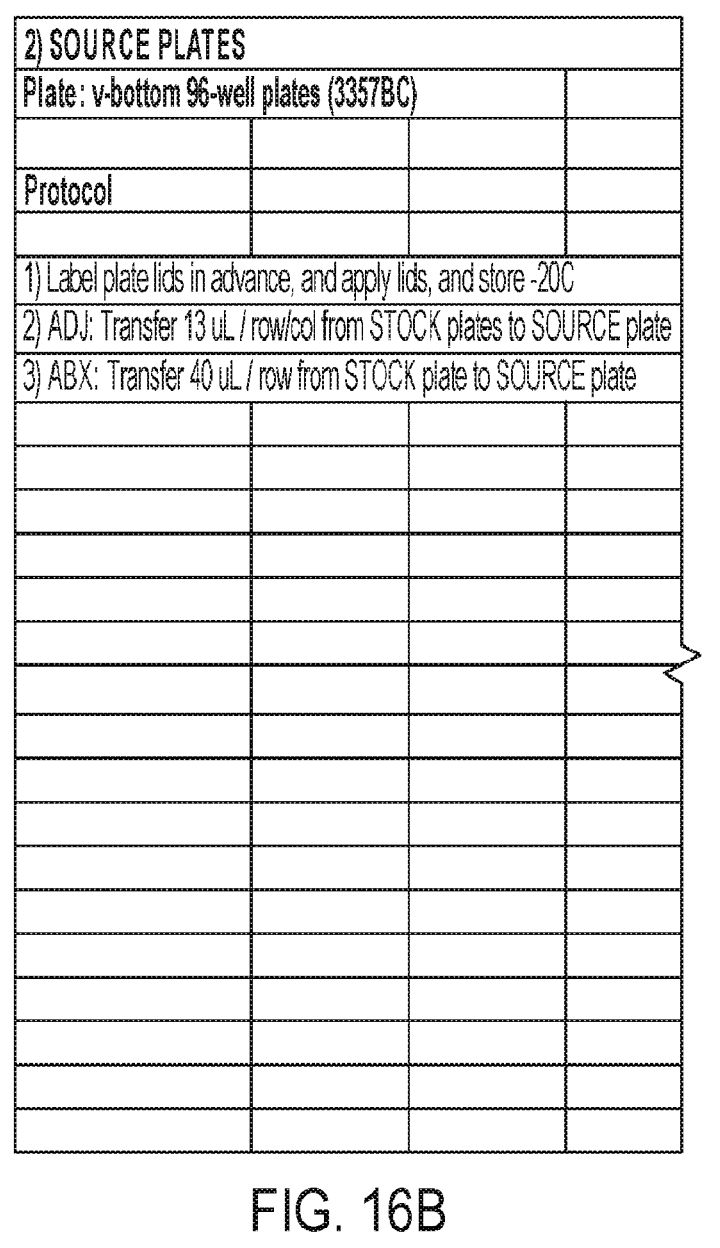

| | | | |
|---|---|---|---|
| 2) SOURCE PLATES | | | |
| Plate: v-bottom 96-well plates (3357BC) | | | |
| | | | |
| Protocol | | | |
| | | | |
| 1) Label plate lids in advance, and apply lids, and store -20C | | | |
| 2) ADJ: Transfer 13 uL / row/col from STOCK plates to SOURCE plate | | | |
| 3) ABX: Transfer 40 uL / row from STOCK plate to SOURCE plate | | | |
| | | | |
| | | | |
| | | | |
| | | | |
| | | | |
| | | | |
| | | | |
| | | | |
| | | | |
| | | | |
| | | | |
| | | | |
| | | | |
| | | | |
| | | | |
| | | | |
| | | | |

FIG. 16B

SOURCE PLATE - Adjuvant transfer

| | 1 | 2 | 3 | 4 | 5 | 6 | 7 |
|---|---|---|---|---|---|---|---|
| A | DMSO | DMSO | Cmp 400 uM | Cmp 400 uM | Cmp 400 uM | Cmp 400 uM | Cmp 400 uM |
| B | DMSO | DMSO | Cmp 200 uM | Cmp 200 uM | Cmp 200 uM | Cmp 200 uM | Cmp 200 uM |
| C | DMSO | DMSO | Cmp 100 uM | Cmp 100 uM | Cmp 100 uM | Cmp 100 uM | Cmp 100 uM |
| D | DMSO | DMSO | Cmp 50 uM | Cmp 50 uM | Cmp 50 uM | Cmp 50 uM | Cmp 50 uM |
| E | DMSO | DMSO | Cmp 25 uM | Cmp 25 uM | Cmp 25 uM | Cmp 25 uM | Cmp 25 uM |
| F | DMSO | DMSO | Cmp 12.5 uM | Cmp 12.5 uM | Cmp 12.5 uM | Cmp 12.5 uM | Cmp 12.5 uM |
| G | DMSO | DMSO | Cmpd 6.25 uM | Cmpd 6.25 uM | Cmpd 6.25 uM | Cmpd 6.25 uM | Cmpd 6.25 uM |
| H | DMSO | DMSO | DMSO | DMSO | DMSO | DMSO | DMSO |

SOURCE PLATE - Antibiotics

| | 1 | 2 | 3 | 4 | 5 | 6 | 7 |
|---|---|---|---|---|---|---|---|
| A | Ab 50 | DMSO | DMSO | Ab 0.7 | Ab 1.5 | Ab 3.125 | Ab 6.25 |
| B | Ab 25 | DMSO | DMSO | Ab 0.7 | Ab 1.5 | Ab 3.125 | Ab 6.25 |
| C | Ab 12.5 | DMSO | DMSO | Ab 0.7 | Ab 1.5 | Ab 3.125 | Ab 6.25 |
| D | Ab 6.25 | DMSO | DMSO | Ab 0.7 | Ab 1.5 | Ab 3.125 | Ab 6.25 |
| E | Ab 3.125 | DMSO | DMSO | Ab 0.7 | Ab 1.5 | Ab 3.125 | Ab 6.25 |
| F | Ab 1.5 | DMSO | DMSO | Ab 0.7 | Ab 1.5 | Ab 3.125 | Ab 6.25 |
| G | Ab 0.7 | DMSO | DMSO | Ab 0.7 | Ab 1.5 | Ab 3.125 | Ab 6.25 |
| H | DMSO | DMSO | DMSO | Ab 0.7 | Ab 1.5 | Ab 3.125 | Ab 6.25 |

FIG. 16B
CONTINUED

| | 8 | 9 | 10 | 11 | 12 |
|---|---|---|---|---|---|
| | Cmp 400 uM | Cmp 400 uM | Cmp 400 uM | DMSO | Cmp 400 uM |
| | Cmp 200 uM | Cmp 200 uM | Cmp 200 uM | DMSO | Cmp 200 uM |
| | Cmp 100 uM | Cmp 100 uM | Cmp 100 uM | DMSO | Cmp 100 uM |
| | Cmp 50 uM | Cmp 50 uM | Cmp 50 uM | DMSO | Cmp 50 uM |
| | Cmp 25 uM | Cmp 25 uM | Cmp 25 uM | DMSO | Cmp 25 uM |
| | Cmp 12.5 uM | Cmp 12.5 uM | Cmp 12.5 uM | DMSO | Cmp 12.5 uM |
| | Cmpd 6.25 uM | Cmpd 6.25 uM | Cmpd 6.25 uM | DMSO | Cmpd 6.25 uM |
| | DMSO | DMSO | DMSO | DMSO | DMSO |

| | 8 | 9 | 10 | 11 | 12 |
|---|---|---|---|---|---|
| | Ab 12.5 | Ab 25 | Ab 50 | DMSO | DMSO |
| | Ab 12.5 | Ab 25 | Ab 50 | DMSO | DMSO |
| | Ab 12.5 | Ab 25 | Ab 50 | DMSO | DMSO |
| | Ab 12.5 | Ab 25 | Ab 50 | DMSO | DMSO |
| | Ab 12.5 | Ab 25 | Ab 50 | DMSO | DMSO |
| | Ab 12.5 | Ab 25 | Ab 50 | DMSO | DMSO |
| | Ab 12.5 | Ab 25 | Ab 50 | DMSO | DMSO |
| | Ab 12.5 | Ab 25 | Ab 50 | DMSO | DMSO |
| | Ab 12.5 | Ab 25 | Ab 50 | DMSO | DMSO |

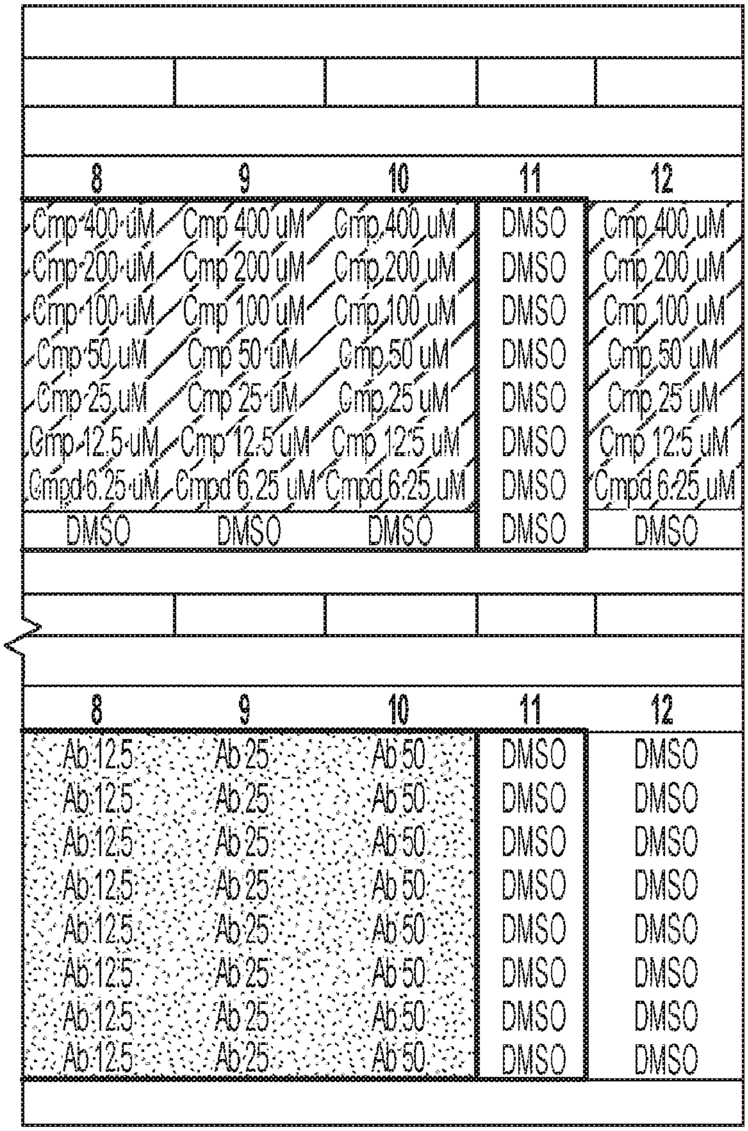

FIG. 16B
CONTINUED

3) CHECKERBOARD PLATES

Plate: v-bottom 96-well plates (3357BC)

Protocol

1) Use the Bravo to transfer 1 uL 1-1 from each SOURCE plate to checkerboard plate 2) Label plate lids in advance, and apply lids, and store -20C Checkerboard Plate

| | 1 | 2 | 3 | 4 | 5 | 6 | 7 | 8 | 9 | 10 | 11 | 12 |
|---|---|---|---|---|---|---|---|---|---|---|---|---|
| A | Ab 50 | DMSO | Cmp 400 uM | | | | | | | | DMSO | Cmp 400 uM |
| B | Ab 25 | DMSO | Cmp 200 uM | | | | | | | | DMSO | Cmp 200 uM |
| C | Ab 12.5 | DMSO | Cmp 100 uM | | | | | | | | DMSO | Cmp 100 uM |
| D | Ab 6.25 | DMSO | Cmp 50 uM | | | | | | | | DMSO | Cmp 50 uM |
| E | Ab 3.125 | DMSO | Cmp 25 uM | | | | | | | | DMSO | Cmp 25 uM |
| F | Ab 1.5 | DMSO | Cmp 12.5 uM | | | | | | | | DMSO | Cmp 12.5 uM |
| G | Ab 0.7 | DMSO | Cmpd 6.25 uM | | | | | | | | DMSO | Cmpd 6.25 uM |
| H | DMSO | DMSO | DMSO | Ab 0.7 | Ab 1.5 | Ab 12.5 | Ab 6.25 | Ab 12.5 | Ab 25 | Ab 50 | DMSO | DMSO |

FIG. 16C

| ID | Chip | Label | Structure | Net growth inhibition | Vancomycin | Cycloserin | Fosfomycin |
|---|---|---|---|---|---|---|---|
| 0 | Plate: BR88914Block: B2Z': n/a | G3 | *Clobenpropit dihydrobromide* | 0.34 | -0.2 | 0.04 | -0.4 |
| 1 | Plate: BR88914Block: B3Z': n/a | B9 | *5,6-Dihydro-5-aza-2'-deoxycytidine* | 0.01 | 0.05 | 0.22 | -0.2 |
| 2 | Plate: BR88914Block: B3Z': n/a | G10 | *Iodophenpropit dihydrobromide* | 0.33 | -0.1 | 0 | -0.3 |
| 3 | Plate: BR88916Block: B2Z': n/a | G2 | *Pasireotide (ditrifluoroacetate)* | 0.22 | 0.06 | 0.28 | 0 |
| 4 | Plate: BR88919Block: B3Z': n/a | E9 | *NVP-BSK805 2HCl* | 0.18 | 0 | 0.38 | -0.5 |
| 5 | Plate: BR88923Block: B2Z': n/a | H8 | *SULFANILAMIDE* | 0.2 | -0.1 | -0.1 | 0 |
| 6 | Plate: BR88925Block: B3Z': n/a | A9 | *NSC 23766* | 0.14 | -0.7 | 0 | -0.5 |
| 7 | Plate: BR88930Block: B1Z': n/a | D7 | *BORNYL ACETATE* | 0 | 0.12 | 0.23 | 1.01 |
| 8 | Plate: BR88930Block: B2Z': n/a | F7 | *SNS-032 (BMS-387032)* | 0.18 | -0.2 | -0.1 | 0 |
| 9 | Plate: BR88951Block: B2Z': n/a | H7 | *ASPIRIN* | 0 | 0 | 0.04 | 1.42 |
| 10 | Plate: BR88973Block: B3Z': n/a | D9 | *Ciglitazone* | 0.49 | 0.77 | 0.21 | -0.3 |
| 11 | Plate: BR88986Block: B2Z': n/a | E3 | *NICERGOLINE* | 0.38 | 0.74 | -0.1 | -0.3 |
| 12 | Plate: BR89003Block: B3Z': n/a | G10 | *PENTETIC ACID* | 0.5 | 0.74 | 0.03 | 0 |
| 13 | Plate: BR89009Block: B3Z': n/a | G9 | *AT7867* | 0.24 | -0.1 | 0.26 | 0.22 |
| 14 | Plate: BR89013Block: B1Z': n/a | C5 | *Indacaterol Maleate* | 0.19 | 0.33 | 0 | -0.2 |
| 15 | Plate: BR89018Block: B1Z': n/a | B5 | *Flucloxacillin sodium* | 0.09 | 0 | -0.1 | 0.44 |
| 16 | Plate: BR89018Block: B1Z': n/a | C4 | *Pivmecillinam hydrochloride* | 0.36 | 0.09 | 0.58 | 0.36 |
| 17 | Plate: BR89024Block: B2Z': n/a | F3 | *Oxacillin sodium monohydrate* | 0.12 | 0.17 | 0.25 | 0.35 |
| 18 | Plate: BR89047Block: B3Z': n/a | D9 | *Acarbose* | 0.17 | 0.76 | 0.67 | 1 |
| 19 | Plate: BR89051Block: B3Z': n/a | C10 | *PRT062607 (P505-15, BIIB057) HCl* | 0.2 | 0 | 0.61 | 0 |

FIG. 17A

| Novobiocin | Erythromycin | Tetraycline | Ampicillin | Trimethoprim | Chlorampheni | Norfloxacin | LogD |
|---|---|---|---|---|---|---|---|
| 0.46 | 0 | 0.03 | 0 | 0.31 | 0.72 | 0.1 | 3.639 |
| 0 | 0.04 | 0.07 | 0.76 | -0.3 | 0.2 | -0.3 | -1.668 |
| 0.78 | 0.63 | 0.02 | -0.1 | 0.61 | 1.03 | 0.18 | 3.874 |
| 0.65 | 0.97 | 0.33 | 0.2 | 0.54 | 0.4 | -0.1 | 1.711 |
| 0.44 | 0.21 | 0.35 | 0.74 | 0.42 | 0.61 | 0.22 | 1.83 |
| -0.1 | 0 | -0.1 | 0 | 0.79 | -0.1 | 0.04 | -0.212 |
| 0.85 | 0.38 | 0.28 | -0.2 | 0.49 | 0.91 | 0 | 3.045 |
| 0.48 | 0.04 | 0.26 | 0.07 | 0.08 | 0.09 | -0.2 | 2.354 |
| 0.37 | 1.11 | 0.24 | 0.08 | 0.14 | 0.82 | 0 | 1.067 |
| 0 | 0.07 | 0.17 | 0.31 | 0.43 | 0.23 | -0.3 | -0.245 |

FIG. 17B

| | | | | | | | |
|---|---|---|---|---|---|---|---|
| 0.4 | 0.03 | 0 | 0.24 | 0.2 | 0.01 | 0.27 | 4.571 |
| 0.17 | 0 | 0 | 0.18 | 0.08 | -0.1 | 0.31 | 1.902 |
| 0.4 | 0.63 | 0.37 | 0.05 | -0.1 | 0.38 | 0.08 | -12.469 |
| 0.52 | 1.21 | 0.38 | 0.16 | 0.36 | 1.06 | 0.25 | 2.807 |
| 0.79 | 1.41 | 0.22 | 0 | 0.61 | 1.29 | 0 | 2.699 |
| 0 | 0.06 | -0.1 | 0.85 | 0.08 | 0.06 | 0.01 | 2.503 |
| -0.1 | 0 | -0.3 | 0.75 | -0.1 | -0.5 | 0 | 2.676 |
| 0.2 | 0.01 | 0.23 | 1.22 | 0.09 | 0.2 | 0.14 | 1.634 |
| 0.47 | 0.65 | 0.24 | 0.14 | 0.24 | 0.32 | 0.39 | -6.84 |
| 0.58 | 0.85 | 0.41 | 0.3 | 0.36 | 0.78 | 0.19 | 0.646 |

FIG. 17B
CONTINUED

| ID | Chip | Label | Structure | Net Growth int | Vancomycin | Cyclimycin | Fantomycin | Novobiocin |
|---|---|---|---|---|---|---|---|---|
| 0 | Plack 581 889 14<br>Block 52<br>Z: n/a | G3 | Clot:?crocit ????? | 0:34 | -0.2 | 0.04 | -0.4 | 0.46 |
| 1 | Plack 581 889 14<br>Block 53<br>Z: n/a | B9 | 5.6-Oilhydro-5-ara-2'de???? | 0.01 | 0.05 | 0.22 | -0.2 | 0 |
| 2 | Plack 581 889 14<br>Block 53<br>Z: n/a | G10 | ??????????????????????? | 0:33 | -0.1 | 0 | -0.3 | 0.78 |
| 3 | Plack 581 889 16<br>Block 52<br>Z: n/a | G2 | ??????????????????????? | 0:22 | 0.06 | 0.28 | 0 | 0.65 |
| 4 | Plack 581 889 19<br>Block 53<br>Z: n/a | E9 | ???????????5HCL | 0.18 | 0 | 0.38 | -0.5 | 0.44 |
| 5 | Plack 581 889 23<br>Block 52<br>Z: n/a | H8 | 8LL FANLAMICE | 0:2 | -0.1 | -0.1 | 0 | -0.1 |
| 6 | Plack 581 889 25<br>Block 53<br>Z: n/a | A9 | NSC 23766 | 0.14 | -0.7 | 0 | -0.5 | 0.85 |

FIG. 17C

| Erythromycin | Tetracycline | Ampicillin | Trimethoprim | Chloramphenicol | Norfloxacin | Log0 | Statu |
|---|---|---|---|---|---|---|---|
| 0 | 0.03 | 0 | 0.31 | 0.72 | 0.1 | 3.639 | |
| 0.04 | 0.07 | 0.76 | -0.3 | 0.2 | -0.3 | -1.668 | |
| 0.63 | 0.02 | -0.1 | 0.61 | 1.03 | 0.18 | 3.874 | |
| 0.97 | 0.33 | 0.2 | 0.54 | 0.4 | -0.1 | 1.711 | |
| 0.21 | 0.35 | 0.74 | 0.42 | 0.61 | 0.22 | 1.83 | |
| 0 | -0.1 | 0 | 0.79 | -0.1 | 0.04 | -0.212 | |
| 0.38 | 0.28 | -0.2 | 0.49 | 0.91 | 0 | 3.045 | |

FIG. 17C
CONTINUED

| | | | | | | | | |
|---|---|---|---|---|---|---|---|---|
| 7 | Plack 581 889 30<br>Block 51<br>Z: n/a | D7 | ??????????? | 0 | 0.12 | 0.23 | 1.01 | 0.48 |
| 8 | Plack 581 889 30<br>Block 52<br>Z: n/a | F7 | SNS-032 BMS-3870321 | 0.18 | -0.2 | -0.1 | 0 | 0.37 |
| 9 | Plack 581 889 51<br>Block 52<br>Z: n/a | H7 | ASMHN | 0 | 0 | 0.04 | 1.42 | 0 |
| 10 | Plack 581 889 73<br>Block 53<br>Z: n/a | D9 | ??????????? | 0.49 | 0.77 | 0.21 | -0.3 | 0.4 |
| 11 | Plack 581 890 36<br>Block 52<br>Z: n/a | E9 | NCEAGOLINE | 0.38 | 0.74 | -0.1 | -0.3 | 0.17 |
| 12 | Plack 581 890 03<br>Block 53<br>Z: n/a | C10 | PENTETIC AOO | 0.5 | 0.74 | 0.03 | 0 | 0.4 |
| 13 | Plack 581 890 09<br>Block 53<br>Z: n/a | C9 | AT7867 | 0.24 | -0.1 | 0.28 | 0.22 | 0.52 |

FIG. 17C
CONTINUED

| | | | | | | |
|---|---|---|---|---|---|---|
| 0.04 | 0.28 | 0.07 | 0.08 | 0.09 | -0.2 | 2.354 |
| 1.11 | 0.24 | 0.08 | 0.14 | 0.82 | 0 | 1.067 |
| 0.07 | 0.17 | 0.31 | 0.43 | 0.23 | -0.3 | -0.245 |
| 0.03 | 0 | 0.24 | 0.2 | 0.01 | 0.27 | 4.571 |
| 0 | 0 | 0.18 | 0.08 | -0.1 | 0.31 | 1.902 |
| 0.63 | 0.37 | 0.05 | -0.1 | 0.38 | 0.08 | -12.489 |
| 1.21 | 0.38 | 0.18 | 0.36 | 1.08 | 0.25 | 2.807 |

FIG. 17C
CONTINUED

| | | | | | | | | |
|---|---|---|---|---|---|---|---|---|
| 14 | Plack 581 890 13<br>Block 53<br>Z: n/a | C5 | ??????????? | 0.19 | 0.33 | 0 | -0.2 | 0.79 |
| 15 | Plack 581 890 18<br>Block 53<br>Z: n/a | B5 | Flucsodium | 0.09 | 0 | -0.1 | 0.44 | 0 |
| 16 | Plack 581 890 18<br>Block 53<br>Z: n/a | C4 | ??????????? | 0.36 | 0.09 | 0.58 | 0.38 | -0.1 |
| 17 | Plack 581 890 24<br>Block 52<br>Z: n/a | P9 | ??????????? | 0.12 | 0.17 | 0.25 | 0.35 | 0.2 |
| 18 | Plack 581 890 47<br>Block 53<br>Z: n/a | C9 | ??????????? | 0.17 | 0.76 | 0.67 | 1 | 0.47 |
| 19 | Plack 581 890 51<br>Block 53<br>Z: n/a | C10 | ??????????? | 0.2 | 0 | 0.81 | 0 | 0.58 |

FIG. 17C
CONTINUED

| | | | | | | |
|---|---|---|---|---|---|---|
| 1.41 | 0.22 | 0 | 0.81 | 1.29 | 0 | 2.899 |
| 0.08 | -0.1 | 0.85 | 0.08 | 0.06 | 0.01 | 2.503 |
| 0 | -0.3 | 0.75 | -0.1 | -0.5 | 0 | 2.878 |
| 0.01 | 0.23 | 1.22 | 0.09 | 0.2 | 0.14 | 1.834 |
| 0.85 | 0.24 | 0.14 | 0.24 | 0.32 | 0.39 | -8.84 |
| 0.85 | 0.41 | 0.3 | 0.36 | 0.78 | 0.19 | 0.848 |

FIG. 17C
CONTINUED

| | Plate type | Adj (Col) | Col ID | Abx (Row) | Row ID | Plate ID 1 | Plate ID 2 | Group | Notes | Status | Result | Validated |
|---|---|---|---|---|---|---|---|---|---|---|---|---|
| | Checkerboard | SNS-032 (BMS-387032) | 87 | Eryth | 81 | 826 | 827 | 10 | | | Synergy | 1 |
| | Checkerboard | SNS-032 (BMS-387032) | 87 | Nov | 80 | 828 | 829 | 10 | | | Synergy | 1 |
| | Checkerboard | SNS-032 (BMS-387032) | 87 | Nor | 86 | 830 | 831 | 10 | | | Neutral | 1 |
| | Checkerboard | 20-Hydroxyecdysone | 88 | Vanc | 77 | 832 | 833 | 10 | | | Neutral | 0 |
| | Checkerboard | 20-Hydroxyecdysone | 88 | Amp | 83 | 834 | 835 | 9 | | | Neutral | 1 |
| | Checkerboard | AT7867 | 89 | Eryth | 81 | 837 | 838 | 8 | | | Synergy | 1 |
| | Checkerboard | AT7867 | 89 | Chlor | 85 | 836 | 839 | 8 | | | Synergy | 1 |
| | Checkerboard | AT7867 | 89 | Tet | 82 | 840 | 841 | 8 | | | Neutral | 1 |
| | Checkerboard | Indacaterol Maleate | 90 | Nov | 80 | 842 | 843 | 7 | | | Synergy | 1 |
| | Checkerboard | Indacaterol Maleate | 90 | Eryth | 81 | 844 | 845 | 8 | | | Synergy | 1 |
| | Checkerboard | Indacaterol Maleate | 90 | Chlor | 85 | 846 | 847 | 7 | | | Synergy | 1 |
| | Checkerboard | Indacaterol Maleate | 90 | Cyc | 78 | 848 | 849 | 6 | | | Neutral | 1 |
| | Checkerboard | Acarbose | 91 | Vanc | 77 | 801 | 802 | 6 | | | Synergy | 1 |
| | Checkerboard | Acarbose | 91 | Eryth | 81 | 803 | 804 | 6 | | | Synergy | 1 |
| | Checkerboard | Acarbose | 91 | Cyc | 78 | 805 | 806 | 5 | | | Synergy | 1 |
| Batch 1 | Checkerboard | Acarbose | 91 | Trim | 84 | 807 | 808 | 5 | | | Neutral | 1 |

FIG. 18A

| | | | | | | | | | | | | |
|---|---|---|---|---|---|---|---|---|---|---|---|---|
| | Checkerboard | PRT062607 (P505-15, BIIB057) HCl | 92 | Eryth | 81 | 809 | 810 | 9 | Top Conc is 200 | ? | Antagonism | 0 |
| | Checkerboard | PRT062607 (P505-15, BIIB057) HCl | 92 | Cyc | 78 | 811 | 812 | 9 | Top Conc is 200 | | Synergy | 1 |
| | Checkerboard | PRT062607 (P505-15, BIIB057) HCl | 92 | Chlor | 85 | 813 | 814 | 9 | Top Conc is 200 | | Synergy | 1 |
| | Checkerboard | PRT062607 (P505-15, BIIB057) HCl | 92 | Nor | 86 | 815 | 816 | 9 | Top Conc is 200 | | Neutral | 1 |
| | Checkerboard | 5,6-Dihydro-5-aza-2'-deoxycytidine | 93 | Amp | 83 | 817 | 818 | 7 | | | Neutral | 0 |
| | Checkerboard | 5,6-Dihydro-5-aza-2'-deoxycytidine | 93 | Tet | 82 | 819 | 820 | 7 | | | Neutral | 1 |
| | Checkerboard | Iodophenpropit dihydrobromide | 94 | Nov | 80 | 821 | 822 | 5 | | | Synergy | 1 |
| | Checkerboard | Iodophenpropit dihydrobromide | 94 | Eryth | 81 | 823 | 824 | 5 | | | Synergy | 1 |
| | Checkerboard | Iodophenpropit dihydrobromide | 94 | Chlor | 85 | 851 | 852 | 5 | | | Synergy | 1 |
| | Checkerboard | Iodophenpropit dihydrobromide | 94 | Nor | 86 | 853 | 854 | 4 | | | Netural | 1 |
| | Checkerboard | NSC 23766 | 95 | Nov | 80 | 855 | 856 | 7 | | | Synergy | 1 |
| | Checkerboard | NSC 23766 | 95 | Chlor | 85 | 857 | 858 | 6 | | | Synergy | 1 |
| | Checkerboard | NSC 23766 | 95 | Tet | 82 | 859 | 860 | 6 | | | Netural | 1 |
| | Checkerboard | Sulbactam | 96 | Amp | 83 | 861 | 862 | 8 | | | Synergy | 1 |
| | Checkerboard | Sulbactam | 96 | Tet | 82 | 863 | 864 | 2 | | | Neutral/Ant | 1 |

FIG. 18A
CONTINUED

| | | | | |
|---|---|---|---|---|
| Batch 2 | Checkerboard | Pasireotide (ditrifluoroacetate) | 65 | Nov |
| | Checkerboard | Pasireotide (ditrifluoroacetate) | 65 | Eryth |
| | Checkerboard | Pasireotide (ditrifluoroacetate) | 65 | Trim |
| | Checkerboard | Pasireotide (ditrifluoroacetate) | 65 | Nor |
| | Checkerboard | NVP-BSK805 2HCl | 66 | Amp |
| | Checkerboard | NVP-BSK805 2HCl | 66 | Tet |
| | Checkerboard | Oxacillin sodium monohydrate | 67 | Amp |
| | Checkerboard | Oxacillin sodium monohydrate | 67 | Tet |
| | Checkerboard | Panobinostat (LBH589) | 68 | Fos |
| | Checkerboard | Panobinostat (LBH589) | 68 | Vanc |
| | Checkerboard | IPAG | 69 | Cyc |
| | Checkerboard | IPAG | 69 | Tet |
| | Checkerboard | SDZ 21009 | 70 | Fos |
| | Checkerboard | SDZ 21009 | 70 | Vanc |
| | Checkerboard | D-Glucose 6-Phosphate Barium Salt Heptahydrate | 71 | Fos |
| | Checkerboard | D-Glucose 6-Phosphate Barium Salt Heptahydrate | 71 | Amp |
| | Checkerboard | Sulbactam (Batch 2) | 72 | Amp |
| | Checkerboard | Sulbactam (Batch 2) | 72 | Tet |

FIG. 18B

| | | | | | | | |
|---|---|---|---|---|---|---|---|
| 80 | 26 | 27 | 3 | Top Conc is 200 | | Synergy | 1 |
| 81 | 28 | 29 | 3 | Top Conc is 200 | | Synergy | 1 |
| 84 | 30 | 31 | 2 | Top Conc is 200 | New CB | | |
| 86 | 32 | 33 | 1 | Top Conc is 200 | | Neutral | 1 |
| 83 | 34 | 35 | 4 | | New CB | | |
| 82 | 36 | 37 | 4 | | | Synergy | 0 |
| 83 | 38 | 39 | 4 | | | Synergy | 1 |
| 82 | 40 | 41 | 4 | | | Neutral | 1 |
| 79 | 42 | 43 | 1 | Small brown precipitates | New CB | | |
| 77 | 44 | 45 | 1 | Small brown precipitates | | Neutral | 1 |
| 78 | 46 | 47 | 3 | | New CB | | |
| 82 | 48 | 49 | 3 | | | Synergy | 0 |
| 79 | 1 | 2 | 2 | | New CB | | |
| 77 | 3 | 4 | 1 | | | Neutral | 1 |
| 79 | 5 | 6 | 3 | | New CB | | |
| 83 | 7 | 8 | 2 | | | Netural | 1 |
| 83 | 9 | 10 | 1 | | | Synergy | 1 |
| 82 | 11 | 12 | 2 | | | Neutral/Ant | 1 |

FIG. 18B
CONTINUED

| | | | | | | | | |
|---|---|---|---|---|---|---|---|---|
| Batch 3 | Checkerboard | SOTALOL HYDROCHLORIDE | 276 | Vanc | 77 | 201 | 202 | |
| | Checkerboard | SOTALOL HYDROCHLORIDE | 276 | Nor | 86 | 203 | 204 | |
| | Checkerboard | SOTALOL HYDROCHLORIDE | 276 | Amp | 83 | 205 | 206 | |
| | Checkerboard | BORNYL ACETATE | 277 | Fos | 79 | 207 | 208 | |
| | Checkerboard | BORNYL ACETATE | 277 | Nor | 86 | 209 | 210 | |
| | Checkerboard | BORNYL ACETATE | 277 | Trim | 84 | 211 | 212 | |
| | Checkerboard | ASPIRIN | 278 | Fos | 79 | 213 | 214 | |
| | Checkerboard | ASPIRIN | 278 | Eryth | 81 | 215 | 216 | |
| | Checkerboard | HEXACHLOROPHENE | 279 | Fos | 79 | 217 | 218 | |
| | Checkerboard | HEXACHLOROPHENE | 279 | Vanc | 77 | 219 | 220 | |
| | Checkerboard | PENICILLIN G POTASSIUM | 280 | Vanc | 77 | 221 | 222 | |
| | Checkerboard | PENICILLIN G POTASSIUM | 280 | Cyc | 78 | 223 | 224 | |
| | Checkerboard | PENICILLIN G POTASSIUM | 280 | Nov | 80 | 13 | 14 | |
| | Checkerboard | PENICILLIN G POTASSIUM | 280 | Chlor | 85 | 15 | 16 | |
| | Checkerboard | Sulbactam (Batch 3) | 281 | Amp | 83 | 17 | 18 | |
| | Checkerboard | Sulbactam (Batch 3) | 281 | Tet | 82 | 21 | 22 | |

FIG. 18C

| | | | | | | |
|---|---|---|---|---|---|---|
| Summary | | | | Vanc | 335706577 | 77 |
| Total compounds | 16.000 | | | Cyc | 335706578 | 78 |
| Validation rate (Compounds) | 0.9375 | *If all synergies invalidated | | Fos | 335706579 | 79 |
| Total CB | 43 | | | Nov | 335706580 | 80 |
| Concordance rate (Pos and Neg) | 0.884 | | | Eryth | 335706581 | 81 |
| Validation rate (Pos only) | 0.916667 | | | Tet | 335706582 | 82 |
| | | | | Amp | 335706583 | 83 |
| | | | | Trim | 335706584 | 84 |
| | | | | Chlor | 335706585 | 85 |
| | | | | Nor | 335706586 | 86 |
| | | | | SNS-032 (BMS-387032) | 335706587 | 87 |
| | | | | 20-Hydroxyecdysone | 335706588 | 88 |
| | | | | AT7867 | 335706589 | 89 |
| | | | | Indacaterol Maleate | 335706590 | 90 |
| | | | | Acarbose | 335706591 | 91 |
| | | | | PRT062607 (P505-15, BIIB057) HCl | 335706592 | 92 |
| | | | | 5,6-Dihydro-5-aza-2'-deoxycytidine | 335706593 | 93 |
| | | | | Iodophenpropit dihydrobromide | 335706594 | 94 |
| | | | | NSC 23766 | 335706595 | 95 |
| | | | | Sulbactam | 335706596 | 96 |

FIG.18D

| | | | | | | |
|---|---|---|---|---|---|---|
| | | | | Pasireotide (ditrifluoroacetate) | 3357065865 | 65 |
| | | | | NVP-BSK805 2HCl | 3357065866 | 66 |
| | | | | Oxacillin sodium monohydrate | 3357065867 | 67 |
| | | | | Panobinostat (LBH589) | 3357065868 | 68 |
| | | | | IPAG | 3357065869 | 69 |
| | | | | SDZ 21009 | 3357065870 | 70 |
| | | | | D-Glucose 6-Phosphate Barium Salt Heptahydrate | 3357065871 | 71 |
| | | | | Sulbactam (Batch 2) | 3357065872 | 72 |
| | | | | SOTALOL HYDROCHLORIDE | 3357065276 | 276 |
| | | | | BORNYL ACETATE | 3357065277 | 277 |
| | | | | ASPIRIN | 3357065278 | 278 |
| | | | | HEXACHLOROPHENE | 3357065279 | 279 |
| | | | | PENICILLIN G POTASSIUM | 3357065280 | 280 |
| | | | | Sulbactam (Batch 3) | 3357065281 | 281 |
| | | | | | | |
| | | | | **New plates** | | |
| | | | | Pasireotide Redo | 3375065227 | 227 |
| | | | | Sulbactam (Batch 2) Redo | 3375065228 | 228 |
| | | | | Penicillin Redo | 3375065229 | 229 |
| | | | | Sulbactam (Batch 3) Redo | 3375065230 | 230 |

FIG.18D
CONTINUED

| | | | | | | | | | |
|---|---|---|---|---|---|---|---|---|---|
| Batch 2 | Checkerboard | Pasireotide Redo | 227 | Nov | 80 | 96 | n/a | 5 | |
| | Checkerboard | Pasireotide Redo | 227 | Eryth | 81 | Not made | n/a | | |
| | Checkerboard | Pasireotide Redo | 227 | Trim | 84 | 97 | n/a | 5 | |
| | Checkerboard | Pasireotide Redo | 227 | Nor | 86 | 98 | n/a | 5 | |
| | Checkerboard | NVP-BSK805 2HCl | 66 | Amp | 83 | 76 | n/a | 1 | |
| | Checkerboard | NVP-BSK805 2HCl | 66 | Tet | 82 | 77 | n/a | 1 | |
| | Checkerboard | Oxacillin sodium monohydrate | 67 | Amp | 83 | Not made | n/a | | |
| | Checkerboard | Oxacillin sodium monohydrate | 67 | Tet | 82 | Not made | n/a | | |
| | Checkerboard | Panobinostat (LBH589) | 68 | Fos | 79 | 78 | n/a | 1 | |
| | Checkerboard | Panobinostat (LBH589) | 68 | Vanc | 77 | 79 | n/a | 1 | |
| | Checkerboard | IPAG | 69 | Cyc | 78 | 80 | n/a | 1 | |
| | Checkerboard | IPAG | 69 | Tet | 82 | 81 | n/a | 2 | |
| | Checkerboard | SDZ 21009 | 70 | Fos | 79 | 82 | n/a | 2 | |
| | Checkerboard | SDZ 21009 | 70 | Vanc | 77 | 83 | n/a | 2 | |
| | Checkerboard | D-Glucose 6-Phosphate Barium Salt Hep | 71 | Fos | 79 | 84 | n/a | 2 | |
| | Checkerboard | D-Glucose 6-Phosphate Barium Salt Hep | 71 | Amp | 83 | 85 | n/a | 2 | |
| | Checkerboard | Sulbactam (Batch 2) Redo | 228 | Amp | 83 | 235 | n/a | 6 | F1 out |
| | Checkerboard | Sulbactam (Batch 2) Redo | 228 | Tet | 82 | 234 | n/a | 6 | |

FIG. 18E

| | | | | | | | | | |
|---|---|---|---|---|---|---|---|---|---|
| Batch 3 | Checkerboard | SOTALOL HYDROCHLORIDE | 276 | Vanc | 77 | 93 | n/a | 4 | |
| | Checkerboard | SOTALOL HYDROCHLORIDE | 276 | Nor | 86 | 94 | n/a | 4 | |
| | Checkerboard | SOTALOL HYDROCHLORIDE | 276 | Amp | 83 | 95 | n/a | 4 | |
| | Checkerboard | BORNYL ACETATE | 277 | Fos | 79 | 90 | n/a | 3 | |
| | Checkerboard | BORNYL ACETATE | 277 | Nor | 86 | 91 | n/a | 3 | |
| | Checkerboard | BORNYL ACETATE | 277 | Trim | 84 | 92 | n/a | 3 | |
| | Checkerboard | ASPIRIN | 278 | Fos | 79 | 86 | n/a | 3 | |
| | Checkerboard | ASPIRIN | 278 | Eryth | 81 | 87 | n/a | 3 | |
| | Checkerboard | HEXACHLOROPHENE | 279 | Fos | 79 | 88 | n/a | 4 | |
| | Checkerboard | HEXACHLOROPHENE | 279 | Vanc | 77 | 89 | n/a | 4 | |
| | Checkerboard | Penicillin Redo | 229 | Vanc | 77 | 99 | n/a | 5 | |
| | Checkerboard | Penicillin Redo | 229 | Cyc | 78 | 100 | n/a | 5 | |
| | Checkerboard | Penicillin Redo | 229 | Nov | 80 | 237 | n/a | 6 | |
| | Checkerboard | Penicillin Redo | 229 | Chlor | 85 | 236 | n/a | 6 | |
| | Checkerboard | Sulbactam (Batch 3) Redo | 230 | Amp | 83 | 233 | n/a | 6 | F1 out |
| | Checkerboard | Sulbactam (Batch 3) Redo | 230 | Tet | 82 | 241 | n/a | 6 | |

FIG. 18E
CONTINUED

| | Plate ID 1 | Plate ID 2 | Plate type | Adjuvant | Col ID | Antibiotic |
|---|---|---|---|---|---|---|
| 0 | 826 | 827 | Checkerboard | SNS-032 (BMS-387032) | 87 | Eryth |
| 1 | 828 | 829 | Checkerboard | SNS-032 (BMS-387032) | 87 | Nov |
| 2 | 830 | 831 | Checkerboard | SNS-032 (BMS-387032) | 87 | Nor |
| 3 | 832 | 833 | Checkerboard | 20-Hydroxyecdysone | 88 | Vanc |
| 4 | 834 | 835 | Checkerboard | 20-Hydroxyecdysone | 88 | Amp |
| 5 | 837 | 838 | Checkerboard | AT7867 | 89 | Eryth |
| 6 | 836 | 839 | Checkerboard | AT7867 | 89 | Chlor |
| 7 | 840 | 841 | Checkerboard | AT7867 | 89 | Tet |
| 8 | 842 | 843 | Checkerboard | Indacaterol Maleate | 90 | Nov |
| 9 | 844 | 845 | Checkerboard | Indacaterol Maleate | 90 | Eryth |
| 10 | 846 | 847 | Checkerboard | Indacaterol Maleate | 90 | Chlor |
| 11 | 848 | 849 | Checkerboard | Indacaterol Maleate | 90 | Cyc |
| 12 | 801 | 802 | Checkerboard | Acarbose | 91 | Vanc |
| 13 | 803 | 804 | Checkerboard | Acarbose | 91 | Eryth |
| 14 | 805 | 806 | Checkerboard | Acarbose | 91 | Cyc |
| 15 | 807 | 808 | Checkerboard | Acarbose | 91 | Trim |
| 16 | 809 | 810 | Checkerboard | PRT062607 (P505-15, BIIB057) HCl | 92 | Eryth |
| 17 | 811 | 812 | Checkerboard | PRT062607 (P505-15, BIIB057) HCl | 92 | Cyc |
| 18 | 813 | 814 | Checkerboard | PRT062607 (P505-15, BIIB057) HCl | 92 | Chlor |
| 19 | 815 | 816 | Checkerboard | PRT062607 (P505-15, BIIB057) HCl | 92 | Nor |
| 20 | 817 | 818 | Checkerboard | 5,6-Dihydro-5-aza-2-deoxycytidine | 93 | Amp |
| 21 | 819 | 820 | Checkerboard | 5,6-Dihydro-5-aza-2-deoxycytidine | 93 | Tet |
| 22 | 821 | 822 | Checkerboard | Iodophenpropit dihydrobromide | 94 | Nov |

FIG. 19A

| Row ID | Plate ID 1.1 | Group | Primary | P | Validated Bliss Synergy in Plate | Found |
|---|---|---|---|---|---|---|
| 81 | | 10 | 1.116124267 | 6.062241351 | 1 | 1 |
| 80 | | 10 | 0.375456232 | 4.303153741 | 1 | 1 |
| 86 | | 10 | -0.037362035 | 0.443974324 | 0 | 1 |
| 77 | | 10 | 0.109097068 | 0.503902322 | 0 | 1 |
| 83 | | 9 | 0.06295689 | 0.450596655 | 0 | 1 |
| 81 | | 8 | 1.215906725 | 8.60437512 | 1 | 1 |
| 85 | | 8 | 1.06889372 | 8.824273696 | 1 | 1 |
| 82 | | 8 | 0.388768538 | 4.660078389 | 0 | 1 |
| 80 | | 7 | 0.796557226 | 5.491343188 | 1 | 1 |
| 81 | | 8 | 1.418432319 | 8.523968689 | 1 | 1 |
| 85 | | 7 | 1.296247544 | 8.53687021 | 1 | 1 |
| 78 | | 6 | -0.021664708 | 0.368693987 | 0 | 1 |
| 77 | | 6 | 0.769682759 | 5.025547164 | 1 | 1 |
| 81 | | 6 | 0.655958608 | 5.974660471 | 1 | 1 |
| 78 | | 5 | 0.676958647 | 6.025301298 | 0 | 1 |
| 84 | | 5 | 0.247283213 | 2.820394411 | 0 | 1 |
| 81 | | 9 | 0.859238879 | 8.37329604 | 1 | 1 |
| 78 | | 9 | 0.61803562 | 5.667932035 | 1 | 1 |
| 85 | | 9 | 0.786829054 | 9.882609874 | 1 | 1 |
| 86 | | 9 | 0.192304093 | 2.189559226 | 1 | 1 |
| 83 | | 7 | 0.766861567 | 4.780615881 | 0 | 1 |
| 82 | | 7 | 0.074510595 | 0.568608016 | 1 | 1 |
| 80 | | 5 | 0.786550802 | 7.531715221 | 1 | 1 |

FIG. 19A
CONTINUED

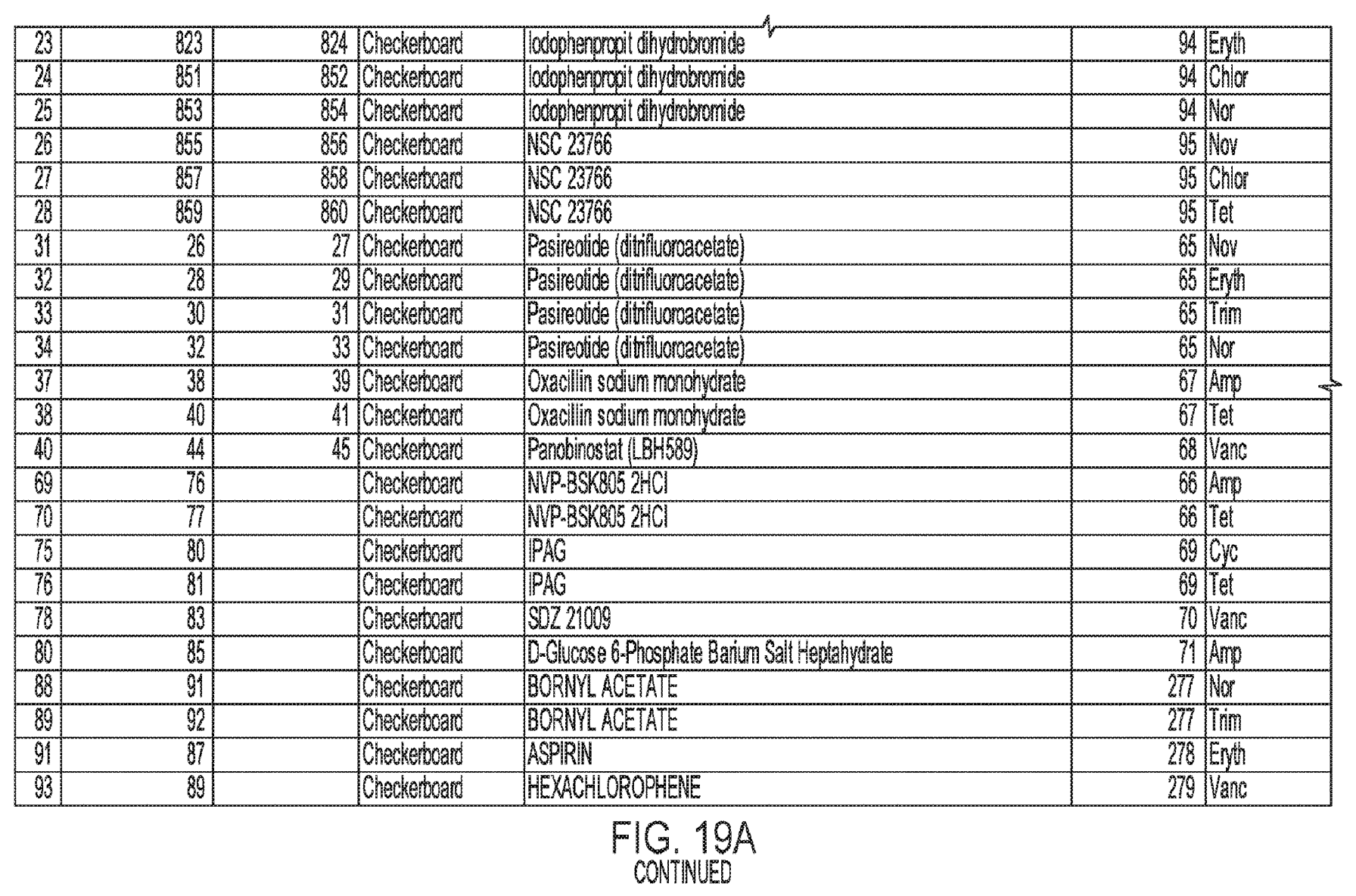

| | | | | | | |
|---|---|---|---|---|---|---|
| 23 | 823 | 824 | Checkerboard | Iodophenpropit dihydrobromide | 94 | Eryth |
| 24 | 851 | 852 | Checkerboard | Iodophenpropit dihydrobromide | 94 | Chlor |
| 25 | 853 | 854 | Checkerboard | Iodophenpropit dihydrobromide | 94 | Nor |
| 26 | 855 | 856 | Checkerboard | NSC 23766 | 95 | Nov |
| 27 | 857 | 858 | Checkerboard | NSC 23766 | 95 | Chlor |
| 28 | 859 | 860 | Checkerboard | NSC 23766 | 95 | Tet |
| 31 | 26 | 27 | Checkerboard | Pasireotide (ditrifluoroacetate) | 65 | Nov |
| 32 | 28 | 29 | Checkerboard | Pasireotide (ditrifluoroacetate) | 65 | Eryth |
| 33 | 30 | 31 | Checkerboard | Pasireotide (ditrifluoroacetate) | 65 | Trim |
| 34 | 32 | 33 | Checkerboard | Pasireotide (ditrifluoroacetate) | 65 | Nor |
| 37 | 38 | 39 | Checkerboard | Oxacillin sodium monohydrate | 67 | Amp |
| 38 | 40 | 41 | Checkerboard | Oxacillin sodium monohydrate | 67 | Tet |
| 40 | 44 | 45 | Checkerboard | Panobinostat (LBH589) | 68 | Vanc |
| 69 | 76 | | Checkerboard | NVP-BSK805 2HCl | 66 | Amp |
| 70 | 77 | | Checkerboard | NVP-BSK805 2HCl | 66 | Tet |
| 75 | 80 | | Checkerboard | IPAG | 69 | Cyc |
| 76 | 81 | | Checkerboard | IPAG | 69 | Tet |
| 78 | 83 | | Checkerboard | SDZ 21009 | 70 | Vanc |
| 80 | 85 | | Checkerboard | D-Glucose 6-Phosphate Barium Salt Heptahydrate | 71 | Amp |
| 88 | 91 | | Checkerboard | BORNYL ACETATE | 277 | Nor |
| 89 | 92 | | Checkerboard | BORNYL ACETATE | 277 | Trim |
| 91 | 87 | | Checkerboard | ASPIRIN | 278 | Eryth |
| 93 | 89 | | Checkerboard | HEXACHLOROPHENE | 279 | Vanc |

FIG. 19A
CONTINUED

| | | | | | | |
|---|---|---|---|---|---|---|
| 81 | | 5 | 0.633884808 | 5.119663169 | 1 | 1 |
| 85 | | 5 | 1.037050918 | 7.54398798 | 1 | 1 |
| 86 | | 4 | 0.180350241 | 1.320660757 | 0 | 1 |
| 80 | | 7 | 0.858029446 | 10.29708933 | 1 | 1 |
| 85 | | 6 | 0.91215776 | 8.564568578 | 1 | 1 |
| 82 | | 6 | 0.2819745 | 3.022780314 | 0 | 1 |
| 80 | | 3 | 0.659751107 | 6.367020204 | 1 | 1 |
| 81 | | 3 | 0.972082676 | 7.618875022 | 1 | 1 |
| 84 | | 2 | 0.541688677 | 5.612423931 | 1 | 1 |
| 86 | | 1 | -0.185143931 | 1.018746851 | 1 | 1 |
| 83 | | 4 | 1.225539172 | 5.587255789 | 1 | 1 |
| 82 | | 4 | 0.230185196 | 1.005083313 | 1 | 1 |
| 77 | | 1 | 0.113980974 | 0.889269322 | 0 | 1 |
| 83 | | | 0.744047949 | 5.89566141 | 1 | 1 |
| 82 | | | 0.359701847 | 3.505749232 | 1 | 1 |
| 78 | | | 0.697028391 | 3.330477402 | 0 | 1 |
| 82 | | | 0.207495052 | 1.986261248 | 1 | 1 |
| 77 | | | -0.1891887 | 0.799580183 | 0 | 1 |
| 83 | | | -0.136955032 | 0.708347296 | 0 | 1 |
| 86 | | | -0.286927536 | 2.779325928 | 0 | 1 |
| 84 | | | 0.087123981 | 1.129456376 | 0 | 1 |
| 81 | | | 0.07269965 | 0.495594825 | 1 | 1 |
| 77 | | | -0.049140226 | 0.469129812 | 0 | 1 |

FIG. 19A
CONTINUED

| | | | | Primary Screening Data | | Plate Validation | |
|---|---|---|---|---|---|---|---|
| Antibiotic | Row ID | Plate ID 1.1 | Group | Primary | P | Bliss | Found |
| Eryth | 81 | | 10 | 1.116124267 | 6.062241351 | 1 | 1 |
| Nov | 80 | | 10 | 0.375456232 | 4.303153741 | 1 | 1 |
| Nor | 86 | | 10 | -0.037362035 | 0.443974324 | 0 | 1 |
| Vanc | 77 | | 10 | 0.109097068 | 0.503902322 | 0 | 1 |
| Amp | 83 | | 9 | 0.06295689 | 0.450596655 | 0 | 1 |
| Eryth | 81 | | 8 | 1.215906725 | 8.60437512 | 1 | 1 |
| Chlor | 85 | | 8 | 1.06889372 | 8.824273696 | 1 | 1 |
| Tet | 82 | | 8 | 0.388768538 | 4.660078389 | 0 | 1 |
| Nov | 80 | | 7 | 0.796557226 | 5.491343188 | 1 | 1 |
| Eryth | 81 | | 8 | 1.418432319 | 8.523968689 | 1 | 1 |
| Chlor | 85 | | 7 | 1.296247544 | 8.53687021 | 1 | 1 |
| Cyc | 78 | | 6 | -0.021664708 | 0.368693987 | 0 | 1 |
| Vanc | 77 | | 6 | 0.769682759 | 5.025547164 | 1 | 1 |
| Eryth | 81 | | 6 | 0.655958608 | 5.974660471 | 1 | 1 |
| Cyc | 78 | | 5 | 0.676958647 | 6.025301298 | 0 | 1 |
| Trim | 84 | | 5 | 0.247283213 | 2.820394411 | 0 | 1 |
| Eryth | 81 | | 9 | 0.859238879 | 8.37329604 | 1 | 1 |
| Cyc | 78 | | 9 | 0.61803562 | 5.567932035 | 1 | 1 |
| Chlor | 85 | | 9 | 0.786829054 | 9.882609874 | 1 | 1 |
| Nor | 86 | | 9 | 0.192304093 | 2.189559226 | 1 | 1 |
| Amp | 83 | | 7 | 0.766861567 | 4.780615881 | 0 | 1 |

FIG. 19B

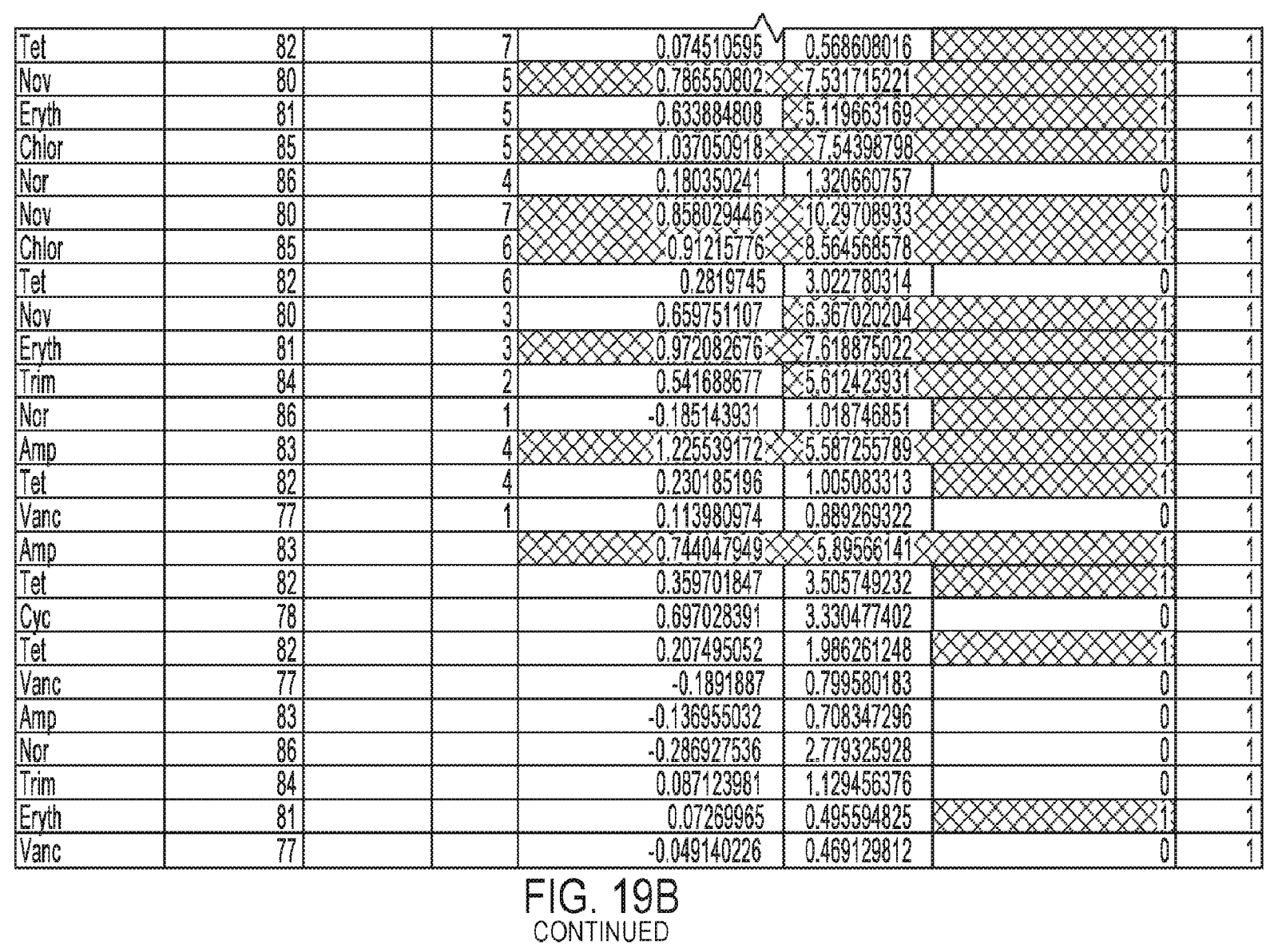

| | | | | | | | |
|---|---|---|---|---|---|---|---|
| Tet | 82 | | 7 | 0.074510595 | 0.568608016 | 1 | 1 |
| Nov | 80 | | 5 | 0.786550802 | 7.531715221 | 1 | 1 |
| Eryth | 81 | | 5 | 0.633884808 | 5.119663169 | 1 | 1 |
| Chlor | 85 | | 5 | 1.037050918 | 7.54398798 | 1 | 1 |
| Nor | 86 | | 4 | 0.180350241 | 1.320660757 | 0 | 1 |
| Nov | 80 | | 7 | 0.858029446 | 10.29708933 | 1 | 1 |
| Chlor | 85 | | 6 | 0.91215776 | 8.564568578 | 1 | 1 |
| Tet | 82 | | 6 | 0.2819745 | 3.022780314 | 0 | 1 |
| Nov | 80 | | 3 | 0.659751107 | 6.367020204 | 1 | 1 |
| Eryth | 81 | | 3 | 0.972082676 | 7.618875022 | 1 | 1 |
| Trim | 84 | | 2 | 0.541688677 | 5.612423931 | 1 | 1 |
| Nor | 86 | | 1 | -0.185143931 | 1.018746851 | 1 | 1 |
| Amp | 83 | | 4 | 1.225539172 | 5.587255789 | 1 | 1 |
| Tet | 82 | | 4 | 0.230185196 | 1.005083313 | 1 | 1 |
| Vanc | 77 | | 1 | 0.113980974 | 0.889269322 | 0 | 1 |
| Amp | 83 | | | 0.744047949 | 5.89566141 | 1 | 1 |
| Tet | 82 | | | 0.359701847 | 3.505749232 | 1 | 1 |
| Cyc | 78 | | | 0.697028391 | 3.330477402 | 0 | 1 |
| Tet | 82 | | | 0.207495052 | 1.986261248 | 1 | 1 |
| Vanc | 77 | | | -0.1891887 | 0.799580183 | 0 | 1 |
| Amp | 83 | | | -0.136955032 | 0.708347296 | 0 | 1 |
| Nor | 86 | | | -0.286927536 | 2.779325928 | 0 | 1 |
| Trim | 84 | | | 0.087123981 | 1.129456376 | 0 | 1 |
| Eryth | 81 | | | 0.07269965 | 0.495594825 | 1 | 1 |
| Vanc | 77 | | | -0.049140226 | 0.469129812 | 0 | 1 |

FIG. 19B
CONTINUED

| | | | | | |
|---|---|---|---|---|---|
| | Plate ID 1 | Plate ID 2 | Plate type | Adjuvant | Col ID |
| 0 | 826 | 827 | Checkerboard | SNS-032 (BMS-387032) | 87 |
| 1 | 828 | 829 | Checkerboard | SNS-032 (BMS-387032) | 87 |
| 2 | 830 | 831 | Checkerboard | SNS-032 (BMS-387032) | 87 |
| 3 | 832 | 833 | Checkerboard | 20-Hydroxyecdysone | 88 |
| 4 | 834 | 835 | Checkerboard | 20-Hydroxyecdysone | 88 |
| 5 | 837 | 838 | Checkerboard | AT7867 | 89 |
| 6 | 836 | 839 | Checkerboard | AT7867 | 89 |
| 7 | 840 | 841 | Checkerboard | AT7867 | 89 |
| 8 | 842 | 843 | Checkerboard | Indacaterol Maleate | 90 |
| 9 | 844 | 845 | Checkerboard | Indacaterol Maleate | 90 |
| 10 | 846 | 847 | Checkerboard | Indacaterol Maleate | 90 |
| 11 | 848 | 849 | Checkerboard | Indacaterol Maleate | 90 |
| 12 | 801 | 802 | Checkerboard | Acarbose | 91 |
| 13 | 803 | 804 | Checkerboard | Acarbose | 91 |
| 14 | 805 | 806 | Checkerboard | Acarbose | 91 |
| 15 | 807 | 808 | Checkerboard | Acarbose | 91 |
| 16 | 809 | 810 | Checkerboard | PRT062607 (P505-15, BIIB057) HCl | 92 |
| 17 | 811 | 812 | Checkerboard | PRT062607 (P505-15, BIIB057) HCl | 92 |
| 18 | 813 | 814 | Checkerboard | PRT062607 (P505-15, BIIB057) HCl | 92 |
| 19 | 815 | 816 | Checkerboard | PRT062607 (P505-15, BIIB057) HCl | 92 |
| 20 | 817 | 818 | Checkerboard | 5,6-Dihydro-5-aza-2'-deoxycytidine | 93 |
| 21 | 819 | 820 | Checkerboard | 5,6-Dihydro-5-aza-2'-deoxycytidine | 93 |
| 22 | 821 | 822 | Checkerboard | Iodophenpropit dihydrobromide | 94 |
| 23 | 823 | 824 | Checkerboard | Iodophenpropit dihydrobromide | 94 |

FIG. 19C

| | | | | | |
|---|---|---|---|---|---|
| 24 | 851 | 852 | Checkerboard | Iodophenpropit dihydrobromide | 94 |
| 25 | 853 | 854 | Checkerboard | Iodophenpropit dihydrobromide | 94 |
| 26 | 855 | 856 | Checkerboard | NSC 23766 | 95 |
| 27 | 857 | 858 | Checkerboard | NSC 23766 | 95 |
| 28 | 859 | 860 | Checkerboard | NSC 23766 | 95 |
| 31 | 26 | 27 | Checkerboard | Pasireotide (ditrifluoroacetate) | 65 |
| 32 | 28 | 29 | Checkerboard | Pasireotide (ditrifluoroacetate) | 65 |
| 33 | 30 | 31 | Checkerboard | Pasireotide (ditrifluoroacetate) | 65 |
| 34 | 32 | 33 | Checkerboard | Pasireotide (ditrifluoroacetate) | 65 |
| 37 | 38 | 39 | Checkerboard | Oxacillin sodium monohydrate | 67 |
| 38 | 40 | 41 | Checkerboard | Oxacillin sodium monohydrate | 67 |
| 40 | 44 | 45 | Checkerboard | Panobinostat (LBH589) | 68 |
| 69 | 76 | | Checkerboard | NVP-BSK805 2HCl | 66 |
| 70 | 77 | | Checkerboard | NVP-BSK805 2HCl | 66 |
| 75 | 80 | | Checkerboard | IPAG | 69 |
| 76 | 81 | | Checkerboard | IPAG | 69 |
| 78 | 83 | | Checkerboard | SDZ 21009 | 70 |
| 80 | 85 | | Checkerboard | D-Glucose 6-Phosphate Barium Salt Heptahydrate | 71 |
| 88 | 91 | | Checkerboard | BORNYL ACETATE | 277 |
| 89 | 92 | | Checkerboard | BORNYL ACETATE | 277 |
| 91 | 87 | | Checkerboard | ASPIRIN | 278 |
| 93 | 89 | | Checkerboard | HEXACHLOROPHENE | 279 |

FIG. 19C
CONTINUED 97194 microwells
48 x 48 cross
73.90 cm2

9.96 cm 7.42 cm 49200 microwells
32 x 32 cross
44.64 cm2

7.20 cm 6.20 cm 148.6 um 271.4 um

Microwell

Injection of pooled
droplets and oil washes

Neodymium magnet

Hole for bolt
(clamping)

Acrylic housing

Drainage of excess droplets

Microwell chip

Hydrophobic glass slide

Plastic spacer

Chip (FIC ≤ 0.3125)

| Ampicillin (μg/ml) \ Subactam (ug/ml) | 0 | 4 | 8 | 16 | 32 | 64 | 128 | 256 |
|---|---|---|---|---|---|---|---|---|
| 512 | 0.268 | 0.135 | 0.101 | 0.060 | 0.050 | 0.034 | 0.025 | 0.010 |
| 256 | 0.510 | 0.251 | 0.179 | 0.120 | 0.070 | 0.059 | 0.033 | 0.019 |
| 128 | 0.926 | 0.515 | 0.384 | 0.234 | 0.163 | 0.102 | 0.057 | 0.040 |
| 64 | 1.052 | 1.901 | 0.725 | 0.510 | 0.378 | 0.236 | 0.153 | 0.074 |
| 32 | 1.030 | 1.034 | 0.985 | 0.872 | 0.764 | 0.608 | 0.401 | 0.199 |
| 16 | 1.053 | 1.011 | 1.028 | 0.988 | 0.963 | 0.840 | 0.662 | 0.374 |
| 8 | 1.033 | 1.016 | 1.030 | 0.997 | 1.030 | 0.945 | 0.759 | 0.534 |
| 0 | 1 | 1.010 | 1.007 | 0.994 | 1.020 | 1.006 | 0.922 | 0.675 |

Plate (FIC ≤ 0.5)

| Ampicillin (μg/ml) \ Subactam (ug/ml) | 0 | 4 | 8 | 16 | 32 | 64 | 128 | 256 |
|---|---|---|---|---|---|---|---|---|
| 512 | 0.606 | 0.382 | 0.280 | 0.181 | 0.111 | 0.081 | 0.059 | 0.022 |
| 256 | 0.827 | 0.530 | 0.427 | 0.300 | 0.166 | 0.112 | 0.082 | 0.058 |
| 128 | 0.934 | 0.747 | 0.606 | 0.507 | 0.388 | 0.265 | 0.127 | 0.100 |
| 64 | 1 | 0.848 | 0.784 | 0.723 | 0.595 | 0.490 | 0.332 | 0.186 |
| 32 | 0.990 | 0.956 | 0.889 | 0.870 | 0.815 | 0.721 | 0.511 | 0.332 |
| 16 | 0.952 | 0.919 | 0.926 | 0.883 | 0.846 | 0.772 | 0.754 | 0.458 |
| 8 | 0.877 | 0.889 | 0.842 | 0.847 | 0.851 | 0.793 | 0.740 | 0.560 |
| 0 | 0.806 | 0.855 | 0.829 | 0.801 | 0.740 | 0.762 | 0.712 | 0.634 |

FIG. 27

| | |
|---|---|
| Antibiotic | Erythromycin |
| Compound | SNS-032 (BMS-387032) |
| Primary Bliss | 1.12 |
| Log10 P-value | 6.06 |
| Primary Hit | 1 |
| Plate Bliss | 1.25 |
| Plate FIC | ≤0.625 |
| Plate Hit | 1 |

| | |
|---|---|
| Antibiotic | Novobiocin |
| Compound | SNS-032 (BMS-387032) |
| Primary Bliss | 0.375 |
| Log10 P-value | 4.3 |
| Primary Hit | 0 |
| Plate Bliss | 0.717 |
| Plate FIC | ≤1 |
| Plate Hit | 1 |

| | |
|---|---|
| Antibiotic | Norfloxacin |
| Compound | SNS-032 (BMS-387032) |
| Primary Bliss | -0.0374 |
| Log10 P-value | 0.444 |
| Primary Hit | 0 |
| Plate Bliss | 0.0479 |
| Plate FIC | n/a |
| Plate Hit | 0 |

| | |
|---|---|
| Antibiotic | Vancomycin |
| Compound | 20-Hydoxyecdysone |
| Primary Bliss | 0.109 |
| Log10 P-value | 0.504 |
| Primary Hit | 0 |
| Plate Bliss | 0.19 |
| Plate FIC | ≤1 |
| Plate Hit | 0 |

| | |
|---|---|
| Antibiotic | Ampicillin |
| Compound | 20-Hydoxyecdysone |
| Primary Bliss | 0.063 |
| Log10 P-value | 0.451 |
| Primary Hit | 0 |
| Plate Bliss | 0.0865 |
| Plate FIC | ≤1 |
| Plate Hit | 0 |

| | |
|---|---|
| Antibiotic | Erythromycin |
| Compound | AT7867 |
| Primary Bliss | 1.22 |
| Log10 P-value | 8.6 |
| Primary Hit | 1 |
| Plate Bliss | 0.771 |
| Plate FIC | 0.75 |
| Plate Hit | 1 |

| | |
|---|---|
| Antibiotic | Chloramphenicol |
| Compound | AT7867 |
| Primary Bliss | 1.07 |
| Log10 P-value | 8.82 |
| Primary Hit | 1 |
| Plate Bliss | 0.978 |
| Plate FIC | 1 |
| Plate Hit | 1 |

| | |
|---|---|
| Antibiotic | Tetracycline |
| Compound | AT7867 |
| Primary Bliss | 0.389 |
| Log10 P-value | 4.66 |
| Primary Hit | 0 |
| Plate Bliss | 0.0662 |
| Plate FIC | 1 |
| Plate Hit | 0 |

| | |
|---|---|
| Antibiotic | Novobiocin |
| Compound | Indacaterol Maleate |
| Primary Bliss | 0.797 |
| Log10 P-value | 5.49 |
| Primary Hit | 1 |
| Plate Bliss | 1.15 |
| Plate FIC | 0.5 |
| Plate Hit | 1 |

| | |
|---|---|
| Antibiotic | Erythromycin |
| Compound | Indacaterol Maleate |
| Primary Bliss | 1.42 |
| Log10 P-value | 8.52 |
| Primary Hit | 1 |
| Plate Bliss | 1.51 |
| Plate FIC | 0.375 |
| Plate Hit | 1 |

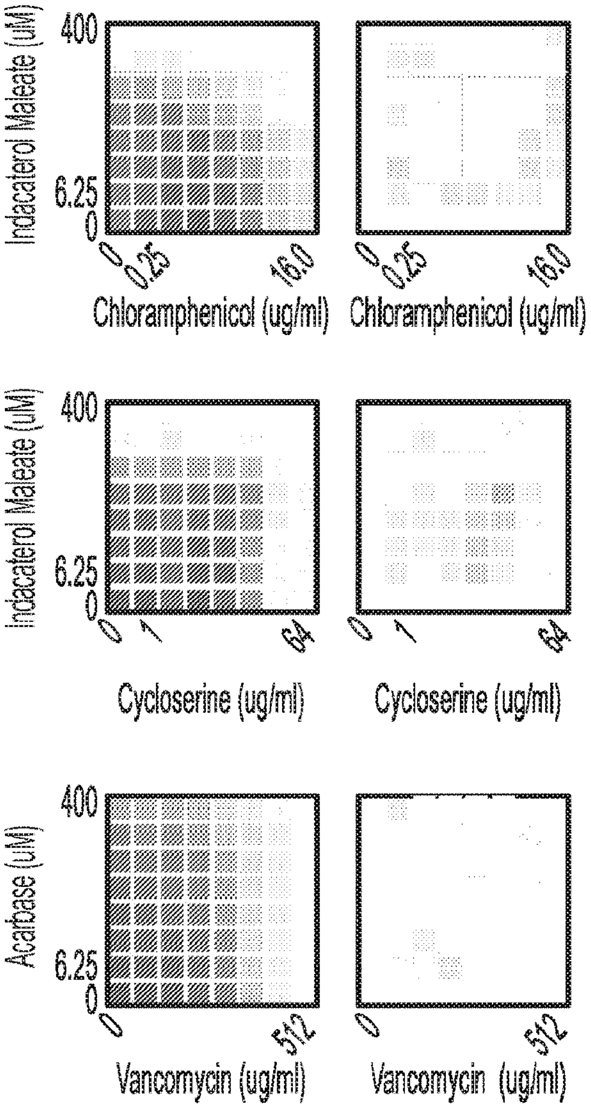

| | |
|---|---|
| Antibiotic | Chloramphenicol |
| Compound | Indacaterol Maleate |
| Primary Bliss | 1.3 |
| Log10 P-value | 8.54 |
| Primary Hit | 1 |
| Plate Bliss | 1.5 |
| Plate FIC | 0.75 |
| Plate Hit | 1 |

| | |
|---|---|
| Antibiotic | Cycloserine |
| Compound | Indacaterol Maleate |
| Primary Bliss | -0.0217 |
| Log10 P-value | 0.369 |
| Primary Hit | 0 |
| Plate Bliss | 0.0938 |
| Plate FIC | 1 |
| Plate Hit | 0 |

| | |
|---|---|
| Antibiotic | Vancomycin |
| Compound | Acarbose |
| Primary Bliss | 0.77 |
| Log10 P-value | 5.03 |
| Primary Hit | 1 |
| Plate Bliss | 0.453 |
| Plate FIC | ≤0.531 |
| Plate Hit | 1 |

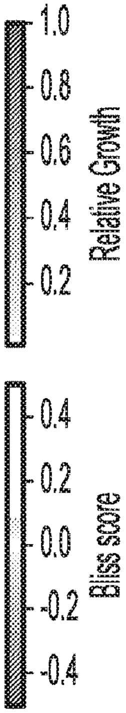

FIG. 31C

| | |
|---|---|
| Antibiotic | Erythromycin |
| Compound | Acarbose |
| Primary Bliss | 0.656 |
| Log10 P-value | 5.97 |
| Primary Hit | 0 |
| Plate Bliss | 0.381 |
| Plate FIC | ≤1 |
| Plate Hit | 0 |

| | |
|---|---|
| Antibiotic | Cycloserine |
| Compound | Acarbose |
| Primary Bliss | 0.677 |
| Log10 P-value | 6.03 |
| Primary Hit | 0 |
| Plate Bliss | 0.249 |
| Plate FIC | ≤1 |
| Plate Hit | 0 |

| | |
|---|---|
| Antibiotic | Trimethoprim |
| Compound | Acarbose |
| Primary Bliss | 0.247 |
| Log10 P-value | 2.82 |
| Primary Hit | 0 |
| Plate Bliss | 0.0791 |
| Plate FIC | ≤0.75 |
| Plate Hit | 0 |

| | |
|---|---|
| Antibiotic | Erythromycin |
| Compound | PRT062607 (P505-15, BIIB057) HCl |
| Primary Bliss | 0.859 |
| Log10 P-value | 1 |
| Primary Hit | 0 |
| Plate Bliss | 0.328 |
| Plate FIC | 0.75 |
| Plate Hit | 0 |

| | |
|---|---|
| Antibiotic | Cycloserine |
| Compound | PRT062607 (P505-15, BIIB057) HCl |
| Primary Bliss | 0.618 |
| Log10 P-value | 5.67 |
| Primary Hit | 0 |
| Plate Bliss | 0.364 |
| Plate FIC | 1 |
| Plate Hit | 0 |

| | |
|---|---|
| Antibiotic | Chloramphenicol |
| Compound | PRT062607 (P505-15, BII057) HCL |
| Primary Bliss | 0.787 |
| Log10 P-value | 9.88 |
| Primary Hit | 1 |
| Plate Bliss | 1.2 |
| Plate FIC | 0.75 |
| Plate Hit | 1 |

| | |
|---|---|
| Antibiotic | Norfloxacin |
| Compound | PRT062607 (P505-15, BIIB057) HCL |
| Primary Bliss | 0.192 |
| Log10 P-value | 2.19 |
| Primary Hit | 0 |
| Plate Bliss | 0.482 |
| Plate FIC | ≤0.625 |
| Plate Hit | 1 |

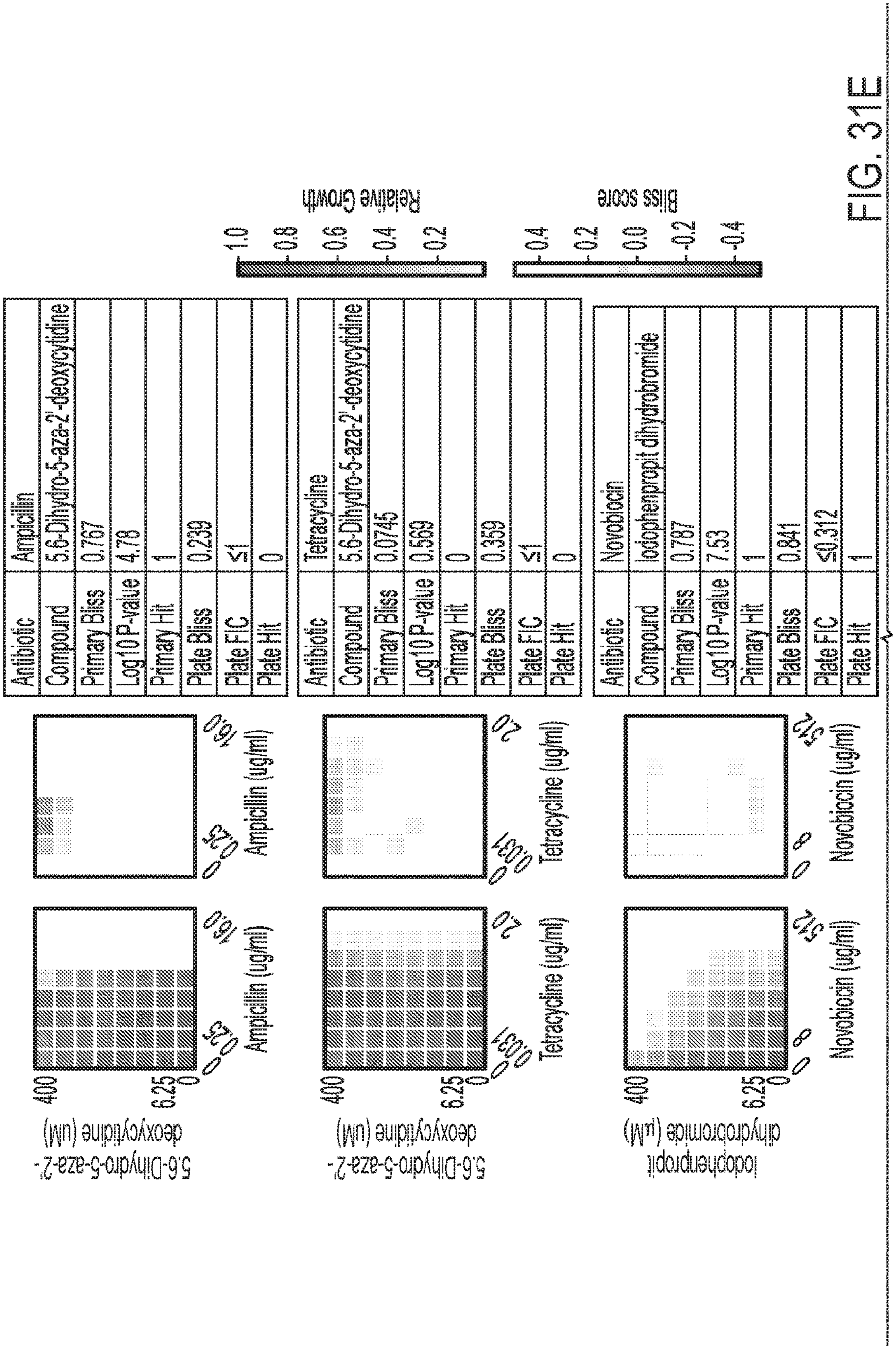

| | |
|---|---|
| Antibiotic | Ampicillin |
| Compound | 5,6-Dihydro-5-aza-2'-deoxycytidine |
| Primary Bliss | 0.767 |
| Log10 P-value | 4.78 |
| Primary Hit | 1 |
| Plate Bliss | 0.239 |
| Plate FIC | ≤1 |
| Plate Hit | 0 |

| | |
|---|---|
| Antibiotic | Tetracycline |
| Compound | 5,6-Dihydro-5-aza-2'-deoxycytidine |
| Primary Bliss | 0.0745 |
| Log10 P-value | 0.569 |
| Primary Hit | 0 |
| Plate Bliss | 0.359 |
| Plate FIC | ≤1 |
| Plate Hit | 0 |

| | |
|---|---|
| Antibiotic | Novobiocin |
| Compound | Iodophenpropit dihydrobromide |
| Primary Bliss | 0.787 |
| Log10 P-value | 7.53 |
| Primary Hit | 1 |
| Plate Bliss | 0.841 |
| Plate FIC | ≤0.312 |
| Plate Hit | 1 |

FIG. 31E

| | |
|---|---|
| Antibiotic | Erythromycin |
| Compound | Iodophenpropit dihydrobromide |
| Primary Bliss | 0.634 |
| Log10 P-value | 5.12 |
| Primary Hit | 0 |
| Plate Bliss | 0.577 |
| Plate FIC | ≤0.5 |
| Plate Hit | 1 |

| | |
|---|---|
| Antibiotic | Chloramphenicol |
| Compound | Iodophenpropit dihydrobromide |
| Primary Bliss | 1.04 |
| Log10 P-value | 7.54 |
| Primary Hit | 1 |
| Plate Bliss | 0.966 |
| Plate FIC | ≤0.5 |
| Plate Hit | 1 |

| | |
|---|---|
| Antibiotic | Norfloxacin |
| Compound | Iodophenpropit dihydrobromide |
| Primary Bliss | 0.18 |
| Log10 P-value | 1.32 |
| Primary Hit | 0 |
| Plate Bliss | 0.13 |
| Plate FIC | ≤1 |
| Plate Hit | 0 |

| | |
|---|---|
| Antibiotic | Novobiocin |
| Compound | NSC 23766 |
| Primary Bliss | 0.858 |
| Log10 P-value | 10.3 |
| Primary Hit | 1 |
| Plate Bliss | 1.84 |
| Plate FIC | ≤0.375 |
| Plate Hit | 1 |

| | |
|---|---|
| Antibiotic | Chloramphenicol |
| Compound | NSC 23766 |
| Primary Bliss | 0.912 |
| Log10 P-value | 8.56 |
| Primary Hit | 1 |
| Plate Bliss | 1.64 |
| Plate FIC | ≤0.625 |
| Plate Hit | 1 |

| | |
|---|---|
| Antibiotic | Tetracycline |
| Compound | NSC 23766 |
| Primary Bliss | 0.282 |
| Log10 P-value | 3.02 |
| Primary Hit | 0 |
| Plate Bliss | 0.225 |
| Plate FIC | ≤0.516 |
| Plate Hit | 0 |

| | |
|---|---|
| Antibiotic | Novobiocin |
| Compound | Pasireotide (ditrifluoroacelate) |
| Primary Bliss | 0.66 |
| Log10 P-value | 6.37 |
| Primary Hit | 0 |
| Plate Bliss | 1.51 |
| Plate FIC | ≤0.312 |
| Plate Hit | 1 |

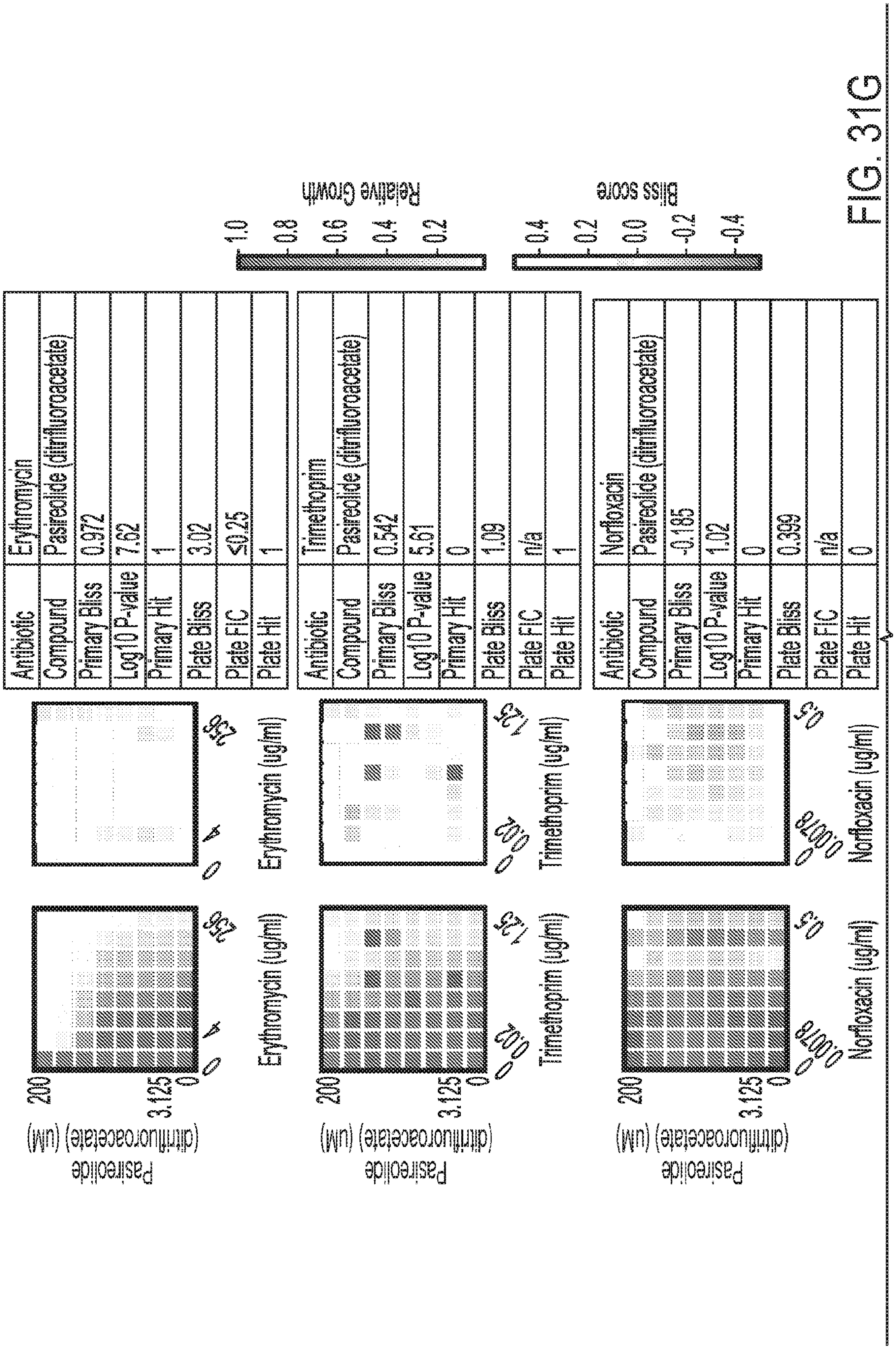

| | |
|---|---|
| Antibiotic | Erythromycin |
| Compound | Pasireolide (ditrifluoroacetate) |
| Primary Bliss | 0.972 |
| Log10 P-value | 7.62 |
| Primary Hit | 1 |
| Plate Bliss | 3.02 |
| Plate FIC | ≤0.25 |
| Plate Hit | 1 |

| | |
|---|---|
| Antibiotic | Trimethoprim |
| Compound | Pasireolide (ditrifluoroacetate) |
| Primary Bliss | 0.542 |
| Log10 P-value | 5.61 |
| Primary Hit | 0 |
| Plate Bliss | 1.09 |
| Plate FIC | n/a |
| Plate Hit | 1 |

| | |
|---|---|
| Antibiotic | Norfloxacin |
| Compound | Pasireolide (ditrifluoroacetate) |
| Primary Bliss | -0.185 |
| Log10 P-value | 1.02 |
| Primary Hit | 0 |
| Plate Bliss | 0.399 |
| Plate FIC | n/a |
| Plate Hit | 0 |

FIG. 31G

| | |
|---|---|
| Antibiotic | Ampicillin |
| Compound | Oxacillin sodium monohydrate |
| Primary Bliss | 1.23 |
| Log10 P-value | 5.59 |
| Primary Hit | 1 |
| Plate Bliss | 1.64 |
| Plate FIC | ≤0.625 |
| Plate Hit | 1 |

| | |
|---|---|
| Antibiotic | Tetracycline |
| Compound | Oxacillin sodium monohydrate |
| Primary Bliss | 0.23 |
| Log10 P-value | 1.01 |
| Primary Hit | 0 |
| Plate Bliss | 0.342 |
| Plate FIC | ≤1 |
| Plate Hit | 0 |

| | |
|---|---|
| Antibiotic | Vancomycin |
| Compound | Panobinostat |
| Primary Bliss | 0.114 |
| Log10 P-value | 0.889 |
| Primary Hit | 0 |
| Plate Bliss | -0.0986 |
| Plate FIC | ≤1 |
| Plate Hit | 0 |

| | |
|---|---|
| Antibiotic | Ampicillin |
| Compound | NVP-BSK805 2HCl |
| Primary Bliss | 0.744 |
| Log10 P-value | 5.9 |
| Primary Hit | 1 |
| Plate Bliss | 0.451 |
| Plate FIC | 0.75 |
| Plate Hit | 1 |

| | |
|---|---|
| Antibiotic | Tetracycline |
| Compound | NVP-BSK805 2HCl |
| Primary Bliss | 0.36 |
| Log10 P-value | 3.51 |
| Primary Hit | 0 |
| Plate Bliss | 1.02 |
| Plate FIC | 1 |
| Plate Hit | 1 |

| | |
|---|---|
| Antibiotic | Cycloserine |
| Compound | IPAG |
| Primary Bliss | 0.697 |
| Log10 P-value | 3.33 |
| Primary Hit | 0 |
| Plate Bliss | 0.0598 |
| Plate FIC | 1 |
| Plate Hit | 0 |

| | |
|---|---|
| Antibiotic | Tetracycline |
| Compound | IPAG |
| Primary Bliss | 0.207 |
| Log10 P-value | 1.99 |
| Primary Hit | 0 |
| Plate Bliss | 1.64 |
| Plate FIC | 0.75 |
| Plate Hit | 1 |

| | |
|---|---|
| Antibiotic | Vancomycin |
| Compound | SDZ 21009 |
| Primary Bliss | -0.189 |
| Log10 P-value | 0.8 |
| Primary Hit | 0 |
| Plate Bliss | 0.028 |
| Plate FIC | ≤1 |
| Plate Hit | 0 |

| | |
|---|---|
| Antibiotic | Ampicillin |
| Compound | D-Glucose 6-Phosphate |
| Primary Bliss | -0.137 |
| Log10 P-value | 0.708 |
| Primary Hit | 0 |
| Plate Bliss | 0.000546 |
| Plate FIC | ≤1 |
| Plate Hit | 0 |

| | |
|---|---|
| Antibiotic | Norfloxacin |
| Compound | BORNYL ACETATE |
| Primary Bliss | -0.287 |
| Log10 P-value | 2.78 |
| Primary Hit | 0 |
| Plate Bliss | 0.0566 |
| Plate FIC | n/a |
| Plate Hit | 0 |

Relative Growth

| | 1.0 | 0.8 | 0.6 | 0.4 | 0.2 |

Bliss score

| | 0.4 | 0.2 | 0.0 | -0.2 | -0.4 |

| Antibiotic | Trimethoprim |
|---|---|
| Compound | BORNYL ACETATE |
| Primary Bliss | 0.0871 |
| Log10 P-value | 1.13 |
| Primary Hit | 0 |
| Plate Bliss | 0.102 |
| Plate FIC | n/a |
| Plate Hit | 0 |

| Antibiotic | Erythromycin |
|---|---|
| Compound | ASPIRIN |
| Primary Bliss | 0.0727 |
| Log10 P-value | 0.496 |
| Primary Hit | 0 |
| Plate Bliss | 0.343 |
| Plate FIC | ≤1 |
| Plate Hit | 0 |

| | |
|---|---|
| Antibiotic | Vancomycin |
| Compound | HEXACHLOROPHENE |
| Primary Bliss | -0.0491 |
| Log10 P-value | 0.469 |
| Primary Hit | 0 |
| Plate Bliss | 0.0268 |
| Plate FIC | 1 |
| Plate Hit | 0 |

| Antobiotic | FIC |
|---|---|
| Novobiocin | ≤ 0.625 |
| Erythromycin | ≤ 0.531 |
| Chloramphenicol | ≤ 0.5 |
| Tetracycline | ≤ 1.0 |

COMPOSITIONS AND METHODS FOR COMBINATORIAL DRUG DISCOVERY IN NANOLITER DROPLETS

CROSS REFERENCE TO RELATED APPLICATIONS

This application is a divisional application of U.S. patent application Ser. No. 16/754,668, having a 371 (c) date of Apr. 8, 2020, which is a national stage application, filed under 35 U.S.C. § 371, of International Application No. PCT/US18/54916, filed Oct. 9, 2018, which claims the benefit of priority of U.S. Provisional Application No. 62/578,140, filed Oct. 27, 2017; U.S. Provisional Application No. 62/570,585, filed Oct. 10, 2017; and U.S. Provisional Application No. 62/570,014, filed Oct. 9, 2017. The contents of each of these prior applications are hereby incorporated by reference in their entirety.

FIELD OF THE DISCLOSURE

The disclosure relates to compositions and methods for combinatorial drug discovery in nanoliter droplets. More particularly, the disclosure relates to the identification and characterization of novel synergistic agents that increase efficacy of antibiotic agents to treat bacterial infection.

BACKGROUND OF THE DISCLOSURE

Many human diseases are increasingly recognized as multifactorial in origin and therapeutic strategies increasingly leverage combination therapy or polytherapy. Combination therapy is a therapy that uses more than one therapeutic agent or medication or modality. This is in contrast to a monotherapy that uses only a single therapeutic agent or medication or modality. In general, a combination therapy refers to the use of more than one therapeutic agent or medication to treat a single disease. Combination therapies are currently used to treat a variety of indications (e.g., cancer, HIV/AIDS, tuberculosis, leprosy, and the like).

Despite their utility, identification of novel drug combinations for use in combination therapy has been slowed by the complexity, cost, and high compound consumption of the combinatorics of tests required. For example, testing all pairs of drugs from a modest library of 2000 drugs (e.g., FDA approved drugs) requires 2 million pairwise combinations, and many more combinations if the compounds are titrated during the screening process. As another example, testing 2000 drugs in combination with 2000 antibiotics at four concentrations would require 32 million pairwise combinations. Experiments of this scale are restricted to specialized labs and facilities, often with prohibitive costs and complexity (e.g., total liquid handling steps, plate layout, workflow design, and the like). Additionally, since such combinatorial screens test each compound in pairwise combinations with thousands of other compounds, thousands-fold more compound is consumed relative to a typical single-compound screen. Unfortunately, this means that a combinatorial screen has the potential to deplete an entire compound inventory in a single experiment. Current methods for combinatorial drug discovery work around these issues by either leveraging computational predictions of drug synergies to reduce screening scale, or combining multiple tests in pools with subsequent deconvolution of hits from high-scoring pools. Accordingly, there is an urgent need for compositions and methods for identifying combinations of therapeutic agents or medications in a scalable, cost-efficient manner.

SUMMARY OF THE DISCLOSURE

In one aspect, the disclosure provides a composition comprising an antibiotic selected from the group consisting of novobiocin, erythromycin, chloramphenicol, and combinations thereof and a compound having the following formula:

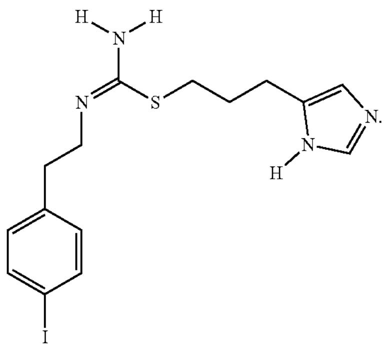 [SMILES: N/C(=N/CCc1ccc(I)cc1)SCCCc1cnc[nH]1]

In embodiments, the antibiotic is novobiocin or erythromycin or chloramphenicol.

In one aspect, the disclosure provides a composition comprising an antibiotic selected from the group consisting of novobiocin, erythromycin, and combinations thereof and a compound having the following formula:

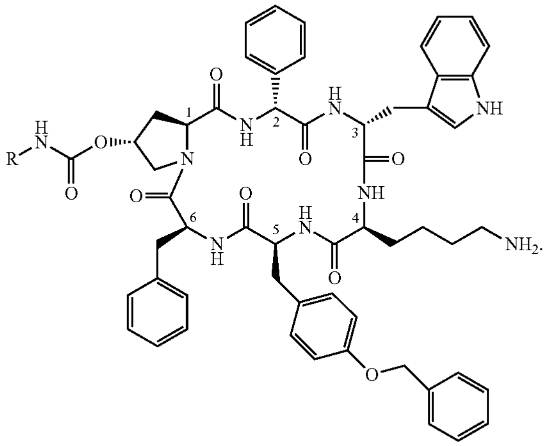

In embodiments, the composition has the following structure:

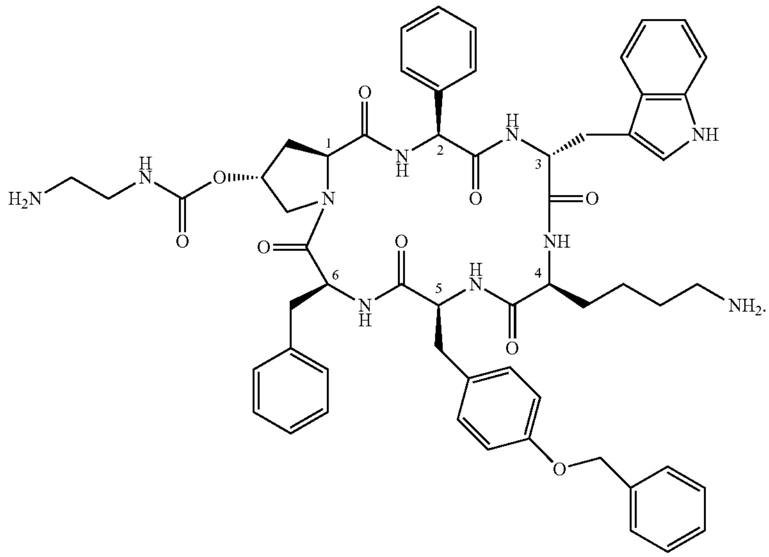 [SMILES: NCCCC[C@@H]1NC(=O)[C@@H](Cc2c[nH]c3ccccc23)NC(=O)[C@H](c2ccccc2)NC(=O)[C@@H]2C[C@@H](OC(=O)NCCN)CN2C(=O)[C@H](Cc2ccccc2)NC(=O)[C@H](Cc2ccc(OCc3ccccc3)cc2)NC1=O]

In embodiments, the antibiotic is novobiocin or erythromycin.

In one aspect, the disclosure provides a composition comprising an antibiotic selected from the group consisting of novobiocin, erythromycin, and combinations thereof and a compound having the following structure:

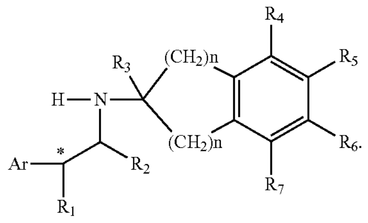

In an embodiment, the compound has the following structure:

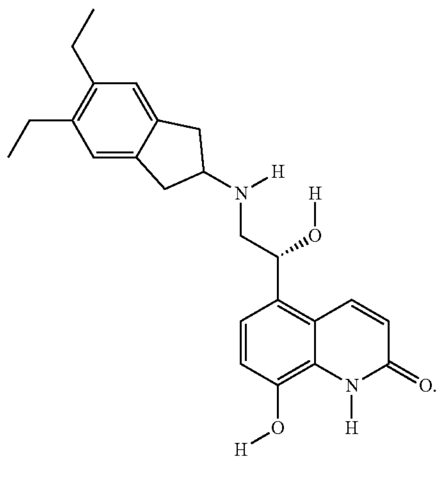 [SMILES: CCc1cc2c(cc1CC)CC(NC[C@H](O)c1ccc(O)c3[nH]c(=O)ccc13)C2]

In embodiments, the antibiotic is erythromycin or novobiocin.

In one aspect, the disclosure provides a composition comprising novobiocin and a compound of formula:

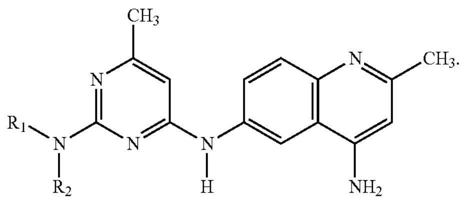

In embodiments, $R_1$ to $R_2$ are independently selected from the group consisting of H, —X-Alk, —X-Alk-X', and —X—Y—X'; wherein X is —CR7R8; X' is —CHR7R8; Alk is a C2-C18 substituted or unsubstituted hydrocarbon chain; Y is a C2-C8 substituted or unsubstituted alkylene chain; R6 is H or (C1-C4) alkyl; and R7 and R8 are independently selected from the group consisting of H or (C1-C4) alkyl or a salt of.

In embodiments, the compound has the following structure:

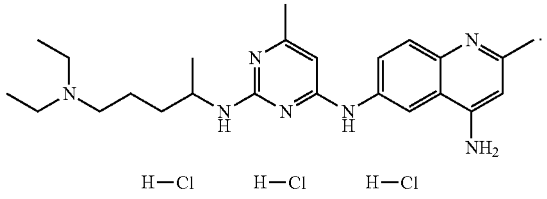 [SMILES: CCN(CC)CCCC(C)Nc1nc(C)cc(Nc2ccc3nc(C)cc(N)c3c2)n1 ; Cl ; Cl ; Cl]

In one aspect, the disclosure provides a composition comprising an antibiotic selected from the group consisting of vancomycin, novobiocin, erythromycin, and combinations thereof and a compound of the following structure:

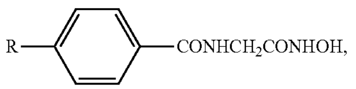

wherein R is nitro or chloro.

In embodiments, the compound is:

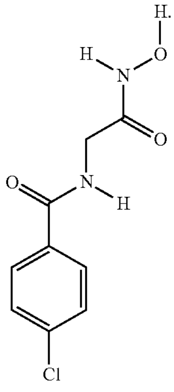

In embodiments, the antibiotic is vancomycin or novobiocin or erythromycin.

In one aspect, the disclosure provides a composition comprising chloramphenicol and a compound of the following structure:

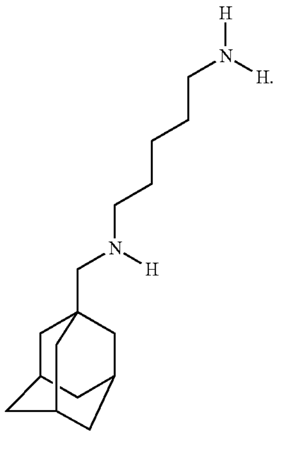

In one aspect, the disclosure provides a composition comprising chloramphenicol and a compound of the following structure:

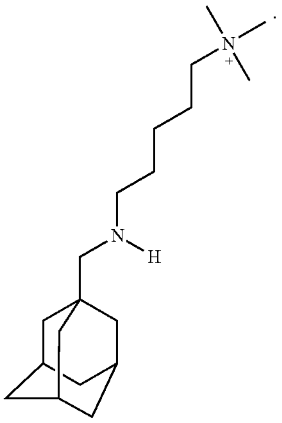

In one aspect, the present disclosure provides a composition comprising an H3 histamine antagonist and an antibiotic selected from the group consisting of novobiocin, erythromycin, chloramphenicol, and combinations thereof.

In embodiments, the H3 histamine antagonist is selected from the group consisting of A-349,821, ABT-239, Betahistine, Burimamide, Ciproxifan, Clobenpropit, Conessine, Failproxifan, Impentamine, Iodophenpropit, Irdabisant, Pitolisant, Thioperamide (also an H4 antagonist), VUF-5681, and combinations thereof.

In embodiments, the H3 histamine antagonist is Iodophenpropit and the antibiotic is novobiocin.

In embodiments, the H3 histamine antagonist is Iodophenpropit and the antibiotic is erythromycin.

In embodiments, the H3 histamine antagonist is Iodophenpropit and the antibiotic is chloramphenicol.

In one aspect, the present disclosure provides a composition comprising a somatostatin receptor agonist and an antibiotic selected from the group consisting of novobiocin, erythromycin, and combinations thereof.

In embodiments, the somatostatin receptor agonist it selected from the group consisting of Octreotide, Lanreotide, Pasireotide, and combinations thereof.

In embodiments, the somatostatin receptor agonist is Pasireotide and the antibiotic is novobiocin.

In embodiments, the somatostatin receptor is Pasireotide and the antibiotic is erythromycin.

In one aspect, the disclosure provides a composition comprising an adrenergic receptor agonist and an antibiotic selected from the group consisting of novobiocin, erythromycin, and combinations thereof.

In embodiments, the adrenergic receptor agonist is selected from the group consisting of Salbutamol, Albuterol, Terbutaline, Salmeterol, Formoterol, Pirbuterol, Indacaterol, and combination thereof.

In embodiments, the somatostatin receptor is Indacaterol and the antibiotic is erythromycin.

In embodiments, the somatostatin receptor is Indacaterol and the antibiotic is novobiocin.

In one aspect, the present disclosure provides a composition comprising a RAC1 inhibitor and novobiocin.

In embodiments, the RAC1 inhibitor is NSC23766.

In one aspect, the present disclosure provides a composition comprising a bacterial urease inhibitor and an antibiotic selected from the group consisting of vancomycin, novobiocin, erythromycin, and combinations thereof.

In embodiments, the bacterial urease inhibitor is 2-(para-chlorobenzamide)-acetohydroxamic acid.

In embodiments, the bacterial urease inhibitor is benurestat and the antibiotic is vancomycin.

In embodiments, the bacterial urease inhibitor is benurestat and the antibiotic is novobiocin.

In embodiments, the bacterial urease inhibitor is benurestat and the antibiotic is erythromycin.

In one aspect, the present disclosure provides a composition comprising a glutamate receptor antagonist and chloramphenicol.

In embodiments, the glutamate receptor antagonist is selected from the group consisting of IEM 1754 and IEM 1460.

In embodiments, the glutamate receptor antagonist is IEM 1754.

In one aspect, the present disclosure provides a method of treating a subject having a bacterial infection comprising administering to the subject any of the aforementioned compositions.

In one aspect, the present disclosure provides a method of potentiating antibacterial activity of an antibiotic in a subject having a bacterial infection comprising administering the antibiotic with a synergistic agent selected from the group consisting of an H3 histamine antagonist, a somatostatin receptor agonist, an adrenergic receptor agonist, a RAC1 inhibitor, a bacterial urease inhibitor, and a glutamate receptor antagonist.

In embodiments, the H3 histamine antagonist is selected from the group consisting of A-349,821, ABT-239, Betahistine, Burimamide, Ciproxifan, Clobenpropit, Conessine, Failproxifan, Impentamine, Iodophenpropit, Irdabisant, Pitolisant, Thioperamide (also an H4 antagonist), VUF-5681, and combinations thereof.

In embodiments, the somatostatin receptor agonist it selected from the group consisting of Octreotide, Lanreotide, Pasireotide, and combinations thereof.

In embodiments, the adrenergic receptor agonist is selected from the group consisting of Salbutamol, Albuterol, Terbutaline, Salmeterol, Formoterol, Pirbuterol, Indacaterol, and combination thereof.

In embodiments, the RAC1 inhibitor is NSC23766.

In embodiments, the bacterial urease inhibitor is 2-(parachlorobenzamide)-acetohydroxamic acid.

In embodiments, the glutamate receptor antagonist is selected from the group consisting of IEM 1754 and IEM 1460.

Definitions

By "agent" or "therapeutic agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease or a symptom thereof.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

As used herein, "changed as compared to a control" sample or subject is understood as having a level of the analytic or diagnostic or therapeutic indicator to be detected at a level that is statistically different than a sample from a normal, untreated, or control sample. Control samples include, for example, cells in culture, one or more laboratory test animals, or one or more human subjects. Methods to select and test control samples are within the ability of those in the art. An analytic substance can be a naturally occurring substance that is characteristically expressed or produced by the cell or organism (e.g., pathogenic bacteria, antibodies, pathogenic peptides or particles, and the like) or a substance produced by a reporter construct (e.g., β-galactosidase or luciferase). Depending on the method used for detection the amount and measurement of the change can vary. Determination of statistical significance is within the ability of those skilled in the art.

As used herein, the term "co-administering," or "co-administration," and the like refers to the act of administering two or more agents (e.g., an antibiotic or therapeutic agent with a synergistic agent), compounds, therapies, or the like, at or about the same time. The order or sequence of administering the different agents of the disclosure, e.g., antibiotics or synergistic agent may vary and is not confined to any particular sequence. Co-administering may also refer to the situation where two or more agents (e.g., an antibiotic or therapeutic agent with a synergistic agent) are administered to different regions of the body or via different delivery schemes, e.g., where a first agent is administered systemically and a second agent is administered orally, or where a first agent is administered orally and a second agent is administering systemically into the blood or proximally to a tissue of interest. Co-administering may also refer to two or more agents administered via the same delivery scheme, e.g., where a first agent is administered systemically and a second agent is administered systemically or at the same time, via the same mechanism (e.g., the antibiotic and synergistic agent are present as a composition within the same tablet or pill).

As used herein, the terms "comprises," "comprising," "containing" and "having" and the like are open-ended as defined by U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

"Contacting a cell" is understood herein as providing an agent (e.g., an antibiotic or therapeutic agent with a synergistic agent) to a cell e.g., a bacterial cell to be treated in culture, ex vivo, or in a subject or animal, such that the agent can interact with the cell (e.g., bacterial cell to be treated), potentially be taken up by the cell, and have an effect on the cell. The agent (e.g., an antibiotic and a synergistic agent) can be delivered to the cell directly (e.g., by addition of the agent to a subject or culture medium or by injection into a cell, tissue, or area of interest), or by delivery to the organism by a topical or parenteral route of administration for delivery to the cell by vascular, lymphatic, or other means. One of ordinary skill in the art will readily understand that administration of an agent of the disclosure to a subject involves contacting the agent with a cell, fluid, or tissue of the subject.

As used herein, the term "coupled," as in reference to two or more agents being "coupled" together, refers to a covalent or otherwise stable association between the two or more agents (e.g., an antibiotic or therapeutic agent with a synergistic agent). For example, an antibiotic agent may be coupled with a synergistic agent via a covalent bond, a covalently tethered linker moiety, or non-covalently through ionic interactions or hydrogen bonding. One or more agents that are coupled together retain substantial their same independent functions and characteristics. For example, the antibiotic agent when coupled to a synergistic agent may retain its same antibacterial activity as if it were independent, but that activity will be increased or multiplied.

By "cycle" or "drug cycle" is meant the administration of repetitive dosing for a defined period of time, which may range from minute to hours to days to weeks to months or even years.

As used herein, "detecting," "detection," and the like are understood to mean that an assay is performed to determine one or more characteristics of a sample, e.g. identifying the presence, absence or amount of the analyte to be detected. For example, detection can include identification of a specific analyte in a sample or an activity of an agent in a sample. Detection can include the determination of the presence of nucleic acid, protein (e.g., antibody, cytokine, and the like) by PCR, immunoassay (e.g., ELISA), microscopy, pathogen challenge, and the like.

The amount of analyte or activity detected in the sample can be none or below the level of detection of the assay or method.

By "disease" is meant any condition or disorder that damages or interferes with the normal function of a cell, tissue, or organ. An exemplary disease is a bacterial infection.

The terms "effective amount," "therapeutically effective amount," or "pharmaceutically effective amount," as used herein, refer to an amount of an agent or compound that is sufficient to treat a disorder, e.g., a bacterial infection. In some embodiments, the result is a reduction in and/or alleviation of the signs, symptoms, or causes of a disorder, or any other desired alteration of a biological system. For example, an "effective amount" for therapeutic uses is the amount of the composition comprising a compound as disclosed herein required to provide a clinically significant decrease in a disorder (e.g., a reduction or elimination of a bacterial infection). An "effective amount" or therapeutically effective amount of an agent or combination of agents of the disclosure may also be that amount or dose that is effective to substantially shrink or destroy a tumor, or permit its surgical removal. An appropriate "effective" amount in any individual case is determined using any suitable technique, (e.g., a dose escalation study) and will depend on the judgment of the practitioner. However, suitable dosage ranges are readily determinable by one skilled in the art.

More than one dose may be required to provide an effective dose. It is understood that an effective dose in one population may or may not be sufficient in all populations. Thus, in connection with the administration of an agent of the disclosure (e.g., an antibiotic or therapeutic agent with a synergistic agent), the agent is "effective against" a disease or condition (e.g., a bacterial infection) when administration in a clinically appropriate manner results in a beneficial effect for at least a statistically significant fraction of subjects, such as a prevention of disease onset, improvement of symptoms, a cure, a reduction in disease signs or symptoms, extension of life, improvement in quality of life, or other effect generally recognized as positive by medical doctors familiar with treating the particular type of disease or condition.

By "enhances" is meant a positive alteration of at least 10%, 25%, 50%, 75%, 100%, or any number therebetween.

As used herein, an "immunoassay" is a detection method based on the specific binding of at least one antibody to an antigen, e.g., ELISA, RIA, western blot, and the like.

"Infection" means that a subject is suffering from the presence of a higher number of one or more microorganisms than would be expected in a healthy subject. An infection may be localized (restricted to a particular region, organ, system or the like of the subject) or systemic (affecting a number of regions, organs, systems or the like of the subject). Exemplary types of infections that may be treated by antibiotics include anthrax (*Bacillus anthracis*), lyme disease (*Borrelia burgdorferi*), brucellosis (*Brucella*), enteritis (*Campylobacter jejuni*), *Clostridium difficile* infections, *Clostridium perfringens* infections, diphtheria (*Corynebacterium diphtheriae*), nosocomial infections (e.g. caused by *Enterococcus faecalis* or *Enterococcus faecium*), *Escherichia coli* infections (including by Enterotoxigenic *E. coli* or Enteropathogenic *E. coli*), tularemia (*Francisella tularensis*), *Haemophilus* influenza infections, *Helicobacter pylori* infections, Legionnaire's disease (*Legionella pneumophila*), leptospirosis (*Leptospira interrogans*), listeriosis (*Listeria monocytogenes*), leprosy (*Mycobacterium leprae*), tuberculosis (*Mycobacterium tuberculosis*), gonorrhea (*Neisseria gonorrhoeae*), meningococcal disease (*Neisseria meningitides*), *pseudomonas* infection (*Pseudomonas aeruginosa*), typhoid fever or *salmonellosis* (*Salmonella typhi, Salmonella typhimurium*), shigellosis (*Shigella sonnei*), staphylococcal infections (*Staphylococcus aureus, Staphylococcus epidermis, Staphylococcus saprophyticus*), *streptococcus* infections (*Streptococcus agalactiae, Streptococcus pneumoniae, Streptococcus pyogenes*), syphilis (*Treponema pallidum*), plague (*Yersinia pestis*), or the like. In some embodiments, the infection is a bacterial infection. In some embodiments, the infection is caused by a combination of a bacterial infection and an infection with one or more other types of microorganisms.

"Obtaining" is understood herein as manufacturing, purchasing, synthesizing, isolating, purifying, or otherwise coming into possession of.

The term "pharmaceutically acceptable" as used herein, refers to a material, (e.g., a carrier or diluent), which does not abrogate the biological activity or properties of the compounds described herein, and is relatively nontoxic (i.e., the material is administered to an individual without causing undesirable biological effects or interacting in a deleterious manner with any of the components of the composition in which it is contained).

The phrase "pharmaceutically acceptable carrier, excipient, or diluent" is art recognized and includes a pharmaceutically acceptable material, composition or vehicle, suitable for administering compounds of the present disclosure to mammals. As used herein, the term "pharmaceutically acceptable" means being approved by a regulatory agency of the Federal or a state government or listed in the U.S. Pharmacopia, European Pharmacopia or other generally recognized pharmacopia for use in mammals, e.g., humans.

As used herein, the term "pharmaceutically effective regimen" refers to a systematic plan for the administration of one or more therapeutic agents, which includes aspects such as type of therapeutic agent, therapeutic agent concentrations, synergistic antibacterial enhancer concentrations, amounts or levels based on the bacteria type, location or size, timing, and repetition, and any changes therein made during the course of the drug administration, which when administered is effective in treating an infection, mitigating disease symptoms, and/or providing antibacterial activity.

Such considerations depend on the judgment of the practitioner and are readily determinable by one skilled in the art.

A "polypeptide" or "peptide" as used herein is understood as two or more independently selected natural or non-natural amino acids joined by a covalent bond (e.g., a peptide bond). A peptide can include 2, 3, 4, 5, 6, 7, 8, 9, 10, 11, 12, 13, 14, 15, 16, 17, 18, 19, 20, or more natural or non-natural amino acids joined by peptide bonds. Polypeptides as described herein include full length proteins (e.g., fully processed proteins) as well as shorter amino acids sequences (e.g., fragments of naturally occurring proteins or synthetic polypeptide fragments).

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

By "reduces" is meant a negative alteration of at least 10%, 25%, 50%, 75%, 100%, or any number therebetween.

By "reference" is meant a standard or control condition.

As used herein, the term "regimen" refers to the various parameters that characterize how a drug or agent is administered, including, the dosage level, timing, and iterations, as well as the ratio of different drugs or agents to one another. The term "pharmaceutically effective regimen" refers to a particular regimen which provides a desired therapeutic result or effect, including substantial shrinkage and/or destruction of the tumor or cells that have metastasized therefrom. The term "iterations" refer to the general concept of repeating sets of administering one or more agents. For example, a combination of drug X (e.g., an antibiotic) and drug Y (e.g., a synergistic agent) may be given (co-administered at or about at the same time and in any order) to a patient on a first day at dose Z. Drugs X and Y may then be administered (co-administered at or about at the same time and in any order) again at dose Z, or another dose, on a second day. The timing between the first and second days can be 1 day or anywhere up to several days, or a week, or several weeks, or months. The iterative administrations may also occur on the same day, separated by a specified number of minutes (e.g., 10 minutes, 20 minutes, 30 minutes or more) or hours (e.g., 1 hour, 2 hours, 4 hours, 6 hours, 12 hours). An effective dosing regimen may be determinable by those of ordinary skill in the art, e.g., prescribing physician, using standard practices.

A "sample" as used herein refers to a biological material that is isolated from its environment (e.g., blood or tissue from an animal, cells, or conditioned media from tissue culture). In embodiments, the sample is suspected of containing, or known to contain an analyte, such as an infectious agent or a protein of interest (e.g., pathogenic bacteria, antibody, cytokine, and the like). A sample can also be a partially purified fraction of a tissue or bodily fluid. A reference sample can be a "normal" sample, from a donor not having the disease or condition fluid, or from a normal tissue in a subject having the disease or condition, or an untreated subject (e.g., a subject not treated with an antibiotic or an antibiotic with a synergistic agent). A reference sample can also be taken at a "zero time point" prior to contacting the cell or subject with the agent or therapeutic intervention to be tested.

By "specifically binds" is meant recognition and binding to a target (e.g., polypeptide, cell, and the like), but which does not substantially recognize and bind other molecules in a sample, for example, a biological sample.

The term "subject", as used herein, refers to any organism that is capable of developing a bacterial infection. Such organisms include, but are not limited to, human, dog, cat, horse, cow, sheep, goat, mouse, rat, guinea pig, monkey, avian, reptiles, etc.

By "synergistic agent" or "synergistic therapeutic agent" is meant any small molecule chemical compound, antibody, nucleic acid molecule, or polypeptide, or fragments thereof that potentiates the activity or function of an agent (e.g., an antibiotic). In general, a synergistic agent may be characterized by a "fractional inhibitory concentration" (hereafter "FIC") interaction coefficient $\leq 0.5$. Additionally, a synergistic agent as disclosed herein may generally be characterized by a positive BLISS score (see e.g., Borisy et al., Proc. Natl. Acad. Sci. USA. 100 (13): 7977-7982 (2003); and Buck et al., Mol. Cancer. Ther. 5 (11) (2006)).

As used herein, the terms "treatment", "treating", and the like, refer to obtaining a desired pharmacologic and/or physiologic effect (e.g., reducing and/or eliminating a bacterial infection). The effect may be prophylactic in terms of completely or partially preventing a disease or symptom thereof and/or may be therapeutic in terms of a partial or complete cure for a disease and/or adverse effect attributable to the disease. "To treat an infection" or "Treating an infection" in a mammal means one or more of alleviating a symptom of, correcting an underlying molecular or physiological disorder of, or reducing the frequency or severity of a pathological or deleterious physiological consequence of an infection in a subject. By way of example, and not by limitation, the deleterious physiological consequences of an infection can include uncontrolled proliferation, metastasis and invasion of bacteria, fungi, parasites, and/or viruses into fluids, tissues, and/or cells of a subject, and suppression of an immune response of the subject. Thus, treatment of infection includes, but is not limited to, inhibiting growth of infectious agents (e.g. bacteria, fungi, viruses, and parasites), inhibiting proliferation of infectious agents, reducing infectious agent volume, or inhibiting the spread of infectious agents to other parts of the body (sepsis).

As used herein and in the appended claims, the singular forms "a," "and," and "the" include plural reference unless the context clearly dictates otherwise. Thus, for example, reference to "a gene" is a reference to one or more genes and includes equivalents thereof known to those skilled in the art, and so forth.

Unless specifically stated or obvious from context, as used herein, the term "or" is understood to be inclusive.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Other definitions appear in context throughout this disclosure.

Any therapeutic agents, compositions, or methods provided herein can be combined with one or more of any of the other therapeutic agents, compositions, and methods provided herein.

Where applicable or not specifically disclaimed, any one of the embodiments described herein are contemplated to be able to combine with any other one or more embodiments, even though the embodiments are described under different aspects of the disclosure.

These and other embodiments are disclosed and/or encompassed by, the following Detailed Description.

BRIEF DESCRIPTION OF THE DRAWINGS

The following detailed description, given by way of example, but not intended to limit the disclosure solely to the specific embodiments described, may best be understood in conjunction with the accompanying drawings, in which:

FIG. 1A is a schematic showing that compounds used in the screening process of an exemplary embodiment may be barcoded by the ratio of three fluorescent dyes (e.g., red, green, and blue fluorescent dye barcodes). FIG. 1B is a schematic in which a sample from each well is emulsified into 1 nanoliter aqueous droplets in a surrounding fluorocarbon oil and stabilizing surfactant. FIG. 1C is a schematic that shows that standard micropipette techniques may be used to pool and load the emulsions into a microwell array such that each microwell captures two droplets at random (right panel). FIG. 1D is an image showing a low-magnification (2-4×) fluorescence microscopy image that identifies the compound in each droplet according to an exemplary embodiment. FIG. 1E is an image showing that pairs of droplets may be merged by applying a high voltage AC electric current to induce droplet merging, and the array may then be incubated to allow for cells to respond to the pair of compounds. FIG. 1F is an image showing that an optical phenotype may be assayed and mapped to the pair of compounds previously identified in each well to identify an effect on, for example, cell growth inhibition. FIG. 1G is a schematic depicting an overview of a combinatorial drug screening based on parallel droplet processing according to an exemplary embodiment of the disclosure. FIG. 1H shows a droplets-based platform for combinatorial drug screening. Section I of FIG. 1H shows that compounds, cells, and fluorescence red/green/blue (RGB) barcodes are emulsified into nanoliter droplets and subsequently pooled. Section II of FIG. 1H shows that a microwell array (FIG. 20) pairs random combinations of droplets (Movie 1, Movie 2). Once loaded, surfactant that mediates compound exchange can be washed out of the array. Low magnification fluorescence microscopy identifies the compounds carried by each droplet. Pairs of droplets in each well are merged and incubated, and a second scan measures an optical assay (such as, e.g., cell growth inhibition). Section III of FIG. 1H shows photographs of microwell array assembly during and after loading. Section IV of FIG. 1H shows 3-color fluorescence micrograph droplets in microwell array, paired with subsequent cell growth assay (fluorescence from GFP).

FIGS. 2A-2K show a series of graphs, dot plots, schematics, and tables. FIG. 2A shows graphs measuring exchange at each step of a combinatorial drug screening process according to an exemplary embodiment of the disclosure. FIG. 2B shows graphs depicting growth rates of *Staphylococcus aureus, Escherichia coli*, and *Pseudomonas aeruginosa*. FIG. 2C shows dot plots depicting antibiotic drug responses according to an exemplary embodiment of the disclosure. FIG. 2D shows graphs measuring the relationship of noise contributed by variability between different runs by assessing antibiotic response curves from 6-12 different antibiotics from the same pool of droplets floated across to technical replicate microwell arrays. FIG. 2E depicts tables in which a canonical pair of compounds, ampicillin and sulbactam, were tested for synergistic activity against *P. aeruginosa* via FIC analysis. FIG. 2F-FIG. 2K show characterization of microarray system performance. FIG. 2F shows a model for assessing cross-contamination of screening compounds. The transfer of the fluorescent dye resorufin was tracked (e.g., carried by "source droplets") to empty droplets ("sink droplets"). FIG. 2G depicts graphs of exchange of dye measured over time by fraction of total observed dye fluorescence measured in source droplets (red lines) and sink droplets (gray lines) as a function of surfactant concentration (0%, 0.5%, and 2% w/w surfactant). The effect of compartmentalization is measured by comparing the rates of dye accumulation in sink droplets when co-compartmentalized in wells with source (dotted lines) or other sink droplets (solid lines). Transfer that occurred during the pooling and loading is measured by the fraction of total fluorescence in sink droplets at the first time point in the assay (FIG. 22C). FIG. 2H shows measurement of cell growth by monitoring accumulation of constitutively expressed GFP in both conventional Erlenmeyer flasks (dotted lines) and an exemplary embodiment of a microdroplet platform as disclosed herein (solid lines). Error bars represent standard deviations of microwell measurements. Measurements from Erlenmeyer flask cultures are linearly transformed to the same scale as microwell measurements FIG. 2I shows an experimental setup for measuring comparing antibiotic response curves and measuring technical noise between 96-well broth culture format and the microdroplet format. FIG. 2K depicts a series of graphs of bacterial growth over time. The three graphs on the first row of FIG. 2K display estimated $IC_{50}$ for each antibiotic compared between both platforms (FIGS. 23-25). Dotted lines show the diagonal. The three graphs on the section row of FIG. 2K show a comparison of growth values determined from both technical replicates on the microdroplet platform. Dotted lines show a line of best fit. The three graphs on the third row of FIG. 2K show the relationship between well-level replication and technical noise, estimated by bootstrap resampling of the second row data set in FIG. 2K and FIGS. 23-25. Error bars represent 10-$90^{th}$ percentile bootstrapped $R^2$ values. Dotted lines represent $R^2$ values between technical replicates in 96-well broth culture plates (FIGS. 26A-26C). FIG. 2J is a chart of the data shown in the data set for the first row of graphs in FIG. 2K. Reported were root mean square (RMS) differences between log 10 IC50 values for antibiotic growth curves measured between an exemplary embodiment of the microdroplet platform disclosed herein and a 96-well broth culture format. RMS differences between technical replicates in each format are shown for comparison (FIG. 26A-FIG. 26C). For data shown in the second row of graphs in FIG. 2K, the value of $R^2$ values measured between technical replicates was reported.

FIG. 3A shows that drug-antibiotic synergies were assessed by evaluating a shift of a 3-point antibiotic dose response, and quantified by the Bliss synergy metric according to an exemplary embodiment of the disclosure. FIG. 3B shows data indicating that of the drug-antibiotic combinations, the median level of well-level replication was 13, and 3.82% had <5 replicates (gray line is antibiotic alone; blue line is antibiotic+compound tested). FIG. 3B shows that the final numbers of analyzed combinations, after accounting for losses and quality filtering (FIG. 28A-FIG. 28B). FIG. 3B also shows a histogram (blue bars) and cumulative distribution (red line) of the number of microwells observed for each compound×antibiotic combination. (Bottom panel) The panel beneath the histogram in FIG. 3B depicts mean number of microwells of all antibiotic×compound combinations for a given chip. FIG. 3C shows that the distribution of Bliss scores of the negative controls across all antibiotics was well described by a T-distribution. The top right panel of FIG. 3C shows 28 compound-antibiotic combination hits determined by thresholding Bliss scores (gray contours) for each pair on effect size (Bliss score >0.7, red dotted line) and statistical significance (p<1e-4, red dotted line, FIG. 30A-FIG. 30B). The top left panel of FIG. 3C shows compound-antibiotic sensitivity to positive controls (blue: sulbactam, green: erythromycin) as determined by statistical significance threshold. The bottom right panel of FIG. 3C shows effect of size distributions of positive and negative (black: blank) controls. FIG. 3D shows the threshold Bliss score used to identify 22 compound hits of significance. FIG. 3E is a series of graphs showing that each hit yields a signature of antibiotic potentiation. FIG. 3F is a schematic showing that 3-point dose response curves were generated to measure antibiotic potentiation for 10 different antibiotics in combination (FIG. 10A) with 4,160 compounds (each at single concentration, 100 μM) from a drug repurposing library, as well as positive controls (sulbactam and erythromycin) and negative controls (blank). Each chip constructed all pairwise combinations of two input sets: 1) 3 antibiotics×10 concentrations (FIG. 10A)+2 controls (32 total) 2) 24-28 compounds+4-8 controls (32 total). Hits were validated by performing 8-point checkerboard assays to determine Bliss synergy and FIC. FIG. 3G is a series of graphs showing that primary screening data yielded antibiotic response curves in combination with each compound (blue: sulbactam; green: erythromycin; black: blank) that were compared to response curves of the antibiotic alone (gray, dotted). This comparison is made quantitative by calculating a Bliss Score; and FIGS. 4A-4J show data summarizing validation results. FIG. 4A depicts validation results as tested in plates and with plate validation concordance, as well as validation by FIC. FIG. 4B shows a table listing six identified compounds according to an exemplary embodiment of the disclosure. FIG. 4C shows data indicating synergistic enhancement of the action of novobiocin, erythromycin, and cycloserine by Iodophenpropit. FIG. 4D shows data indicating synergistic enhancement of the action of novobiocin, erythromycin, and chloramphenicol by Iodophenpropit. FIG. 4E-FIG. 4J show validation of hits from primary screening. FIG. 4E displays Bliss score data from 8-point checkerboard assays. A total of 46 drug-antibiotic combinations (19 distinct compounds) were tested, of which 17 combinations (11 distinct compounds) scored as hits (Bliss score >0.7 and p-value <10-4) in the primary screen (FIG. 31A-FIG. 31J). Combinations that scored positive (blue) and negative (black) are shown with their primary screening data. FIG. 4F shows a chart and images of targets, statuses, antibiotic synergies (FIC method), and representative structures from validated hits (FIG. 31A-FIG. 31J, FIG. 32, FIG. 33). FIG. 4G shows graphs of primary screening data (top panel) and calculated bliss scores (bottom) for three different hits. FIG. 4H shows heat maps of relative growth data (top panel) and calculated bliss scores (bottom panel) from checkerboard assay for NSC 23766×novobiocin (synergy predicted) (left column) and NSC 23766×tetracycline (no synergy predicted) (right column). FIG. 4I shows checkerboard data for screening hit indacaterol×erythromycin (color scale bars in (FIG. 4H)). FIG. 4J shows checkerboard data for screening hit benurestat×vancomycin (color scale bars in (FIG. 4H)).

FIGS. 5A-5E show an exemplary protocol for a two-step Assay Ready Plates (ARP) process that was used for processing. FIG. 5A shows that compounds were stocked in 384 well plates. In the first step compounds in each of four quadrants were echoed into 96-well plate ARPs as shown in FIG. 5B. In the second step a second plate of controls and dyes were added as shown in FIG. 5C. FIG. 5D details construction of the source plate and controls. Outlines for dye plates and details on loading of wells is detailed in FIG. 5E.

FIGS. 6A-6B show a map of a dye plate master plate (FIG. 6A) and an adjuvant plate (FIG. 6B), respectively.

FIG. 8 provides an example of a compound concentration model.

FIGS. 9A-9B are tables elaborating exemplary methods for creating fluorescent Alexa dye stocks for Alexa 555, Alexa 594, and Alexa 647. Nanodrop software was used for normalizing florescent Alexa concentrations.

FIGS. 10A-10F provide exemplary antibiotic protocols according to the disclosure. Stock antibiotic concentration formulations for vancomycin, cycloserine, fosfomycin, novobiocin, erythromycin, tetracycline, ampicillin, trimethoprim, chloramphenicol, and norflaxacin are detailed in FIG. 10A. Standard curves for these antibiotics against *E. coli* are shown in FIG. 10B. An example of data from antibiotics at various concentrations before droplets were merged is given in FIG. 10C. Stock dilutions of 1×, 10×, and 100× concentrations were made as shown in FIG. 10D. Examples of plate maps for antibiotic concentrations were made as shown in FIG. 10E. Details regarding plate assembly with antibiotics are given in FIG. 10F.

FIGS. 12A-12D depict primary hit data. FIGS. 12A-12C show three segments of a chart detailing primary hit information from a combination of antibiotics and adjuvants against bacterial models. FIG. 12D displays this hit data graphically.

FIGS. 13A-13C show exemplary checkerboard parameters. Checkerboards of concentrations of antibiotics used for different screening runs were created as shown in FIG. 13A. Example concentrations of antibiotics used for screening against *E. coli* were made as shown in FIG. 13B. Barcode identifiers were made for each antibiotic as shown in FIG. 13C.

FIGS. 14A-14F show adjuvant and antibiotic checkerboards. Three batches of adjuvants were run during several screens as shown in FIG. 14A. Molar mass, mass, DMSO volume, plate volume, and DMSO solubility of the compounds were recorded for adjuvant compounds used during screens as shown in FIG. 14B. In some instances 800 microliter deep well plates were used for screening as shown in FIG. 14C. An exemplary plate map is shown in FIG. 14D. Exemplary antibiotic counts are listed in FIG. 14E. An exemplary annotated source plate is shown in FIG. 14F.

FIGS. 15A-B shows exemplary pipetting protocols for the adjuvant transfer (transfer 1), the antibiotic transfer (transfer 2), and the adjuvant stock.

FIGS. 16A-16D depict an exemplary checkerboards workflow. FIG. 16A details a protocol for generating stock plates according to an exemplary embodiment of the invention.

FIG. 16B details a protocol for generating source plates according to an exemplary embodiment of the invention. FIG. 16C details a protocol for generating checker board plates according to an exemplary embodiment of the invention. FIG. 16D details a protocol for adding bacteria to a checker board plate.

FIGS. 17A-17C depict primary hits identified by an exemplary embodiment of the disclosure.

FIGS. 18A-18E depict exemplary checkerboard final barcodes.

FIGS. 19A-C depict exemplary Bliss scores for antibiotic-compound combinations. The chart in FIG. 19A is zoomed in and split into two parts as shown in FIG. 19B and FIG. 19C.

FIG. 21A depicts a graph displaying barcoding performance. To measure the performance of the barcode classification, droplets were created from a set of 60 barcodes with different ratios of 3 fluorescent dyes (Color 1 (Alexa Fluor 555), Color 2 (Alexa Fluor 647), Color 3 (Alexa Fluor 647)). The set of 60 was divided into 4 sets of 15 barcodes and split across different chips (blue, orange, green, or red). The 3-color fluorescence values of each droplet (n=164,024 across 82,012 wells) are shown as a 2-dimensional projection. FIG. 21B shows a histogram where droplets were determined to be misclassified if they were assigned to a cluster that was not present on the chip. A histogram shows the fraction of total droplets that were misclassified as function of each droplet's distance to its assigned cluster centroid. FIG. 21C shows a graph where wells with at least one droplet exceeding a distance threshold are removed to improve classification performance. The fraction of wells misclassified is estimated by multiplying the number of wells with at least 1 misclassified droplet by 4/3, since misassignment can only be detected to the 45 of 60 total clusters not present on each chip.

FIG. 22A is a pair of graphs. In one graph, exchange of resorufin between neighboring droplets is monitored in wells containing a single source and sink droplet (FIG. 2F), by tracking the accumulation of dye in the sink droplets (solid) and the depletion of dye from the sink droplets (dashed). In another graph, kinetics of exchange exhibit a single exponential at early time points, and a power law at later timepoints. Exchange kinetic constants (k) for each surfactant were estimated from data from the first 2 hours. FIG. 22B is a pair of graphs. In one graph, during the pooling phase (FIG. 1H, Section I), droplets form a 3-dimensional sphere packing that increases the transport surface area. To measure the relationship of surface area and exchange kinetics, wells were constructed that hold 7 total droplets, with stochastic loading of source or sink droplets. The exchange kinetics were measured between source and sink droplets that shared the same well, as a function of the number of source droplets. In another graph exchange kinetic constants (k) were measured as function of the number of source droplets by fitting to a single exponential to the first two hours. FIG. 22C is another pair of graphs. In one graph, the exchange kinetic constants show a linear relationship with the number of source droplets. In another graph, the exchange during pooling was predicted by linearly extrapolating the fit kinetic constants in (B) by the number of source droplets neighboring a given sink droplet in the 3-dimensional sphere-packing. In the experiment described in FIG. 2F, source and sink droplets were pooled in a 1:1 ratio for 10 minutes. At the first timepoint, the fraction of resorufin dye in the sink droplets in sink only wells (0% w/w surfactant) was measured as 0.096 (FIG. 2G).

FIG. 26A is a scatterplot comparison of 96-well plate technical replicate measurements of relative GFP fluorescence, from FIG. 23-FIG. 25. Lines of best fit (gray, dotted) and corresponding R2 values are shown. R2 values obtained are also drawn in FIG. 2K (gray, dotted) and reported in FIG. 2J. FIG. 26B and FIG. 26C are scatterplot comparisons of fit IC50 values from technical replicate antibiotic dose responses (FIG. 23-FIG. 25), compared to the diagonal (red, dotted). The root mean square of the log 10 error (RMS log 10 (E)) was reported, which represents the log 10 difference from the diagonal (red, dotted). These values are also reported in FIG. 2J.

FIG. 27 is a graph of a comparison checkerboard assay between 96-well plates and microwell array platform. Comparison of checkerboard drug interaction assay in *P. aeruginosa* for ampicillin and a beta-lactamase inhibitor, sulbactam. Each point shows a relative growth value normalized to the maximum growth value on the 64-point matrix. Both platforms report a synergistic interaction as described by the FIC method.

FIG. 28A shows histograms of a quality scoring procedure for a representative microwell array chip based on calculation of Z-factor (Z') between microwells representing the top (blank control, red) and bottom (cycloserine 16 μg/mL, blue) of the growth assay dynamic range. Histograms show median GFP growth values (abs) computed from samples bootstrapped from original sample of replicate microwells. FIG. 28B is a graph where each point represents the Z-factor (Z') computed for each microwell array chip, computed as shown in (A). 108 chips passed our quality threshold (Z'>0.21), and 16 chips failed.

FIG. 30A is a histogram of the test statistic for all blank negative control—antibiotic pairs (n=140×10 antibiotics=1400; blue), compared to the fit T-distribution (11.2 degrees of freedom, scale=0.992; red). FIG. 30B is a graph. To determine the quality of the fit, ordered values were compared of the test-statistic with theoretical quantiles estimated for the fit T-distribution. Theoretical quantiles are estimated by Filliben's estimate. The diagonal (gray) is shown for comparison.

FIG. 31A is section one of the checkerboard validation assays. FIG. 31B is section two of the checkerboard validation assays. FIG. 31C is section three of the checkerboard validation assays. FIG. 31D is section four of the checkerboard validation assays. FIG. 31E is section five of the checkerboard validation assays. FIG. 31F is section six of the checkerboard validation assays. FIG. 31G is section seven of the checkerboard validation assays. FIG. 31H is section eight of the checkerboard validation assays. FIG. 31I is section nine of the checkerboard validation assays. FIG. 31J is section ten of the checkerboard validation assays.

DETAILED DESCRIPTION OF THE DISCLOSURE

Figure 1A:
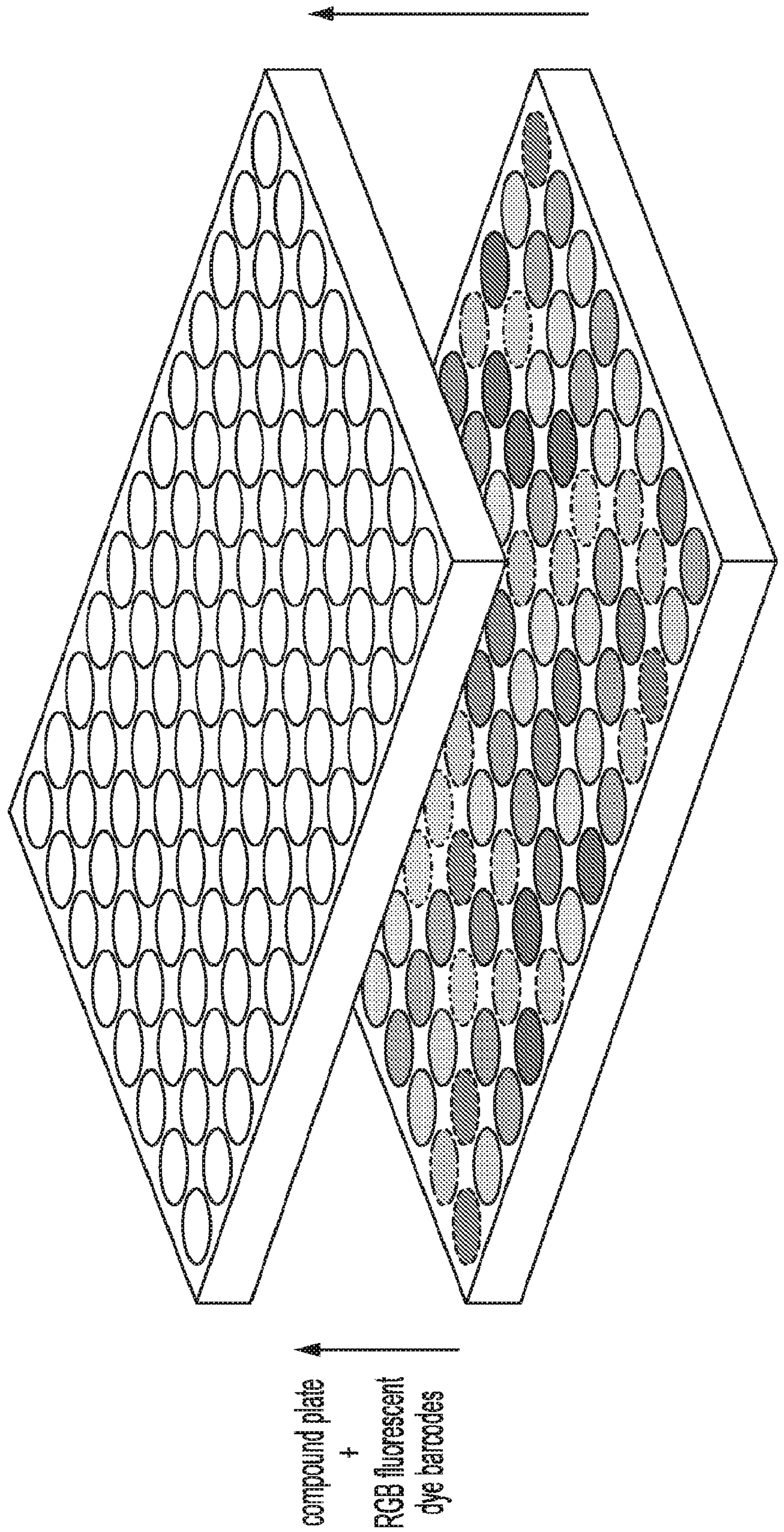
FIGS. 1A-1H show a series of schematics and diagrams pertaining to an exemplary combinatorial drug screening process as described herein.

The present disclosure is based, at least in part, on the discovery that a microfluidics-based platform that implements parallel droplet processing may be used in a scalable, high throughput method to identify agents (e.g., synergistic agents) that potentiate or enhance the activity/function of an antibiotic. The present disclosure provides synergistic agents that potentiate the activity of a variety of antibiotics (e.g., novobiocin, erythromycin, chloramphenicol, vancomycin, and the like). Advantageously, the synergistic agents disclosed herein may increase the efficacy of known antibiotics, and mitigate issues arising from bacterial strains that have acquired drug or multi-drug resistance. The techniques herein provide a new microscale assay platform for rapidly screening drug combinations with order of magnitude improvements over the state of the art. In particular, the techniques herein have allowed identification of novel synergistic agents that potentiate antibiotic activity (e.g., novobiocin, erythromycin, vancomycin, chloramphenicol, and the like).

Overview

Human diseases are increasingly recognized as multifactorial in origin. Combination treatments involving multiple drug compounds are increasingly used across several therapeutic areas, including cancer, immunotherapy, antibacterials, and antivirals. Antimicrobial treatments that combine inhibitors of specific resistance mechanisms (e.g. beta-lactamase enzymes) with antibiotics now make up a substantial fraction of drugs in clinical development.

Biological networks are complex and nonlinear, yet conventional medical approaches seek to perturb such networks to treat disease in a one-drug/one-target paradigm that is out of sync with the opportunity to leverage the best understanding of biology for the treatment of disease. Some existing drugs are known to be imperfectly specific (e.g., amiodarone) or to idiosyncratically engage multiple specific targets that collectively drive observed therapeutic effects (e.g., papaverine). Multiple drug compounds are currently used in combination across several therapeutic areas including cancer, antibacterials, and antivirals. In particular, combination antimicrobial treatments that overcome drug resistance by targeting known resistance elements (e.g. beta-lactamase enzymes) in addition to essential pathways make up a substantial fraction of antibiotic treatments in clinical development today.

Despite their applicability, identification of novel drug combinations by high throughput screening has been slowed by the high complexity, cost, and compound consumption of conventional combinatorial screening. For example, testing all pairs of drugs from a modest library of 2000 drugs (e.g. FDA approved drugs) requires 2 million pairwise combinations, and far more if compounds are titrated in the screen. Experiments of this scale are restricted to specialized labs and facilities, often with prohibitive costs and complexity (total liquid handling steps, plate layout and workflow design). Additionally, since these screens test each compound across thousands of others, thousands-fold more compound is consumed compared with single-compound screening and can deplete an entire inventory in one experiment. Current methods for combinatorial discovery work around these issues, either by leveraging computational predictions of drug synergies to reduce screening scale, or by combining multiple tests in pools with subsequent deconvolution of hits from high-scoring pools. However, these methods fall short of allowing rapid screening methods that might identify drug combinations having synergistic effects.

The techniques herein provide a high-throughput system for nanoliter-scale phenotypic screening that stabilizes a chemical library in micro-droplet emulsions and automates the formulation of chemical combinations en mass in parallel. This system was used to predict synergy against *E. coli* between more than 4000 investigational and approved drugs and a panel of 10 antibiotics. A range of drugs not previously indicated for infectious disease were identified that synergize with antibiotics against *E. coli*, an important Gram-negative pathogen. The hits include drugs that synergize with the antibiotics vancomycin, erythromycin, and novobiocin, which are used today against Gram positive bacteria but are not effective by themselves to resolve Gram negative infections. In particular, 6 novel potentiators of antibiotics against Gram-negative bacterial pathogens were identified.

Screening Methodology

Combinatorial screening of molecular species in the presence of cells (e.g. bacteria) and a reporter construct (e.g. fluorescence protein) is used to rapidly measure the effect of combined species. In the case of evaluating antibiotic-compound synergy, a set of antibiotics is screened in combination with a set of compounds, over a range of different antibiotic and compound combinations, rapidly and in replicates. Each molecular species to be tested is placed in a microplate well. Mono-disperse droplets comprising the species to be screened are formed using an aqueous and an oil input channel. The molecular species droplets are then loaded onto a microfluidic device. Each molecular species is labeled with a barcode. When two or more droplets are merged, the combined molecular barcodes identify which molecular species are present in the merged droplet. The barcode is an optically detectable barcode visualized with light or fluorescence microscopy or an oligonucleotide barcode that is detected off-chip.

Bacteria, against which an antibiotic to be screened is targeted, are loaded into one set of droplets and merged with droplet(s) comprising the antibiotic and compound to be screened. These cellular droplets are formed from an aqueous solution comprising the appropriate growth media. Reporter systems or reporter cells incorporated in the cellular droplets express an optically detectable marker (e.g. fluorescent protein) as a marker of biological activity (e.g. cell viability or metabolic activity). After the droplets containing cells, antibiotic, and compound of interest are merged, the identity of the molecular species in each well is determined by optically scanning each microwell to read the optical barcode. Optical measurement of the reporter system occurs simultaneously with optical scanning of the barcode. Thus, simultaneous gathering of experimental data and molecular species identification occurs with use of this combinatorial screening system. In some cases, the microfluidic device is incubated for a period of time prior to imaging and imaged at multiple time points to track changes in the measured amount of reporter over time. Additionally, for some experiments, merged droplets are eluted off of the microfluidic device for off-chip evaluation (see e.g., International Publication No. WO2016/149661, hereby incorporated by reference in its entirety for all purposes).

Synergy Between Drug Combinations

Fractional Inhibitory Concentration for Drug Synergy

As used herein, unless otherwise indicated, "minimum inhibitory concentration" (hereafter "MIC") means the minimum concentration of a particular substance or agent necessary to inhibit the growth of a particular microbial organism. MIC may relate to inhibition of microorganisms including, but not limited to *Pseudomonas aeruginosa* and/or *Staphylococcus aureus* organisms.

As used herein, unless otherwise indicated, "fractional inhibitory concentration" (hereafter "FIC") is an interaction coefficient indicating whether the combined inhibitory effect of a particular combination of agents is synergistic, additive or antagonistic. Thus, for example, FIC=A+B; wherein A=(MIC of combination X+Y)/(MIC of agent X alone), and B=(MIC of combination X+Y)/(MIC of agent Y alone). The FIC is generally considered to be synergistic when $A+B<0.5$, partially synergistic when $0.5<A+B<1.0$, additive when $A+B=1$ and antagonistic when $1<A+B<4$.

BLISS Scoring for Drug Synergy

The BLISS scoring is a criterion often used in the evaluation of the synergistic effect of drugs used in combination (Borisy et al., Proc. Natl. Acad. Sci. USA. 100 (13): 7977-7982 (2003); and Buck et al., Mol. Cancer. Ther. 5 (11) (2006)). This BLISS scoring was used to analyze the biostatic activity of a set of antibiotics when combined with a set of compounds.

The rate of cell growth in each well was calculated according to the following expression. Rate of cell growth G=((Gt−G0)/(Gc−G0), where Gc=untreated control cells, Gt=treated cells, G0=initial number of cells. The percent rate of inhibition of cell growth in each well was calculated according to the following expression. Rate of inhibition of cell growth GI (%)=100×(1−G). Assuming that the first test compound and the second test compound each acted as a single agent (i.e., the rate of cell growth when the concentration of either of the compounds was 0), the theoretical BLISS independence (BLISSin) of each well can be calculated according to the following expression: BLISSin=G (First test compound)×G(Second test compound). The BLISS score of each well can be determined from the difference between the theoretical value BLISSin and the actually measured value of the rate of cell growth. If the BLISS score is a positive number, the synergistic effect appears to be present.

As detailed below, the techniques described herein were used to screen for potentiation of a panel of 10 antibiotics with diverse mechanisms at three different combinations and biochemical target locations by a "drug repurposing" library of 4,160 drugs against the Gram-negative model pathogen *E. coli*. This effort resulted in the measurement of 100,800 combinations in 1.1+ million microwell-level measurements performed in two phases over the course of 10 days. Including controls, the total number of combinations screened was 159,744. Analysis determined compound-antibiotic synergies by evaluating a shift of a 3-point antibiotic dose response, and quantified by the Bliss synergy metric for each compound-antibiotic pair. Hits from the screen were then validated in 8-point checkerboard assays and quantified by the FIC method. The screen yielded 28 hit compound-antibiotic combinations (0.098%) from 20 distinct library compounds (0.70%) that passed both the significance and the effect size thresholds. Seventeen hit combinations were selected from eleven distinct compounds for confirmation in 8-point "checkerboards" measured in conventional 96-well microplate assays. For comparison, an additional 29 combinations were measured. Of the hit combinations, 16 out of 17 scored as synergistic (94.1%, p0.0039 binomial with 29 positive synergy out of 46 total tests, FIG. 4E).

By applying the more stringent synergy criterion of FIC<=0.5 to the hits as detailed in the below Examples, a set of six compounds were identified that synergize with at least one antibiotic against *E. coli*: Iodophenpropit, Pasireotide, Indacaterol, NSC23766, Benurestat, and IEM1754.

Iodophenpropit

Iodophenpropit was originally identified as a Histamine H3 receptor agonist. Histamine H3 receptors are expressed in the peripheral and central nervous system (CNS). H3 receptors express about 22% and 20% homology with both H1 and H2 receptors respectively. H3 receptors function as autoreceptors in presynaptic histaminergic neurons and control histamine turnover by feedback inhibition of histamine synthesis and release. H3 receptors are also capable of presynaptically inhibiting the release of a number of other neurotransmitters, e.g. dopamine, GABA, acetylcholine, noradrenaline, histamine and serotonin.

The histamine H3 receptor's involvement in the neuronal mechanism behind many cognitive H3R-disorders and the location of H3 receptors in the CNS has made H3 receptors potential therapeutic targets. More than 20 H3 receptor isoforms have been discovered. At least six of these H3 isoforms are specific to the human body. Rats have six subtypes identified and mice have three reported isoforms of H3. These subtypes all have subtle differences in their pharmacology and presumably distribution, but the exact physiological role of these isoforms has yet to be discovered.

Known agonists for H3 receptors include but are not limited to (R)-α-methylhistamine, Cipralisant, Imbutamine (also a H4 agonist), Immepip, Imetit, Immethridine, Methimepip, and Proxyfan. Known antagonists for H3 receptors include but are not limited to A-349821, ABT-239, Betahistine (also a weak H1 agonist), Burimamide (also a weak H2 antagonist), Ciproxifan, Clobenpropit (also a H4 antagonist), Conessine, Failproxifan, Impentamine, Iodophenpropit, Irdabisant, Pitolisant, Thioperamide (also H4 antagonist), VUF-5681 (4-[3-(1H-Imidazol-4-yl)propyl]piperidine). Specifically, the H3 receptor antagonist, iodophenpropit, is commonly radio labelled and used for mapping the distribution of H3 receptors in the body. As an $H_3$ agonist, iodophenpropit is commonly used for competition binding experiments in research.

Iodophenpropit was first synthesized in 1992 by Menge et al. J. Labeled Compounds and Radiopharmaceuticals. 31: 781-86, and has the following chemical structure:

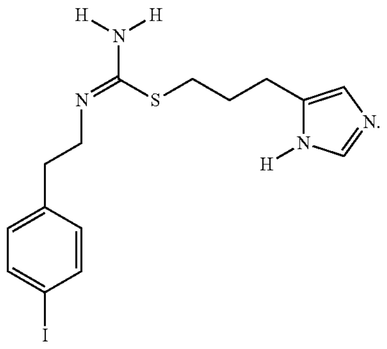 [SMILES: N/C(=N/CCc1ccc(I)cc1)SCCCc1cnc[nH]1]

Iodophenpropit, its structure, and/or useful derivatives thereof and other related structures and agents are described in detail in WO0076500, U.S. Pat. Nos. 7,915,271, 7,846,922, 8,357,700, 8,357,709, 8,466,281, 8,399,494, 8,710,076, 8,669,272, 9,029,364, 9,676,751, 7,485,647, US Publication No. 2016102073, U.S. Pat. No. 9,624,197, US Publication No. 2016304490, U.S. Pat. Nos. 9,586,950, 9,546,152, 9,556,145, US Publication No. 2016016935, U.S. Pat. Nos. 9,586,934, 9,156,819, 9,643,955, US Publication No. 2010029736, U.S. Pat. No. 9,688,630, US Publication No. 2015322040, US Publication No. 2006205774, U.S. Pat. No. 9,493,438, US Publication No. 2008194494, U.S. Pat. No. 9,550,786, US Publication No. 2008076805, U.S. Pat. Nos. 7,160,886, 7,618,987, 7,329,673, 7,652,024, US Publication No. 2014287002, US Publication No. 2016235807, U.S. Pat. Nos. 7,879,802, 8,969,514, US Publication No. 2011015181, US Publication No. 2009105318, US Publication No. 2008262046, US Publication No. 2009258903, U.S. Pat. No. 7,541,477, US Publication No. 2016002255, US Publication No. 2016332968, U.S. Pat. Nos. 9,527,875, 7,390,835, US Publication No. 2006052597, U.S. Pat. No. 7,365,079, US Publication No. 2007060566, U.S. Pat. Nos. 7,696,193, 8,207,331, 7,105,526, 9,126,976, 8,153,813, 7,576,110, 7,667,053, 7,446,103, 7,276,520, US Publication No. 2011243940, US Publication No. 2016185784, US Publication No. 2009131395, U.S. Pat. No. 7,514,068, US Publication No. 2009258902, U.S. Pat. Nos. 8,410,142, 8,618,102, 7,858,560, US Publication No. 2009005323, US Publication No. 2010081642, U.S. Pat. Nos. 7,652,049, 8,293,721, 8,865,707, US Publication No. 2007066601, US Publication No. 2008255084, US Publication No. 2007099884, US Publication No. 2006148721, US Publication No. 2006160834, US Publication No. 2004122033, US Publication No. 2008200376, US Publication No. 2009312302, U.S. Pat. Nos. 9,486,494, 9,353,101, 9,221,834, 8,796,258, 8,895,596, 7,553,964, 8,829,041, 8,030,495, US Publication No. 2010136614, US Publication No. 2009181948, US Publication No. 2010324049, US Publication No. 2009176789, U.S. Pat. No. 8,685,961, US Publication No. 2016318923, U.S. Pat. No. 7,423,067, US Publication No. 2009186834, U.S. Pat. Nos. 8,623,863, 8,497,240, US Publication No. 2009118503, U.S. Pat. Nos. 9,616,097, 9,663,534, 8,871,738, 7,521,455, 8,263,545, 8,895,498, 8,445,538, 7,687,534, 9,688,989, US Publication No. 2016068514, US Publication No. 2012028970, U.S. Pat. Nos. 7,723,342, 7,906,652, 9,511,054, US Publication No. 2002132755, US Publication No. 2009286723, US Publication No. 2016068510, U.S. Pat. Nos. 8,541,595, 7,504,412, 8,884,020, US Publication No. 2009088452, U.S. Pat. No. 8,106,086, US Publication No. 2016060226, U.S. Pat. Nos. 8,592,457, 9,242,995, 7,727,998, 7,494,979, US Publication No. 2008125403, U.S. Pat. No. 8,173,629, US Publication No. 2009305993, US Publication No. 2008280955, U.S. Pat. Nos. 7,772,188, 8,779,090, US Publication No. 2009054319, U.S. Pat. Nos. 9,480,695, 9,023,881, US Publication No. 2009156474, U.S. Pat. No. 8,394,765, US Publication No. 2006167075, US Publication No. 2007244048, U.S. Pat. Nos. 7,750,015, 9,290,517, US Publication No. 2015203487, U.S. Pat. Nos. 9,382,243, 9,556,193, 9,540,364, 9,527,839, US Publication No. 2009042862, U.S. Pat. Nos. 8,394,969, 9,650,375, 8,524,730, 6,869,966, 8,486,621, 7,728,031, US Publication No. 2016176858, US Publication No. 2010143383, U.S. Pat. Nos. 8,263,586, 9,593,155, US Publication No. 2008023345, US Publication No. 2009104210, U.S. Pat. Nos. 8,653,066, 8,124,126, 9,433,625, US Publication No. 2014134248, U.S. Pat. Nos. 9,226,901, 9,198,867, US Publication No. 2015290211, U.S. Pat. No. 9,498,444, US Publication No. 2015306040, U.S. Pat. Nos. 9,387,177, 9,402,813, 9,399,022, US Publication No. 2015328210, U.S. Pat. No. 9,393,207, US Publication No. 2015328212, U.S. Pat. No. 9,427,407, US Publication No. 2016051474, US Publication No. 2016106755, US Publication No. 2016375013, US Publication No. 2016375014, US Publication No. 2016375015, US Publication No. 2017173037, US Publication No. 2013030000, U.S. Pat. Nos. 8,728,522, 9,526,704, US Publication No. 2009005321, US Publication No. 2012040397, U.S. Pat. Nos. 7,592,347, 8,288,389, 7,414,057, 7,419,990, 8,940,898, 9,556,190, 9,108,959, 9,580,471, US Publication No. 2017129925, US Publication No. 2009118200, US Publication No. 2012065205, U.S. Pat. Nos. 8,703,770, 8,003,797, 7,732,456, US Publication No. 2011245209, U.S. Pat. No. 8,242,121, US Publication No. 2010144764, U.S. Pat. No. 8,389,720, US Publication No. 2014343023, U.S. Pat. Nos. 8,138,197, 7,410,976, 7,935,712, US Publication No. 2015342931, U.S. Pat. Nos. 7,271,266, 7,485,732, 6,972,295, US Publication No. 2010113492, US Publication No. 2005154202, U.S. Pat. Nos. 7,951,797, 8,153,626, US Publication No. 2009137529, US Publication No. 2008269279, U.S. Pat. Nos. 7,091,216, 7,795,265, 8,193,228, 7,759,352, 8,106,070, US Publication No.

2004248956, U.S. Pat. No. 7,728,141, US Publication No. 2010075953, US Publication No. 2006247227, U.S. Pat. No. 7,999,107, US Publication No. 2009253673, US Publication No. 2010063032, US Publication No. 2010029697, U.S. Pat. Nos. 7,405,221, 8,093,389, US Publication No. 2007105914, U.S. Pat. No. 7,691,860, US Publication No. 2009247499, US Publication No. 2012196901, US Publication No. 2012101106, U.S. Pat. No. 9,376,408, US Publication No. 2016185768, U.S. Pat. Nos. 9,617,246, 8,349,872, 8,138,219, US Publication No. 2016145307, U.S. Pat. No. 9,370,516, US Publication No. 2011130425, U.S. Pat. No. 7,960,544, and US Publication No. 2013273081, all of which are hereby incorporated by reference in their entirety for all purposes. The identification of Iodophenpropit as a synergistic potentiator of antibiotic activity was unexpected as this molecule, or class of molecules, was not previously known to synergize with antibiotic agents.

In embodiments, a compound of structure:

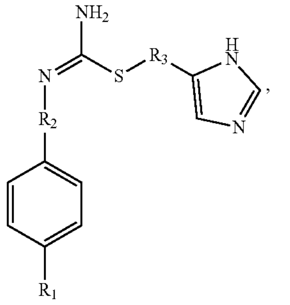

wherein $R_1$ is I, Cl, F, Br, or At, and $R_2$ and $R_3$ are each independently $C_{1-6}$ alkyl, alkenyl, and alkynyl, may function as a synergistic agent to potentiate activity of an antibiotic selected from the group consisting of vancomycin, cycloserine, fosfomycin, novobiocin, clarithromycin, tetracycline, ampicillin, trimethoprim, chloramphenicol, and norfloxacin.

Pasireotide

Pasireotide was originally identified as a somatostatin analog. Somatostatin, also known as growth hormone-inhibiting hormone (GHIH), is a peptide hormone involved in regulating the endocrine system and affecting neurotransmission and cell proliferation in various areas of the body. Somatostatin effects these systems and cellular processes through interaction with G protein-coupled somatostatin receptors and inhibition of the release of numerous secondary hormones. For example, somatostatin inhibits insulin and glucagon secretion.

Somatostatin has two active forms produced by alternative cleavage of a single preproprotein. One somatostatin form is of 14 amino acids and the other is 28 amino acids. Six different somatostatin genes exist in vertebrates, SS1, SS2, SS3, SS4, SS5, and SS6. Zebrafish have all six genes while humans only have one somatostatin gene. The six different genes along with the five different somatostatin receptors allows somatostatin to possess a large range of functions in various vertebrates.

Somatostatin is secreted at several locations in the digestive system including delta cells in the pyloric antrum, the duodenum and the pancreatic islets. Somatostatin released in the pyloric antrum travels by way of the portal venous system to the heart. Once in the heart, somatostatin enters systemic circulation and provides inhibitory effects throughout the body. In some cases, somatostatin release, particularly from delta cells, acts in a paracrine manner.

Somatostatin acts directly on the acid-producing parietal cells in the stomach via a G-protein coupled receptor to reduce acid secretion. Specifically, somatostatin activity ultimately inhibits adenylate cyclase, thus effectively antagonizing the stimulatory effect of histamine. Somatostatin can also indirectly decrease stomach acid production and slow the digestive process by preventing the release of other hormones, including gastrin, secretin and histamine.

Neurons of the ventromedial nucleus of the hypothalamus produce somatostatin. These neurons project to the median eminence, where somatostatin is released through neuron axons from neurosecretory nerve endings into the hypothalamo-hypophysial system. Somatostatin is then carried to the anterior pituitary gland and inhibits the secretion of growth hormone from somatotrope cells.

The somatostatin neurons in the periventricular nucleus mediate negative feedback effects of growth hormone. During this process, somatostatin neurons respond to high circulating concentrations of growth hormone and somatomedins by increasing the release of somatostatin. Increased release of somatostatin then reduces the rate of secretion of growth hormone. Somatostatin receptors are expressed at many different sites in the brain. In particular, there are populations of somatostatin neurons in the arcuate nucleus, the hippocampus, and the brainstem nucleus of the solitary tract.

In the anterior pituitary gland, the effects of somatostatin include but are not limited to inhibiting the release of growth hormone (GHXthus opposing the effects of growth hormone-releasing hormone (GHRH)), inhibiting the release of thyroid-stimulating hormone (TSH), inhibiting adenylyl cyclase in parietal cells, and inhibiting the release of prolactin (PRL).

In the gastrointestinal system, somatostatin is homologous with cortistatin and suppresses the release of gastrointestinal hormones, e.g. Gastrin, Cholecystokinin (CCK), Secretin, Motilin, Vasoactive intestinal peptide (VIP), Gastric inhibitory polypeptide (GIP), Enteroglucagon. Somatostatin aids in decreasing the rate of gastric emptying, and reducing smooth muscle contractions and blood flow within the intestine. Somatostatin also suppresses the release of pancreatic hormones, suppresses the exocrine secretory action of the pancreas and inhibits the release of glucagon. In the pancreas, somatostatin release is triggered by the pancreatic beta cell peptide Urocortin3 (Ucn3) to inhibit insulin release.

Somatostatin acts by binding the somatostatin receptor. There are five known somatostatin receptors, SST1 (SSTR1), SST2 (SSTR2), SST3 (SSTR3), SST4 (SSTR4), and SST5 (SSTR5). All somatostatin receptors are G protein-coupled seven transmembrane receptors. As somatostatin is an inhibitory hormone, somatostatin analogues can mimic somatostatin's inhibitory actions. Known somatostatin analogues include Octreotide, Lanreotide, and Pasireotide. Information about these analogues is detailed below.

Octreotide is an octapeptide that mimics natural somatostatin pharmacologically. Octreotide is a more potent inhibitor of growth hormone, glucagon, and insulin than the natural somatostatin hormone and has a much longer half-life of 90 minutes, compared to the 2-3 minute half-life for somatostatin. The gut absorbs octreotide poorly. Thus, octreotide is administered parenterally, subcutaneously, intramuscularly, or intravenously. Octreotide is indicated for symptomatic treatment of carcinoid syndrome and acromegaly. Octreotide is also finding increased use in polycystic diseases of the liver and kidney.

Lanreotide is a medication used in the management of acromegaly and symptoms caused by neuroendocrine tumors, most notably carcinoid syndrome. Lanreotide is a long-acting analog of somatostatin, like octreotide. Lanreotide is administered in multiple countries, including the United Kingdom, Australia, and Canada. Lanreotide was approved for sale in the United States by the Food and Drug Administration (FDA) on Aug. 30, 2007.

Pasireotide is a somatostatin analog with high binding affinity to somatostatin receptors 1, 2, 3, and 5. Pasireotide potently suppresses growth hormone (GH), insulin-like growth factor-1 (IGF-1) and adrenocorticotropic hormone (ACTH) secretion. Pasireotide is administered via intramuscular injection. Currently, pasireotide (SOM230, trade name Signifor) is an orphan drug approved in the United States and Europe for the treatment of Cushing's disease in patients who fail or are ineligible for surgical therapy. Pasireotide is a somatostatin analog with a 40-fold increased affinity to somatostatin receptor 5 compared to other somatostatin analogs.

Pasireotide was approved for Cushing's disease by the EMEA in October 2009 and by the FDA in December 2012. Additionally, pasireotide LAR was approved by the FDA for treatment of acromegaly in December 2014, and had been approved for this indication by the EMEA one month earlier. Pasireotide has the following structure:

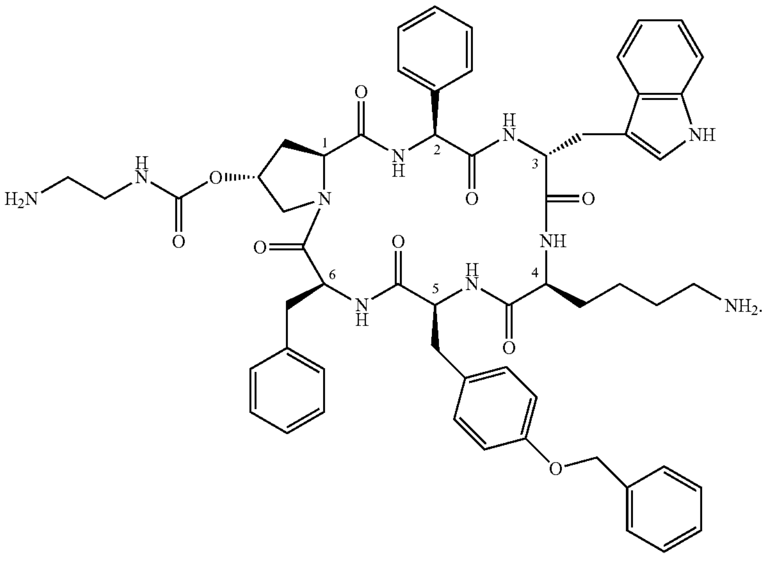 [SMILES: NCCCC[C@@H]1NC(=O)[C@@H](Cc2c[nH]c3ccccc23)NC(=O)[C@H](c2ccccc2)NC(=O)[C@@H]2C[C@@H](OC(=O)NCCN)CN2C(=O)[C@H](Cc2ccccc2)NC(=O)[C@H](Cc2ccc(OCc3ccccc3)cc2)NC1=O]

Pasireotide is also called cyclo[{4-(NH2-C2H4-NH—CO—O-)Pro}-Phg-DTrp-Lys-Tyr(4-Bzl)-Phe] and may comprise diastereoisomers and mixtures thereof, in free form, in salt or complex form or in protected form. Phg means —HN—CH(C6H5)-CO— and Bzl means benzyl.

Pasireotide in protected form corresponds to the above molecule wherein at least one of the amino groups is protected and which by deprotection leads to Pasireotide, preferably physiologically removable. Suitable amino protecting groups are e.g. as disclosed in "Protective Groups in Organic Synthesis", T. W. Greene, J. Wiley & Sons NY (1981), 219-287, the contents of which being incorporated herein by reference. Example of such an amino protecting group is acetyl.

When Pasireotide exists in complex form, it may conveniently be Pasireotide bearing a chelating group on the side chain amino group of Pro and complexed with a detectable or radiotherapeutic element. Pasireotide bearing a chelating group is referred to hereinto as conjugated Pasireotide.

Examples of chelating groups include, for example, those derived from poly-aminopolycarboxylic acids or anhydrides, e.g. those derived from non cyclic ligands e.g. diethylene triamine pentaacetic acid (DTPA), ethylene glycol-0,0'-bis(2-aminoethyl)-N,N,N',N'-tetraacetic acid (EGTA), N,N'-bis(hydroxybenzyl)ethylenediamine-N,N'-diacetic acid (HBED) and triethylenetetramine hexaacetic acid (TTHA), those derived from substituted DTPA, e.g. p-isothiocyanato-benzyl-DTPA, those derived from macrocyclic ligands, e.g. 1,4,7,10-tetra-azacyclododecane-N,N',N",N'"-tetraacetic acid (DOTA) and 1,4,8,11-tetraazacyclotetradecane-N,N',N",N'"-tetraacetic acid (TETA), or 1,4,7,10-tetraazacyclotridecane-N,N',N",N'"-tetra-acetic acid (TITRA).

The chelating group may be attached either directly or through a spacer to the side chain amino group of Pro. Suitable spacers include those known in the art, e.g. as disclosed in GB-A-2,225,579, for example the divalent residue of an amino-carboxylic acid, for example β-Ala or a divalent residue derived from 6-amino-caproic acid. Preferred chelating groups are those derived from DTPA, DOTA or TETA. Chelating groups derived from DTPA or DOTA are most preferred.

Somatostatin analogues of particular interest have been described in, e.g., International Publication No. WO 1997/001579 and WO 2002/010192. For example, where -(D/L)Trp-Lys-$X_1$—$X_2$— wherein $X_1$ is a radical of formula (a) or (b)

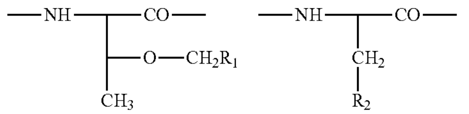

$R_2$ is —$Z_1$—$CH_2$—$R_1$, —$CH_2$—CO—O—$CH_2$—$R_1$,

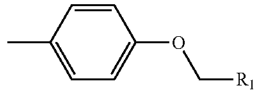 or 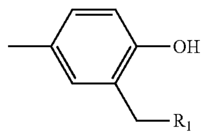

wherein R1 is a phenyl optionally substituted by halogen, methyl, ethyl methoxy or ethoxy. Z1 is O or S, and X2 is an α-amino acid having an aromatic residue on the Cα side chain, or an amino acid unit selected from Dab, Dpr, Dpm, His, (Bzl)HyPro, thienyl-Ala, cyclohexyl-Ala and t-butyl-Ala, the residue Lys of said sequence corresponding to the residue Lys9 of the native somatostatin-14.

Additional useful Pasireotide derivatives may be based on a compound of formula:

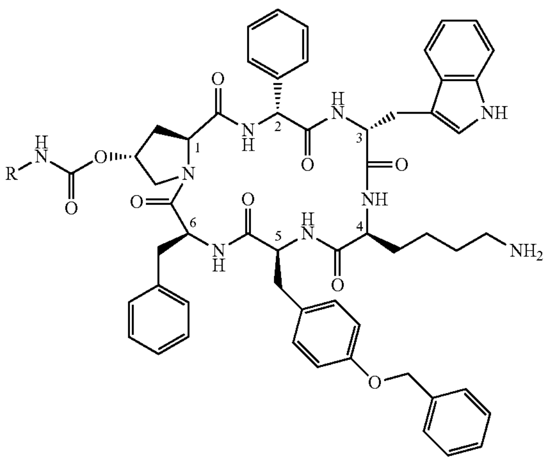

wherein R is NR1R2-C2-6alkylene or guanidine-C2-6alkylene, and each of R1 and R2 independently is H or C1-4alkyl, in free form, in salt form or complex form, or in protected form. Preferably R is NR1R2-C2-6alkylene. A preferred compound of the above formula is the compound wherein R is 2-amino-ethyl, also called cyclo[{4-(NH2-C2H4-NH—CO—O-)Pro}-DPhg-DTrp-Lys-Tyr(4-Bzl)-Phe], and may be present in free form, in salt or complex form or in protected form. Phg and Bzl are as defined above.

Pasireotide, its structure, and/or useful derivatives thereof and other related structures and agents are described in detail in U.S. Pat. No. 7,473,761, US Publication No. 2006234922, U.S. Pat. Nos. 7,615,609, 7,939,625, US Publication No. 2010069296, US Publication No. 2010273719, U.S. Pat. Nos. 9,035,021, 8,822,637, 9,555,118, 9,585,959, 9,579,364, US Publication No. 2014113879, US Publication No. 2014114051, US Publication No. 2014127271, US Publication No. 2013303450, U.S. Pat. Nos. 9,149,510, 9,351,923, 8,835,123, US Publication No. 2015037359, U.S. Pat. Nos. 9,333,234, 9,408,887, US Publication No. 2015218223, U.S. Pat. No. 9,605,070, US Publication No. 2015259420, US Publication No. 2016264732, US Publication No. 2016271227, US Publication No. 2016108123 and US Publication No. 2016346408, and International Publications WO 1997/001579 and WO 2002/010192, all of which are hereby incorporated by reference in their entirety for all purposes. The identification of Pasireotide as a synergistic potentiator of antibiotic activity was unexpected as this molecule, or class of molecules, was not previously known to synergize with antibiotic agents.

Indacaterol

Indacaterol was originally identified as a beta-adrenoceptor agonist. The adrenergic receptors (also known as adrenoceptors) are a class of G protein-coupled receptors that are targets of the catecholamines, such as norepinephrine (noradrenaline) and epinephrine (adrenaline). Adrenergic receptors have several subtypes but the two primary groups are α and β receptors. There are two subclasses of α-receptor, α1 and α2 which are further subdivided into α1A, α1B, α1D, α2A, α2B and α2C. The α2C receptor has been re-classed from α1C, due to its greater homology with the α2 class, giving rise to the somewhat confusing nomenclature. The β receptors are divided into β1, β2 and β3. The receptors are classed physiologically. However, pharmacological selectivity for receptor subtypes exists and is important in the clinical application of adrenergic agonists and antagonists.

From an overall perspective, α1 receptors activate phospholipase C (via Gq), increasing the activity of protein kinase C (PKC). Adrenergic α2 receptors inhibit adenylate cyclase (via Gi), decreasing the activity of protein kinase A (PKA). Adrenergic β receptors activate adenylate cyclase (via Gs), thus increasing the activity of PKA. Adrenergic β2 receptors also couple to Gi. Coupling to Gi causes an increase in the intracellular concentration of the second messenger cAMP. cAMP increase can result in increasing activity of PKA as PKA is a downstream effectors of cAMP. Ultimately, PKA activity mediates intracellular events following hormone binding.

Many cells possess adrenergic receptors, and the binding of a catecholamine to the receptors stimulates the sympathetic nervous system (fight-or-flight response). Stimulation of the sympathetic nervous system results in responses such as pupil dilation, heart rate increases, energy mobilization, and blood flow diversion from non-essential organs to skeletal muscle.

Epinephrine reacts with both α- and β-adrenoreceptors, causing vasoconstriction and vasodilation, respectively. Adrenergic α receptors are less sensitive to epinephrine. However, when α receptors are activated at pharmacologic doses, they override the vasodilation mediated by β-adrenoreceptors as there are more peripheral α1 receptors than β-adrenoreceptors. Thus, high levels of circulating epinephrine cause vasoconstriction. At lower levels of circulating epinephrine, β-adrenoreceptor stimulation dominates. β-adrenoreceptor domination occurs as epinephrine has a higher affinity for the β2 adrenoreceptor than the α1 adrenoreceptor, which ultimately results in vasodilation followed by decrease of peripheral vascular resistance.

An adrenergic agent is a drug, or other substance, which has effects similar to, or the same as, epinephrine. Thus, adrenergic agents are a kind of sympathomimetic agent. Alternatively, an adrenergic agent may refer to something susceptible to epinephrine, or similar substances, such as a biological receptor (specifically, the adrenergic receptors).

Adrenergic agonists act on adrenergic receptors and may stimulate responses from the adrenergic receptors. All adrenergic receptors are G-protein coupled and activate signal transduction pathways. The G-protein receptor can affect the function of adenylate cyclase or phospholipase C. An agonist of the receptor will upregulate the effects on the downstream pathway (an agonist will not necessarily upregulate the pathway itself). The five main categories of adrenergic receptors (α1, α2, β1, β2, and β3) and their subtypes elicit varying specificity to different adrenergic agonists. In the body, epinephrine and norepinephrine are endogenous and have broad-spectrum functionality. Thus, selective adrenergic agonists are useful pharmacologically for medical use.

Numerous drugs are available which can affect adrenergic receptors. Each drug has its own receptor specificity giving it a unique pharmacological effect. Some drugs affect the uptake and storage mechanisms of adrenergic catecholamines, prolonging their action. Drugs can have mixed, indirect, or direct action on adrenergic receptors. Ephedrine and pseudoephedrine have mixed action on one or more adrenergic receptors.

Indirectly acting adrenergic agonists affect the uptake and storage mechanisms involved in adrenergic signaling. Two primary uptake mechanisms exist terminate the action of adrenergic catecholamines (uptake 1 and uptake 2). Uptake 1 occurs at the presynaptic nerve terminal and removes the neurotransmitter from the synapse. Uptake 2 occurs at postsynaptic and peripheral cells and prevent the neurotransmitter from diffusing laterally. Indirectly acting adrenergic agonists can also effect enzymatic degradation of the catecholamines by two main enzymes (monoamine oxidase and catechol-o-methyl transferase). Respectively, these enzymes oxidize monoamines (including catecholamines) and methylate the hydroxyl groups of the phenyl moiety of catecholamines. Inhibitors of these enzymes act as indirect agonists of adrenergic receptors, as they prolong the action of catecholamines at the receptors. In general, a primary or secondary aliphatic amine separated by 2 carbons from a substituted benzene ring is minimally required for high agonist activity. Drugs that act indirectly on adrenergic receptors include but are not limited to amphetamines, cocaine, methylenedioxymethamphetamine (MDMA), tyramine, nicotine, caffeine, and methylphenidate. These indirectly adrenergic receptor-influencing compounds are agents that increase neurotransmission in endogenous chemicals, in this case epinephrine and norepinephrine.

The following drugs are examples of compounds that act directly on one or more adrenergic receptors. These drugs have been split into two types of receptor selectivity (non-selective and selective). Non-selective drugs act on one or more receptors and include but are not limited to adrenaline (acts on nearly all adrenergic receptors), aoradrenaline (acts on α1, α2, β1), isoprenaline (acts on β1, β2, β3), and dopamine (acts on α1, α2, β1, D1, D2). Selective drugs act on a single receptor only and are further classified into a selective and β selective. Selective al drugs include but are not limited to phenylephrine, methoxamine, midodrine, and oxymetazoline. Selective α2 drugs include but are not limited to α-methyl dopa, clonidine, and brimonidine. Selective β1 drugs include but are not limited to dobutamine. Selective β2 drugs include but are not limited to salbutamol/albuterol, terbutaline, salmeterol, formoterol, and pirbuterol.

An adrenoceptor agonist of clinical interest is indacaterol. Indacaterol is an ultra-long-acting beta-adrenoceptor agonist. Stimulation of β2 adrenergic receptors of bronchial smooth muscle cells induces relaxation by activation of the Gs-adenylyl cyclase-cyclic adenosine monophosphate (cAMP)-protein kinase A (PKA) pathway.

Indacaterol (INN) is a long-acting beta-adrenoceptor agonist developed by Novartis. It was approved by the European Medicines Agency (EMA) under the trade name Onbrez Breezhaler® on Nov. 30, 2009, and by the United States Food and Drug Administration (FDA), under the trade name Arcapta Neohaler®, on Jul. 1, 2011. It needs to be taken only once a day, unlike the related drugs formoterol and salmeterol. It is proscribed only for the treatment of chronic obstructive pulmonary disease (COPD) (long-term data in patients with asthma are thus far lacking). It is delivered as an aerosol formulation through a dry powder inhaler.

A Phase III trial published in March 2010 examined the efficacy and safety of indacaterol in COPD patients. This study, conducted in the U.S., New Zealand, and Belgium, compared indacaterol dry-powder inhaler to placebo in 416 COPD patients, mostly moderate to severe (mean FEV1 of 1.5 L). Indacaterol produced statistically improved FEV1 (both trough and AUC) and decreased use of rescue medication compared to placebo, but with safety and tolerability similar to those of placebo.

A year-long, placebo-controlled trial published in July 2010 suggests indacaterol may be significantly more effective than twice-daily formoterol in improving FEV1. There were some reductions in the need for rescue medication, but these were not significantly different; nor was there any difference in the rate of exacerbation between the 2 active treatments.

A study published in October, 2011 in the European Respiratory Journal compared indacaterol with tiotropium over the study period of 12 weeks. The study found no statistical difference between the effects of the two drugs on FEV1. Indacaterol yielded greater improvements in transition dyspnoea index (TDI) total score and St. George's Respiratory Questionnaire (SGRQ) total score.

Indacaterol has the following generic structure

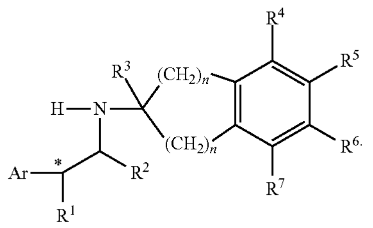

in free or salt or solvate form, where Ar is a group of formula

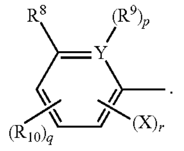

wherein,

R1 is hydrogen, hydroxy, or alkoxy,

R1 and R3 are each independently hydrogen or alkyl,

R4, R5, R6 and R7 are each independently hydrogen, halogen, cyano, hydroxy, alkoxy, aryl, alkyl, alkyl substituted by one or more halogen atoms or one or more hydroxy or alkoxy groups, alkyl interrupted by one or more hetero atoms, alkenyl, trialkylsilyl, carboxy, alkoxycarbonyl, or —CONR11R12 where R11 and R12 are each independently hydrogen or alkyl, or R4 and R5, R5 and R6, or R6 and R7 together with the carbon atoms to which they are attached denote a carbocyclic or heterocyclic ring, R8 is halogen, —OR13, —CH2OR13 or —NHR13 where R13 is hydrogen, alkyl, alkyl interrupted by one or more heteroatoms, —COR14, where R14 is hydrogen, —N(R15)R16, alkyl or alkyl interrupted by one or more hetero atoms, or aryl and R15 and R16 are each independently hydrogen, alkyl or alkyl interrupted by one or more hetero atoms, or R13 is —C(═NH)R17, —SOR17 or —SO2R17 where R17 is alkyl or alkyl interrupted by one or more hetero atoms, and R9 is hydrogen, or R8 is —NHR18 where —NHR18 and R9, together with the carbon atoms to which they are attached, denote a 5- or 6-membered heterocycle, R10 is —OR19 or —NHR19 where R19 is hydrogen, alkyl, alkyl interrupted by one or more hetero atoms, or —COR20, where R20 is —N(R21)R22, alkyl or alkyl interrupted by one or more hetero atoms, or aryl, and R21 and R22 are each independently hydrogen, alkyl or alkyl interrupted by one or more hetero atoms, X is halogen or halomethyl or alkyl, Y is carbon or nitrogen, n is 1 or 2, p is zero when Y is nitrogen or 1 when Y is carbon, q and r are each zero or 1, the sum of q+r is 1 or 2; and the carbon atom marked with an asterisk* has the R or S configuration, or a mixture thereof, when R1 is hydroxy or alkoxy.

In embodiments, Indacaterol has the following structure:

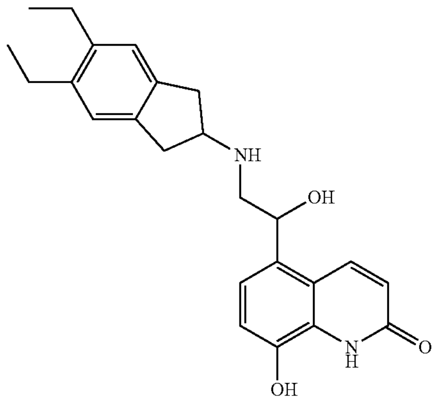 [SMILES: CCc1cc2c(cc1CC)CC(NCC(O)c1ccc(O)c3[nH]c(=O)ccc13)C2]

Indacaterol, its structure, and/or useful derivatives thereof and other related structures and agents are described in detail in U.S. Pat. Nos. 6,878,721, 8,067,437, 8,658,673, and 8,796,307, and in U.S. Pat. Nos. 6,878,721, 6,670,379, 6,921,757, 6,800,643, 7,109,202, 7,034,042, 7,259,173, 7,008,951, 7,273,875, 7,622,483, 7,687,637, 7,288,537, 7,524,880, US Publication No. 2006106075, U.S. Pat. Nos. 7,468,370, 7,622,484, US Publication No. 2006167025, U.S. Pat. Nos. 7,417,056, 7,683,048, 8,017,608, US Publication No. 2006229305, U.S. Pat. No. 8,426,475, US Publication No. 2006247292, U.S. Pat. Nos. 7,534,890, 7,605, 267, US Publication No. 2007015750, US Publication No. 2007015761, US Publication No. 2007032487, US Publication No. 2007041911, US Publication No. 2007043013, US Publication No. 2007060563, U.S. Pat. No. 7,947,730, US Publication No. 2007129358, US Publication No. 2007129359, U.S. Pat. No. 7,745,462, US Publication No. 2007185172, US Publication No. 2007213355, US Publication No. 2007225335, US Publication No. 2007249586, U.S. Pat. Nos. 7,691,841, 7,880,042, 7,893,089, 7,939,547, 7,943,651, 7,951,823, US Publication No. 2008039444, U.S. Pat. Nos. 7,999,108, 8,003,663, 8,182,792, US Publication No. 2008096943, US Publication No. 2008146606, US Publication No. 2008167332, U.S. Pat. Nos. 7,482,347, 7,666,878, 8,076,489, US Publication No. 2008176891, US Publication No. 2008176901, US Publication No. 2008188666, US Publication No. 2008200519, US Publication No. 2008207577, US Publication No. 2008207596, US Publication No. 2008207638, US Publication No. 2008207650, US Publication No. 2008207718, US Publication No. 2008207725, US Publication No. 2008227797, US Publication No. 2008227820, US Publication No. 2008242683, U.S. Pat. Nos. 7,579,335, 7,667,039, 7,678, 826, 7,728,030, 7,834,185, 7,985,740, 8,030,340, 8,114,877, 8,163,754, 8,183,251, US Publication No. 2008249077, US Publication No. 2008260726, US Publication No. 2008267886, US Publication No. 2008269335, US Publication No. 2008274189, US Publication No. 2008275027, US Publication No. 2008279948, US Publication No. 2008286363, U.S. Pat. No. 8,431,703, US Publication No. 2008292561, US Publication No. 2008306064, US Publication No. 2008306067, US Publication No. 2008306109, US Publication No. 2008312212, US Publication No. 2008312229, US Publication No. 2008312322, US Publication No. 2008317862, U.S. Pat. Nos. 7,803,804, 7,902,375, 7,910,708, 7,989,629, 8,202,891, US Publication No. 2009007907, U.S. Pat. No. 8,474,453, US Publication No. 2009012125, US Publication No. 2009018109, US Publication No. 2009020114, US Publication No. 2009023733, US Publication No. 2009023769, US Publication No. 2009041675, US Publication No. 2009042942, US Publication No. 2009054413, US Publication No. 2009054653, U.S. Pat. Nos. 7,723,356, 7,754,746, 8,012,979, US Publication No. 2009093451, US Publication No. 2009093633, US Publication No. 2009099214, US Publication No. 2009105225, US Publication No. 2009105268, US Publication No. 2009105476, US Publication No. 2009123391, US Publication No. 2009124585, US Publication No. 2009124588, US Publication No. 2009124596, US Publication No. 2009124607, US Publication No. 2009130026, U.S. Pat. No. 8,530,463, US Publication No. 2009131457, US Publication No. 2009137506, U.S. Pat. Nos. 7,960,385, 7,998,984, 8,093,281, 8,178,573, 8,394,958, US Publication No. 2009151722, US Publication No. 2009156625, U.S. Pat. Nos. 8,263,585, 8,940,771, US Publication No. 2009163534, US Publication No. 2009170871, US Publication No. 2009170898, US Publication No. 2009176815, US Publication No. 2009181934, US Publication No. 2009181935, U.S. Pat. No. 8,314,112, US Publication No. 2009181950, US Publication No. 2009182033, US Publication No. 2009186923, US Publication No. 2009197914, U.S. Pat. No. 8,420,657, US Publication No. 2009203777, US Publication No. 2009209502, U.S. Pat. No. 8,268,990, US Publication No. 2009209552, U.S. Pat. Nos. 7,858,640, 7,989,458, 8,017,617, 8,114,881, 8,168,673, US Publication No. 2009215732, U.S. Pat. No. 8,343,966, US Publication No. 2009221604, US Publication No. 2009229608, US Publication No. 2009233907, US Publication No. 2009233938, US Publication No. 2009233965, US Publication No. 2009238770, U.S. Pat. No. 8,268,834, US Publication No. 2009240045, US Publication No. 2009258882, US Publication No. 2009264388, U.S. Pat. No. 8,822,468, US Publication No. 2009264459, US Publication No. 2009264461, US Publication No. 2009281127, U.S. Pat. Nos. 7,884,114, 7,888,383, 7,998,990, 8,153,669, US Publication No. 2009286779, U.S. Pat. Nos. 8,383,625, 8,772,495, US Publication No. 2009298824, US Publication No. 2009298875, US Publication No. 2009318410, US Publication No. 2009318494, US Publication No. 2009325952, US Publication No. 2010009934, U.S. Pat. No. 8,629,168, US Publication No. 2010010034, US Publication No. 2010010039, US Publication No. 2010016331, US Publication No. 2010016338, US Publication No. 2010022613, US Publication No. 2011008252, U.S. Pat. Nos. 7,754,758, 7,902,181, 8,097,626, 8,163,724, 8,188,100, 8,198,450, US Publication No. 2010035917, US Publication No. 2010035926, U.S. Pat. No. 8,273,774, US Publication No. 2010041662, US Publication No. 2010048633, US Publication No. 2010056565, U.S. Pat. No. 8,293,915, US Publication No. 2010063080, US Publication No. 2010068288, US Publication No. 2010069407, U.S. Pat. No. 8,697,730, US Publication No. 2010075965, US Publication No. 2010080786, US Publication No. 2010087432, U.S. Pat. Nos. 7,750,027, 7,820,694, 7,989,497, 7,994,170, 8,168,654, 8,207,193, 8,211,930, US Publication No. 2010093751, U.S. Pat. Nos. 8,318,935, 8,273,882, US Publication No. 2010113510, US Publication No. 2010113540, U.S. Pat. No. 8,633,211, US Publication No. 2010120730, U.S. Pat. No. 8,258,122, US Publication No. 2010120733, U.S. Pat. No. 8,304,436, US Publication No. 2010120895, US Publication No. 2010135956, US Publication No. 2010137268, US Publication No. 2010137300, US Publication No. 2010137405, US Publication No. 2010137406, US Publication No. 2010143312, US Publication No. 2010144654, US Publication No. 2010144786, US Publication No. 2010152205, US Publication No. 2010152224, US Publication No. 2010152278, US Publication No. 2010160271, US Publication No. 2010160272, US Publication No. 2010160347, U.S. Pat. Nos. 7,799,810, 7,947,727, 7,994,211, 8,012,980, 8,039,472, 8,071,584, 8,129,541, 8,173,812, 8,183,281, 8,227,462, 8,236,959, US Publication No. 2010179139, US Publication No. 2010184770, US Publication No. 2010190766, US Publication No. 2010197644, US Publication No. 2010197763, US Publication No. 2010204203, U.S. Pat. Nos. 8,470,848, 8,440,834, 8,455,645, 8,367,662, US Publication No. 2010216799, US Publication No. 2010222349, U.S. Pat. Nos. 8,053,574, 8,084,463, 8,143,253, 8,193,164, 8,232,296, US Publication No. 2010234355, US Publication No. 2010239551, US Publication No. 2010240669, US Publication No. 2010240883, U.S. Pat. No. 8,430,097, US Publication No. 2010247658, U.S. Pat. Nos. 8,414,956, 8,518,444, 8,338,587, US Publication No. 2010256104, US Publication No. 2010256105, US Publication No. 2010261690, U.S. Pat. No. 8,616,201, US Publication No. 2010266696, US Publication No. 2010273744, U.S. Pat. Nos. 8,575,162, 8,580,797, 8,466,284, 8,258,141, 7,919,512, 8,071,565, 8,104,469, 8,193,239, 8,217,035, 8,247,377, US Publication No. 2010298286, US Publication No. 2010298311, U.S. Pat. No. 8,431,578, US Publication No. 2010298343, US Publication No. 2010305113, US Publication No. 2010311729, U.S. Pat. Nos. 8,357,707, 8,293,753, US Publication No. 2011003858, US Publication No. 2011009429, U.S. Pat. No. 8,592,453, US Publication No. 2011020423, U.S. Pat. Nos. 8,445,501, 8,378,121, 8,044,075, 8,701,661, 8,815,917, 8,389,526, 8,450,341, US Publication No. 2011046191, U.S. Pat. Nos. 8,944,055, 8,772,288, US Publication No. 2011056494, US Publication No. 2011059937, U.S. Pat. Nos. 8,664,228, 9,079,897, US Publication No. 2011060026, U.S. Pat. Nos. 8,637,662, 8,410,264, 8,394,836, 8,436,024, 8,580,260, US Publication No. 2011092546, US Publication No. 2011094510, U.S. Pat. Nos. 8,067,437, 8,143,290, 8,236,786, US Publication No. 2011105449, U.S. Pat. No. 8,404,684, US Publication No. 2011105563, U.S. Pat. No. 8,765,743, US Publication No. 2011118309, U.S. Pat. Nos. 8,877,930, 8,563,536, US Publication No. 2011124613, US Publication No. 2011124624, US Publication No. 2011124683, US Publication No. 2011124693, U.S. Pat. Nos. 9,132,084, 8,536,158, US Publication No. 2011160167, US Publication No. 2011160249, U.S. Pat. Nos. 8,163,743, 8,329,729, US Publication No. 2011177055, U.S. Pat. Nos. 8,658,635, 8,524,697, 8,536,169, 8,648,191, US Publication No. 2011190309, US Publication No. 2011192397, U.S. Pat. No. 8,481,517, US Publication No. 2011201581, US Publication No. 2011201608, U.S. Pat. No. 8,609,848, US Publication No. 2011224229, US Publication No. 2011237572, U.S. Pat. Nos. 8,039,489, 8,236,808, 8,247,436, 8,431,592, 8,288,588, 8,329,754, 8,338,469, 8,039,601, US Publication No. 2011262368, U.S. Pat. No. 8,604,049, US Publication No. 2011281909, US Publication No. 2011281917, US Publication No. 2011288154, US Publication No. 2011294766, U.S. Pat. Nos. 8,492,548, 8,563,577, 8,629,160, 8,173,676, 8,242,138, US Publication No. 2011319446, U.S. Pat. No. 8,318,750, US Publication No. 2012004247, U.S. Pat. No. 8,426,581, US Publication No. 2012004281, US Publication No. 2012004282, U.S. Pat. No. 8,354,539, US Publication No. 2012010272, US Publication No. 2012016010, US Publication No. 2012016011, US Publication No. 2012022142, US Publication No. 2012022143, U.S. Pat. Nos. 8,969,568, 8,969,350, US Publication No. 2012029054, U.S. Pat. No. 9,358,224, US Publication No. 2012035237, US Publication No. 2012035247, U.S. Pat. No. 8,198,304, US Publication No. 2013172349, U.S. Pat. No. 9,062,045, US Publication No. 2013324526, US Publication No. 2014051698, U.S. Pat. No. 9,050,339, US Publication No. 2014121208, U.S. Pat. No. 9,409,895, US Publication No. 2014171404, U.S. Pat. No. 9,139,586, US Publication No. 2014187550, U.S. Pat. Nos. 9,115,087, 9,034,879, 9,132,127, US Publication No. 2011098311, US Publication No. 2011132355, U.S. Pat. No. 9,011,923, US Publication No. 2012041041, US Publication No. 2012046286, U.S. Pat. No. 9,072,734, US Publication No. 2012058984, US Publication No. 2012065173, US Publication No. 2012077801, US Publication No. 2012083531, US Publication No. 2012108555, US Publication No. 2012156259, U.S. Pat. No. 9,045,472, US Publication No. 2012207751, U.S. Pat. No. 8,987,257, US Publication No. 2012220775, US Publication No. 2012225904, U.S. Pat. No. 8,993,560, US Publication No. 2012232101, US Publication No. 2012234316, US Publication No. 2012245171, US Publication No. 2012269872, US Publication No. 2012277275, US Publication No. 2012277279, U.S. Pat. Nos. 9,018,175, 9,499,487, US Publication No. 2012316138, US Publication No. 2012316142, US Publication No. 2012322728, US Publication No. 2012329780, U.S. Pat. No. 9,499,535, US Publication No. 2013005695, US Publication No. 2013005716, U.S. Pat. Nos. 8,674,099, 8,686,184, 8,697,687, 8,722,925, 8,741,909, 8,754,085, 8,772,314, 8,791,256, 8,796,307, 8,809,340, 8,815,837, 8,815,901, 8,816,085, 8,846,687, 8,901,134, 8,927,557, 8,937,069, 8,937,073, 8,415,333, 8,436,017, 8,449,890, 8,450,314, 8,450,362, 8,471,040, 8,476,268, 8,476,269, 8,481,044, 8,492,407, 8,497,368, 8,501,964, 8,507,676, 8,513,244, 8,524,751, 8,536,175, 8,557,797, 8,563,512, 8,563,549, 8,586,536, 8,658,673, 8,163,905, 8,283,362, 8,299,246, 8,338,424, 8,362,064, 8,372,845, 8,372,855, 8,372,875, 8,394,830, 8,399,436, US Publication No. 2010316724, US Publication No. 2010326432, US Publication No. 2010263665, US Publication No. 2010275909, U.S. Pat. Nos. 9,016,221, 8,997,799, US Publication No. 2010239707, US Publication No. 2010258118, U.S. Pat. Nos. 9,074,212, 9,067,031, US Publication No. 2010218760, U.S. Pat. No. 9,358,242, US Publication No. 2010083964, US Publication No. 2010055045, US Publication No. 2010063016, US Publication No. 2009314291, US Publication No. 2010015238, US Publication No. 2010018524, US Publication No. 2009298802, US Publication No. 2009250058, US Publication No. 2009215734, US Publication No. 2009170775, US Publication No. 2009118249, US Publication No. 2009025722, US Publication No. 2008251411, US Publication No. 2008253970, US Publication No. 2008214440, U.S. Pat. No. 9,138,407, US Publication No. 2008138397, US Publication No. 2007293429, U.S. Pat. No. 8,985,100, US Publication No. 2008004247, US Publication No. 2007183982, U.S. Pat. Nos. 8,776,788, 8,800,554, 8,636,000, 8,653,052, 8,656,910, 8,656,911, 8,578,933, 8,590,529, 8,512,753, 8,534,281, 8,479,725, 8,479,730, 8,420,787, 8,251,056, 8,168,606, 8,158,152, 8,119,156, 8,119,612, 8,101,182, 8,087,286, 8,061,350, 8,071,127, 8,048,910, 8,025,051, 7,939,508, 7,943,592, 7,950,388, 7,905,852, 7,823,584, 7,718,632, 7,611,072, US Publication No. 2014357641, U.S. Pat. No. 9,115,129, US Publication No. 2014357724, US Publication No. 2014378463, U.S. Pat. Nos. 9,056,867, 9,040,559, 9,452,139, US Publication No. 2014308214, U.S. Pat. No. 9,169,251, US Publication No. 2014147393, U.S. Pat. Nos. 8,992,916, 9,050,267, US Publication No. 2013323237, US Publication No. 2013330281, US Publication No. 2013274232, US Publication No. 2013237564, U.S. Pat. No. 9,174,012, US Publication No. 2013004542, U.S. Pat. No. 9,345,848, US Publication No. 2012269799, US Publication No. 2012272951, US Publication No. 2012283334, U.S. Pat. No. 9,211,383, US Publication No. 2012304991, U.S. Pat. No. 9,381,189, US Publication No. 2012208882, U.S. Pat. No. 9,125,999, US Publication No. 2012156194, US Publication No. 2012171126, U.S. Pat. No. 9,597,531, US Publication No. 2012093947, US Publication No. 2012095104, US Publication No. 2012097159, US Publication No. 2012097160, US Publication No. 2012101077, US Publication No. 2012107414, U.S. Pat. No. 9,095,670, US Publication No. 2012129820, U.S. Pat. Nos. 8,985,102, 9,604,018, US Publication No. 2012046258, US Publication No. 2012046284, U.S. Pat. No. 9,155,851, US Publication No. 2012055469, US Publication No. 2012058198, US Publication No. 2012064126, US Publication No. 2012065174, US Publication No. 2012070417, U.S. Pat. No. 9,327,088, US Publication No. 2012022032, US Publication No. 2012027756, US Publication No. 2011206765, US Publication No. 2011253138, US Publication No. 2011259323, U.S. Pat. No. 9,289,565, US Publication No. 2011262543, US Publication No. 2011120464, US Publication No. 2011132357, US Publication No. 2011135737, US Publication No. 2011144209, US Publication No. 2011146677, U.S. Pat. No. 9,637,840, US Publication No. 2011150782, US Publication No. 2011150783, US Publication No. 2011150784, U.S. Pat. No. 9,545,401, US Publication No. 2011182830, US Publication No. 2011189183, U.S. Pat. No. 9,028,864, US Publication No. 2011104259, US Publication No. 2011020412, US Publication No. 2011020454, U.S. Pat. Nos. 9,463,161, 8,961,965, 8,974,831, 8,840,930, 8,877,251, 8,808,713, 8,815,258, 8,815,325, 8,820,318, 8,771,744, 8,703,956, 8,568,719, 8,518,918, 8,387,614, 8,404,750, 8,414,915, 8,324,266, 8,372,838, 8,268,347, US Publication No. 2015065490, US Publication No. 2015072961, US Publication No. 2015005311, U.S. Pat. No. 9,174,985, US Publication No. 2015094312, US Publication No. 2015141387, U.S. Pat. Nos. 9,522,149, 9,475,772, US Publication No. 2015231142, U.S. Pat. Nos. 9,474,762, 9,650,438, US Publication No. 2015297604, U.S. Pat. No. 9,630,945, US Publication No. 2015374623, U.S. Pat. Nos. 9,604,981, 9,073,932, 9,643,983, US Publication No. 2016168119, US Publication No. 2016184318, US Publication No. 2016101097, US Publication No. 2017027908, US Publication No. 2017029414, US Publication No. 2017037030, US Publication No. 2017037032, US Publication No. 2017042889, US Publication No. 2017007547, US Publication No. 2017007614, US Publication No. 2017015628, US Publication No. 2016303132, U.S. Pat. No. 9,682,935, US Publication No. 2016354388 and US Publication No. 2017143705, all of which are hereby incorporated by reference in their entirety for all purposes.

The identification of Indacaterol as a synergistic potentiator of antibiotic activity was unexpected as this molecule, or class of molecules, was not previously known to synergize with antibiotic agents.

In embodiments, a compound of structure:

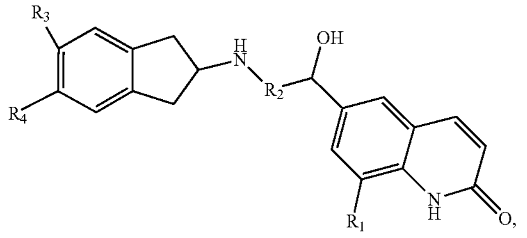

wherein $R_1$ is hydroxyl, hydrogen, amine, $C_{1-3}$ alkyl, alkenyl, and alkynyl and R2, R3, and R4 are each independently C1.4 alkyl, alkenyl, and alkynyl may function as a synergistic agent to potentiate activity of an antibiotic selected from the group consisting of vancomycin, cycloserine, fosfomycin, novobiocin, clarithromycin, tetracycline, ampicillin, trimethoprim, chloramphenicol, and norfloxacin.

NSC23766

NSC23766 was originally identified as an inhibitor of Rac1. Rac1, also known as Ras-related C3 botulinum toxin substrate 1, is a protein found in humans and encoded by the RAC1 gene. This gene can produce a variety of alternatively spliced versions of the Rac1 protein, which carry out different functions. Rac1 is a small (~21 kDa) signaling G protein (more specifically a GTPase). Rac1 is a member of the Rac subfamily of the Rho family of GTPases. Members of this superfamily regulate a diverse array of cellular events including the control of GLUT4 translocation to glucose uptake, cell growth, cytoskeletal reorganization, antimicrobial cytotoxicity, and activation of protein kinases. Rac1 is a pleiotropic regulator of many cellular processes, including the cell cycle, cell-cell adhesion, actin network motility, and epithelial differentiation.

Rac1 role in glucose transport: Rac1 is expressed in significant amounts in insulin sensitive tissues, such as adipose tissue and skeletal muscle. In these tissues Rac1 regulates the translocation of glucose transporting GLUT4 vesicles from intracellular compartments to the plasma membrane. This function allows for blood glucose to enter the cell to lower blood glucose in response to insulin. In conditions of obesity and type 2 diabetes, Rac1 signaling in skeletal muscle is dysfunctional, suggesting that Rac1 contributes to the progression of the disease. Rac1 protein is also necessary for glucose uptake in skeletal muscle activated by exercise and muscle stretching.

Rac1 role in cellular motility: Along with other subfamily of Rac and Rho proteins, Rac1 exerts an important regulatory role specifically in cell motility and cell growth. Rac1 has ubiquitous tissue expression, and drives cell motility by formation of lamellipodia. Deregulation of cell motility allows for cancer cells to grow, invade, and metastasize in local and distant tissues. Additionally, activating mutations in Rac1 have been recently discovered in large-scale genomic studies involving melanoma and non-small cell lung cancer. As a result, Rac1 is considered a therapeutic target for these diseases.

In in vivo experiments, overexpression of a constitutively active Rac1 V12 in mice resulted in tumor formation that was phenotypically indistinguishable from human Kaposi's sarcoma. Activating or gain-of-function mutations of Rac1 have been shown to play active roles in promoting mesenchymal-type of cell movement assisted by neural precursor cell expressed developmentally down-regulated protein 9 (NEDD9) and dedicator of cytokinesis 3 (DOCK3) protein complex. Such abnormal cell motility may result in epithelial mesenchymal transition (EMT). EMT is a driving mechanism for tumor metastasis as well as drug-resistant tumor relapse. A few recent studies have also exploited targeted therapy to suppress tumor growth by pharmacological inhibition of Rac1 activity in metastatic melanoma and liver cancer as well as in human breast cancer. For example, Rac1-dependent pathway inhibition resulted in the reversal of tumor cell phenotypes, suggesting Rac1 as a predictive marker and therapeutic target for trastuzumab-resistant breast cancer. However, given Rac1's role in glucose transport, drugs that inhibits Rac1 could potentially be harmful to glucose homeostasis.

NSC 23766 is an inhibitor of Rac1, a Rho-family GTPase. The compound blocks activation by the guanine nucleotide exchange factors Trio and Tiam1, but does not affect interactions with RhoA or Cdc42. NSC23766 blocks ADP-mediated platelet aggregation. Inhibition of Rac1 by NSC23766 restores sensitivity to trastuzumab by restoring down-regulation of ErbB2.

NSC 23766 has the following structure:

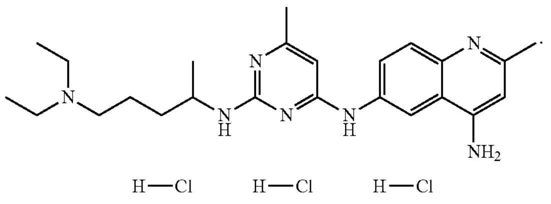 [SMILES: CCN(CC)CCCC(C)Nc1nc(C)cc(Nc2ccc3nc(C)cc(N)c3c2)n1 ; Cl ; Cl ; Cl]

NSC 23766 may be expressed in the following generic formula:

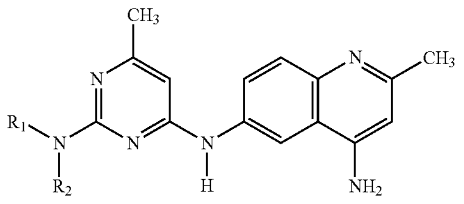

wherein,

R1 to R2 are independently selected from the group consisting of H, —X-Alk, —X-Alk-X', and —X—Y—X'; wherein X is —CR7R8; X is —CHR7R8; Alk is a C2-C18 substituted or unsubstituted hydrocarbon chain; Y is a C2-C8 substituted or unsubstituted alkylene chain; R6 is H or (C1-C4) alkyl; and R7 and R8 are independently selected from the group consisting of H or (C1-C4) alkyl or a salt of a compound of formula (IIa).

Alk may be substituted with halo, halo (C1-C4) alkoxy, (C3-C8) cycloalkyl, hydroxy, or acetyl. Y may be substituted with an NR6 group.

Interestingly, US 2013/0172552 identified EHop-016 as "a 100-fold more efficient inhibitor of Rac activity than NSC23766." EHop-016 is an "inhibitor of Rac activity based on the structure of the established Rac/Rac-GEF inhibitor NSC23766," and has the following structure:

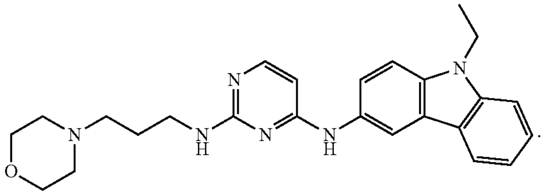 [SMILES: CCn1c2ccccc2c2cc(Nc3ccnc(NCCCN4CCOCC4)n3)ccc21]

NSC 23766, its structure, and/or useful derivatives thereof and other related structures and agents are described in detail in WO 2007/016539, and in U.S. Pat. Nos. 7,517,890, 7,524,851, 7,612,080, 7,826,982, and US Publication No. 2009/093471, all of which are hereby incorporated by reference in their entirety for all purposes. The identification of NSC23766 as a synergistic potentiator of antibiotic activity was unexpected as this molecule, or class of molecules, was not previously known to synergize with antibiotic agents.

In embodiments, a compound of structure:

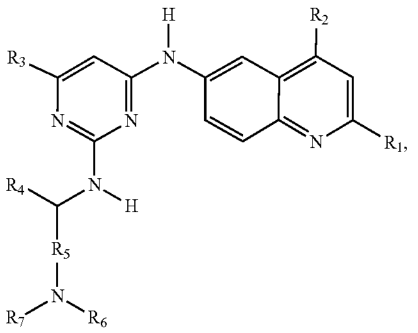

wherein $R_1$, $R_2$, and $R_3$ are each independently selected from $C_{1-3}$ alkyl, alkenyl, alkynyl, amine, hydrogen, and hydroxyl, and $R_4$ and $R_5$ are each independently selected from $C_{1-6}$ alkyl, alkenyl, and alkynyl, and $R_6$ and R7 are each independently selected from C1.4 alkyl, alkenyl, and alkynyl may function as a synergistic agent to potentiate activity of an antibiotic selected from the group consisting of vancomycin, cycloserine, fosfomycin, novobiocin, clarithromycin, tetracycline, ampicillin, trimethoprim, chloramphenicol, and norfloxacin.

Benurestat

Benurestat was originally identified as a urease inhibitor. Ureases belong to the superfamily of amidohydrolases and phosphotriesterases and are nickel-containing metalloenzymes of high molecular weight. Active sites require nickel in jack-bean and several bacteria. However, in vitro activation also has been achieved with manganese and cobalt. Urease is an enzyme that catalyzes the hydrolysis of urea into carbon dioxide and ammonia. The reaction occurs as follows: (NH2)2CO+H2O→CO2+2NH3, where N=nitrogen. H=hydrogen, O=oxygen. Specifically, urease catalyzes the hydrolysis of urea to produce ammonia and carbamate. The carbamate produced is subsequently degraded by spontaneous hydrolysis to produce another ammonia and carbonic acid. Urease activity increases the pH of its environment as urease produces ammonia. Ureases are found in numerous bacteria, fungi, algae, plants and some invertebrates, as well as in soils.

Bacterial ureases are composed of three distinct subunits, one large (α 60-76 kDa) and two small (β 8-21 kDa, γ 6-14 kDa) commonly forming (αβγ)3 trimers stoichiometry with a 2-fold symmetric structure. Bacterial ureases are cysteine-rich enzymes, resulting in the enzyme molar masses between 190 and 300 kDa. All bacterial ureases are solely cytoplasmic, except for *Helicobacter pylori* urease, which along with its cytoplasmic activity, has external activity with host cells.

The presence of urease is used in the diagnosis of *Helicobacter* species. The urease of *Helicobacter* species is an exceptional enzyme composed of two subunits, α(26-31 kDa)-β(61-66 kDa). *Helicobacter* urease has been shown to form a supramolecular dodecameric complex of repeating α-β subunits, each coupled pair of subunits has an active site, for a total of 12 active sites. *Helicobacter* urease plays an essential function for survival, neutralizing gastric acid by allowing urea to enter into periplasm via a proton-gated urea channel.

All plant ureases are cytoplasmic. Fungal and plant ureases are made up of identical subunits (~90 kDa each), most commonly assembled as trimers and hexamers. Jack-bean urease has two structural and one catalytic subunit. The a subunit of jack-bean urease contains the active site. Jack-bean urease is composed of 840 amino acids per molecule (90 cysteines) and its molecular mass without Ni(II) ions amounts to 90.77 kDa. The mass of the jack-bean urease hexamer with the 12 nickel ions is 545.34 kDa. It is structurally related to the (αβγ)3 trimer of bacterial ureases. Other examples of homohexameric structures of plant ureases are those of soybean, pigeon pea and cotton seeds enzymes. The optimum pH for jack-bean urease is 7.4 and the optimum temperature is 60 degrees Celsius. Jack-bean urease has an enzymatic specificity for urea and hydroxyurea. Inhibitors for jack-bean urease include heavy metals (e.g. $Pb^{-}$ & $Pb^{2+}$).

Although composed of different types of subunits, ureases from different sources extending from bacteria to plants and fungi exhibit high homology of amino acid sequences. For example, the active site of all ureases are located in the α (alpha) subunits. When compared, the a subunits of *Helicobacter pylori* urease and other bacterial ureases align with the jack bean ureases, suggesting that all ureases are evolutionary variants of one ancestral enzyme. The urease active site is a bis-p-hydroxo dimeric nickel center, with an interatomic distance of ~3.5 Å. Magnetic susceptibility experiments have indicated that, in jack bean urease, high spin octahedrally coordinated Ni(II) ions are weakly antiferromagnetically coupled. X-ray absorption spectroscopy (XAS) studies of Canavalia *ensiformis* (jack bean), *Klebsiella aerogenes* and *Sporosarcina pasteurii* (*Bacillus pasteurii*) confirm 5-6 coordinate nickel ions with exclusively O/N ligands (two imidazoles per nickel).

In urea binding, water molecules are located towards the opening of the active site and form a tetrahedral cluster that fills the cavity site through hydrogen bonds. Urea binds to the active site for the reaction, displacing the water molecules. Amino acid residues participate in the substrate binding, mainly through hydrogen bonding, stabilize the catalytic transition state and accelerate the reaction. Additionally, amino acid residues involved in the architecture of the active site compose part of the mobile flap of the site, which acts as a gate for the substrate. Cysteine residues are common in the flap region of the enzymes. Cysteine residues are not essential in catalysis; however, they are involved in positioning other key residues in the active site appropriately. In the structure of *Sporosarcina pasteurii* urease, the flap was found in the open conformation. However, the closed conformation of the *Sporosarcina pasteurii* urease, the flap is needed for the reaction. Indeed, the coordination of urea to the active site of urease has never been observed in a resting state of the enzyme.

The kcat/Km of urease in the processing of urea is 1,014 times greater than the rate of the uncatalyzed elimination reaction of urea. The proximity of urea to active groups in the active site along with the correct orientation of urea allow hydrolysis to occur rapidly. Urea alone is very stable due to the resonance forms it adopts. The stability of urea is understood to be due to its resonance energy, which has been estimated at 30-40 kcal/mol. The resonance energy of urea results from the fact that zwitterionic resonance forms of urea all donate electrons to the carbonyl carbon making urea less of an electrophile making and less reactive to nucleophilic attack.

Urease inhibitors are used to temporarily reduce the activity of the enzyme and slow the rate at which urea is hydrolyzed. There are many compounds that can inhibit urease. Urease inhibitors that are non-toxic, effective at low concentrations, chemically stable and able to be mixed with or coated onto urea-containing fertilizers include but are not limited to N-(n-Butyl) thiophosphoric triamide (NBTPT or NBPT) and phosphoric triamide (NBPTO or BNPO). Other widely studied urease inhibitors include phenylphosphorodiamidate (PPD/PPDA) and hydroquinone. Ammonium thiosulfate and some metals can also inhibit urea hydrolysis. There are many other organic compounds, especially structural analogues of urea, capable of inhibiting urease.

In medicine, acetohydroxamic acid (Lithostat) is a urease inhibitor used to dissolve crystals and struvite kidney stones. Lithostat is used to dissolve kidney stones (including struvite stones), prevent crystals from forming new kidney stones, and treat urinary tract infections.

Benurestat is a urease inhibitor that slows the rate at which urea is hydrolyzed. Benurestat is of interest for infected ureolysis therapy. Benurestat has been administered orally to rats. Benurestat, also known as 2-(para-chlorobenzamide)-acetohydroxamic acid, has the following structure:

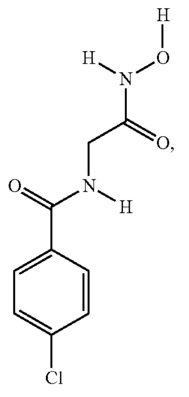

and is described in detail in Andersen J A. *Invest. Urol.* 12: 381-6 and U.S. Pat. No. 3,728,380.

Benurestat was set forth in U.S. Pat. No. 3,728,380 as:

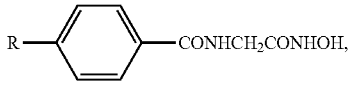

wherein R is nitro or chloro.

Notably, U.S. Pat. No. 4,157,396 identified a further hydroxamic acid derivative having urease inhibitory action:

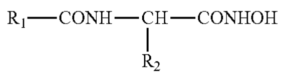

wherein $R_1$ is a residual group selected from the group consisting of a substituted phenyl group represented by a formula:

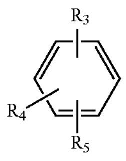

wherein $R_3$, $R_4$ and $R_5$ are selected from the group consisting of hydrogen and a lower alkoxy group, provided that at least one of them is a lower alkoxy group, and two of them may be linked each other to form an alkylene dioxy group; a carbonylaminophenyl group represented by a formula:

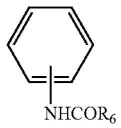

wherein $R_6$ is a lower alkyl group; and a heterocyclic residue selected from the group consisting of furan, thiophene and pyridine, and $R_2$ is hydrogen or methyl group, provided that when $R_1$ is carbonylaminophenyl group, $R_2$ is hydrogen, and its salt of a pharmacologically acceptable base.

Benurestat, its structure, and/or useful derivatives thereof and other related structures and agents are also described in detail in U.S. Pat. Nos. 6,261,537, 6,264,917, 6,331,289, 6,576,636, 6,602,902, US Publication No. 2002102215, U.S. Pat. Nos. 6,680,047, 8,314,077, US Publication No. 2004141922, U.S. Pat. No. 7,199,151, US Publication No. 2005002865, U.S. Pat. No. 8,232,265, US Publication No. 2010304998, US Publication No. 2010305326, U.S. Pat. Nos. 8,343,962, 9,308,162, 5,795,909, 4,256,765, WO9930690, U.S. Pat. Nos. 9,278,134, 8,802,596, 7,175,854, 7,951,398, 9,016,221, US Patent No. Publication No. 2009269772, US Publication No. 2008319092, US Publication No. 2007269379, US Publication No. 2006110428, US Publication No. 2003059471, U.S. Pat. Nos. 8,268,352, 8,263,125, 8,158,152, 7,976,871, 7,905,852, US Publication No. 2014328884, US Publication No. 2014348936, US Publication No. 2014315720, US Publication No. 2014154313, U.S. Pat. No. 9,005,185, US Publication No. 2014113826, US Publication No. 2014050694, US Publication No. 2014051771, US Publication No. 2014052264, U.S. Pat. Nos. 9,308,181, 9,526,824, US Publication No. 2013131628, U.S. Pat. Nos. 9,096,743, 8,632,510, 8,513,304, 8,454,582, 8,480,637, US Publication No. 2015246174, U.S. Pat. No. 9,642,912, US Publication No. 2015306230 and US Publication No. 2016175572, all of which are hereby incorporated by reference in their entirety for all purposes. The identification of Benurestat as a synergistic potentiator of antibiotic activity was unexpected as this molecule, or class of molecules, was not previously known to synergize with antibiotic agents.

In embodiments, a compound of structure:

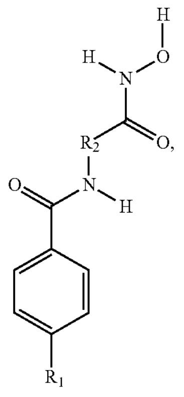

wherein $R_1$ is Cl, F, Br, I, and At, and $R_2$ is $C_{1-4}$ alkyl, alkenyl, or alkynyl may function as a synergistic agent to potentiate activity of an antibiotic selected from the group consisting of vancomycin, cycloserine, fosfomycin, novobiocin, clarithromycin, tetracycline, ampicillin, trimethoprim, chloramphenicol, and norfloxacin.

IEM1754

IEM1754 was originally identified as an AMPA receptor blocker. The α-amino-3-hydroxy-5-methyl-4-isoxazolepropionic acid receptor (also known as AMPA receptor, AMPAR, or quisqualate receptor) is an ionotropic transmembrane receptor for glutamate that mediates fast synaptic transmission in the CNS. The AMPA receptor has been traditionally classified as a non-NMDA-type receptor, along with the kainate receptor. AMPA receptor's name is derived from its activation by the artificial glutamate analog AMPA. AMPARs are located in many parts of the brain and are the most commonly found receptor in the nervous system. The AMPA receptor GluA2 (GluR2) tetramer was the first glutamate receptor ion channel to be crystallized.

AMPARs are composed of four types of subunits, GluA1 (GRIA1), GluA2 (GRIA2), GluA3 (GRIA3), and GluA4 (alternatively called GluRA-D2 or GRIA4). These AMPAR subunits combine to form tetramers. Most AMPARs are heterotetrameric, consisting of symmetric 'dimer of dimers' of GluA2 and either GluA1, GluA3 or GluA4. Dimerization starts in the endoplasmic reticulum with the interaction of N-terminal leucine/isoleucine/valine-binding protein (LIVBP) domains, then "zips up" through the ligand-binding domain into the transmembrane ion pore.

The conformation of the AMPAR subunit protein in the plasma membrane was initially difficult to determine. The amino acid sequence of the subunit indicated four transmembrane domains (parts of the protein that pass through the plasma membrane). However, proteins interacting with the subunit suggested that the N-terminus seemed to be extracellular, while the C-terminus seemed to be intracellular. Yet, if each of the four transmembrane domains went all the way through the plasma membrane, then the two termini would have to be on the same side of the membrane. The reason for these observations is that the second "transmembrane" domain does not cross the membrane at all, but kinks back on itself within the membrane and returns to the intracellular side. When the four subunits of the tetramer come together, this second membranous domain forms the ion-permeable pore of the receptor.

AMPAR subunits differ most in their C-terminal sequence, which determines their interactions with scaffolding proteins. All AMPARs contain PDZ-binding domains; however the PDZ domain AMPARs bind to differs. For instance, GluA1 binds to synapse-associated protein 97 (SAP97) through SAP97's class I PDZ domain, while GluA2 binds to protein interacting with C kinase-1 (PICK1) and glutamate receptor-interacting protein 1 (GRIP)/androgen-binding protein (ABP). Of note, AMPARs cannot directly bind to the common synaptic protein PSD-95 owing to incompatible PDZ domains, although they do interact with PSD-95 via stargazing.

Phosphorylation of AMPARs regulate channel localization, conductance, and open probability. GluA1 has four known phosphorylation sites at serine 818 (S818), S831, threonine 840, and S845. S818 is phosphorylated by protein kinase C, and is necessary for long-term potentiation (LTP). S831 is phosphorylated by calmodulin-dependent protein kinase II (CaMKII) and PKC during LTP, which helps deliver GluA1-containing AMPAR to the synapse and increases single channel conductance. The T840 site has also been implicated in LTD. S845 phosphorylation by PKA regulates the open probability of S845.

Ethanol acts as an antagonist of the NMDA, AMPA and kainate glutamate receptors, along with several antiepileptic drugs. The nootropic compound theanine is an antagonist of the AMPA and kainate receptors. Many dissociative drugs are antagonists of the NMDA glutamate receptor, including but not limited to ketamine, methoxetamine (MXE), phencyclidine (PCP) and dextromethorphan (DXM). Tramadol and ibogaine are dual antagonists of the NMDA glutamate receptor and opioid receptors.

IEM 1754 is a voltage-dependent open-channel blocker of α-amino-3-hydroxy-5-methyl-4-isoxazolepropionic acid (AMPA) receptors. IEM 1754 blocks N-methyl-D-aspartate (NMDA) receptors and is used in neurological research (e.g. competitive binding studies), and has the following structure:

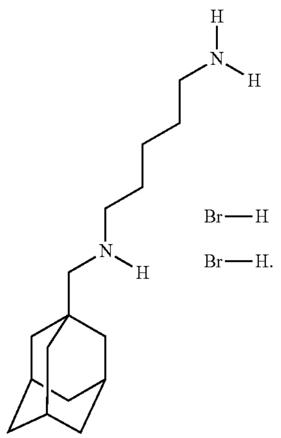

Magazanik et al. J. Physiol. 505: 655-63 describes "[t]he effects of two adamantane derivatives, 1-trimethylammonio-5-(1-adamantane-methyl-ammoniopentane dibromide) (IEM-1460) and 1-ammonio-5-(1-adamantane-methylammoniopentane dibromide) (IEM-1754) on kainate-induced currents were studied in *Xenopus* oocytes expressing recombinant ionotropic glutamate receptors and in freshly isolated neurons from rat hippocampal slices. 2. As described therein, the adamantane derivatives caused use- and voltage-dependent block of open channels of recombinant AMPA receptors. This antagonism was dependent on receptor subunit composition; channels gated by recombinant, homomeric GluR1 and GluR3 receptors exhibited a higher sensitivity to block than those gated by receptors containing edited GluR2 subunits. In the former cases, IEM-1460 had an $IC_{50}$ of 1.6 microM at a holding potential (Vh) of −80 mV and IEM-1754 was 3.8 times less potent than IEM-1460. In contrast, 100 microM IEM-1460 inhibited responses to 100 microM kainate of receptors containing edited GluR2 subunits by only 7.8+/−2.4% (n=5 oocytes at a Vh of −80 mV. 3. Native AMPA/kainate receptors in isolated hippocampal cells were inhibited by adamantane derivatives in a use- and voltage-dependent manner. This antagonism was dependent on cell type: pyramidal neurons were less sensitive to IEM-1460 ($IC_{50}$=1617 microM at Vh=−80 mV) than interneurons ($IC_{50}$=1.6 microM at Vh=−80 mV). IEM-1460 and IEM-1754 were equipotent when applied to pyramidal neurons, but IEM-1754 was less potent (approximately 3 times) than IEM-1460 when applied to interneurons. 4. It was concluded that the presence of the edited GluR2 subunit in recombinant AMPA receptors and native AMPA/kainate receptors inhibits channel block by organic cations and that adamantane derivatives are potentially valuable tools for identifying classes of AMPA/kainate receptors and their roles in synaptic transmission." IEM-1460 has the following structure:

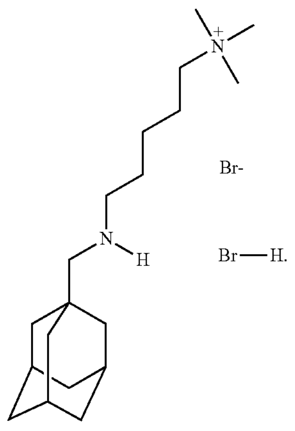

US Publication No. 2013/0046005 identifies IEM-1754 among a number of recited KAR antagonists. For example, US Publication No. 2013/0046005 states "[e]xamples of KAR antagonists that may be administered using the methods of the disclosure include but are not limited to NS102 (5-Nitro-6,7,8,9-tetrahydro-1H-benzo[g]indole-2,3-dione 3-oxime); glutamate derivatives (e.g. pyrrolidine-, isoxazole-, oxa(thia)diazole-, pyrirnidine-, and hexahydrofuropyrane derivatives); tbienol[2,3-djpyrirnidines; 2-aminothiophene-3-carboxylic acid derivatives such as ethyl 2-amion-4-methyl-5-phenylthiophene-3-carboxylate (see Briel et al. 2010 and references therein); LU97175 and IEM-1754 (see Kaczor et al. 2009 (J. Chem. Inf. Model. 49, 1094-1104) and references therein); and those that are described in issued U.S. Pat. Nos. 5,446,051 and 6,156,794, the complete contents of which are herein incorporated by reference. Preferably, the agents (e.g., antagonists) that are used in the practice of the disclosure are specific for the KAR (i.e. they bind only this receptor and no other) or are selective for binding to the KAR (they bind the KAR in preference to any other receptor by at least a factor of 5, 10, 20, 30, 40, 50, 60, 70, 80, 90 or 100 or greater (e.g. several hundred or even 100-fold), i.e. which bind to the receptor with at least 5, 10, etc. fold higher affinity than to other receptors."

IEM 1754, its structure, and/or useful derivatives thereof are described in detail in at least Kaczor et al. 2009 (J. Chem. Inf. Model. 49, 1094-1104) and in US Publication No. 2013/0046005, which is hereby incorporated by reference in its entirety for all purposes. The identification of IEM1754 as a synergistic potentiator of antibiotic activity was unexpected as this molecule, or class of molecules, was not previously known to synergize with antibiotic agents.

In embodiments, a compound of structure:

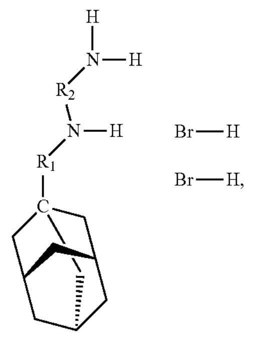

wherein $R_1$ and $R_2$ are each independently $C_{1-6}$ alkyl, alkenyl, or alkynl may function as a synergistic agent to potentiate activity of an antibiotic selected from the group consisting of vancomycin, cycloserine, fosfomycin, novobiocin, clarithromycin, tetracycline, ampicillin, trimethoprim, chloramphenicol, and norfloxacin.

Additional Synergistic Agents

The following compounds were found to function as synergistic agents to potentiate activity of an antibiotic selected from the group consisting of vancomycin, cycloserine, fosfomycin, novobiocin, clarithromycin, tetracycline, ampicillin, trimethoprim, chloramphenicol, and norfloxacin.

The structures of certain compounds that showed activity in the assays presented herein include:

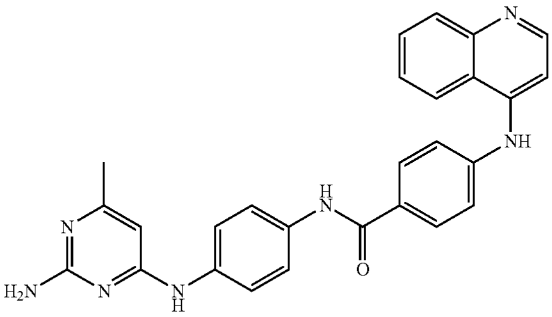
SGI-1027
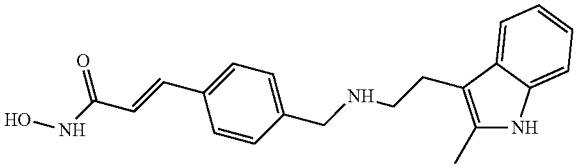
Panobinostat
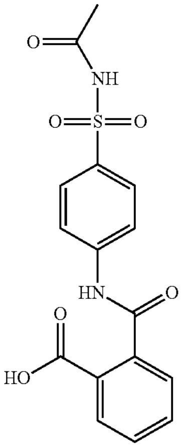
Phthalyl Sulfacetamide
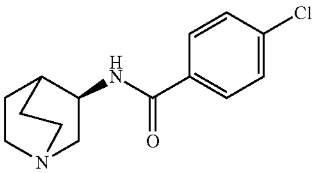
PNU 282987
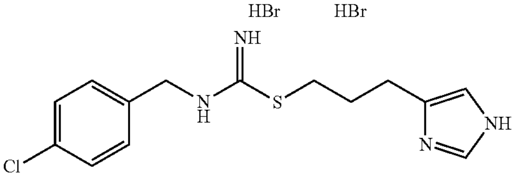
Clobenpropit dihydrobromide
Compound 256
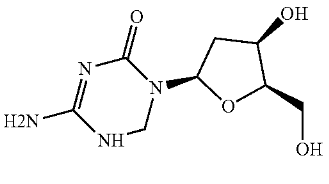
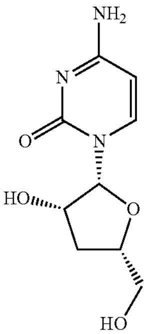
1-(3-Deoxypentofuranosyl)cytosine -continued
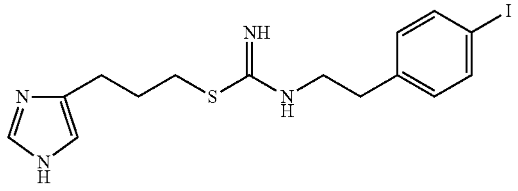
HBr HBr
Iodophenpropit dihydrobromide
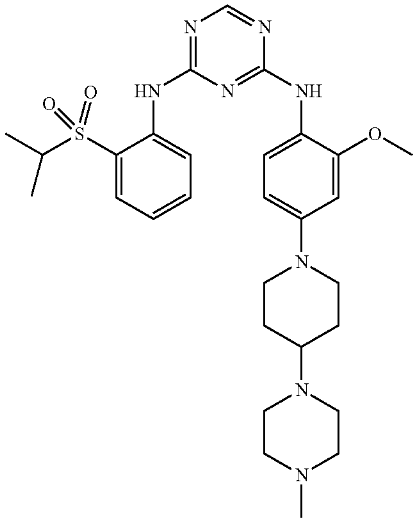
ASP3026
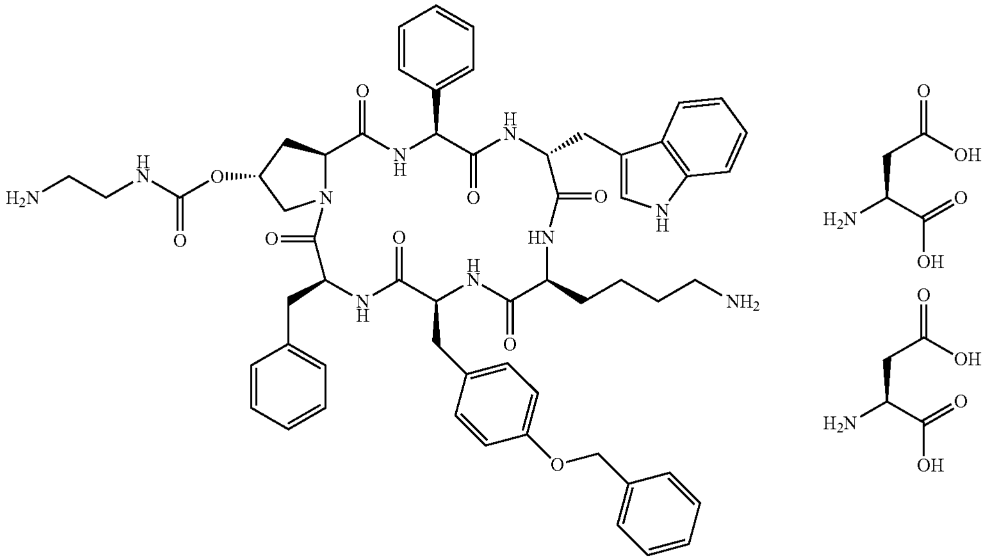
Pasireotide (ditrifluoroacetate)
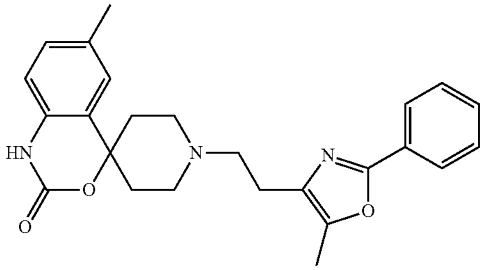
RS 504393
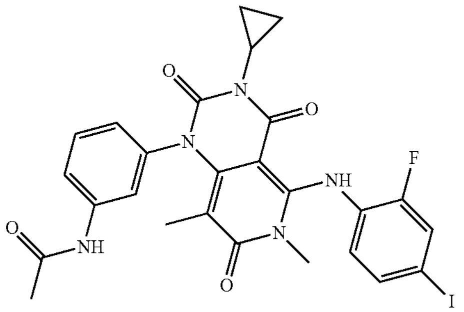
Trametinib (GSK1120212)

-continued
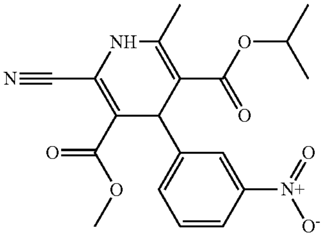
Nilvadipine
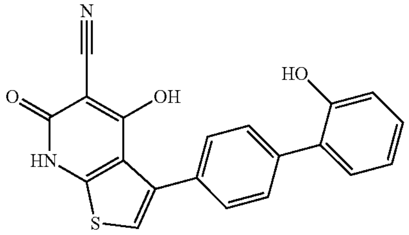
A-769662
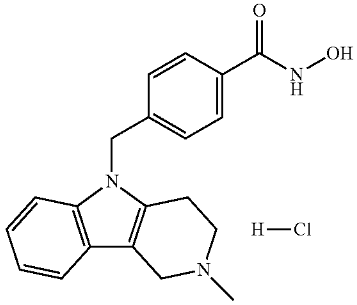
Tubastatin A HCl
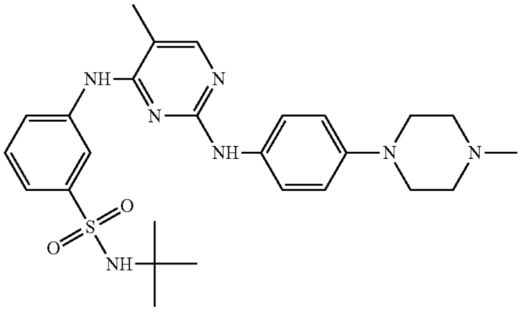
TG101209
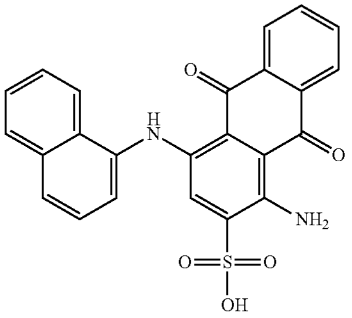
PSB 06126
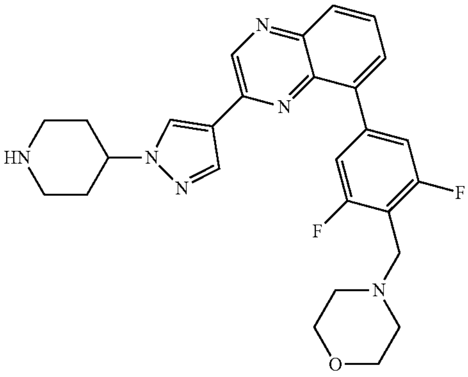
NVP-BSK805 2HCl
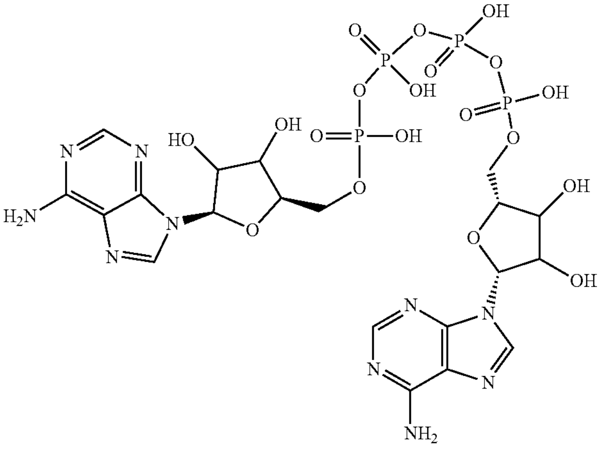
P1,P4-Di(adenosine-5′)tetraphosphate ammonium
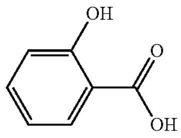
SODIUM SALICYLATE
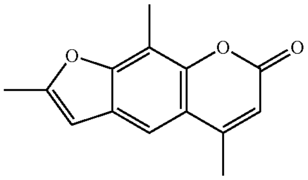
TRIOXSALEN
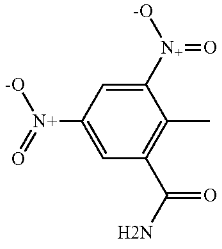
DINITOLMIDE
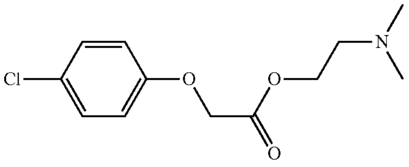
MECLOFENOXATE
HYDROCHLORIDE
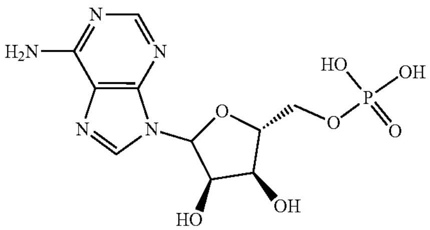
ADENOSINE 5-MONOPHOSPHATE
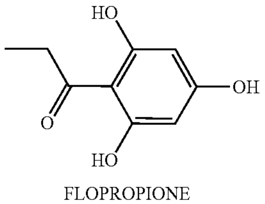
FLOPROPIONE -continued
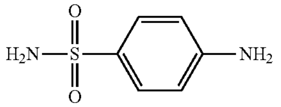
SULFANILAMIDE
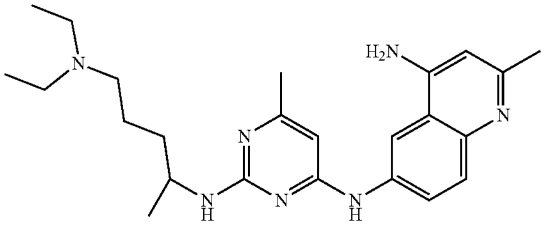
NSC 23766
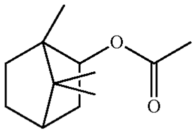
BORNYL ACETATE
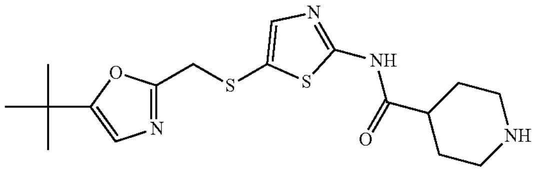
SNS-032 (BMS-387032)
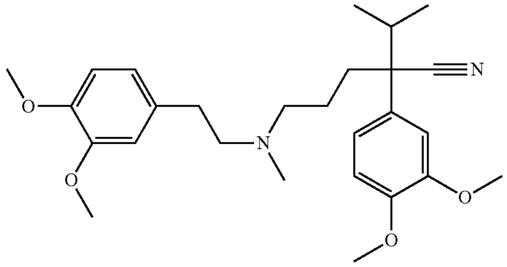
VERAPAMIL HYDROCHLORIDE
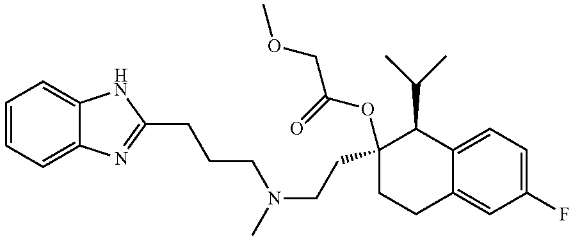
Mibefradil dihydrochloride
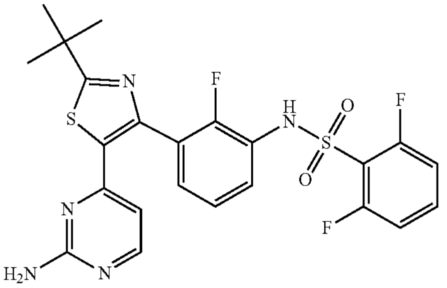
Dabrafenib (GSK2118436)
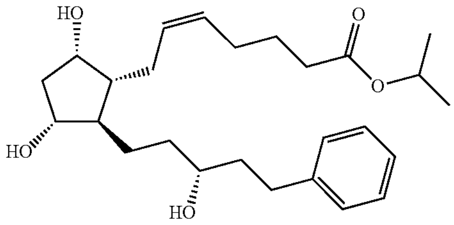
Latanoprost
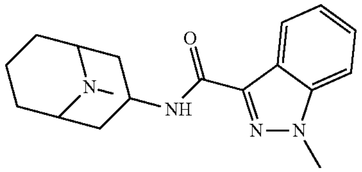
GRANISETRON
HYDROCHLORIDE
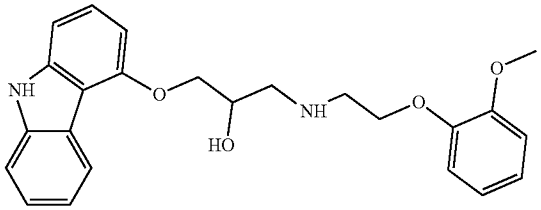
Carvedilol
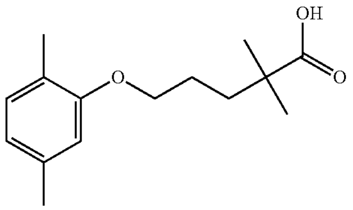
GEMFIBROZIL
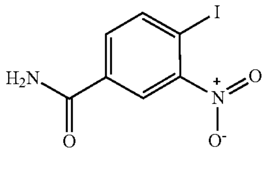
Iniparib (BSI-201)
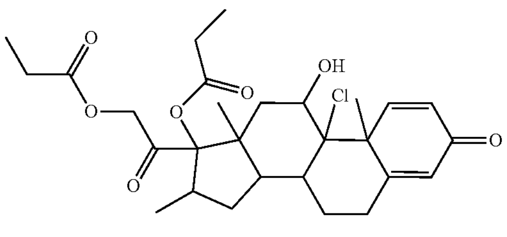
BECLOMETHASONE
DIPROPIONATE
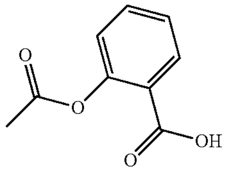
ASPIRIN -continued
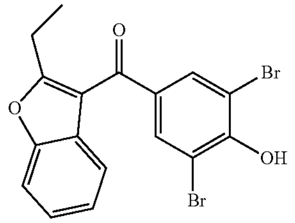
BENZBROMARONE
Compound 773
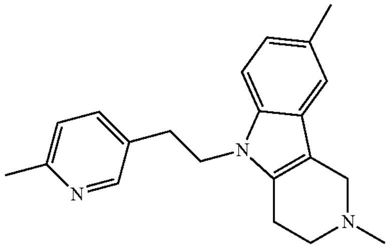
Compound 774
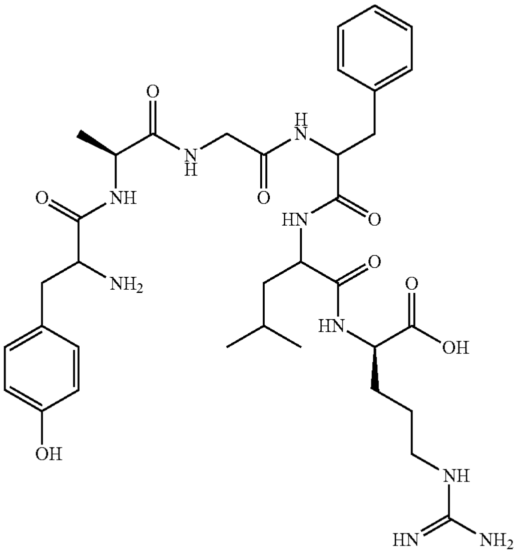
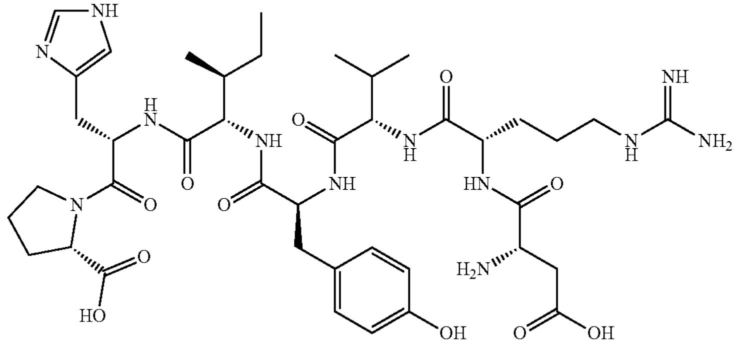
Angiotensin (1-7)
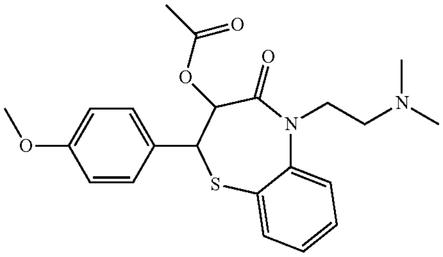
DILTIAZEM HYDROCHLORIDE
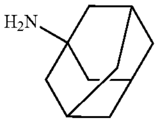
Amantadine HCl
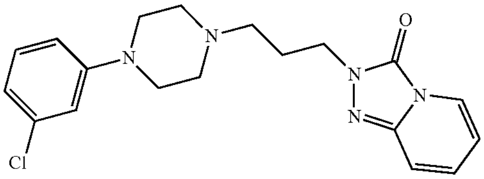
Trazodone HCl -continued
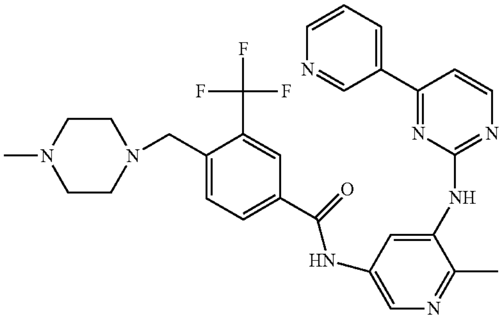
Flumatinib (mesylate)
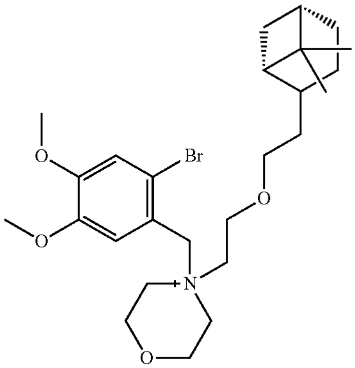
Pinaverium bromide
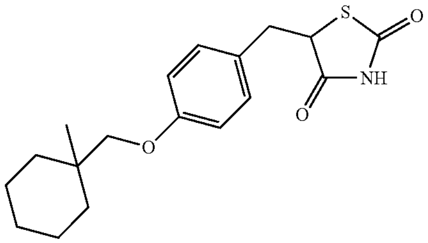
Ciglitazone
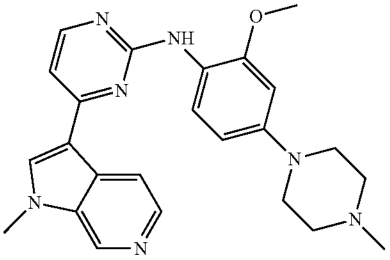
AZ191
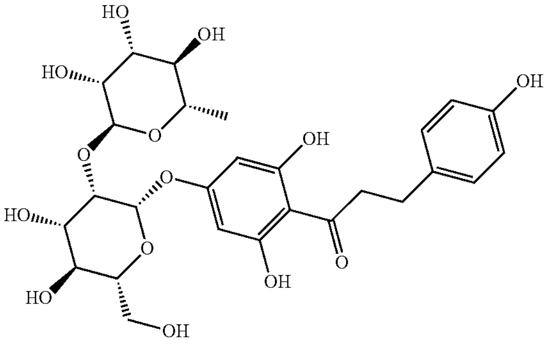
Naringin
Dihydrochalcone
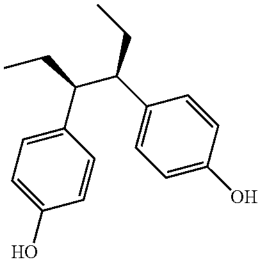
Hexestrol
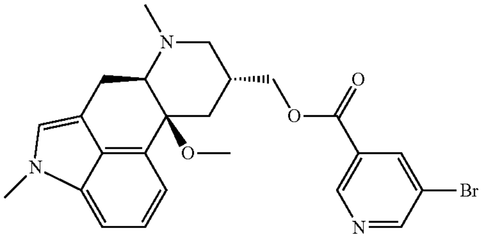
NICERGOLINE
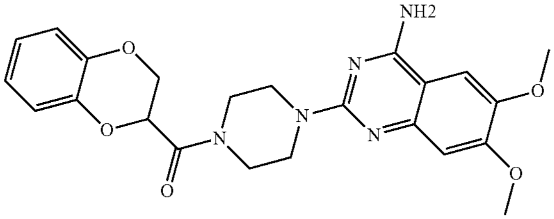
Doxazosin Mesylate
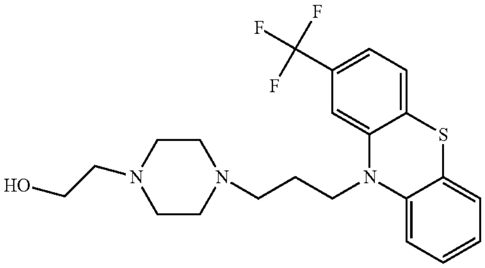
FLUPHENAZINE HYDROCHLORIDE
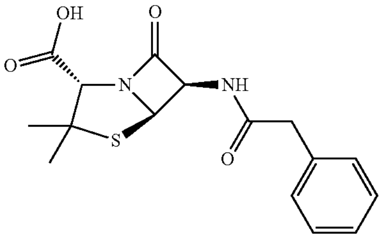
PENICILLIN POTASSIUM -continued
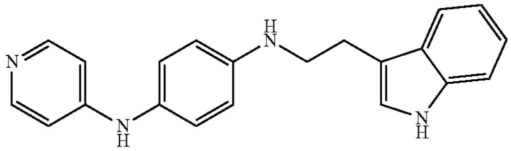
JNJ-26854165 (Serdemetan)
Compound 1233
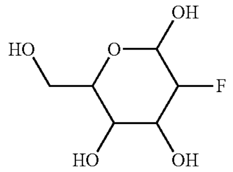
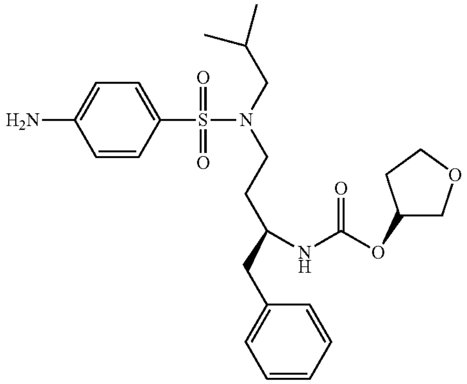
Amprenavir
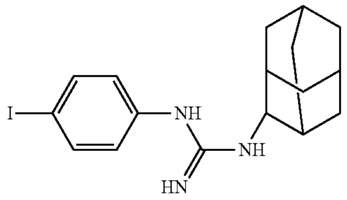
IPAG
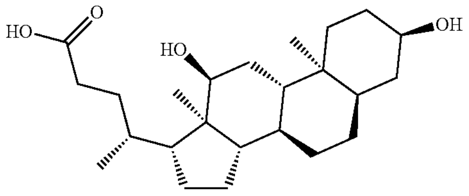
Deoxycholic acid
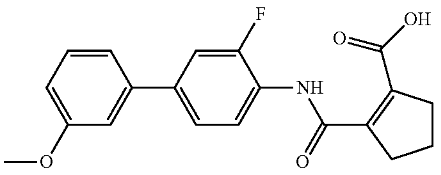
Vidofludimus
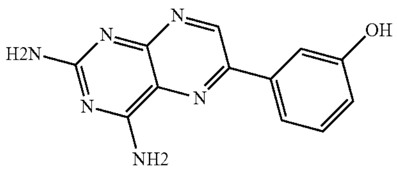
TG100713
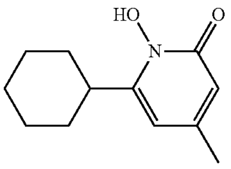
Ciclopirox ethanolamine
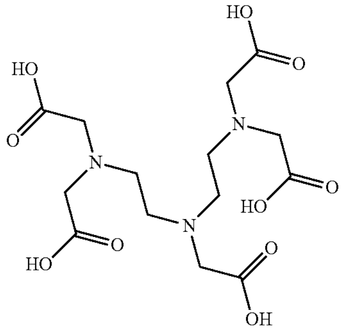
PENTETIC ACID
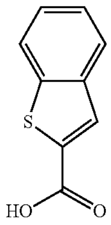
Compound 1633
Compound 1635
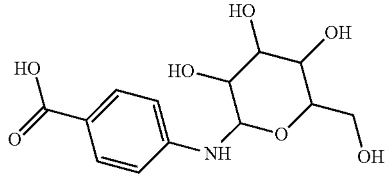

-continued
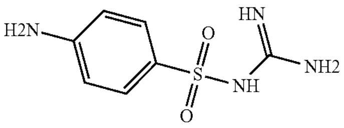
SULFAGUANIDINE
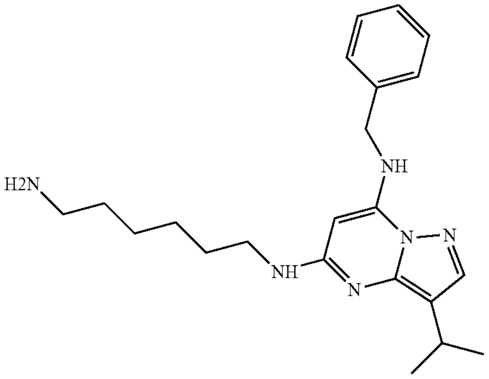
BS-181 HCl
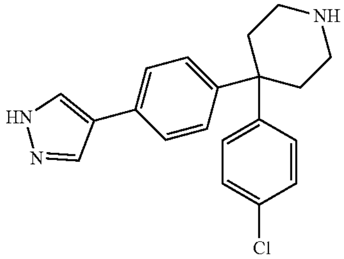
AT7867
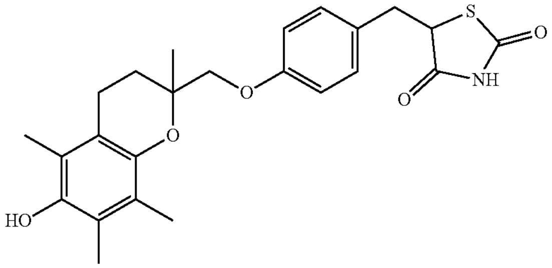
Troglitazone
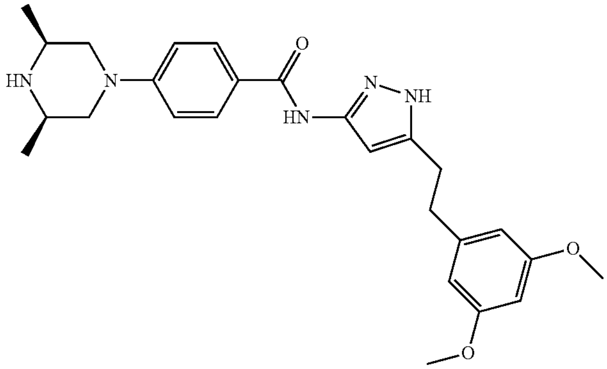
AZD4547
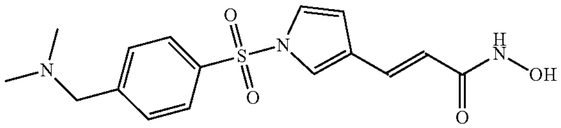
Resminostat
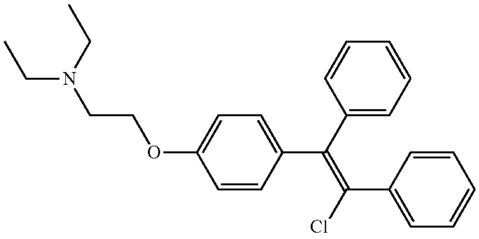
CLOMIPHENE CITRATE
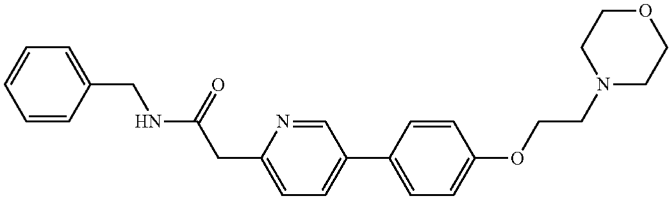
KX2-391

-continued
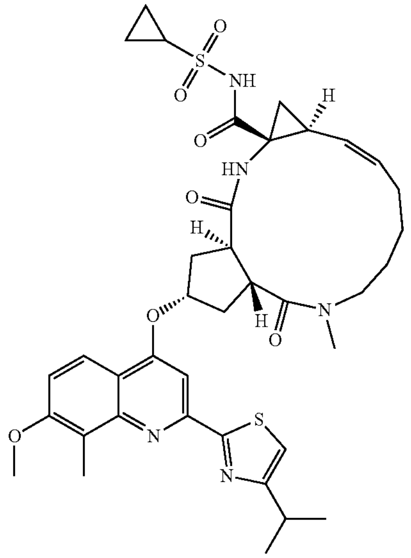
Simeprevir
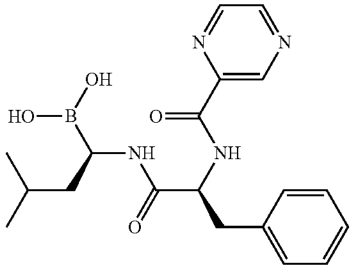
Bortezomib (PS-341)
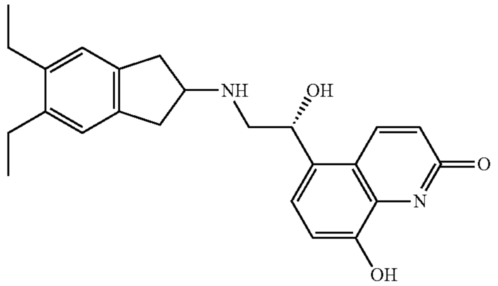
Indacaterol Maleate
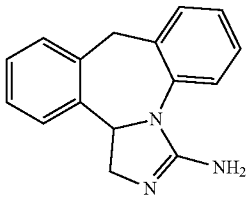
Epinastine HCl
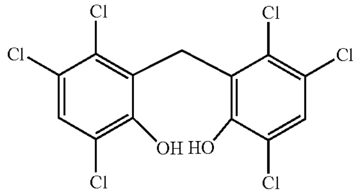
HEXACHLOROPHENE
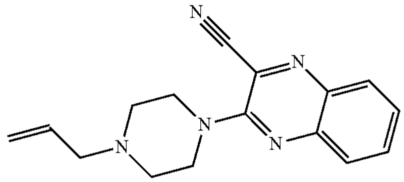
3-AQC
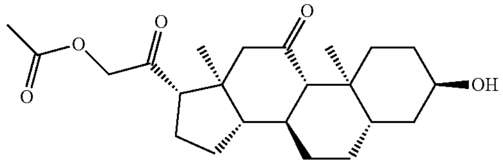
Alfadolone acetate
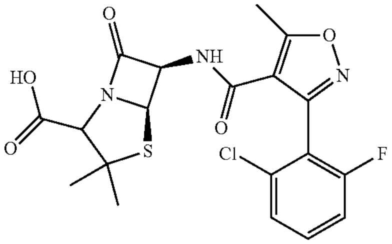
Flucloxacillin sodium
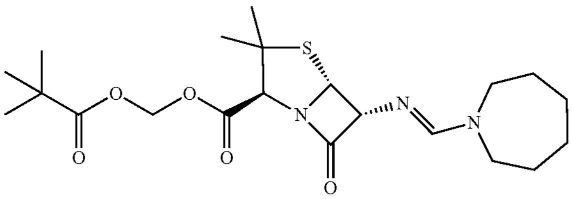
Pivmecillinam hydrochloride
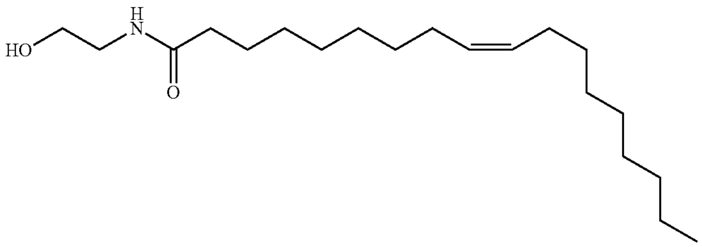
Oleylethanolamide -continued
Compound 2060
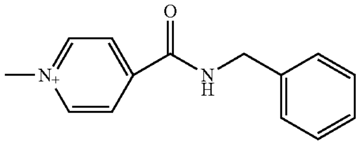
Compound 2171
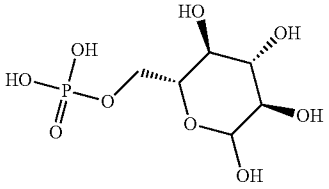
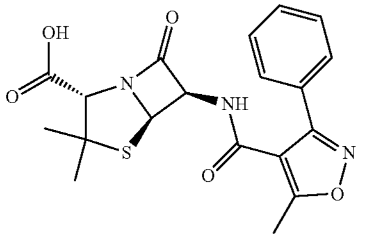
Oxacillin sodium monohydrate
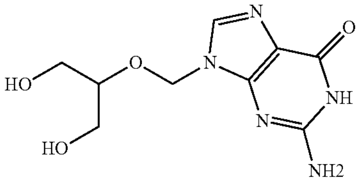
Ganciclovir
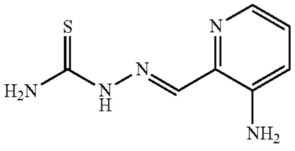
Triapine
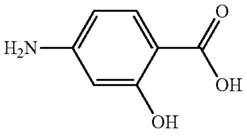
Aminosalicylate Sodium
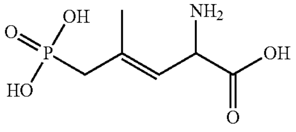
CGP 37849
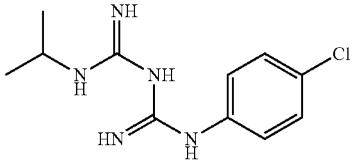
CHLOROGUANIDE HYDROCHLORIDE
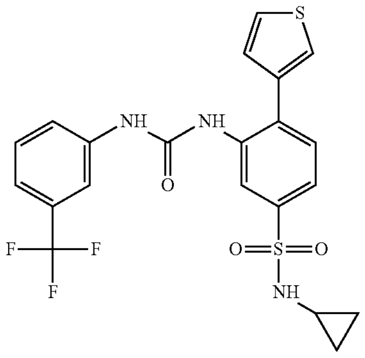
AGI-6780
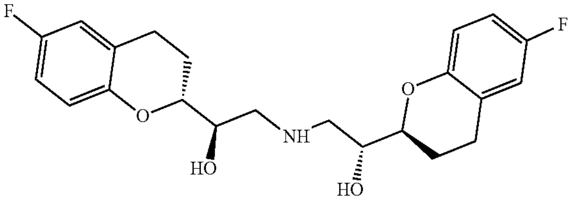
Nebivolol
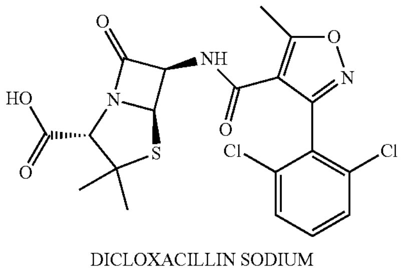
DICLOXACILLIN SODIUM
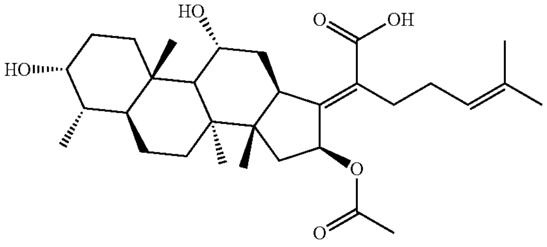
FUSIDIC ACID
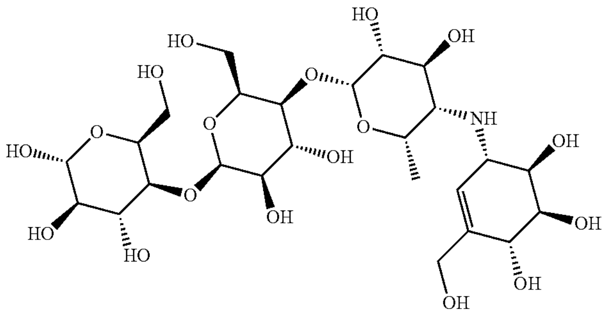
Acarbose -continued

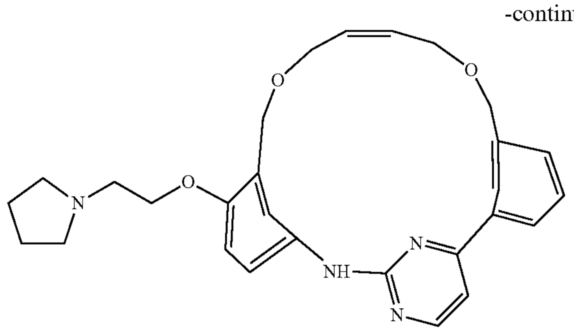

Pacritinib (SB1518)

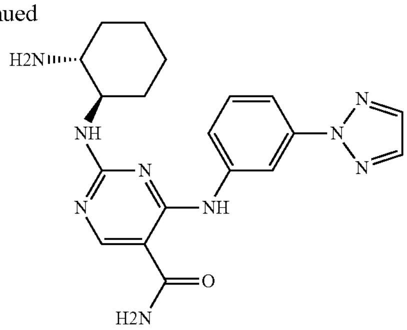

PRT062607 (P505-15, BIIB057) HCl

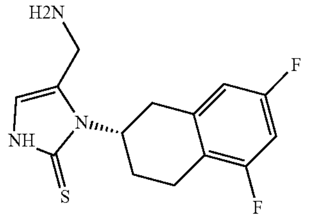

Nepicastat (hydrochloride)

Antibiotics

In some embodiments, a synergistic agent is administered to a subject in conjunction with an antibiotic. In some embodiments, the synergistic agent is administered to a subject in conjunction with an antibiotic to potentiate the effect of the antibiotic and/or to inhibit the development of resistance to the antibiotic in the subject.

In some embodiments, the synergistic agent is administered concurrently with (i.e. at approximately the same time as) the antibiotic. In some embodiments, the synergistic agent is administered separately from (i.e. at a different time than) the antibiotic. In some embodiments, the synergistic agent is administered prior to administration of an antibiotic. In some embodiments, the synergistic agent is administered after administration of an antibiotic. In embodiments in which the synergistic agent and the antibiotic are not administered concurrently, the synergistic agent and the antibiotic should be administered sufficiently close in time that a significant proportion (e.g., greater than 50%) of each compound remains in its active state while both the antibiotic and the anionic phthalocyanine compound are in the subject's system.

The antibiotic and the synergistic agent can be administered in any suitable manner, and need not both be administered in the same manner. In some embodiments, the antibiotic and/or the synergistic agent are administered orally. Suitable methods of administration can be selected by one skilled in the art, and include topical administration, injection or delivery to a desired location (including intravenous or intramuscular injection), or the like. In some embodiments, the antibiotic and/or the synergistic agent are administered by oral, parenteral, cutaneous, rectal, nasal, or vaginal administration.

In some embodiments, the antibiotic is administered at a daily dosage in the range of 0.1 mg/kg to 10 mg/kg. In some embodiments, the synergistic agent is administered at a daily dosage in the range of 1 mg/kg to 20 mg/kg. In some embodiments, the antibiotic is administered at a daily dosage of about 1 mg/kg and the synergistic agent is administered at a daily dosage in the range of about 10 mg/kg.

In some embodiments, the disclosure provides a composition including an antibiotic and a synergistic agent for potentiating the effect of an antibiotic. In some embodiments, the disclosure provides a composition including an antibiotic and a synergistic agent for inhibiting the development of antibiotic resistance. In some embodiments, the composition includes a pharmaceutically effective amount of the antibiotic and a pharmaceutically effective amount of the synergistic agent.

In some embodiments, the composition includes a pharmaceutically acceptable derivative, salt, metabolite or structural or functional analogue of the antibiotic. In some embodiments, the composition includes a pharmaceutically acceptable derivative, salt, metabolite, or structural or functional analogue of the synergistic agent.

In some embodiments, the composition includes a pharmaceutically acceptable carrier. In some embodiments, the composition includes a pharmaceutically effective amount of the antibiotic and a pharmaceutically effective amount of the synergistic agent.

In some embodiments, the disclosure provides a dosage form that includes an antibiotic and a synergistic agent. In some embodiments, the dosage form is a tablet, capsule, granule, powder, syrup, suspension, emulsion, solution, gel, paste, ointment, cream, lotion, plaster, skin patch, drench, suppository, enema, injectable solution, implant, spray or aerosol.

In some embodiments, the dosage form includes a pharmaceutically acceptable carrier. In some embodiments, the dosage form includes a pharmaceutically effective amount of the antibiotic and a pharmaceutically effective amount of the synergistic agent. In some embodiments, the dosage form includes between 1 and 1000 mg of the antibiotic. In some embodiments, the dosage form includes between 10 and 2000 mg of the anionic phthalocyanine compound.

In some embodiments, the antibiotic is an antibiotic that is an activator of the SOS response. In some embodiments, the antibiotic is a bactericidal antibiotic. In some embodiments, the antibiotic is a bacteriostatic antibiotic, for example, rifamycin. In some embodiments, the antibiotic is a bacteriostatic antibiotic that is co-administered together with a synergistic agent that potentiates the activity of the bacteriostatic antibiotic or that causes the bacteriostatic antibiotic to act as a bactericidal antibiotic. In some embodiments, the antibiotic is a bactericidal antibiotic that acts by causing DNA damage. In some embodiments, the antibiotic is a DNA gyrase inhibitor, a topoisomerase inhibitor, or the like. DNA gyrase is a type II topoisomerase.

Exemplary antibiotics that are DNA gyrase inhibitors include quinolones, aminocoumarins, and the like. Exemplary antibiotics that are topoisomerase IV inhibitors include quinolones and fluoroquinolones.

In some embodiments, the antibiotic is an aminoglycoside such as amikacin, arbekacin, apramycin, gentamicin, kanamycin, neomycin, netilmicin, paromomycin, streptomycin, rhodostreptomycin, tobramycin; an aminocoumarin such as novobiocin, coumermycin, clorobiocin; an ansamycin such as geldanamycin, herbimycin; a carbacephem such as loracarbef; a carbapenem such as ertapenem, doripenem, imipenem, meropenem; a cephalosporin such as cefadroxil, cefazolin, cefalotin, cefalexin, cefector, cefamandole, cefoxitin, cefprozil, cefuroxime, cefixime, cefdinir, cefditoren, cefoperazone, cefotaxime, cefpodoxime, ceftazidime, ceftibuten, ceftizoxime, cefiriaxone, cefepime, ceftaroline fosamil, ceftobiprole; a lipopeptide such as daptomycin; a monobactam such as aztreonam; a nitrofuran such as furazolidone, nitrofurantoin; a penicillin such as amdinocillin, amoxicillin, ampicillin, azlocillin, bacampicillin, benzathine, carbenicillin, cloxacillin, cyclacillin, dicloxacillin, flucloxacillin, mezlocillin, methicillin, nafcillin, oxacillin, penicillin G, penicillin V, piperacillin, temocillin, ticarcillin; another β-lactam antibiotic; a polypeptide such as bacitracin, colistin, polymyxin B; a quinolone or fluoroquinolone such as ciprofloxacin, enoxacin, gatifloxacin, levofloxacin, lomefloxacin, moxifloxacin, nalidixic acid, norfloxacin, ofloxacin, trovafloxacin, grepafloxacin, gemifloxacin, sparfloxacin, temafloxacin; vancomycin, metronidazole, co-trimoxazole, telithromycin, clofazimine, dapsone, cycloserine, pyrazinamide, rifampicin, rifabutin, or the like.

In some embodiments, the antibiotic is a tetracycline such as demeclocycline, doxycycline, minocycline, oxytetracycline, tetracycline; a sulfonamide such as mafenide, sulfonamidochrysoidine, sulfacetamid, sulfadiazine, sulfamethizole, sulfamethoxazole, sulfanilamide, sulfsalazine, slufisoxazole, trimethoprim; spectinomycin; chloramphenicol; a lincosamide such as clindamycin, lincomycin; a glycopeptide such as vancomycin, teicoplanin, telavancin, bleomycin, ramoplanin, decaplanin; a macrolide such as azithromycin, clarithromycin, dirithromycin, erythromycin, roxithromycin, troleandomycin, telithromycin, spectinomycin; a streptogramin such as pristinamycin, dalfopristin, quinupristin; trimethoprim, capreomycin, ethambutol, fusidic acid, tigecycline, or the like.

In some embodiments, any of the methods, compositions or dosage forms described above are used to treat a microbial/bacterial infection. In some embodiments, the microbial infection is a bacterial infection. In some embodiments, the methods, compositions or dosage forms described above are used to treat conditions that are typically treated by antibiotics, including for example anthrax (*Bacillus anthracis*), lyme disease (*Borrelia burgdorferi*), brucellosis (*Brucella*), enteritis (*Campylobacter jejuni*), *Clostridium difficile* infections, *Clostridium perfringens* infections, diphtheria (*Corynebacterium diphtheriae*), nosocomial infections (e.g. caused by *Enterococcus faecalis* or *Enterococcus faecium*), *Escherichia coli* infections (including by Enterotoxigenic *E. coli* or Enteropathogenic *E. coli*), tularemia (*Francisella tularensis*), *Haemophilus* influenza infections, *Helicobacter pylori* infections, Legionnaire's disease (*Legionella pneumophila*), leptospirosis (*Leptospira interrogans*), listeriosis (*Listeria monocytogenes*), leprosy (*Mycobacterium leprae*), tuberculosis (*Mycobacterium tuberculosis*), gonorrhea (*Neisseria gonorrhoeae*), meningococcal disease (*Neisseria meningitides*), *pseudomonas* infection (*Pseudomonas aeruginosa*), typhoid fever or *salmonellosis* (*Salmonella typhi, Salmonella typhimurium*), shigellosis (*Shigella sonnei*), staphylococcal infections (*Staphylococcus aureus, Staphylococcus epidermis, Staphylococcus saprophyticus*), *streptococcus* infections (*Streptococcus agalactiae, Streptococcus pneumoniae, Streptococcus pyogenes*), syphilis (*Treponema pallidum*), plague (*Yersinia pestis*), or the like. In some embodiments, more than one antibiotic is used or administered to a subject together with one or more synergistic agents.

In some embodiments, any of the methods, compositions or dosage forms described above are targeted at a Gram positive bacteria. In some embodiments, any of the methods, compositions or dosage forms described above are targeted at a Gram negative bacteria.

Vancomycin is a glycopeptide antibiotic used in the treatment of various bacterial infections. For complicated infections vancomycin is delivered intravenously. Vancomycin is also delivered orally. However, vancomycin is poorly absorbed when taken by mouth. Vancomycin acts by inhibiting proper cell wall synthesis in Gram-positive bacteria. Most Gram-negative bacteria are intrinsically resistant to vancomycin because their outer membranes are impermeable to large glycopeptide molecules. However, vancomycin is active against some nongonococcal species of *Neisseria.*

Novobiocin is a narrow spectrum aminocoumarin antibiotic that is produced by the actinomycete *Streptomyces niveus*. Novobiocin is of the aminocoumarin class of antibiotics and treats mostly Gram-positive bacteria and a few Gram-negative bacteria. Novobiocin strongly inhibits bacterial DNA gyrase through targeting the gyrase B (GyrB) subunit of the enzyme involved in energy transduction. In binding the GyrB subunit, Novobiocin competitively inhibits the ATPase reaction catalyzed by GyrB. Novobiocin is administered intravenously and is used for methicillin-resistant *Staphylococcus aureus* (MRSA) treatment. The oral form of novobiocin has been withdrawn from the market due to lack of efficacy.

Erythromycin is an antibiotic first isolated from the metabolic products of a strain of *Streptomyces erythreus*. Erythromycin is a macrolide antibiotic. The macrolides are a class of natural products that consist of a large macrocyclic lactone ring to which one or more deoxy sugars, usually cladinose and desosamine, may be attached. Erythromycin is administered orally, intravenously, intramuscularly, and topically. Erythromycin is most effective against Gram-positive bacteria but also has some effect on Gram-negative bacteria and some fungi. Erythromycin inhibits bacterial growth through interfering with aminoacyl translocation and preventing the transfer of the transfer ribonucleic acid (tRNA) bound at the A site of the ribosomal RNA (rRNA) complex to the P site of the rRNA complex. Without this translocation, the A site remains occupied and the addition of an incoming tRNA, with an attached amino acid, to the growing polypeptide chain is inhibited. Thus, erythromycin interferes with the bacterial cell protein production, which ultimately inhibits bacterial growth.

Chloramphenicol is a cephalosporin class, broad spectrum antibiotic with Gram-positive and Gram-negative activity. Chloramphenicol is administered orally, intravenously, intramuscularly, and topically. Chloramphenicol functions through inhibiting protein synthesis. Chloramphenicol blocks protein chain elongation by inhibiting the peptidyl transferase activity of the bacterial ribosome. Specifically, chloramphenicol binds to A2451 and A2452 residues in the 23S rRNA of the 50S ribosomal subunit, preventing peptide bond formation. As with most broad spectrum antibiotics, chloramphenicol use has resulted in antibiotic resistance. Three known mechanisms of resistance to chloramphenicol include reduced bacterial membrane permeability, mutation of the 50S ribosomal subunit, and elaboration of chloramphenicol acetyltransferase.

Cyclosporine is commonly used for immune-suppression delivered intravenously, orally, and topically (through eye drops). Cyclosporine inhibits the T-cell receptor signal transduction pathway via the formation of cyclosporin A-cyclophilin complex that inhibits calcineurin. Cyclosporine inhibits nitric oxide synthesis induced by interleukin 1α, lipopolysaccharides and TNFα. Cyclosporine also blocks cytochrome c release from mitochondria.

Cycolserine works as an antibiotic by inhibiting cell-wall biosynthesis in bacteria, and is commonly used to treat tuberculosis. As a cyclic analogue of D-alanine, cycloserine targets two enzymes important in the cytosolic stages of peptidoglycan synthesis: alanine racemase and D-alanine: D-alanine ligase. The first enzyme is a pyridoxal 5'-phosphate-dependent enzyme that converts the L-alanine to the D-alanine form, and the second enzyme is involved in joining two of these D-alanine residues together by catalyzing the formation of the ATP-dependent D-alanine-D-alanine dipeptide bond between the resulting D-alanine molecules. When both of these enzymes are inhibited, D-alanine residues cannot form and previously formed D-alanine molecules cannot be joined together, which effectively leads to inhibition of peptidoglycan synthesis.

Fosfomycin is a phosphoric acid derivative, broad spectrum antibiotic that acts against both Gram-positive and Gram-negative bacteria. Fosfomycin is orally administered and reduces bacterial growth through inhibiting bacterial cell wall biogenesis. Specifically, fosfomycin, as a phosphoenolpyruvate (PEP) analog, limits bacterial growth by inhibiting the enzyme UDP-N-acetylglucosamine-3-enolpyruvyltransferase (MurA) through alkylating an active site cysteine residue.

Tetracycline is a tetracycline class, broad-spectrum antibiotic covering both Gram-positive and Gram-negative bacterial. Tetracycline is typically administered orally. Tetracycline inhibits cell growth by inhibiting translation. More specifically tetracycline bines to the 16S part of the 20S ribosomal subunit to prevent amino-acyl tRNA from binding to the A site of the ribosome. However, wide-spread antibiotic resistance has reduced the usefulness of tetracycline in medicine. Common causes of tetracycline resistance include enzymatic inactivation of tetracycline, efflux, and ribosomal protection mechanisms.

Ampicillin is a penicillin class antibiotic used to treat both Gram-positive and Gram-negative bacteria. Ampicillin was the first broad spectrum, beta-lactam antibiotic with activity against Gram-positive bacteria. Ampicillin is administered orally and intravenously. Ampicillin prevents bacterial growth through irreversibly inhibiting transpeptidase, which is needed by bacteria to make cell wall. Through inhibiting bacterial cell wall synthesis, ampicillin leads to bacterial cell lysis.

Trimethoprim is a sulfonamide antibiotic that is orally administered. Timethoprim has antibiotic activity for most Gram-positive aerobic cocci and some Gram-negative aerobic bacilli. Trimethoprim binds to dihydrofolate reductase and inhibits the reduction of dihydrofolic acid (DHF) to tetrahydrofolic acid (THF). Interference with the THF pathway inhibits bacterial DNA synthesis. Sulfamethoxazole inhibits dihydropteroate synthase, an enzyme involved further upstream in the same pathway. Trimethoprim and sulfamethoxazole are commonly used in combination due to possible synergistic effects, and reduced development of resistance.

Norfloxacin is a synthetic chemotherapeutic antibacterial agent that is classified as a quinolone antibiotic. Norfloxacin is administered topically (for ophthalmic applications) as well as orally. Norfloxacin is a broad-spectrum antibiotic active against both Gram-positive and Gram-negative bacteria. Norfloxacin functions by inhibiting deoxyribonucleic acid (DNA) gyrase and, thereby, inhibiting cell division. Norfloxacin does not bind to DNA gyrase but does bind to the substrate DNA.

Netilmicin is a member of the aminoglycoside family of antibiotics. Netilmicin is active against most Gram-negative, including gentamicin-resistant Gram-negative bacilli, and some Gram-positive bacteria. Netilmicin is not absorbed from the gut and is administered by injection or infusion. Netilmicin is only used in the treatment of serious infections. Netilmicin inhibits protein synthesis in bacteria by binding to the bacterial 30S ribosomal subunit and interfering with messenger RNA (mRNA) binding and the acceptor tRNA site.

Bacterial Strains

*Escherichia coli* (*E. coli*) is a rod-shaped, Gram-negative bacteria. Gram-negative bacteria contain an outer membrane surrounding the cell wall that provides a barrier to certain antibiotics. Most strains of *E. coli* are harmless, but some serotypes cause illnesses such as food poisoning. Harmless strains are part of the normal flora of the gut. An estimated 73,480 illnesses due to *E. coli* infection occur each year in the United States. Currently, antibiotics of choice for treating *E. coli* are fluoroquinolones, azithromycin, and rifaximin.

*Pseudomonas aeruginosa* (*P. aeruginosa*) is a common rod-shaped, Gram-negative bacteria. *P. aeruginosa* is a multidrug resistant pathogen. *P. aeroginosa* is associated with serious illnesses, e.g. sepsis. *P. aeroginosa* is found in soil, water and skin flora. Common first-line antibiotics for treating *P. aeruginosa* are carbapenems, polymyxins, and tigecycline. Treatment of *P. aeruginosa* is difficult due to natural resistance to antibiotics. The low antibiotic susceptibility of *P. aeruginosa* is attributable to a concerted action of multidrug efflux pumps with chromosomally encoded antibiotic resistance genes (e.g., mexAB, mexXY, etc.) and the low permeability of the Gram-negative cellular envelope. In addition to intrinsic resistance, *P. aeruginosa* easily develops acquired resistance either by mutation in chromosomally encoded genes or by the horizontal gene transfer of antibiotic resistance determinants. *Staphylococcus aureus* (*S. aureus*) is a Gram-positive, round-shaped bacterium that is frequently found in the nose, in the respiratory tract, and on the skin. *S. aureus* is a common cause of skin infections, respiratory infections, and food poisoning. Pathogenic strains often produce potent protein toxins and expression of a cell-surface protein that binds and inactivates antibodies. The emergence of antibiotic-resistant strains of *S. aureus* such as MRSA is a worldwide problem in clinical medicine. Each year around 500,000 patients in hospitals of the United States contract a staphylococcal infection, chiefly by *S. aureus*. Up to 50,000 deaths each year in the USA are linked with *S. aureus* infections. The treatment of choice for *S. aureus* infection is penicillin. However, MRSA, one of a number of greatly feared strains of *S. aureus*, has become resistant to most penicillin derivatives, cephalosporins, monobactams, and carbapenems. For this reason, a glycopeptide antibody (e.g. vancomycin) is commonly used to combat MRSA.

Pharmaceutical Compositions

The disclosure provides pharmaceutical compositions for use in any of the methods described herein. The pharmaceutical compositions contain therapeutic agents (e.g. an antimicrobial agent and a synergistic agent).

In embodiments, the pharmaceutical compositions include a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil, olive oil, gel (e.g., hydrogel), and the like. Saline is a preferred carrier when the pharmaceutical composition is administered intravenously. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin, the contents of which are hereby incorporated by reference in its entirety. Such compositions will generally contain a therapeutically effective amount of the therapeutic agent, the intracellular permeation enhancing agent, and/or the immunotherapeutic agent, in purified form, together with a suitable amount of carrier so as to provide the form for proper administration to the patient. The formulation should suit the mode of administration.

In embodiments, the therapeutic agents are administered locally as an immediate release or controlled release composition, for example by controlled dissolution and/or the diffusion of the active substance. Dissolution or diffusion controlled release can be achieved by incorporating the active substance into an appropriate matrix. A controlled release matrix may include one or more of shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

In related embodiments, the controlled release matrix is a hydrogel. A hydrogel is a three-dimensional, hydrophilic or amphiphilic polymeric network capable of taking up large quantities of water. The networks are composed of homopolymers or copolymers, which are insoluble due to the presence of covalent chemical or physical (e.g., ionic, hydrophobic interactions, entanglements) crosslinks. The crosslinks provide the network structure and physical integrity. Hydrogels exhibit a thermodynamic compatibility with water that allows them to swell in aqueous media. The chains of the network are connected in such a fashion that pores exist and that a substantial fraction of these pores are of dimensions between 1 nm and 1000 nm.

The hydrogels can be prepared by crosslinking hydrophilic biopolymers or synthetic polymers. Examples of the hydrogels formed from physical or chemical crosslinking of hydrophilic biopolymers, include but are not limited to, hyaluronans, chitosans, alginates, collagen, dextran, pectin, carrageenan, polylysine, gelatin, agarose, (meth)acrylate-oligolactide-PEO-oligolactide-(meth)acrylate, poly(ethylene glycol) (PEO), poly(propylene glycol) (PPO), PEO-PPO-PEO copolymers (Pluronics), poly(phosphazene), poly (methacrylates), poly(N-vinylpyrrolidone), PL(G)A-PEO-PL(G)A copolymers, poly(ethylene imine), and the like. See Hennink and van Nostrum, Adv. Drug Del. Rev. 54:13-36 (2002); Hoffman, Adv. Drug Del. Rev. 43:3-12 (2002); Cadee et al., J Control. Release 78:1-13 (2002); Surini et al., J. Control. Release 90:291-301 (2003); and U.S. Pat. No. 7,968,085, each of which is incorporated by reference in its entirety. These materials consist of high-molecular weight backbone chains made of linear or branched polysaccharides or polypeptides.

The amount of the pharmaceutical composition of the disclosure which will be effective in the treatment or prevention of bacterial infection may depend on the nature of the infection and can be determined by standard clinical techniques, including imaging techniques. In addition, in vitro assays may optionally be employed to help identify optimal dosage ranges. The precise dose to be employed in the formulation may also depend on the route of administration, and the seriousness of the infection, and should be decided according to the judgment of the practitioner and each patient's circumstances. Effective doses may be extrapolated from dose-response curves derived from in vitro or animal model test systems.

According to another preferred embodiment, the techniques herein may inhibit the bacterial efflux of an antibiotic selected from but not limited to Vancomycin Novobiocin Erythromycin Chloramphenicol Cyclosporine Fosfomycin Tetracycline Ampicillin Trimethoprim Norfloxacin, Netilmicin, ciproflaxacin, levofloxacin, gatifloxacin, moxifloxacin, ofloxacin, norflaxacin, erythromycin, azithromycin, clarithromycin, telitrhomycin, rifamipin and derivatives thereof, tetracycline, minocycline, chloramphenicol, gentamicin, linezolid, penicillin, amoxicillin, ceftriaxone, or imipenem.

If pharmaceutically acceptable salts of the compounds are used, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this disclosure may also be modified by appending appropriate functionalities to enhance selective biological properties. Such modifications are known in the art and include those which increase biological penetration into a given biological system (e.g., blood, lymphatic system, central nervous system, cellular walls), increase oral availability, increase solubility to allow administration by injection, alter metabolism and alter rate of excretion.

Another component of the pharmaceutically acceptable compositions of this disclosure is a pharmaceutically acceptable carrier. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present disclosure may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant or similar alcohol.

The pharmaceutical compositions of this disclosure may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this disclosure may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. Pharmaceutical formulations via nasal inhalation may also be delivered as a dry inhalable powder.

The amount of both, the synergistic agent and the antibiotic that may be combined with the carrier materials to produce a single dosage form will vary depending upon the host treated, the particular mode of administration. Therefore, the amount of antibiotic in such compositions will be less than that required in a monotherapy utilizing only that factor. Preferably, the compositions should be formulated so that a dosage of between 0.01-100 mg/kg body weight/day of the compound can be administered and a dosage of between 0.01-100 mg/kg body weight/day of the antibiotic can be administered to a patient receiving these compositions.

A specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular compound and antibiotic present in the composition.

According to another embodiment, the present disclosure provides a method of treating a bacterial infection in a mammal comprising the step of administering to said mammal a composition of the present disclosure. According to a preferred embodiment, the bacterial infection is caused by a gram-positive or a gram-negative bacteria.

According to another preferred embodiment, the bacterial infection is caused by *Salmonella, Proteus, Acinetobacter, Shigella, Neisseria, Enterobacter, Burkholderia, Pseudomonas, Klebsiella, Haemophilus, Serratia, Providencia, Vibrio, Francisella, Yersinia, Actinobacillus, Kingella, Cardiobacterium, Eikenella corrodens, Brucella, Bartonella, Vibrio, Pasteurella, Edwardsiella, Aeromonas, Plesimonas, Bartonella, Staphylococcus, Streptococcus, Enterococci, Bacillus, Corynebacterium, Actinomyces, Nocardia, Rhodococcus, Aerococcus, Abiotrophia, Erysipelotrix, Listeria, Archanobacterium, Mobiluncus, Gardnerella, Chlamydia, Mycoplasma, Legionella, Coxiella, Rickettsia, Ureaplasma urealyticum, Borrelia, Leptospira, Treponema, Bacteroides, Clostridium, Helicobacter, Campylobacter, Peptostreptococcus, Fusobacterium, Propionibacterium, Prevotella, Porphyromonas*, or Mycobacteria.

According to another preferred embodiment, the bacterial infection is caused by *Streptococcus* (group A), *Streptococcus* (group C), *Stenotrophomonas maltophilia, Archanobacterium haemolyticum, Chlamydia pneumoniae, Neisseria gonorrhoeae, Corynebacterium diphtheriae, Corynebacterium ulcerans, Mycoplasma pneumoniae, Streptococcus pneumoniae, Haemophilus influenzae, Staphylococcus aureus, Moraxella catarrhalis, Pseudomonas aeruginosa, Bordetella pertussis, Bacteroides fragilis, Klebsiella pneumoniae, Mycobacterium tuberculosis, Klebsiella pneumoniae, Burkholderia pseudomallei, Legionella pneumophila, Francisella tularensis, Bacteroides fragilis, Rhodococcus equi, Coxiella burnetti, Rickettsia rickettsii, E. coli, Proteus mirabilis, Salmonella typhi, Salmonella typhimurium, Staphlycoccus saprophyticus, Streptococcus* (group B), *Aerococcus urinae, Morganella morganii, Corynebacterium urealyticum, Ureaplasma urealyticum, Yersinia enterocolitica, Mycobacterium avium, Streptococcus viridans* group, *Streptococcus bovis, Staphylococcus coagulase*-negative, *Stomatococcus mucilaginosus, Actinobacillus actinomycetemcomitans, Cardiobacterium hominis, Eikenella corrodens, Erysipelothrix rhusiopathiae, Coxiella burnetii, Chlamydia psittaci, Corynebacterium diphtheriae, Clostridium perfringens, Borrelia burgdorferi, Neisseria meningitidis, Mycoplasma pneumoniae, Pseudomonas fluorescens, Pseudomonas putida, Serratia marcescens, Campylobacter jejuni, Treponema pallidum, Bacillus cerus, Listeria monocytogenes, Leptospira, Rhodococcus equi, Vibrio vulnicicus, Bacillus anthracis, Francisella tularensis, Pasterurella multocida, Eikenella corrodens, Erysipelothrix rhusiopathiae, Corynebacterium minutissimum, Edwardsiella tarda, Bacillus cereus, Plesimonas shigelloides, Clostridium botulinum, Clostridium perfringrens, Clostridium difficile, Streptococcus beta*-hemolytic groups, *Haemophilus ducreyi, Chlamydia trachomatis, Calymmatobacterium granulomatis, Gardnerella vaginalis, Bartonella henselae, Enterococcus faecalis, Enterococcus faecium, Burkholderia pseudomallei, Treponema carateum*, or *Helicobacter pylori.*

According to an embodiment, the bacterial infection is selected from upper respiratory infections, lower respiratory infections, ear infections, pleuropulmonary and bronchial infections, urinary tract infections, intra-abdominal infections, cardiovascular infections, sepsis, CNS infections, skin and soft tissue infections, GI infections, bone and joint infections, genital infections, eye infections, or granulomatous infections. In embodiments the bacterial infection refers to sepsis.

According to an embodiment, the bacterial infection is selected from pharyngitis, sinusitis, otitis externa, otitis media, bronchitis, empyema, pneumonia, cystitis and pyelonephritis, renal calculi, prostatitis, peritonitis, dialysis-associated peritonitis, visceral abscesses, endocarditis, myocarditis, pericarditis, transfusion-associated sepsis, meningitis, encephalitis, brain abscess, osteomyelitis, arthritis, genital ulcers, urethritis, vaginitis, cervicitis, conjunctivitis, keratitis, or endophthalmitis.

Reference will now be made in detail to exemplary embodiments of the disclosure. While the disclosure will be described in conjunction with the exemplary embodiments, it will be understood that it is not intended to limit the disclosure to those embodiments. To the contrary, it is intended to cover alternatives, modifications, and equivalents as may be included within the spirit and scope of the disclosure as defined by the appended claims.

EXAMPLES

The present disclosure is further illustrated by the following examples, which should not be construed as limiting. The contents of all references, GenBank Accession and Gene numbers, and published patents and patent applications cited throughout the application are hereby incorporated by reference. Those skilled in the art will recognize that the disclosure may be practiced with variations on the disclosed structures, materials, compositions and methods, and such variations are regarded as within the scope of the disclosure.

Example 1

Figure 1B:
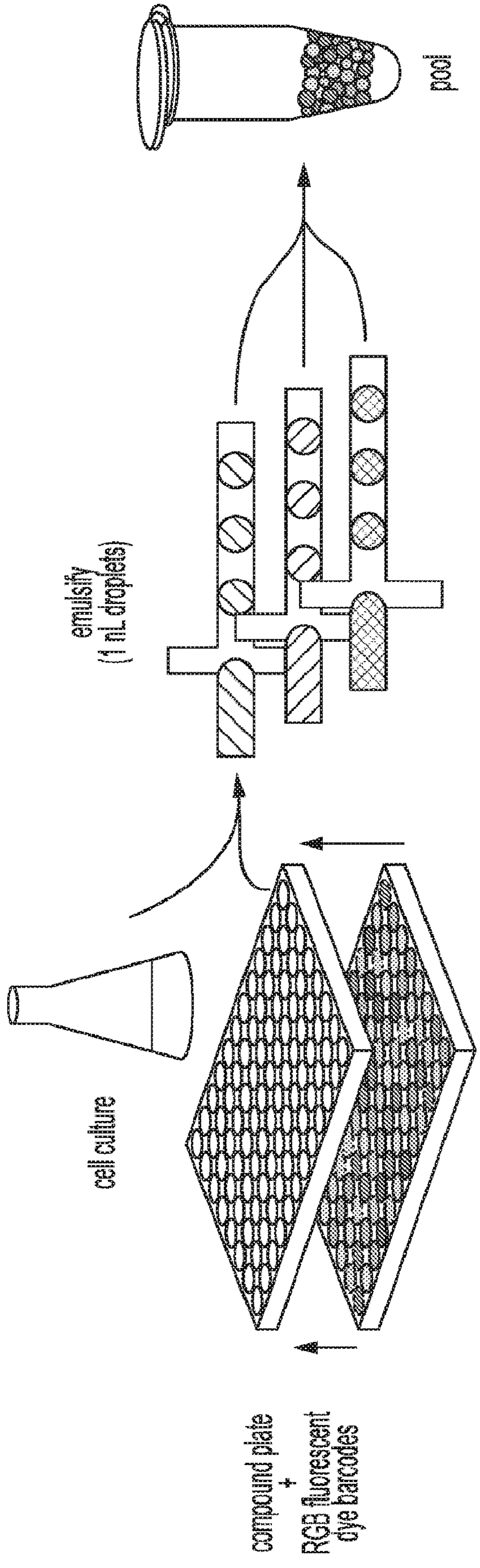
Figure 1C:
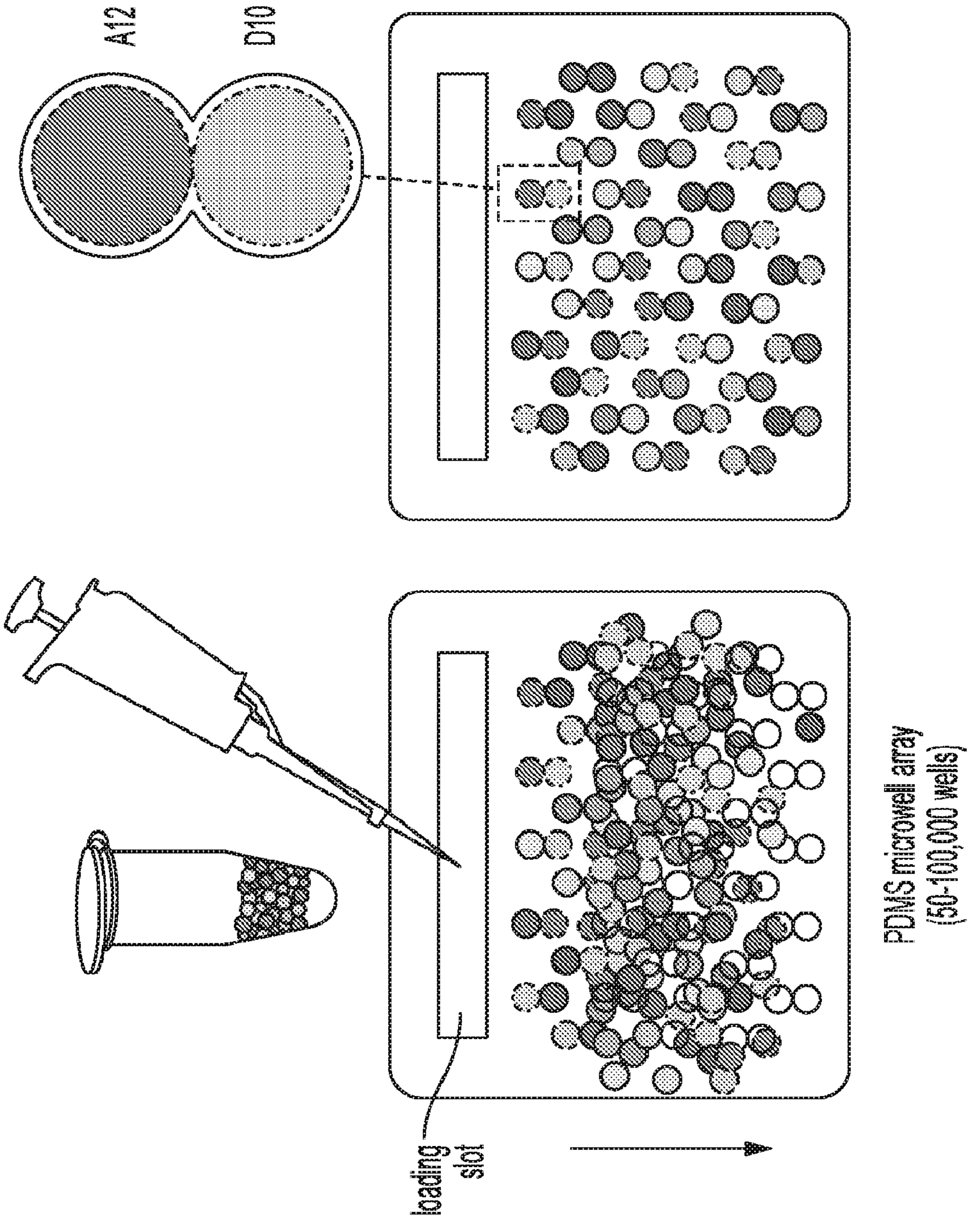
Figure 1D:
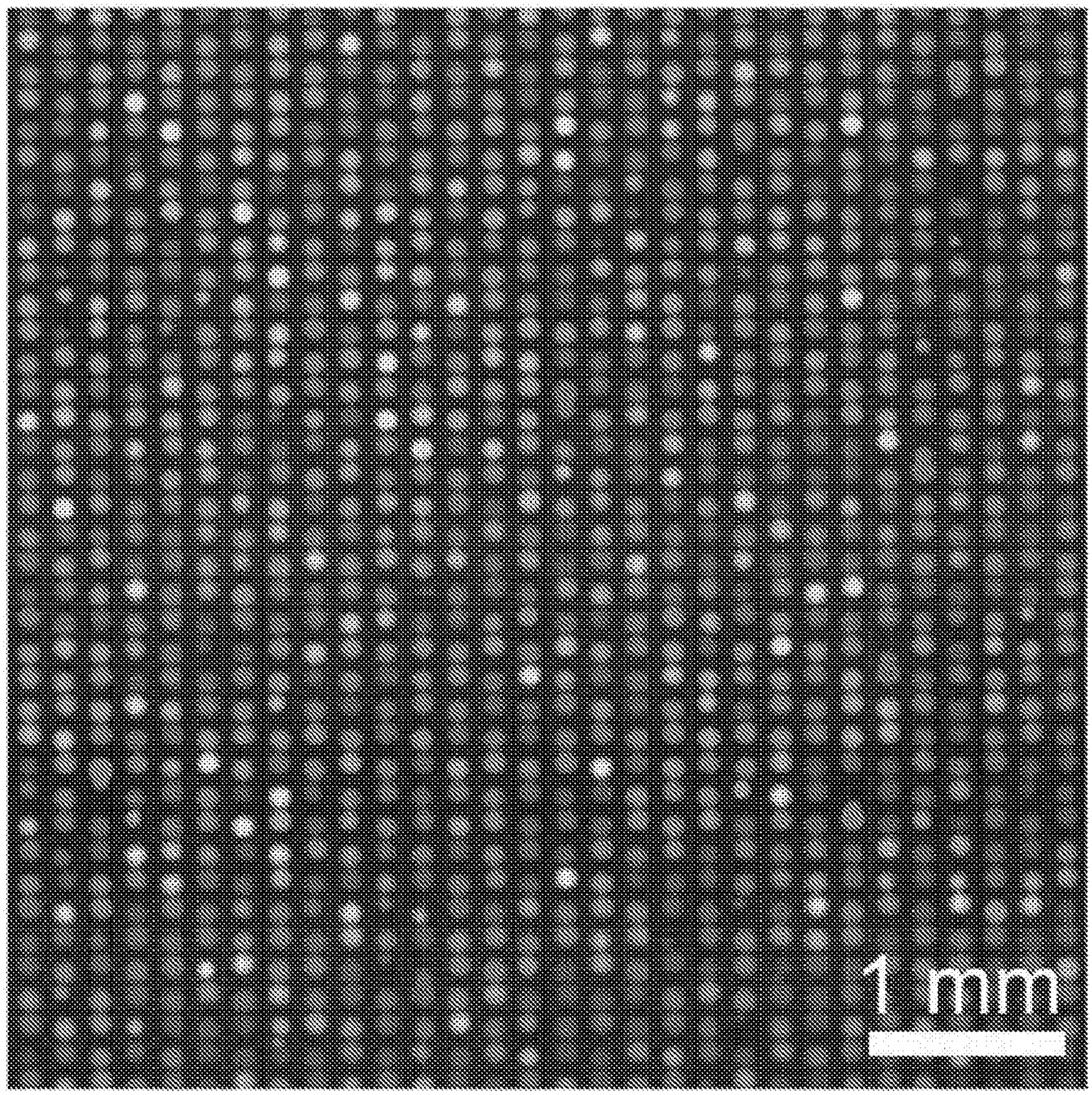
Figure 1E:
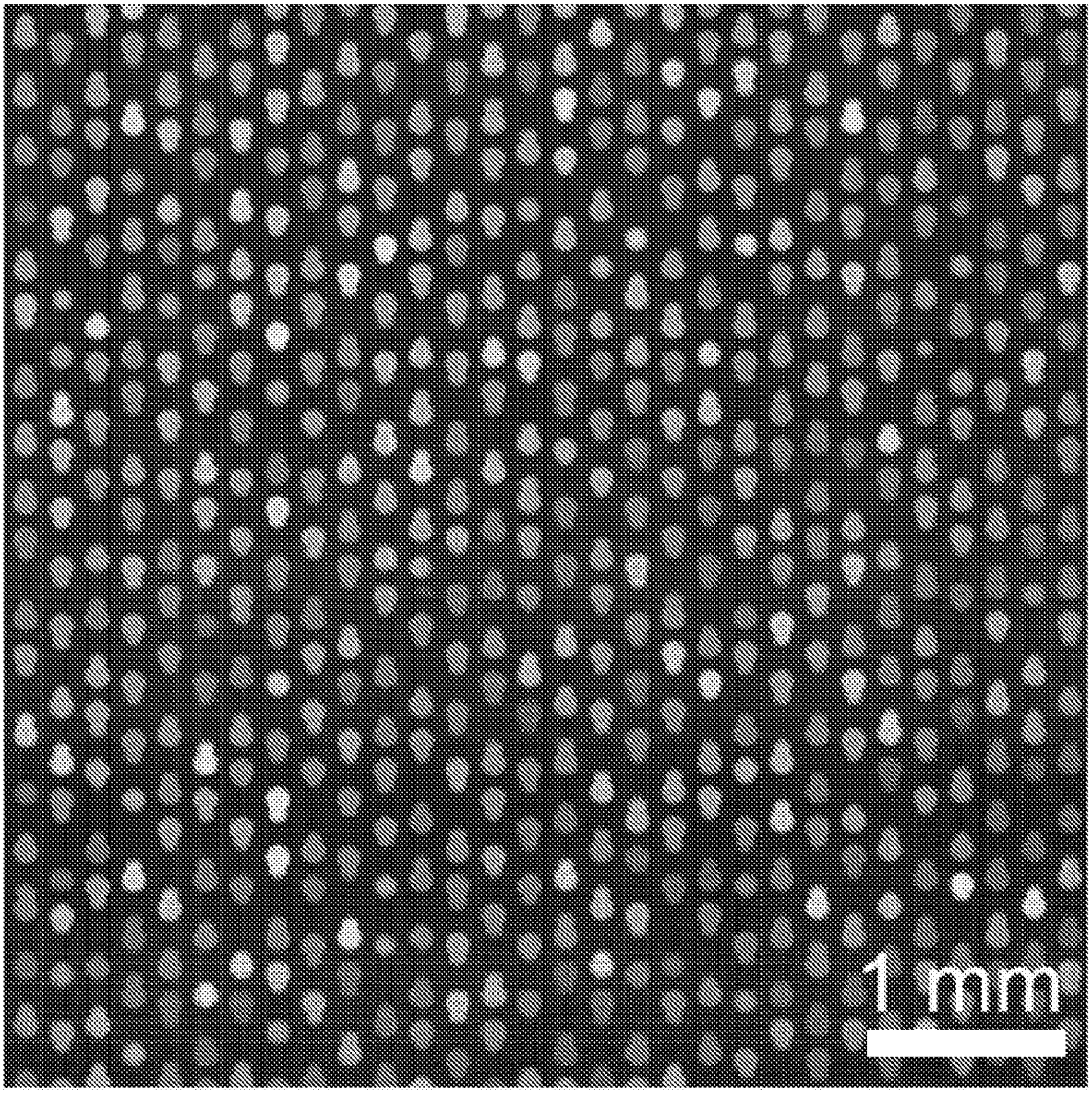
Figure 1F:
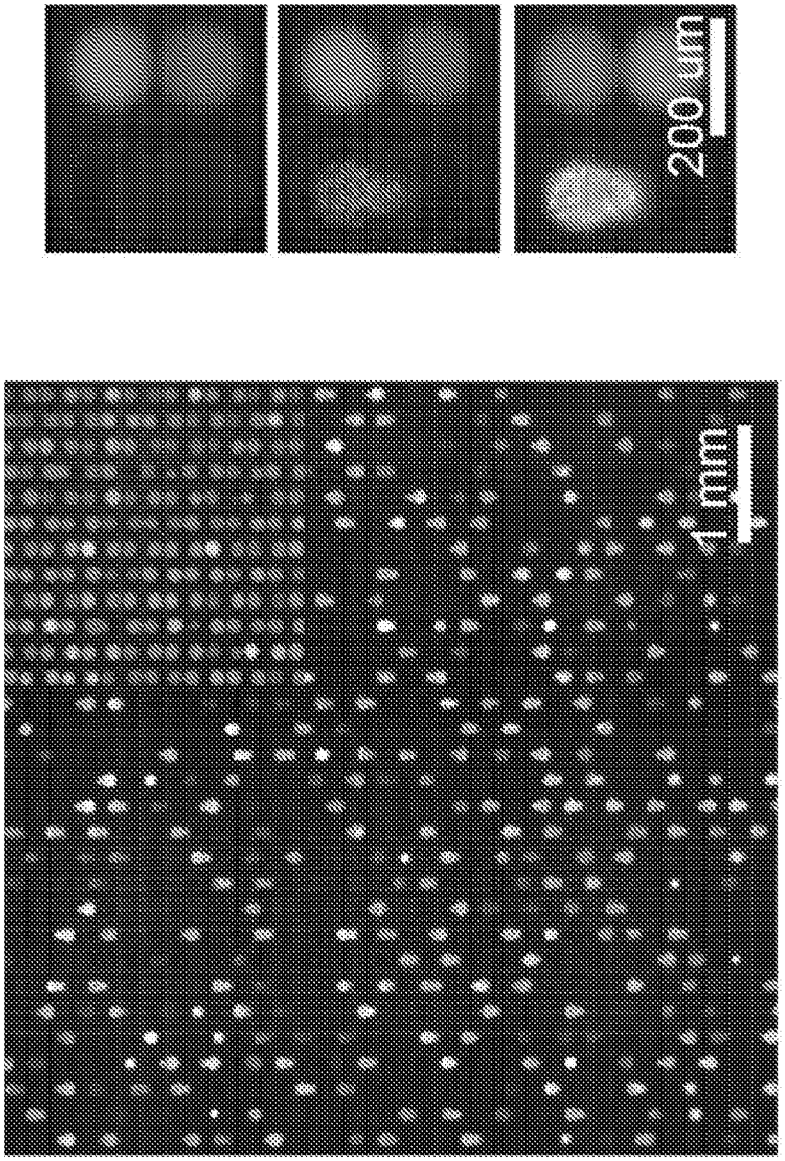
Figure 1G:
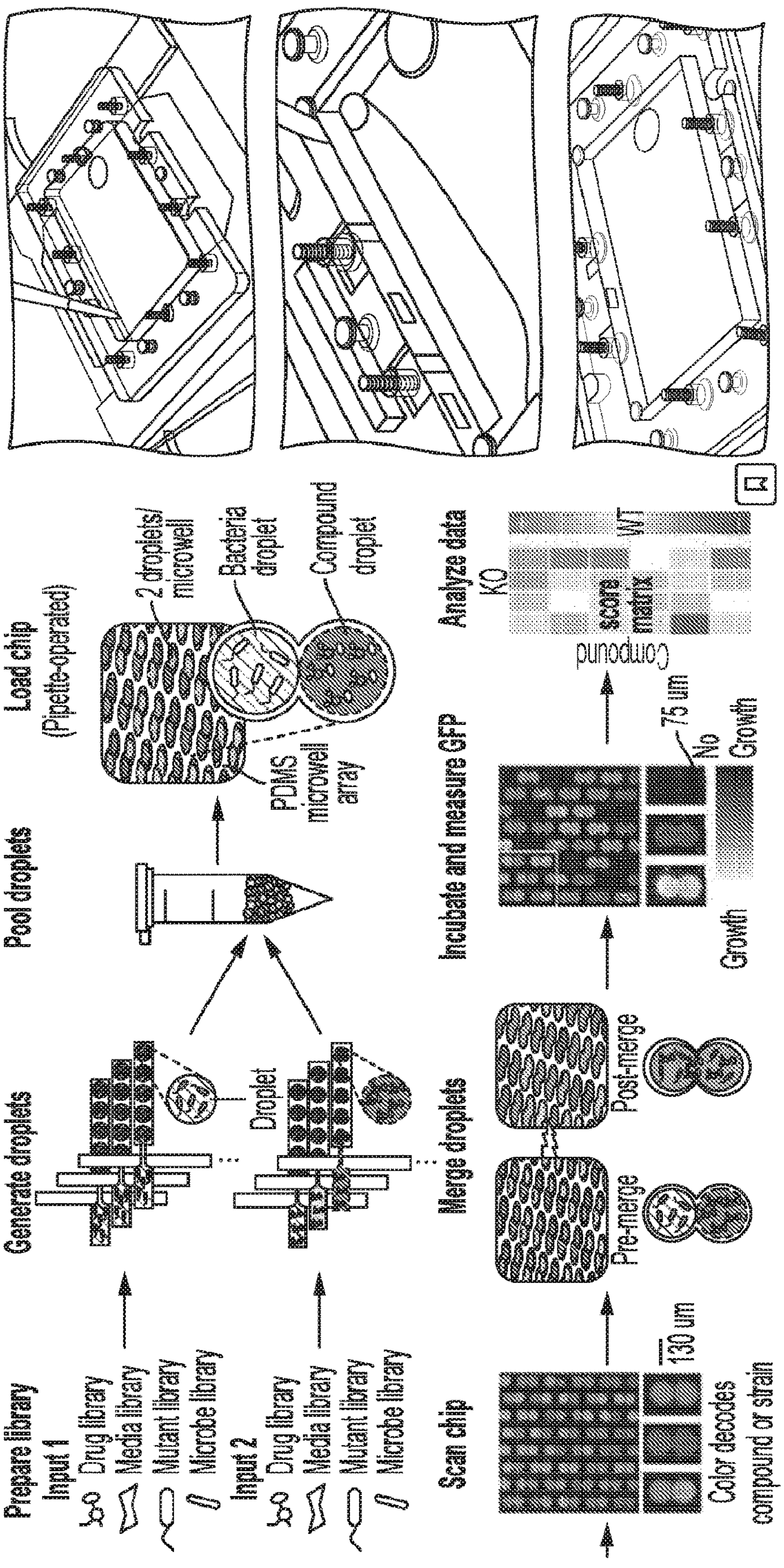
Figure 1H:
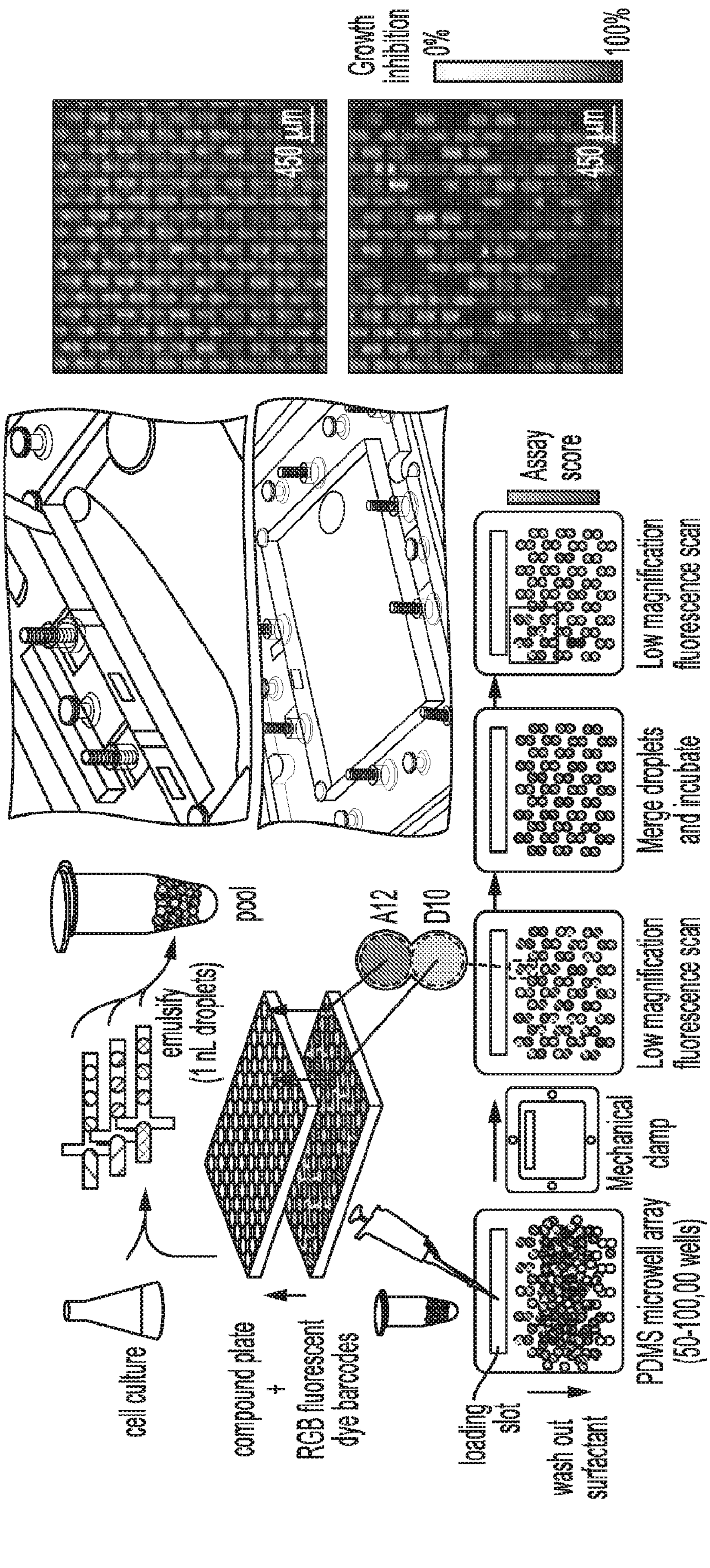

The techniques herein provide a strategy for combinatorial drug screening based on parallel droplet processing. This processing strategy makes order of magnitude improvements in logistical complexity, compound consumption, and demand for capital equipment (FIG. 1H). Recent advances in droplet microfluidics and molecular barcoding are making a major impact in genomics for processing cells and nucleic acid molecules in high speed serial streams of water-in-oil emulsion droplets. With the disclosed processing strategy, parallel handling millions of droplets reaches the scale needed for combinatorial screening. Additionally, the droplets' nanoliter volume reduces compound consumption required for screening. The present disclosure incorporates optical barcodes and parallel manipulation of droplets in large fixed-position spatial arrays to link droplet identity with assay results. A unique advantage of the present system is the parsimonious use of the compounds screened in the 2 nL assay volumes.

Figure 20:
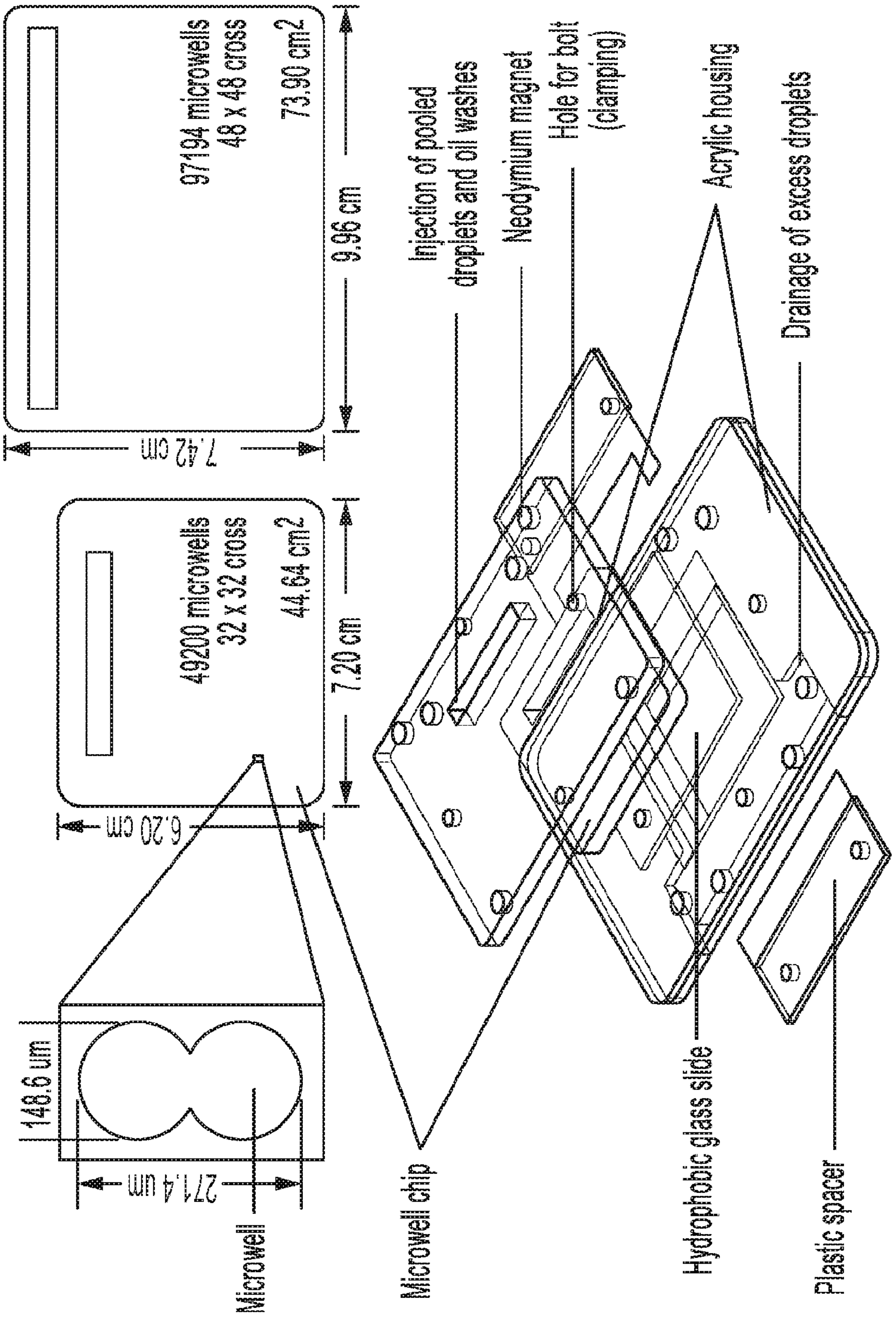
FIG. 20 is an image of a microwell array and assembly design. Two formats for microwell array designs of different sizes (49,200 wells, and 97,194 wells) were created. All data included in this work was collected with the smaller format (the larger format represented in the supplementary movie 1 and movie 2). An assembly of an acrylic clamp and plastic spacers suspends the microwell array above a hydrophobic glass slide to create a wide flow cell in which droplets are loaded. To seal the array against the glass after loading, the spacers are removed, and the acrylic housing top and bottom are bolted together.
Figure 21A:
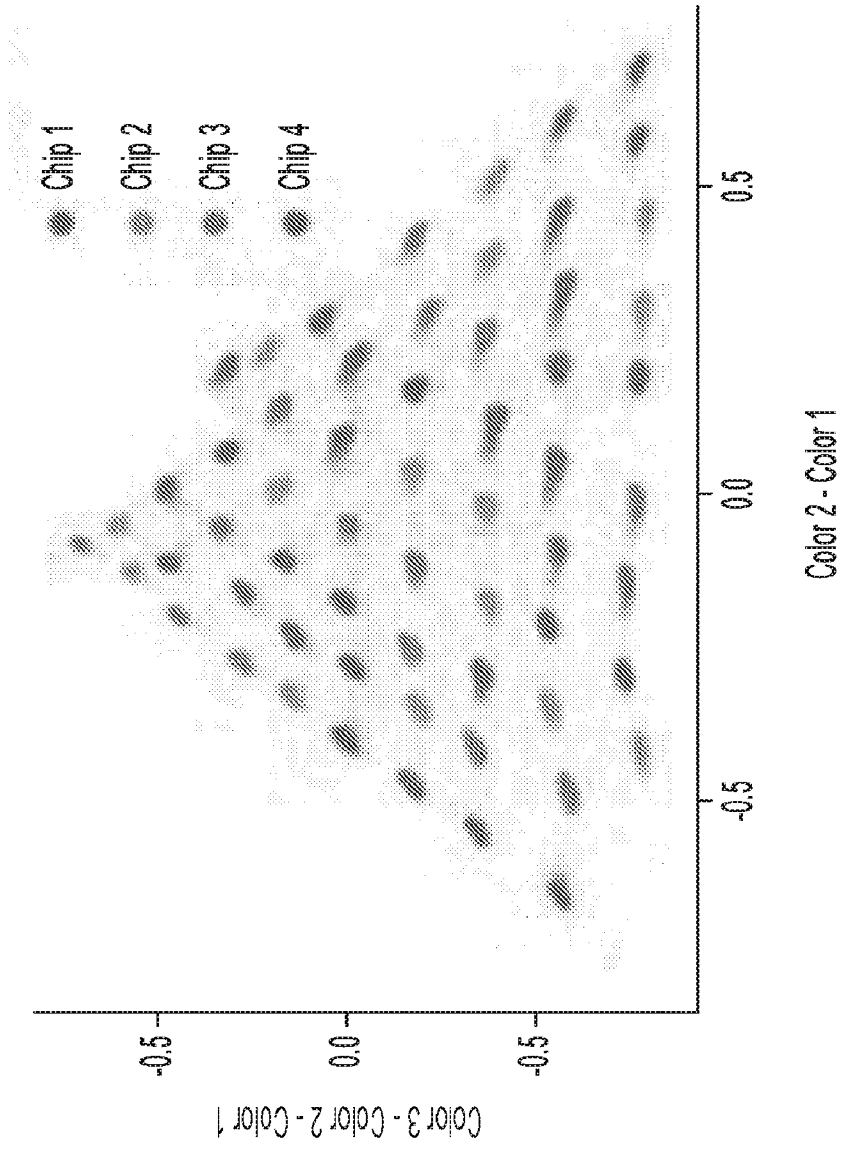
FIGS. 21A-21C are graphs of fluorescence barcoding performance.
Figure 21B:
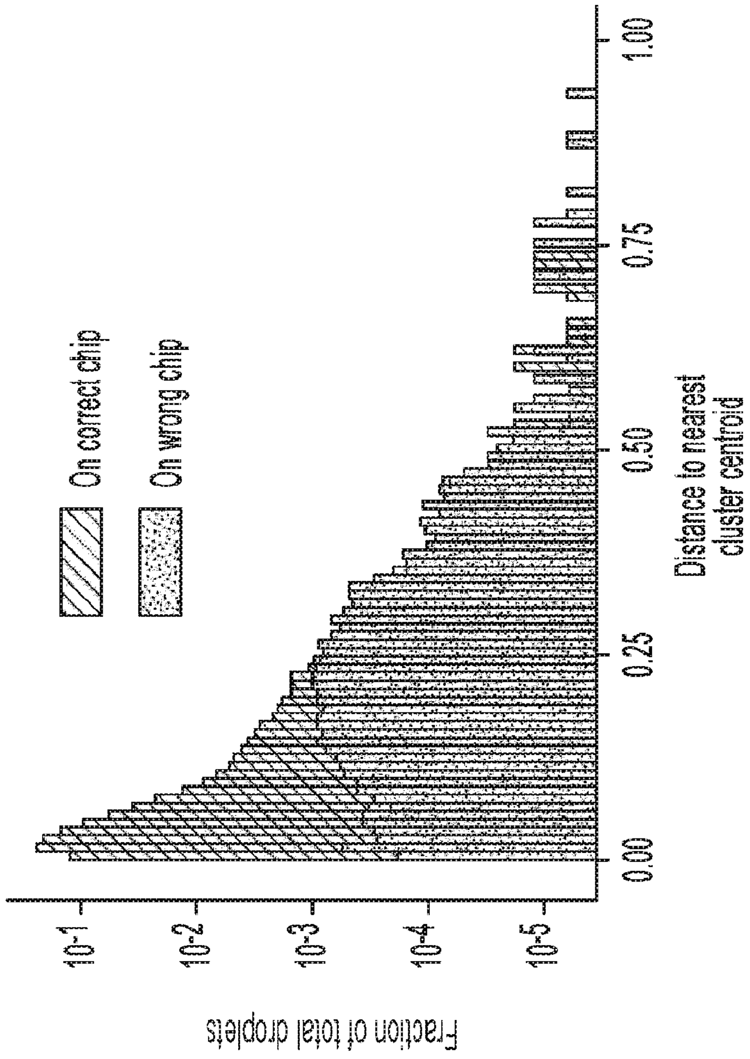
Figure 21C:
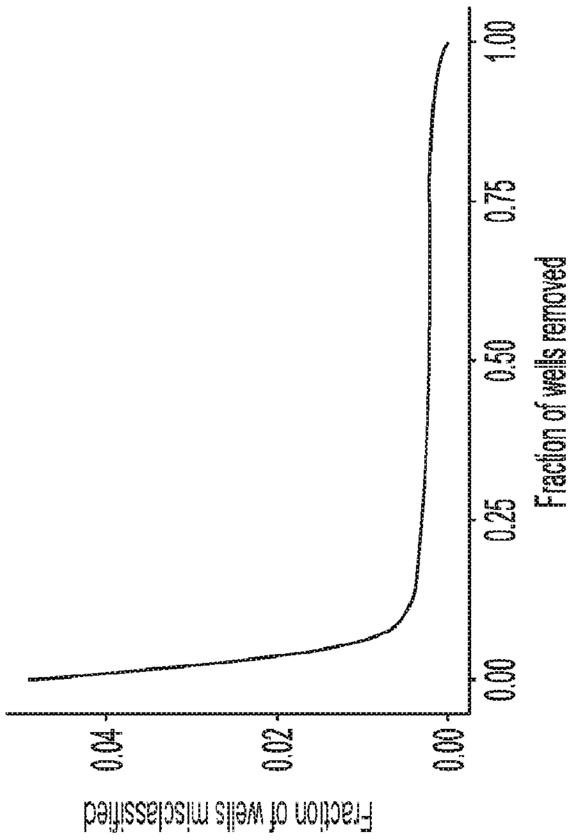

The techniques herein provide a processing platform that tests all pairwise combinations of a set of input compounds in three steps (FIG. 1H). First, concentrated compounds in well plates are combined with a color barcode, cells, and media (FIG. 1H, section I). The concentrated compounds may be barcoded by their ratio of three fluorescent dyes (e.g. red, green, blue, and the like) as shown in FIG. 1A. A sample from each well is then emulsified into 20,000 1 nanoliter aqueous droplets in a surrounding fluorocarbon oil and stabilizing surfactant (FIG. 1B). As shown in FIG. 1C, standard micropipette techniques may be used to combine the droplets into one pool (FIG. 1H, section I) and load the droplets into a microwell array such that each microwell captures two droplets at random. The array is then sealed to the glass bottom using a mechanical clamp (FIG. 1H, sections II-III; FIG. 20; Movie 1; Movie 2). The contents of each droplet are encoded by a color barcode given by the ratio of 3 fluorescent dyes pre-mixed with compounds (FIG. 1H, section I). A low-magnification (2-4×) fluorescence microscope is used to identify the pair of compounds and/or compound in each droplet and/or well (FIG. 1D; FIG. 1H, sections II and IV; FIG. 21A-FIG. 21C). To merge all pairs of droplets, a high voltage AC electric field is applied to induce droplet merging, and then incubate the array to allow for cells to respond to the pair of compounds (FIG. 1E; FIG. 1H, section II). Subsequently, the array is imaged to assay an optical phenotype (e.g. cell growth inhibition) and map this measurement to the pair of compounds previously identified in each well (FIG. 1F, FIG. 1H, sections II and IV). An overview of the screening process as described above is shown in FIG. 1G.

Figure 2A:
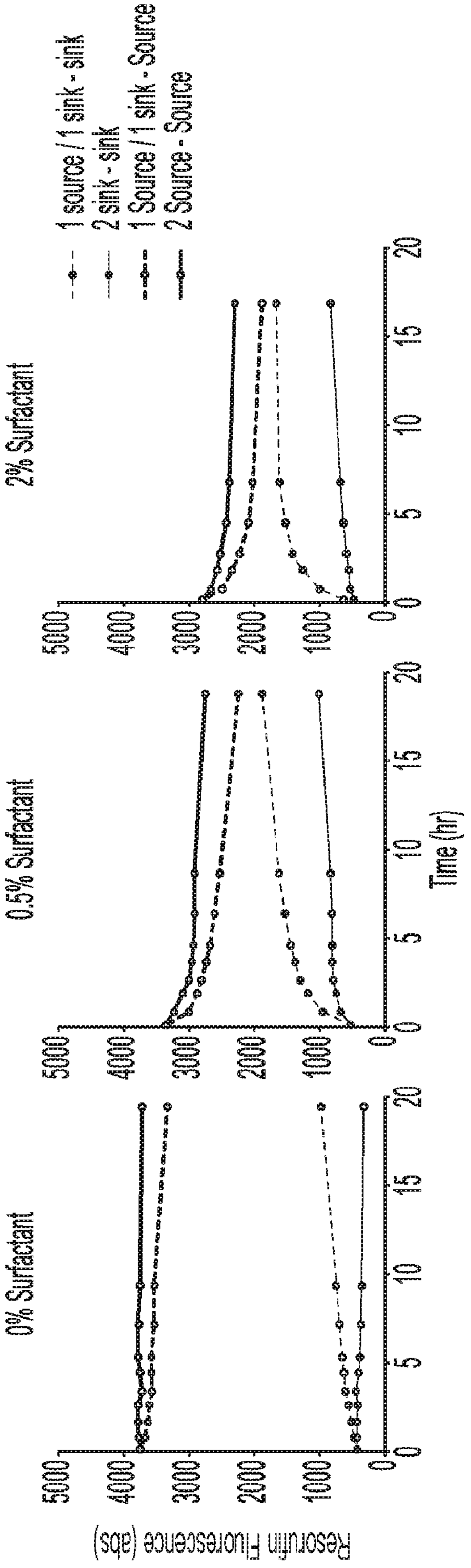
Figure 2B:
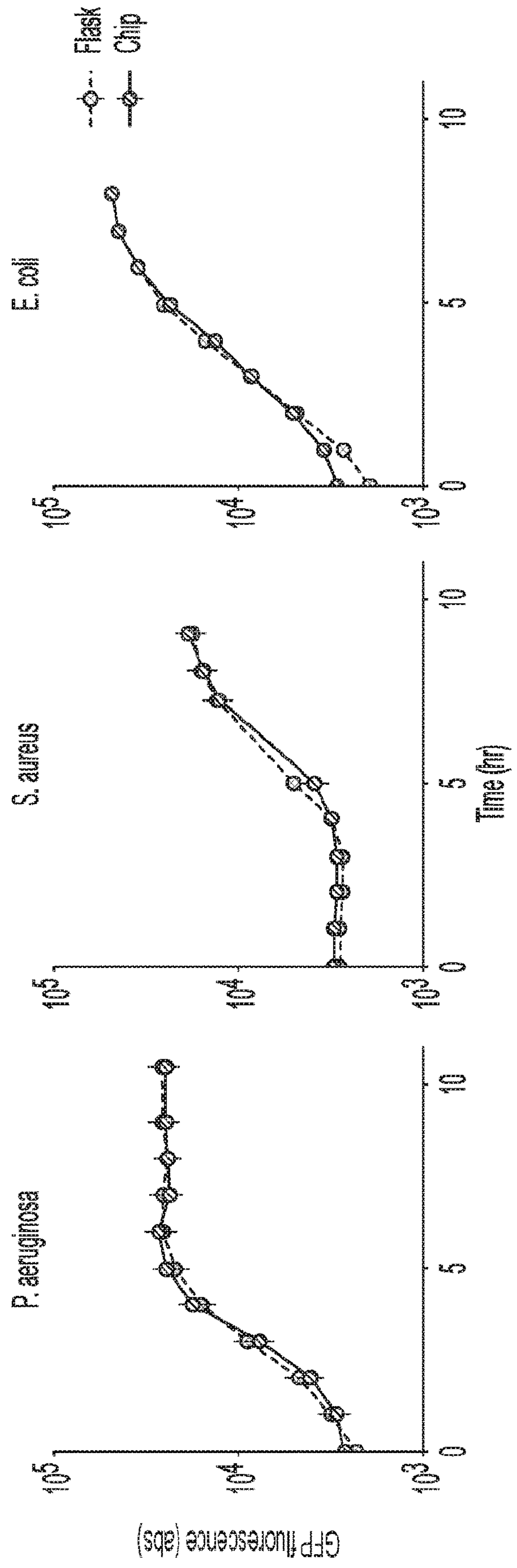
Figure 2C:
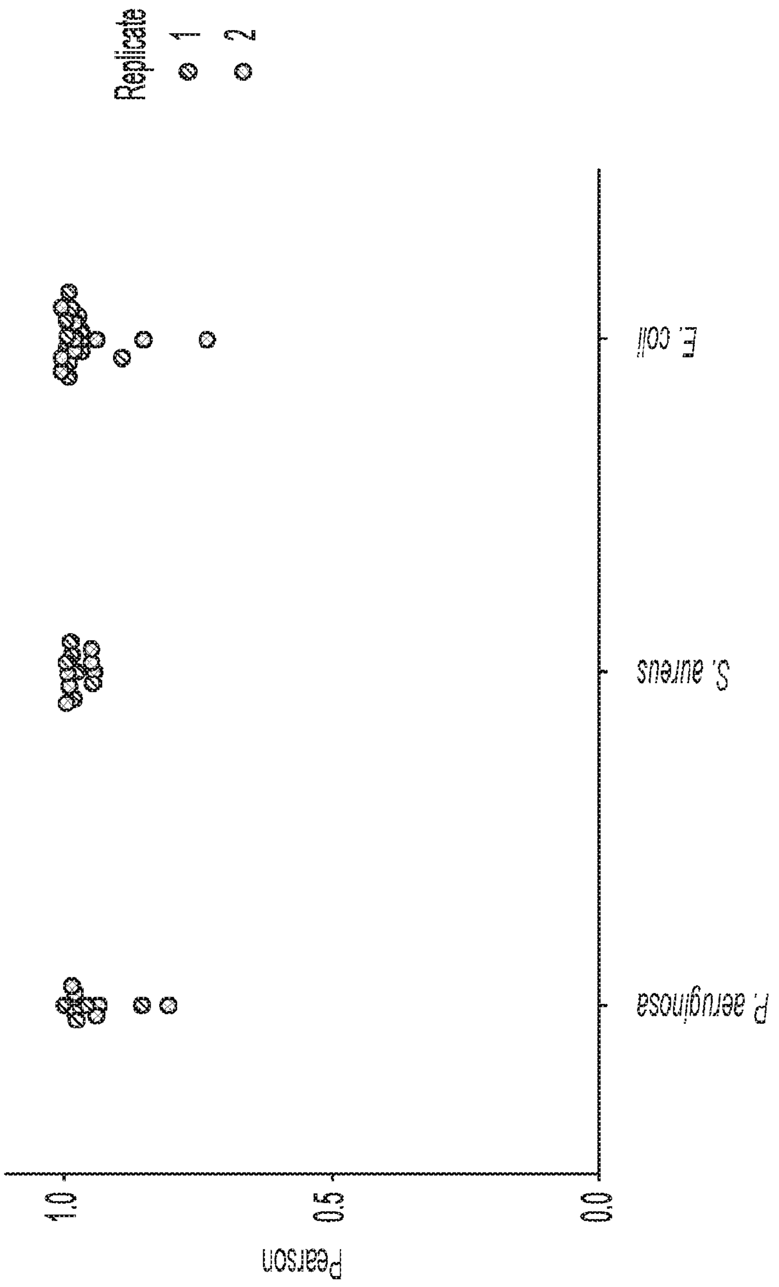
Figure 2D:
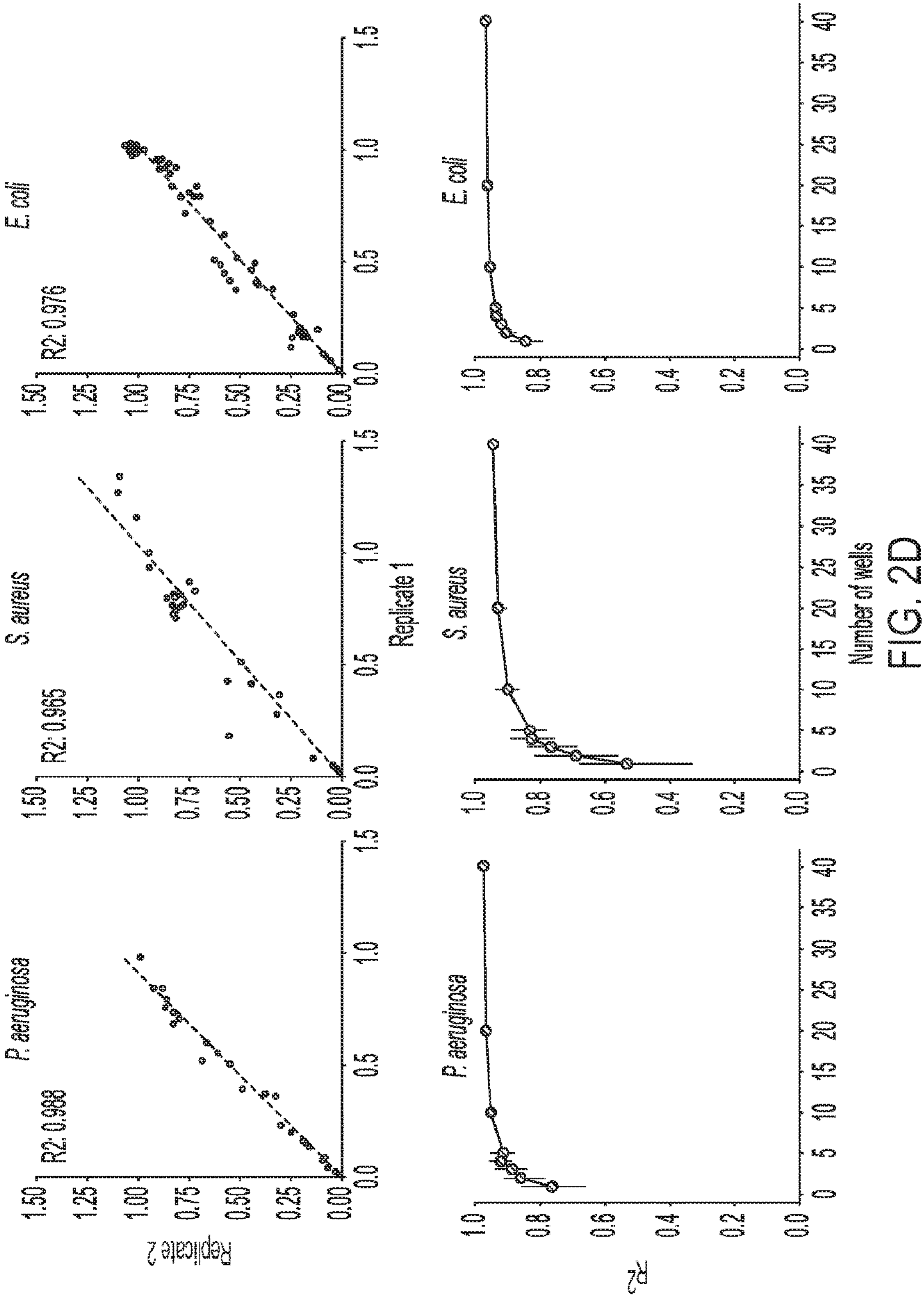
Figure 2F:
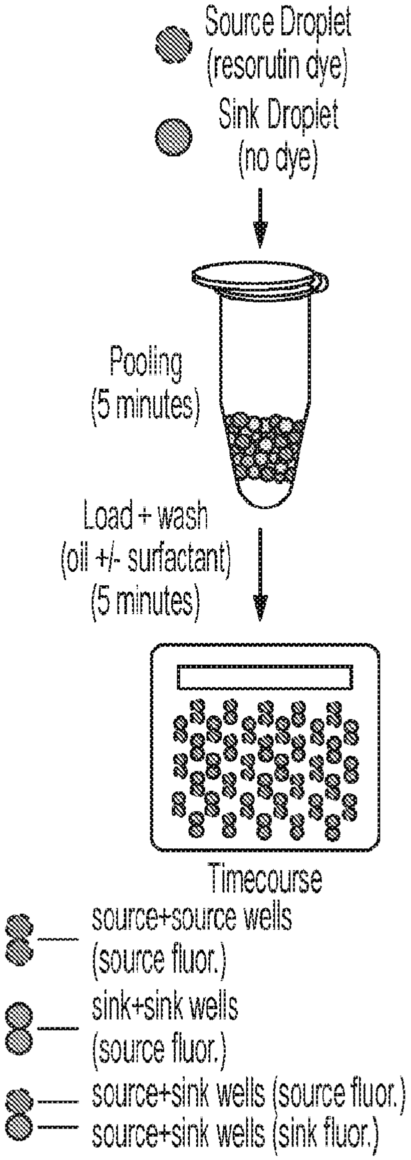
Figure 2G:
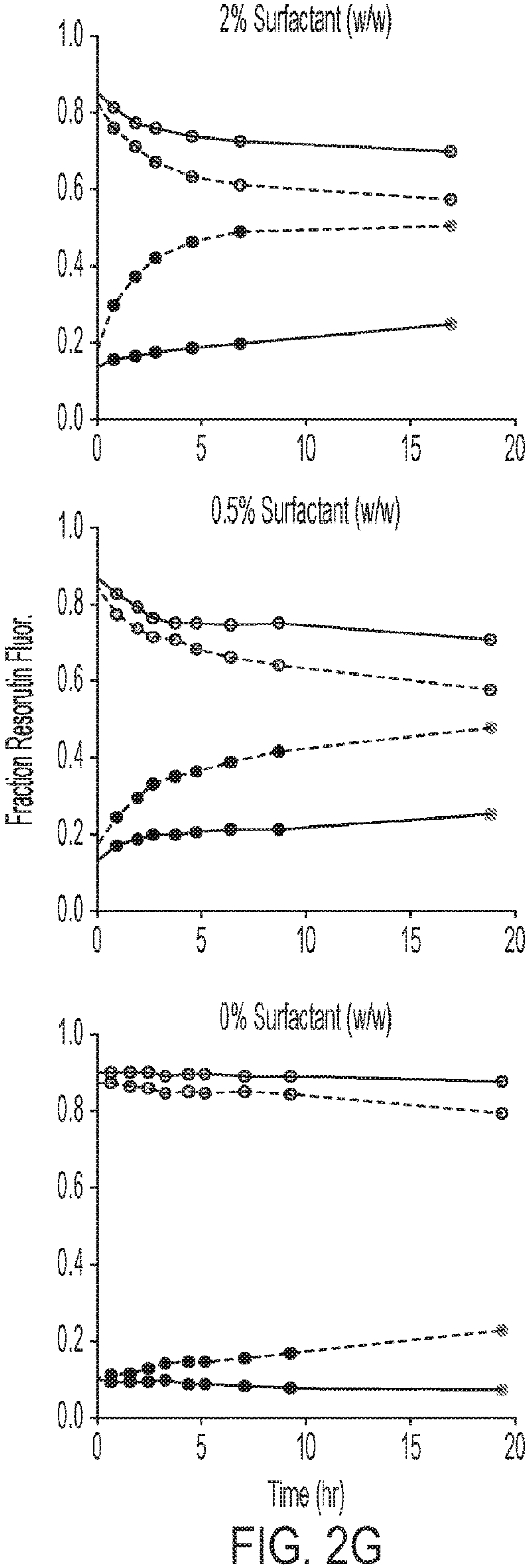
Figure 22A:
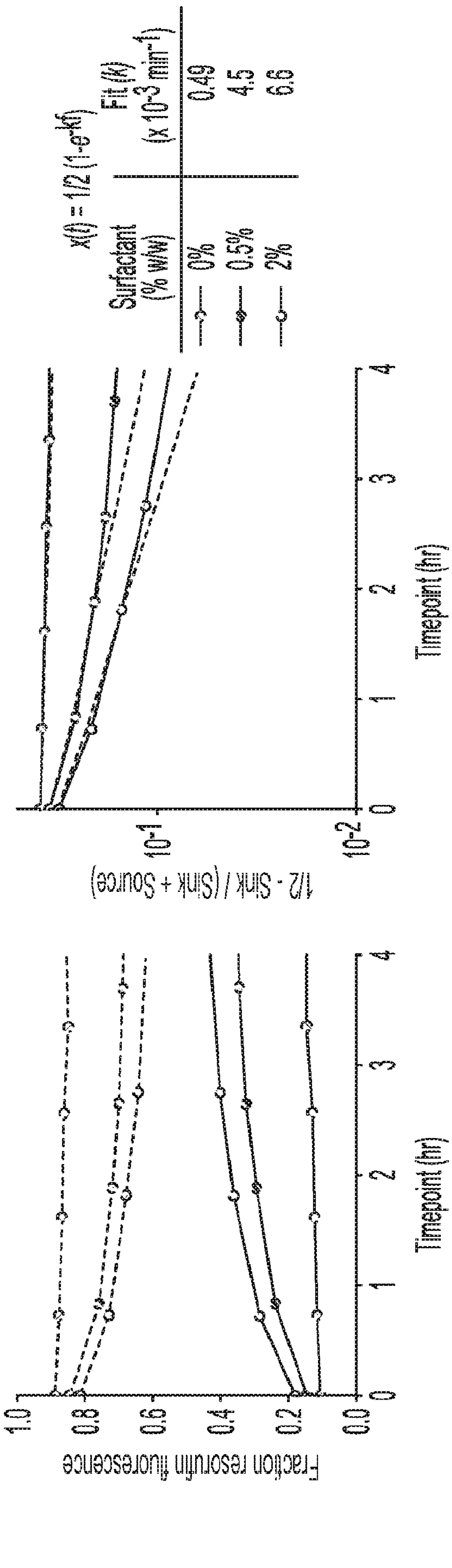
FIGS. 22A-22C are graphs of expected exchange kinetics during pooling phase.
Figure 22B:
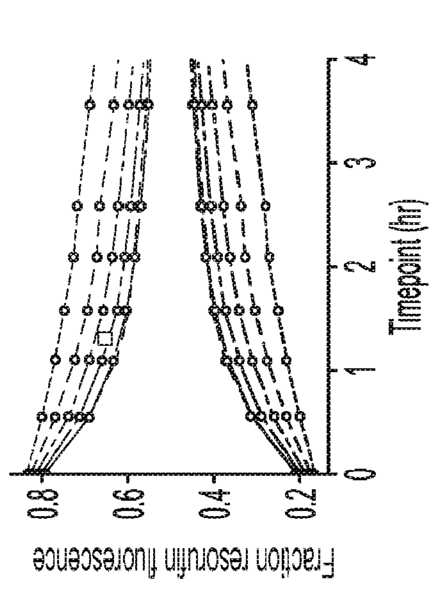
Figure 22B:
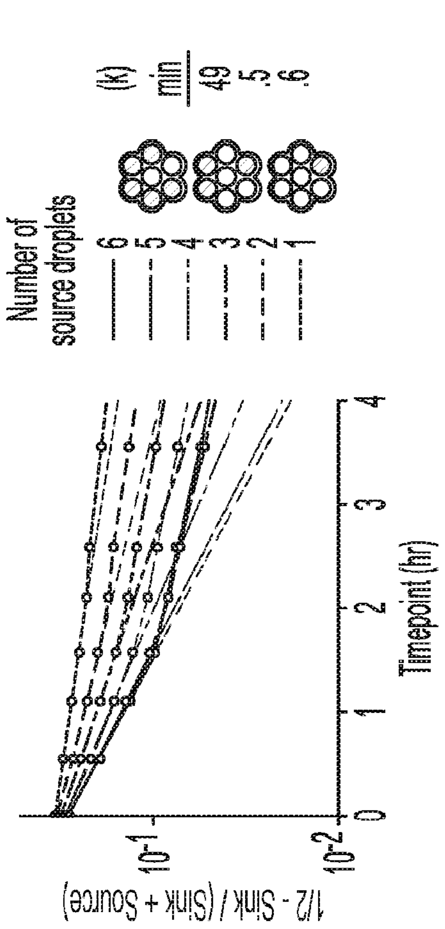
Figure 22C:
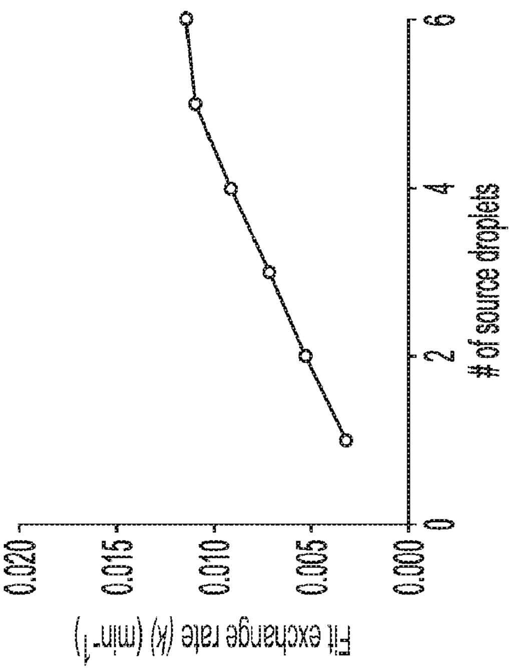
Figure 22C:
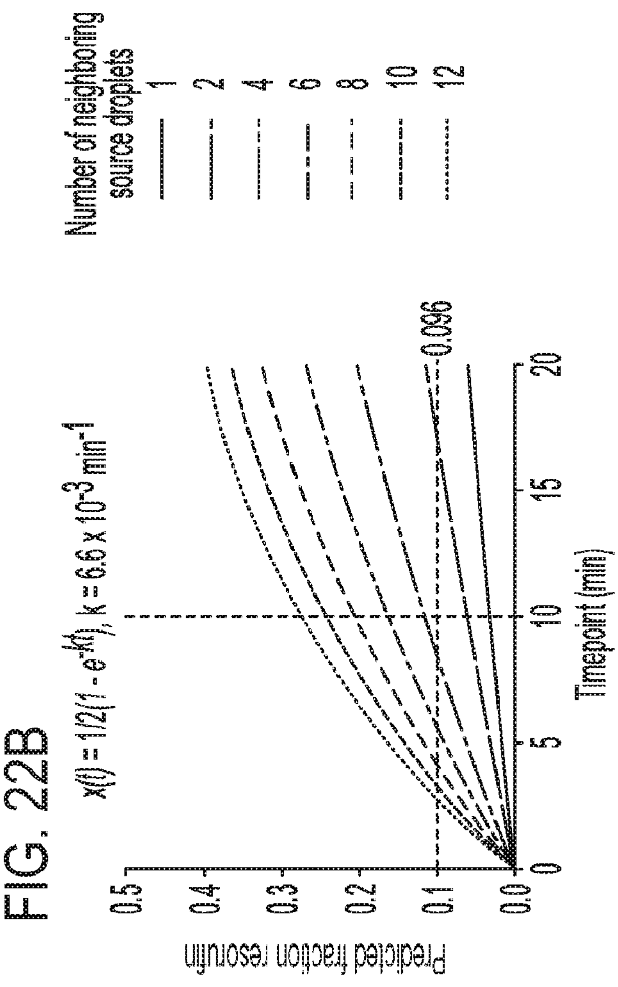

The platform was designed to overcome a critical challenge in droplet microfluidics that has heretofore prevented cell-based compound screening, the exchange of small molecules between droplets on assay-relevant timescales (FIG. 2A). The dynamic equilibrium of surfactant molecules between the aqueous-oil droplet interface and reverse-micelles in the oil phase can carry small molecules between droplets. The design limits this opportunity for compound exchange after loading by compartmentalizing droplet pairs into microwells and subsequent depletion of free surfactant by washing (FIG. 1H, sections I-II). This process occurs as droplets are pooled and loaded into solid PDMS compartments (FIG. 1C). The exchange of a fluorescent dye (e.g., resorufin) between droplets in different wells (FIG. 1H, section II; FIG. 2F) was compared to droplets that share the same microwell as a model of conventional droplet systems. Without depleting surfactant, the microwells limited resorufin exchange compared to exchange between pairs of droplets in the same well (FIG. 2G). Depleting free surfactant further decreased exchange to levels below the detection limit of the experiment (FIG. 2G). In measuring exchange during the pooling and loading process (FIG. 1H, section I; FIG. 2F), the experiments predicted <5% exchange under screening conditions for compounds of similar hydrophobicity to resorufin (FIG. 2G; FIGS. 22A-22C).

In embodiments, once loaded, surfactant is depleted from the system by washing with 0% w/w surfactant and compartmentalization restricts subsequent diffusion of surfactant micelles between wells (FIG. 2A). To measure exchange occurring at each step of the process, the transfer of a fluorescent dye (resorufin) to empty droplets was measured. A ~3% exchange over 10 minutes of pooling and loading was predicted, and no further detectable exchange after loading into wells and depleting surfactant was observed (FIG. 2A).

Example 2

As a first application of the platform, fluorescence-based, growth inhibition phenotypic screening assays, were developed for the three model organisms, bacterial pathogens most often used in antibiotic discovery, *Staphylococcus aureus, Pseudomonas aeruginosa*, and *Escherichia coli*. For each organism, a comparison of growth rates (FIG. 2B, FIG. 2H), antibiotic drug responses (FIG. 2C, FIG. 2I, FIG. 2K, and FIGS. 23-25), and data quality of the microdroplet system with conventional Erlenmeyer flask and microplate broth culture methods were performed (FIG. 2D, FIG. 2I, FIG. 2J, FIG. 2K). In embodiments, growth measurements were determined by measurement of constitutively expressed GFP rates. For example, *P. aeruginosa* cultured on the disclosed platform showed a GFP doubling time of 56+/−5 min on the platform, compared to 62+/−3 min in an Erlenmeyer flask, and other organisms showed similar comparability (FIG. 2B, FIGS. 26A-26C).

Figure 2H:
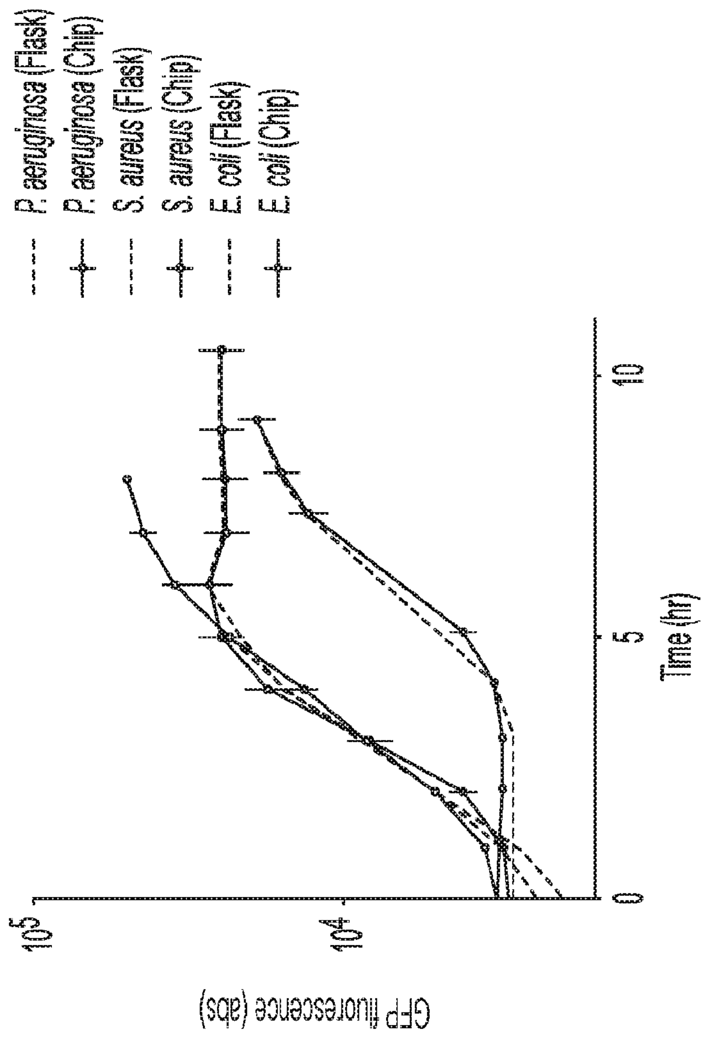
Figure 23:
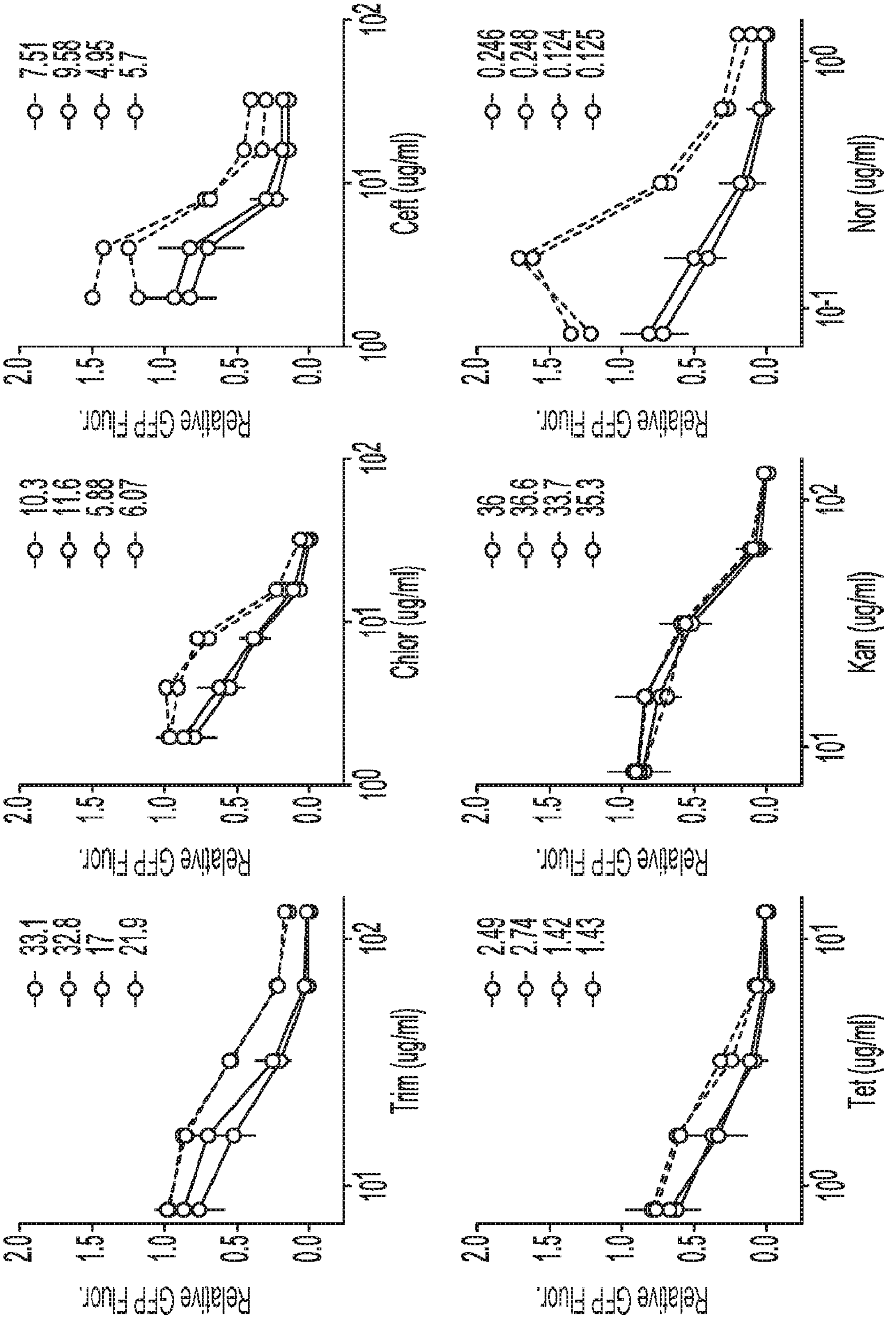
FIG. 23 is a graph of dose response curves. Antibiotic dose response comparison between 96-well plates and the microwell array platform for *P. aeruginosa*. Five-point dose response curves were tested for 6 different antibiotics against *P. aeruginosa* and compared responses in 96-well plates (dotted) with the microwell array platform (solid), for two technical replicates (replicate 1: blue, replicate 2: red). All data are normalized to no-antibiotic controls. Error bars represent standard deviations of replicate microwells for each condition, with samples size (median (25th percentile, 75th percentile)) of n=127 (100, 147.5) (replicate 1), and n=172 (149.5, 193). Legends represent fit IC50 (μg/mL) values for each curve, obtained by non-linear least squares fitting of the Hill curve to each dose response. Data points and IC50 values are also reported in FIG. 2K, FIG. 2J, and FIG. 26A-FIG. 26C.
Figure 24:
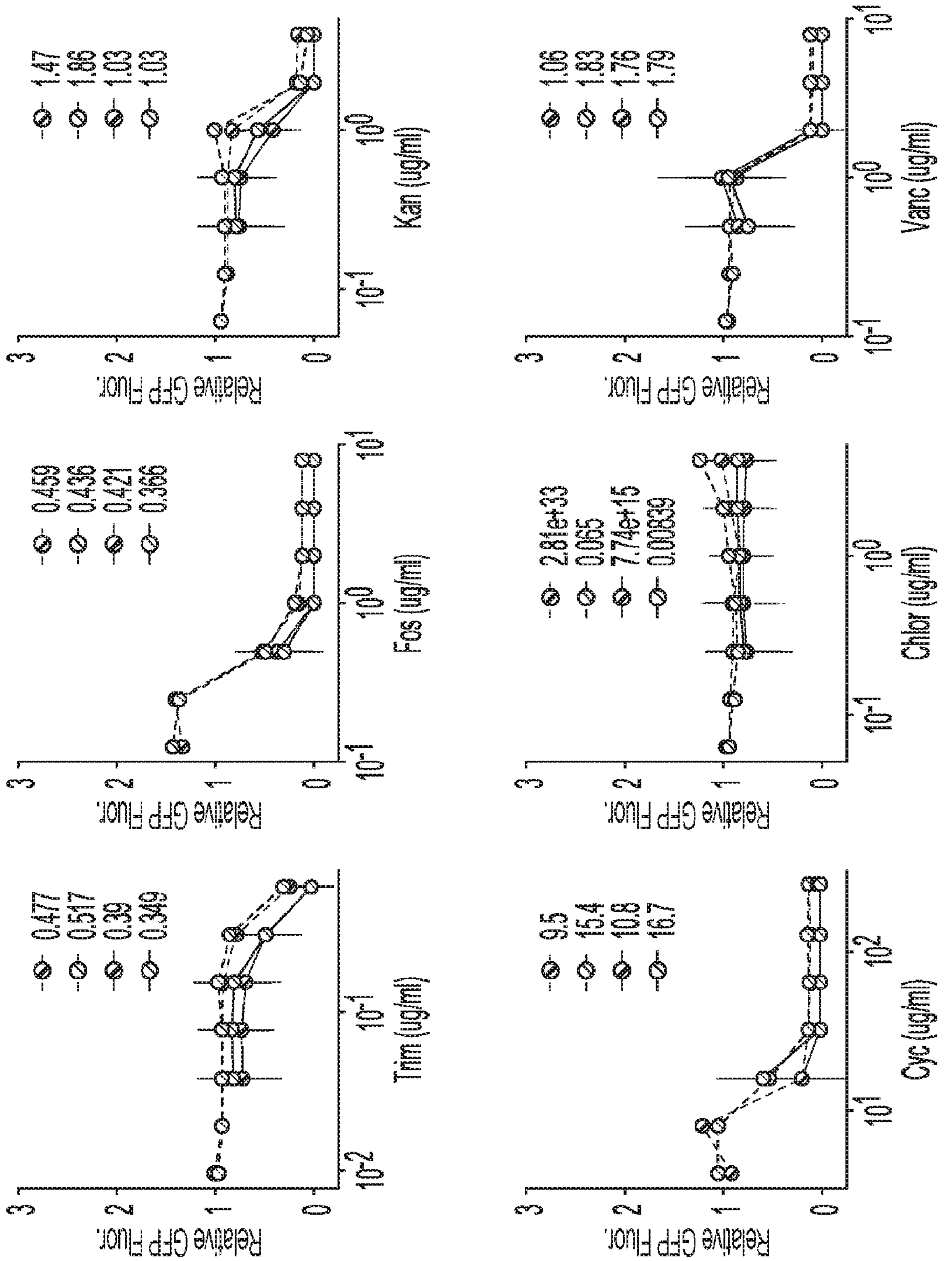
FIG. 24 shows an antibiotic dose response comparison between 96-well plates and the microwell array platform for *S. aureus*. Five-point dose response curves were tested for 12 different antibiotics against *S. aureus* and compared responses in 96-well plates (dotted) with the microwell array platform (solid), for two technical replicates (replicate 1: blue, replicate 2: red). All data are normalized to no-antibiotic controls. Error bars represent standard deviations of replicate microwells for each condition, with samples size (median (25th percentile, 75th percentile)) of n=157.5 (120.25, 190) (replicate 1), and n=142.5 (119, 165.5). Legends represent fit IC50 (μg/mL) values for each curve, obtained by non-linear least squares fitting of the Hill curve to each dose response. Data points and IC50 values are also reported in FIG. 2K, FIG. 2J, and FIG. 27.
Figure 25:
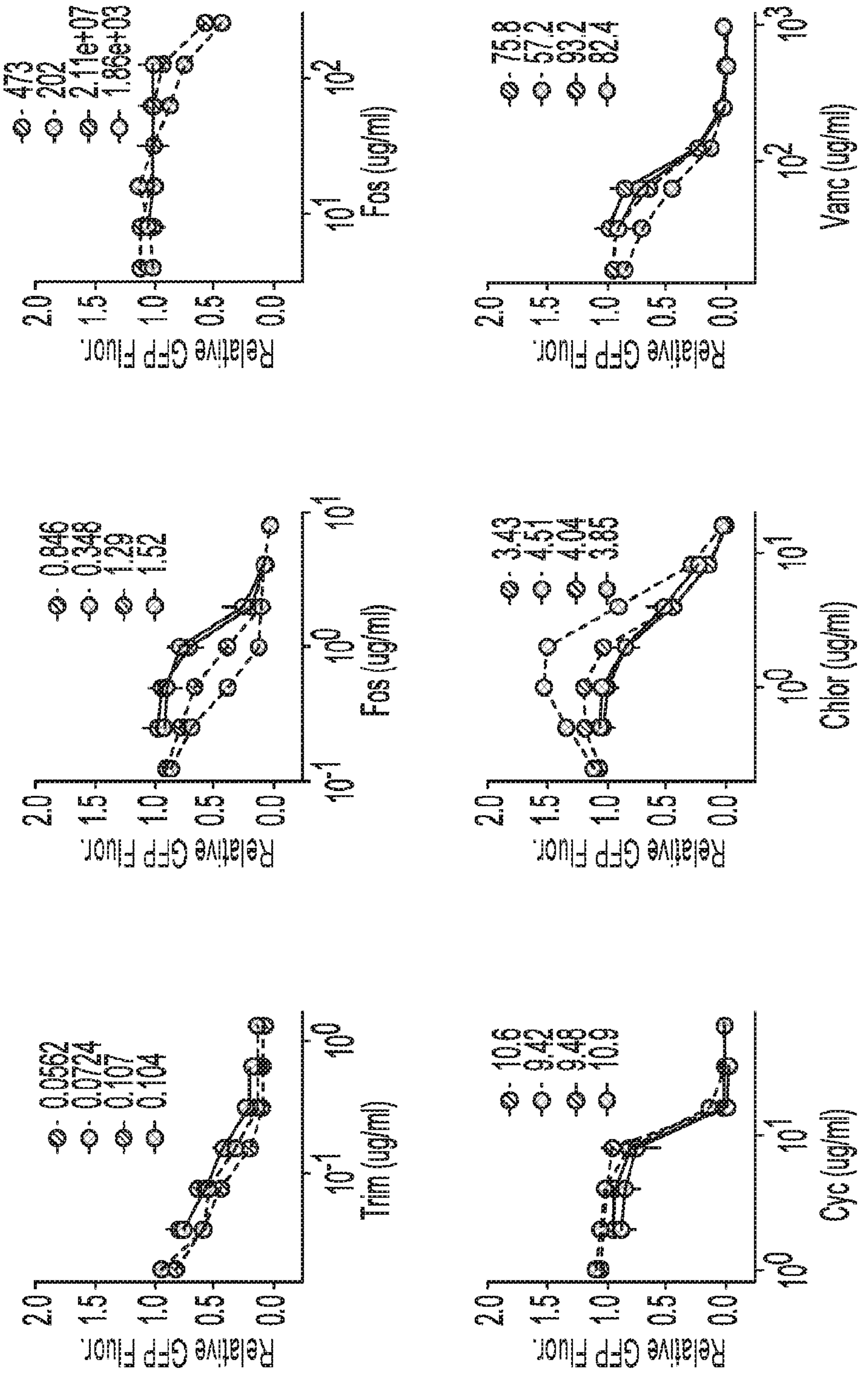
FIG. 25 shows an antibiotic dose response comparison between 96-well plates and the microwell array platform for *E. coli*. Five-point dose response curves were tested for 12 different antibiotics against *E. coli* and compared responses in 96-well plates (dotted) with the microwell array platform (solid), for two technical replicates (replicate 1: blue, replicate 2: red). All data are normalized to no-antibiotic controls. Error bars represent standard deviations of replicate microwells for each condition, with samples size (median (25th percentile, 75th percentile)) of n=171 (137.25, 208.25) (replicate 1), and n=130 (107.5, 149). Legends represent fit IC50 (μg/mL) values for each curve, obtained by non-linear least squares fitting of the Hill curve to each dose response. Data points and IC50 values are also reported in FIG. 2K, FIG. 2J, and FIG. 26A-FIG. 26C.
Figure 25:
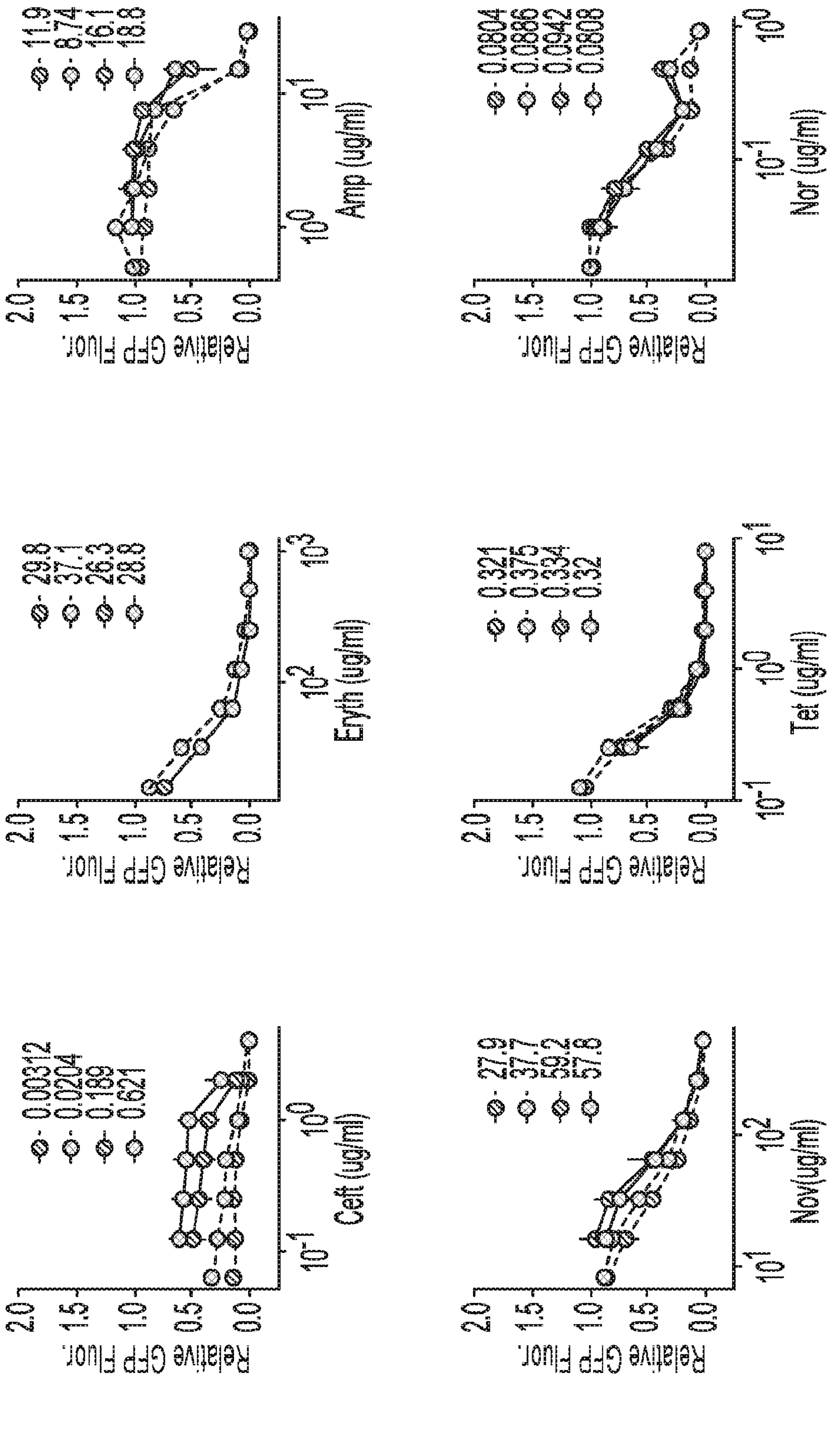
Figure 26A:
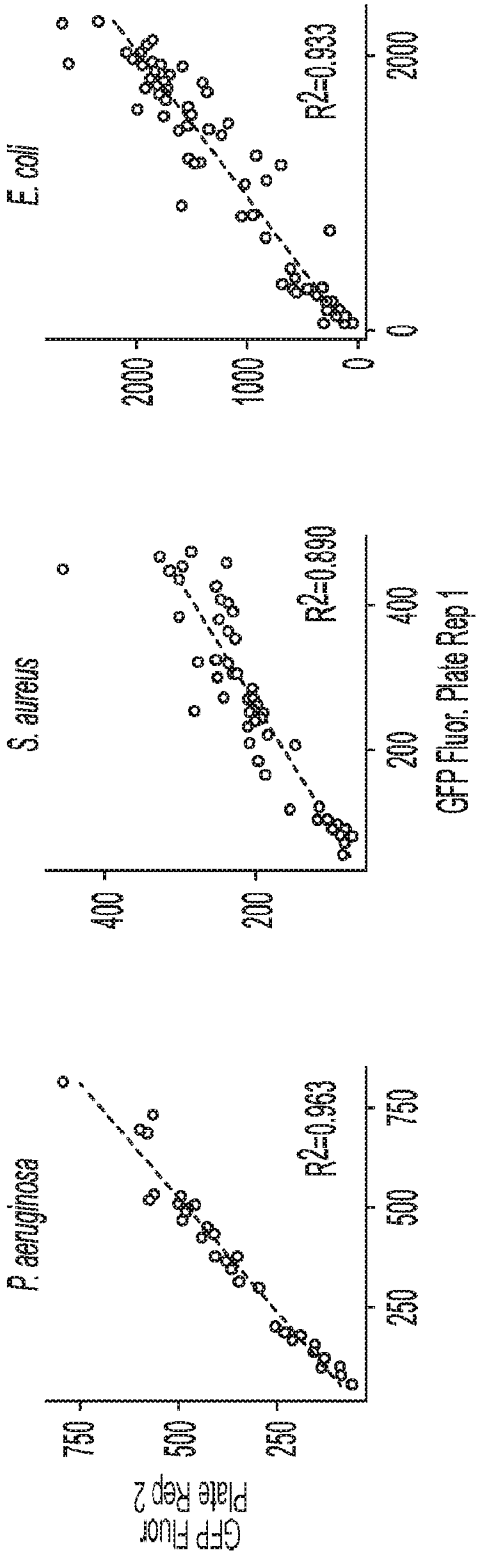
FIGS. 26A-26C show graphs of technical noise estimation of microwell and 96-well plate assays.
Figure 26B:
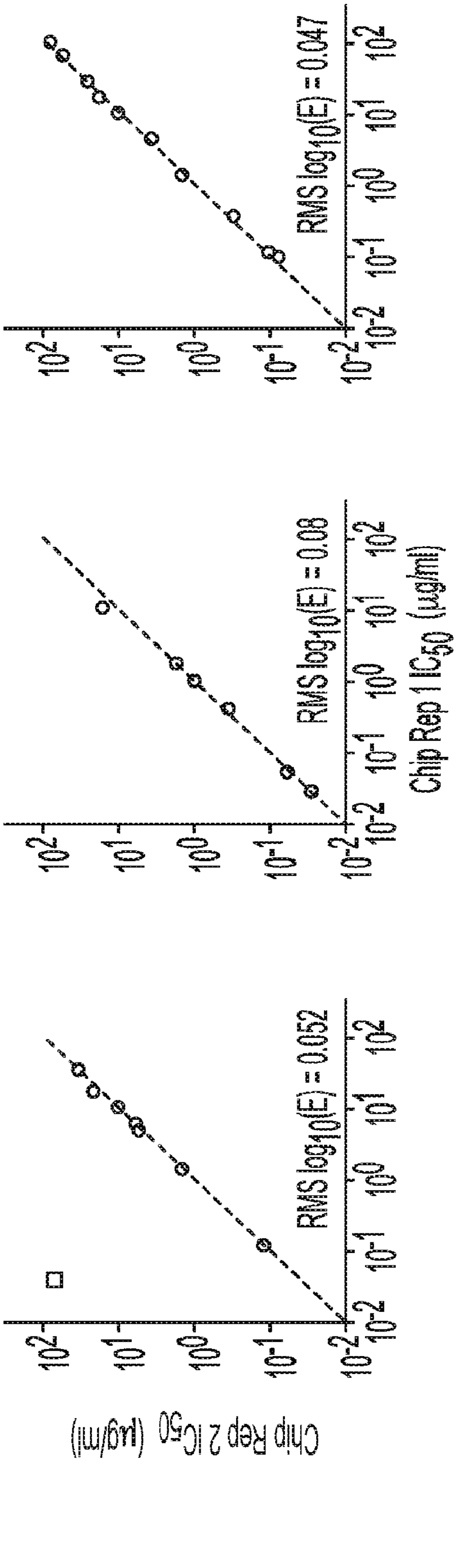
Figure 26C:
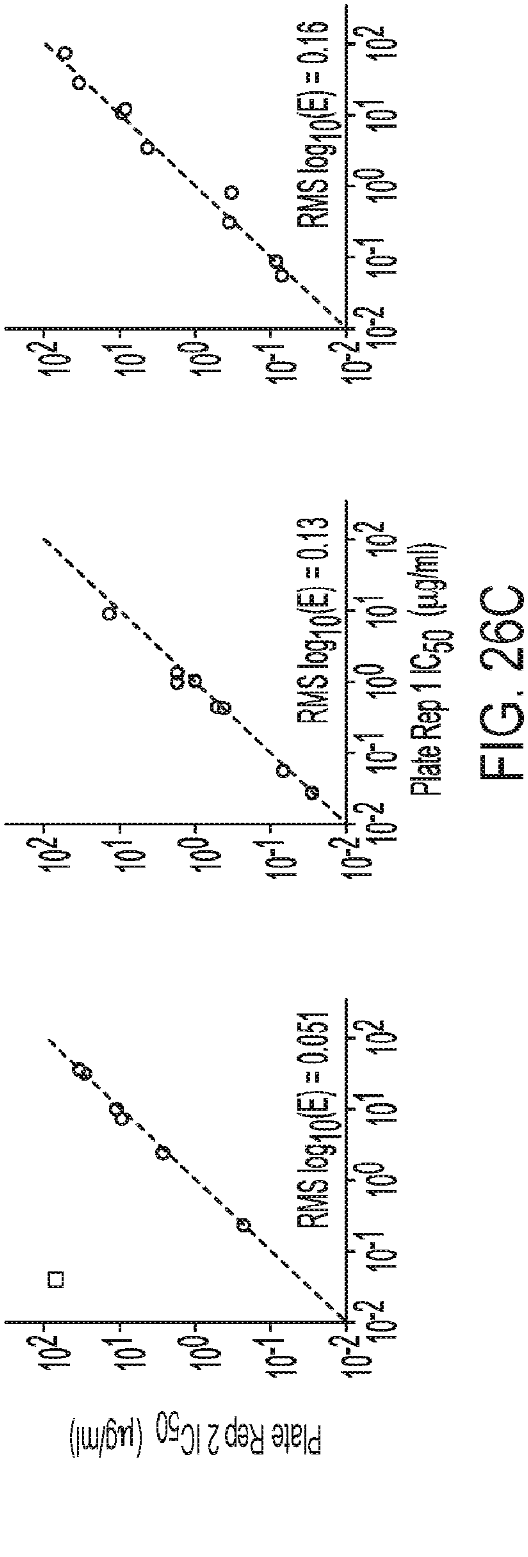

The platform faithfully recapitulates growth curves and antibiotic response curves compared to conventional Erlenmeyer flasks and 96-well broth culture plates (FIG. 2H, FIG. 2I, FIG. 2J, FIG. 2K). Each organism cultured on the microarray platform showed comparable growth dynamics (monitored by GFP) to growth in an Erlenmeyer flask (FIG. 2H). For the experiments, 6-12 antibiotics (see Methods and Materials; FIGS. 23-25) representing different antimicrobial classes with different chemical classes and biochemical targets were chosen, were compared, and had their $IC_{50}$ values estimated from 6-point response curves for the three model pathogens. In assays, these antibiotics were used to measure correlations of 5-point response curves between platforms for each of the three tested model pathogens, *E. coli, S. aureus*, and *P. aeruginosa*. ~90% of correlations between response curves showed ρ>0.9 (Pearson, p value). (FIG. 2C). The microdroplet platform gave results that corresponded closely to the same fluorescence assay in 96-wall broth culture format with similar reproducibility (FIG. 2K, 2J; FIG. 23-25).

Figure 2I:
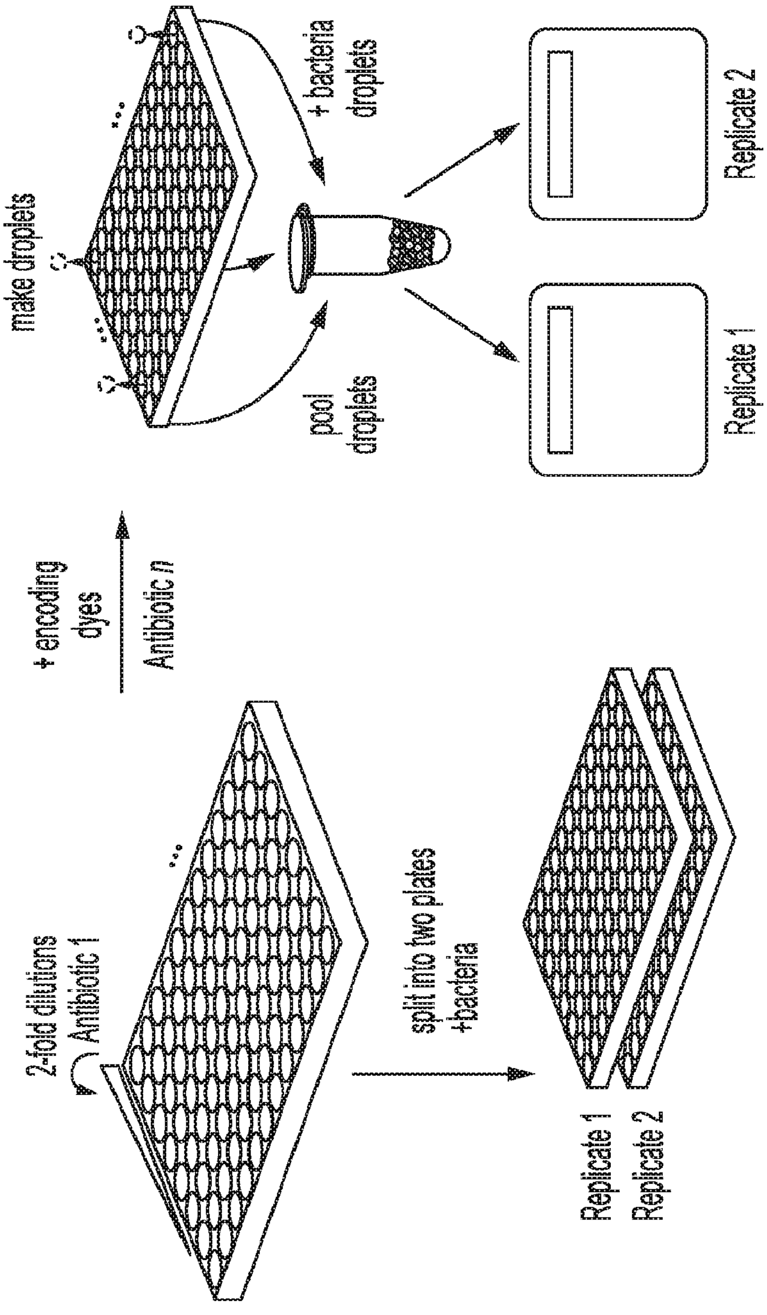
Figure 2K:
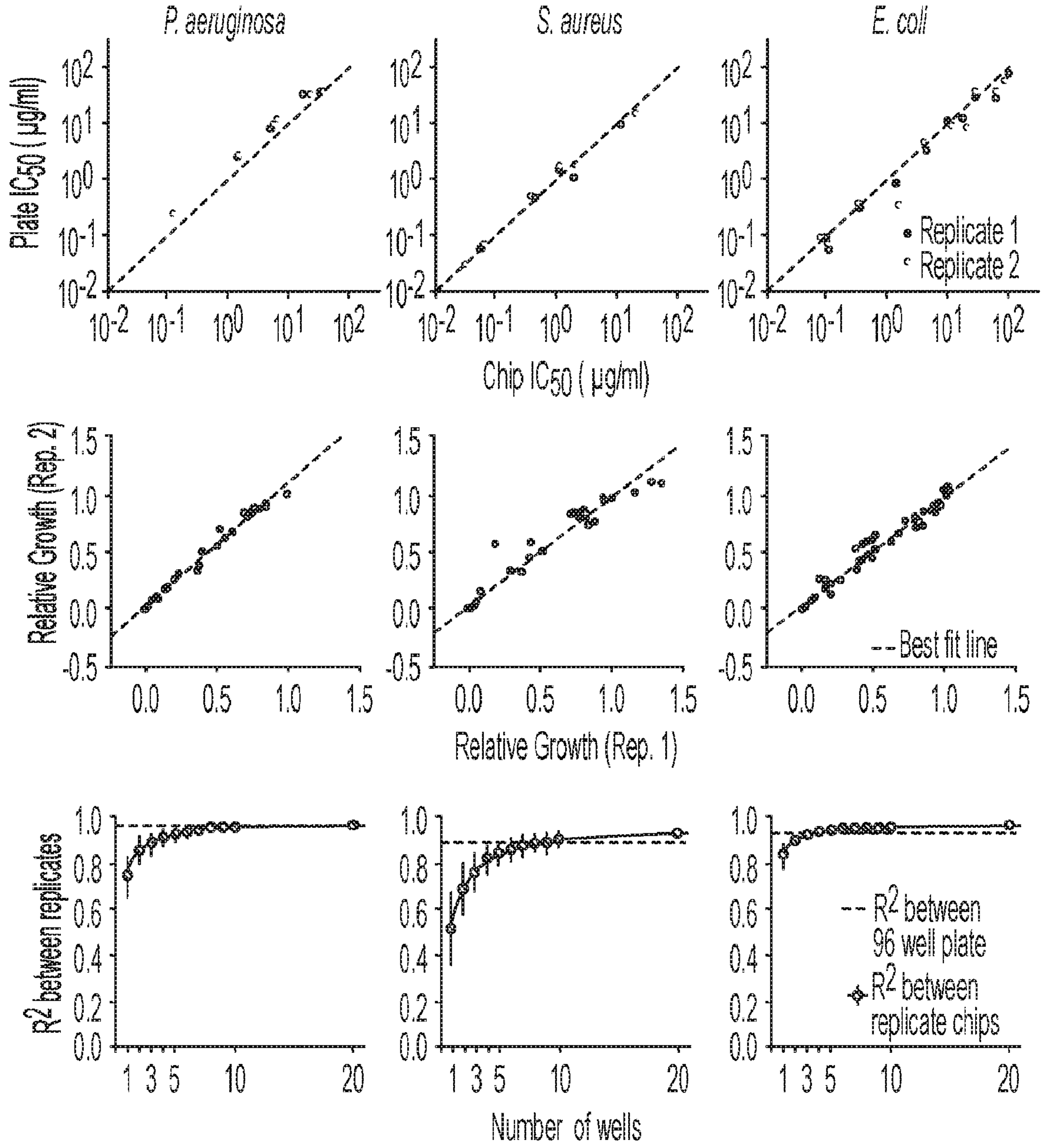

High throughput screening is extremely sensitive to assay noise as hits must be at minimum roughly as frequent as false positives. Noise must also be comparable to conventional 96-well or 384-well assays. Since compound pairs are stochastically assembled in the system, noise levels are tunable by averaging over microwells containing the same compound pair. To characterize this relationship as well as noise contributed by variability between different runs, antibiotic response curves were measured the same pool of droplets loaded across two technical replicate microwell arrays (FIG. 2D; FIG. 2I, FIG. 2J, FIG. 2K). It was observed that noise levels ($R^2$ values between replicates) were comparable to the same fluorescence-based growth assay 96-well broth culture plates for each organism (FIGS. 26A-26C), and there are diminishing improvements past replication levels past 5-10 wells (FIG. 2K).

To evaluate the ability to detect synergy between compounds or compound pairs, a canonically synergistic pair of compounds was tested (ampicillin, a beta-lactam antibiotic, and sulbactam, a beta-lactamase inhibitor) for activity against *P. aeruginosa* (FIG. 2E; FIG. 27. Synergy is commonly assessed by crossing all pairs of a dilution series of two drugs in a "checkerboard" assay matrix, and quantified via the Bliss scoring method or the Fractional Inhibitory Concentration (FIC) method. As shown in FIG. 27, synergy was detected in both 96-well broth culture (FIC<=0.5) and the disclosed microdroplet platform (FIC<=0.3125).

Example 3

The system was then applied to identify compounds that can potentiate the activity of antibiotic drugs. In the face of rising antibiotic resistance, efforts to develop new types of antibiotics have yielded little success. However, many existing antibiotics such as vancomycin, erythromycin, and novobiocin, cannot be used to treat important Gram-negative pathogens such as *E. coli, P. aeruginosa*, and *A. baumannii*, due to their impermeable outer membranes. Coupling drugs developed for other indications with these antibiotics to overcome this intrinsic resistance could have a more rapid clinical impact at lower costs than de novo discovery, but discovery is limited by the combinatorial complexity and compound consumption of screening larger numbers of drug-antibiotic combinations.

Figure 3A:
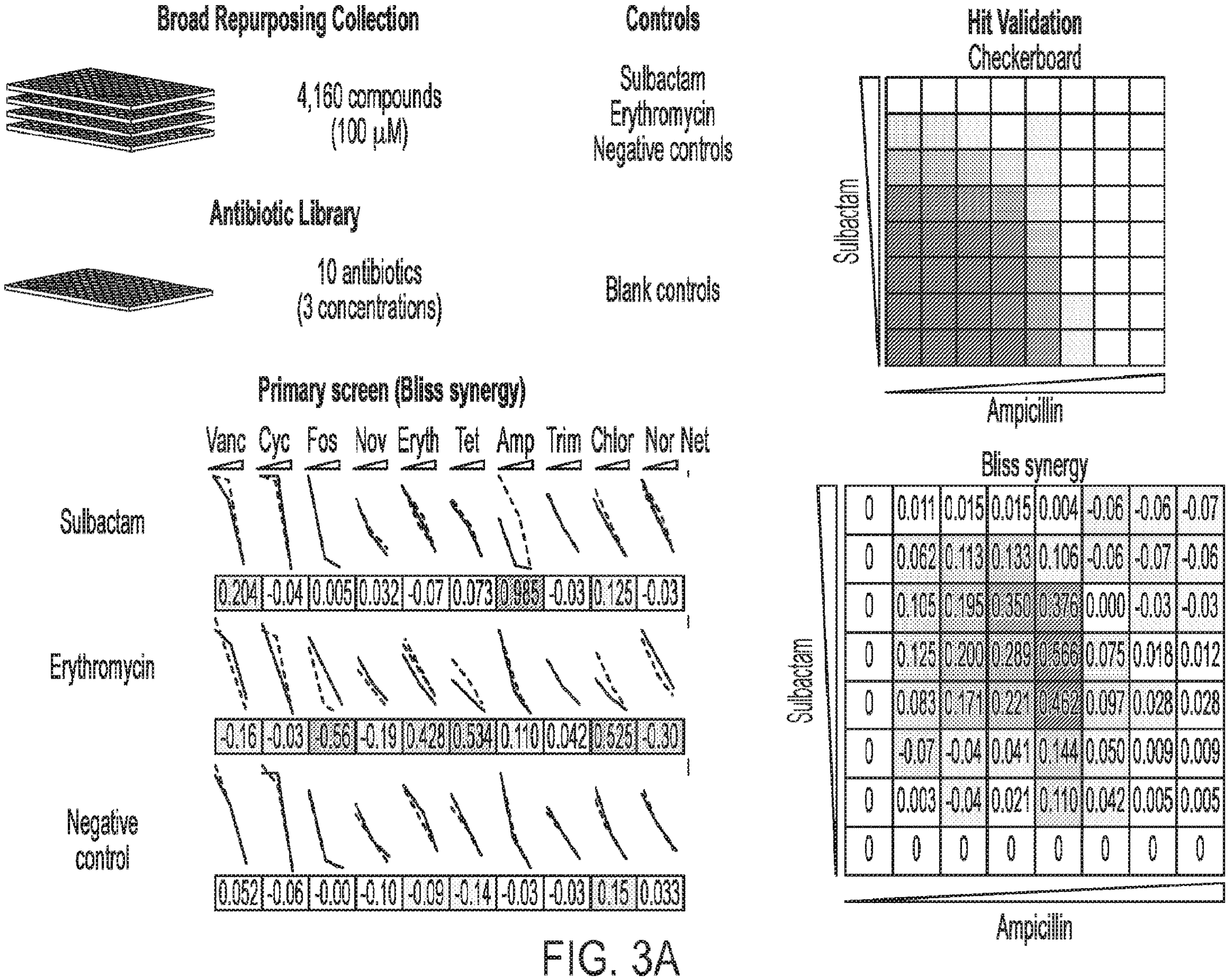
FIGS. 3A-3G depict data from a drug repurposing antibiotic potentiation screen according to an exemplary embodiment of the disclosure.
Figure 3B:
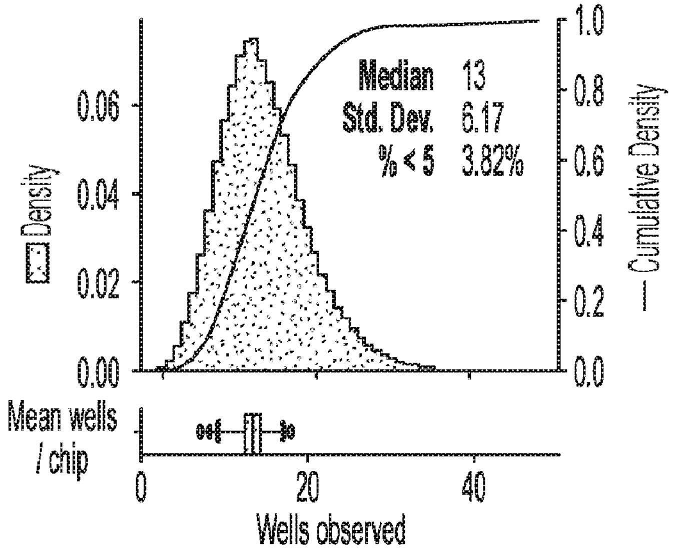
Figure 3C:
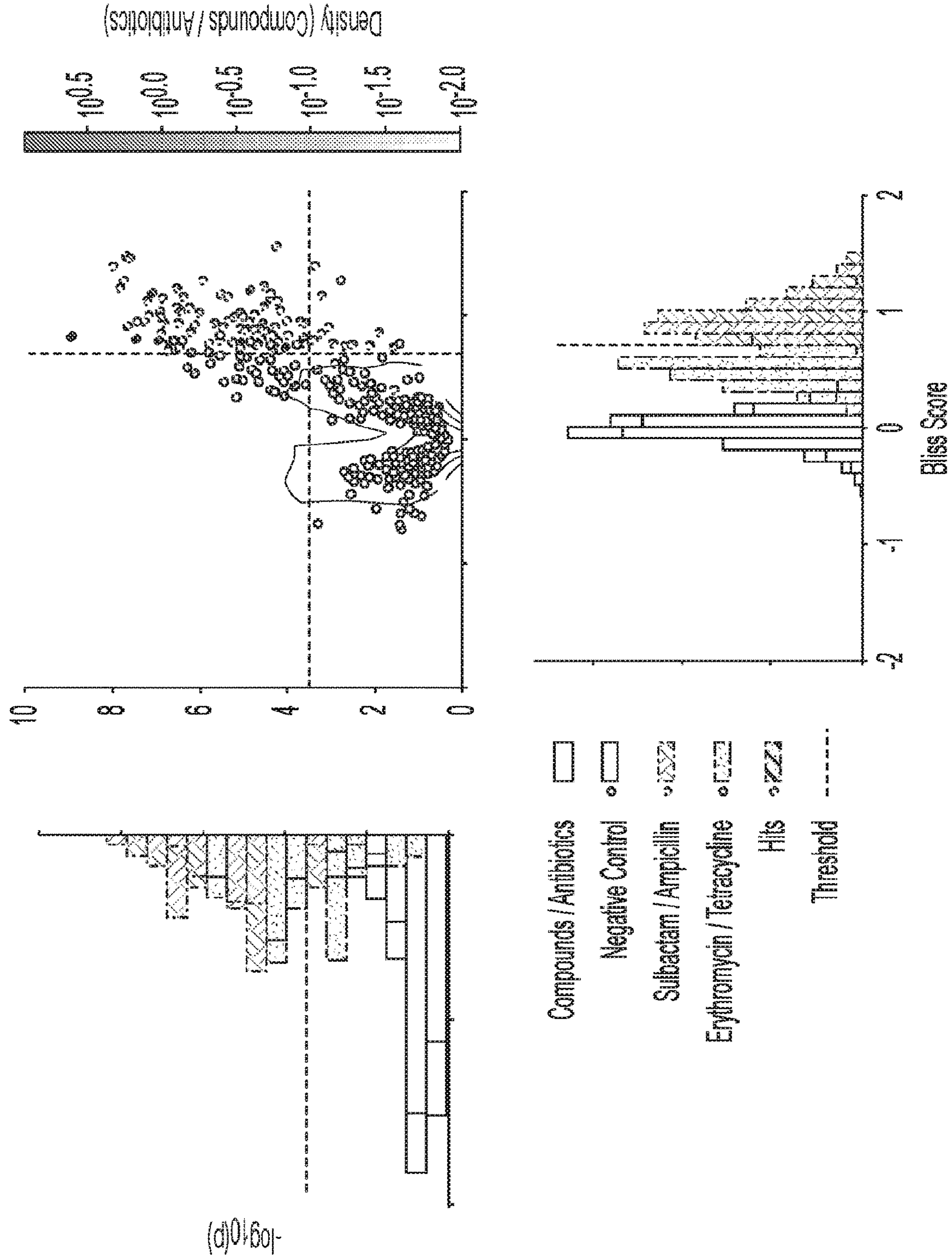
Figure 3D:
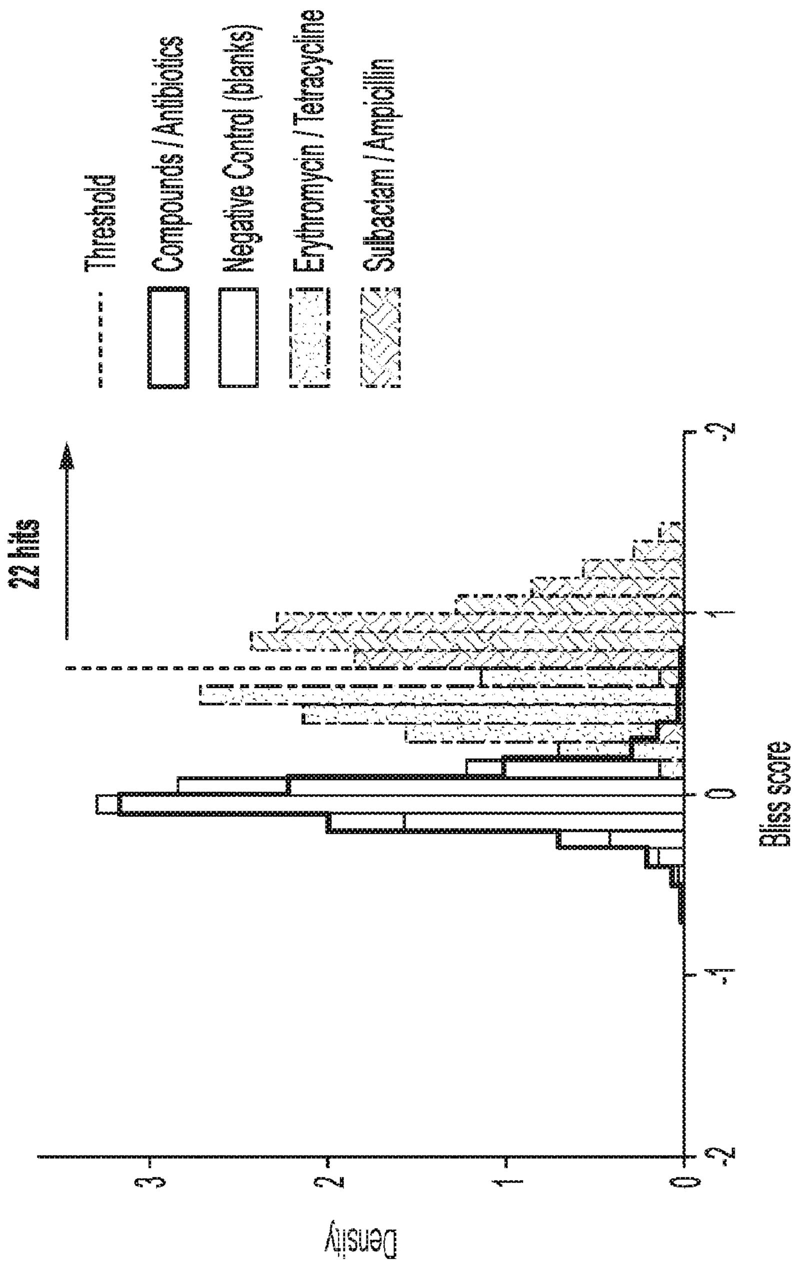
Figure 3E:
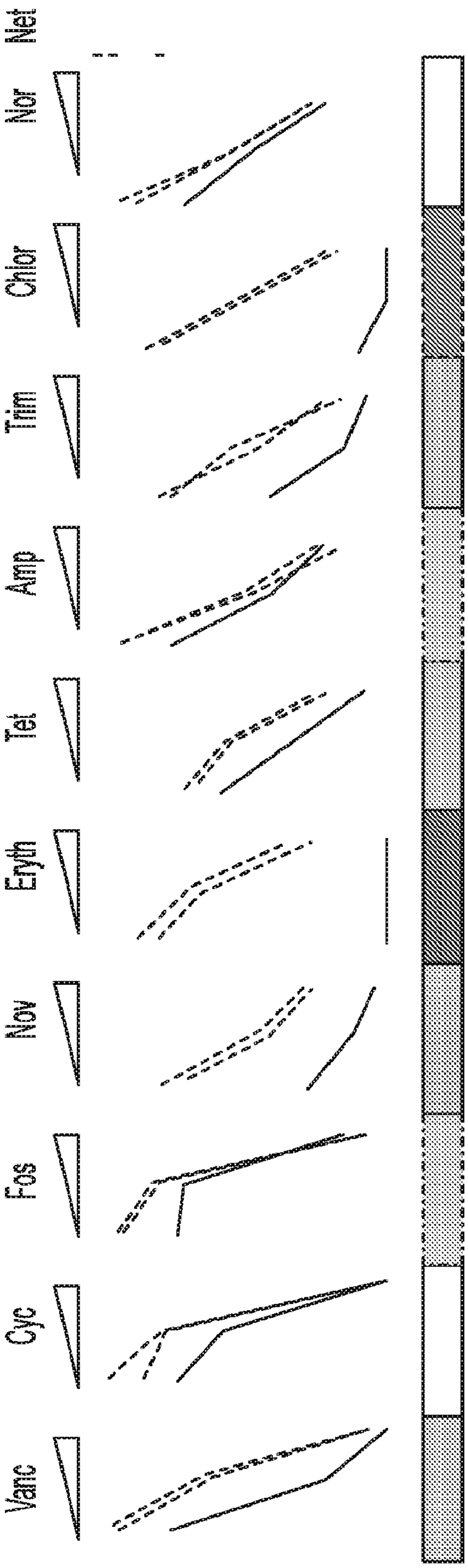
Figure 3F:
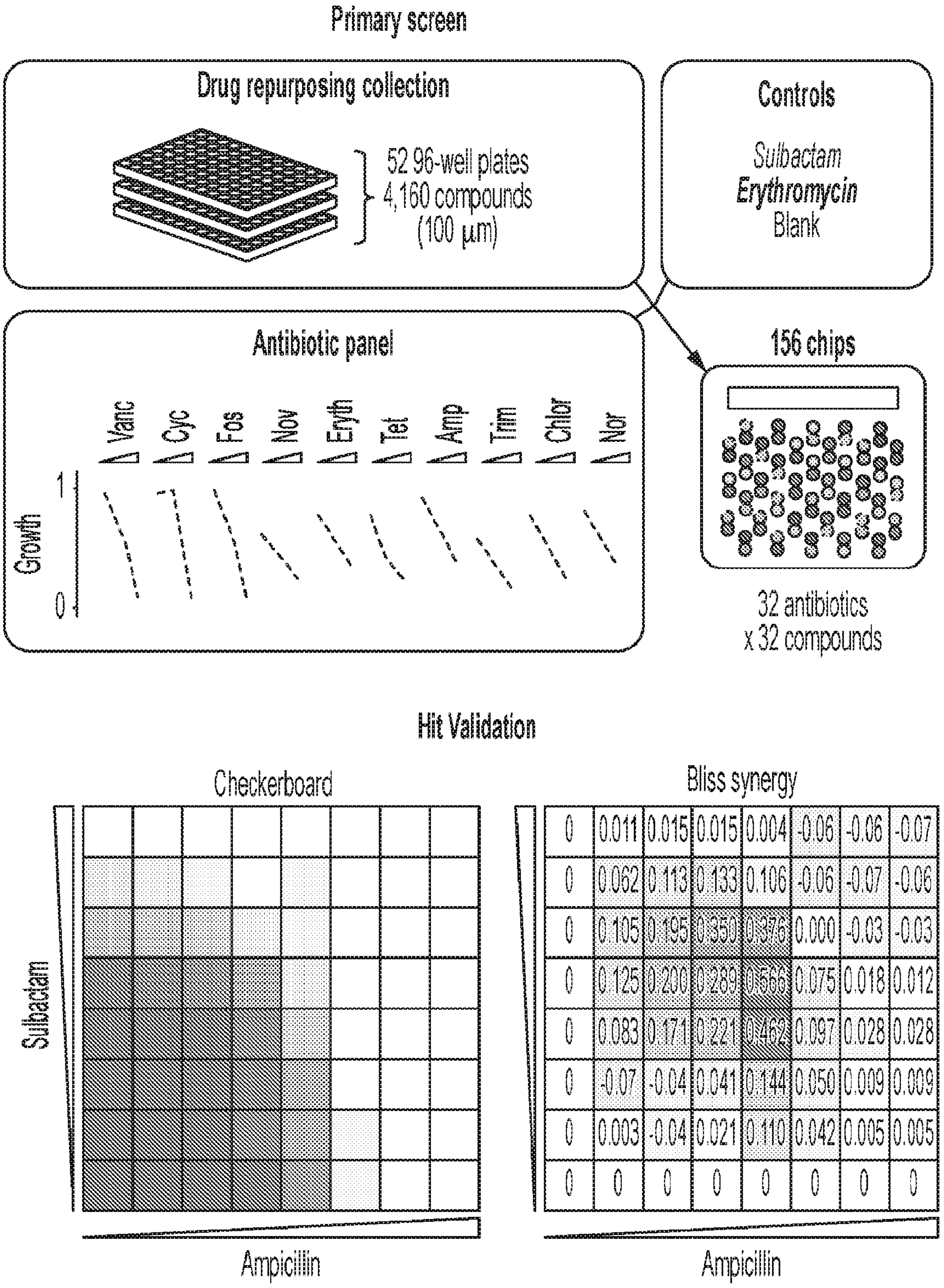

Experiments screened for potentiation of a panel of 10 antibiotics (FIG. 10A) with diverse mechanisms at three different combinations and biochemical target locations by a "drug repurposing" library of 4,160 drugs against the Gram-negative model pathogen *E. coli* (FIG. 3A; FIG. 3F). This curated repurposing library is composed of compounds for which significant development work has been previously completed (ranging from focused preclinical investigation to launched drugs). Hit compounds from the screen would have significant toxicity data available that would enable faster clinical translation for against Gram-negative pathogens more quickly than a de novo hit.

This effort resulted in the measurement of 100,800 combinations in 1.1+ million microwell-level measurements performed in two phases over the course of 10 days (Pilot phase: 800 compounds, 10 antibiotics at three different combinations, 24,000 combinations, 3.33 days; Full scale phase: 3,360 compounds, 10 antibiotics at three different combinations, 100,800 combinations, 7 days). Including controls, the total number of combinations screened was 159,744. Analysis determined compound-antibiotic synergies by evaluating a shift of a 3-point antibiotic dose response (FIG. 10A), and quantified by the Bliss synergy metric for each compound-antibiotic pair (see e.g., FIG. 3A, FIG. 3F, and FIG. 3G). Hits from the screen were then validated in 8-point checkerboard assays and quantified by the FIC method (see e.g., FIG. 3A and FIG. 3F).

Figure 28B:
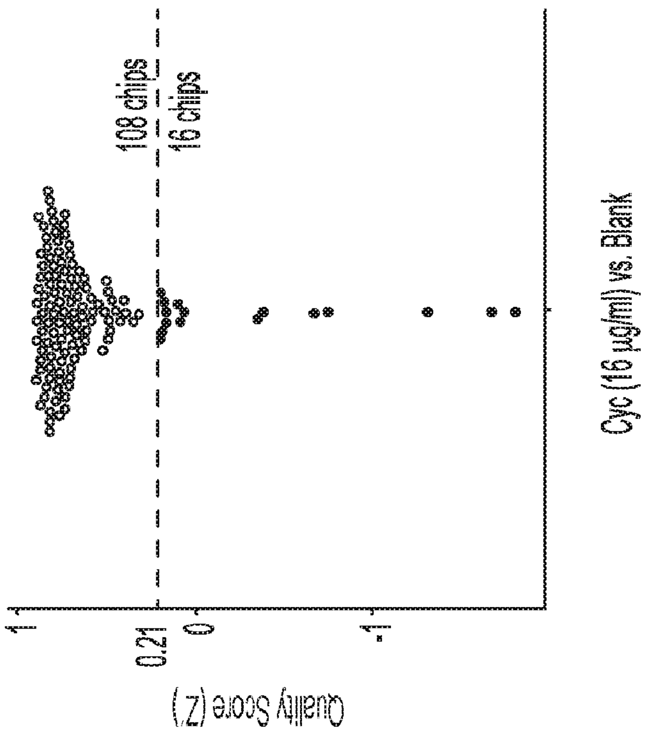
FIGS. 28A-28B show graphs of quality scoring of each microwell array in screen. A quality score is estimated of a microwell array chip by examining the maximum dynamic range in growth values obtained across all conditions. Chips with low quality were then filtered prior to analysis of screening data.
Figure 28A:
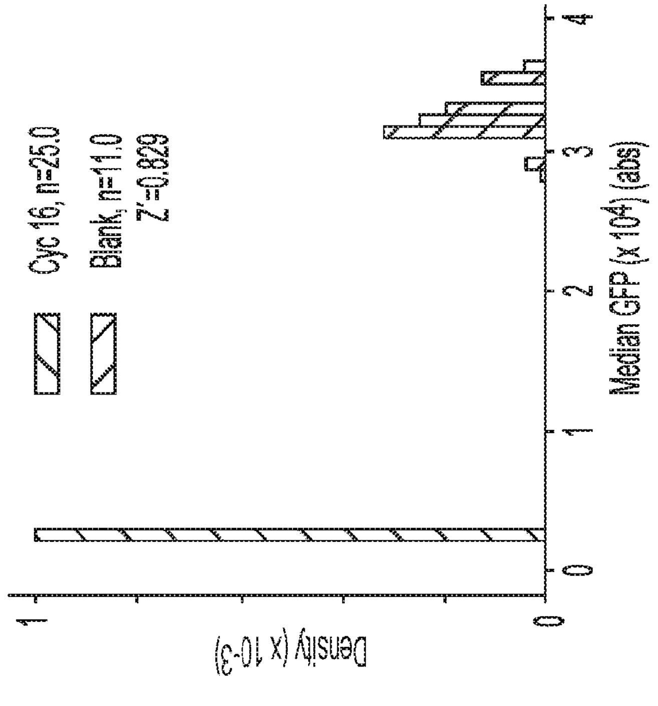

The full scale phase constituted 126 runs and 100,800 combinations from which experiments evaluated screening performance in terms of dropout and data. Of the 126 runs, there were two logistical failures and 16 runs removed for low data quality for a final passing rate of 86.5% (FIG. 3B, FIG. 28A-FIG. 28B). On passing runs, droplet production failed for 1.46% of compounds. Of the 100,800 compound-antibiotic combinations, the median level of well-level replication was 13 (FIG. 3B), with zero microwells observed for 0.0734% of antibiotic-drug pairs and 3.82% of antibiotic-drug pairs were observed with <5 replicates (FIG. 3B). Overall 84.7% of the 100,800 combinations successfully measured (FIG. 3B).

Figure 3G:
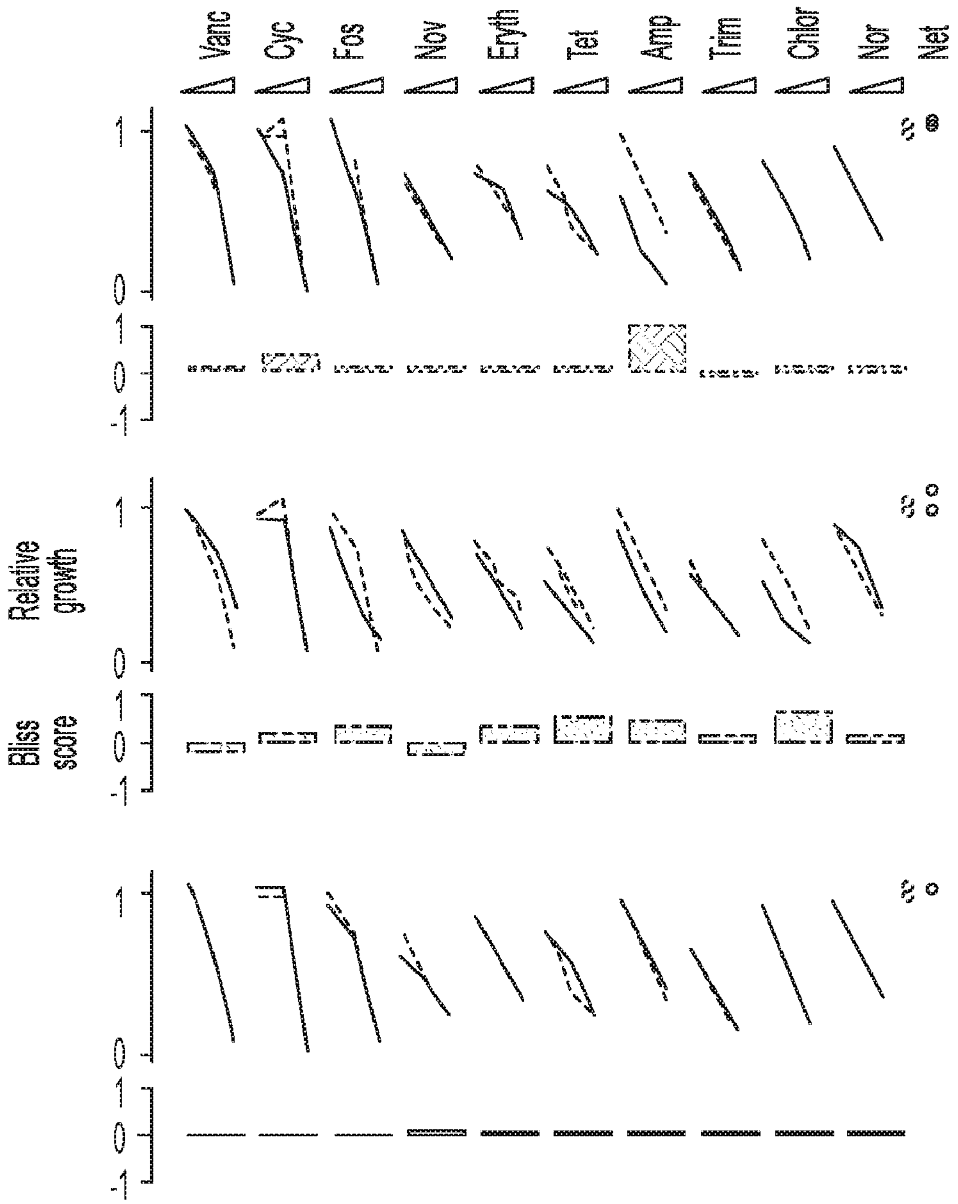
Figure 30A:
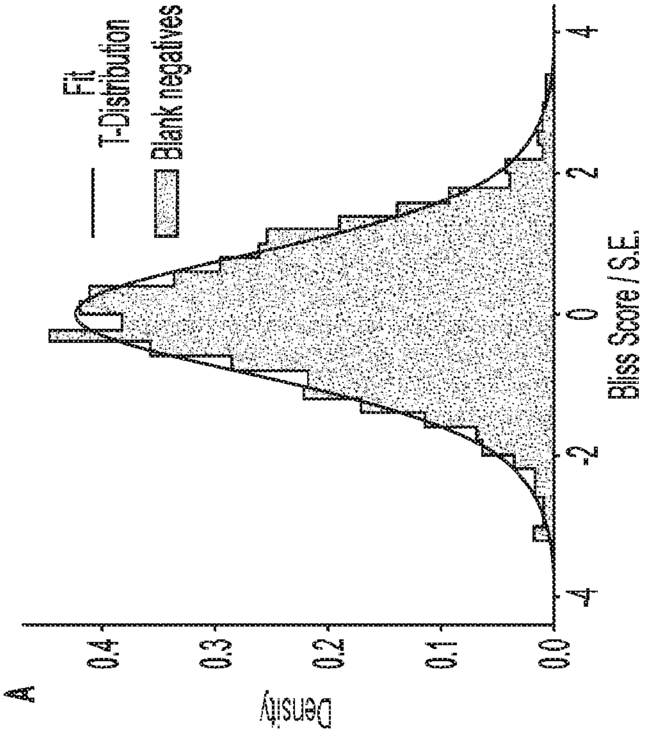
FIGS. 30A-30B show distributions of screening blank negative controls. To estimate the statistical significance of Bliss scores measured for each compound-antibiotic pair, a test statistic was computed from each Bliss score divided by the estimated standard error. A null model was estimated for this test-statistic from all pairs of blank negative controls× antibiotics.
Figure 30B:
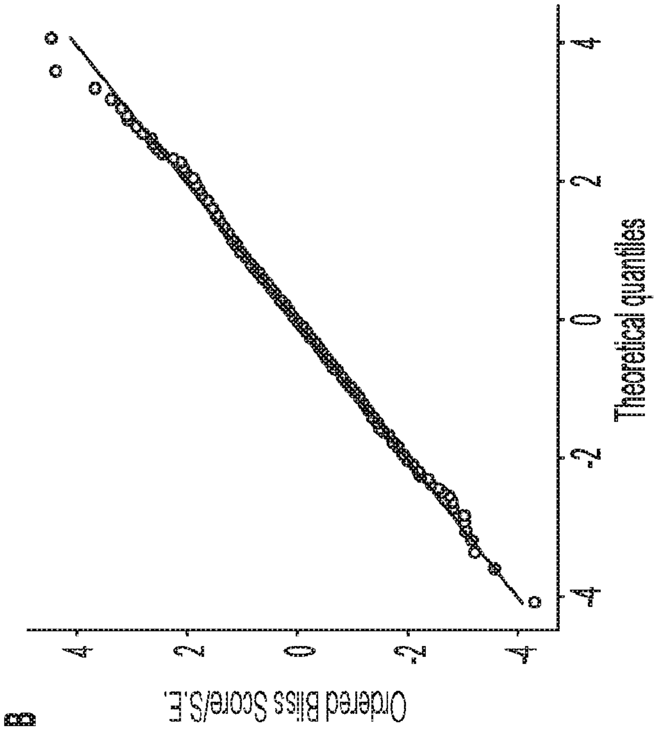
Figure 31A:
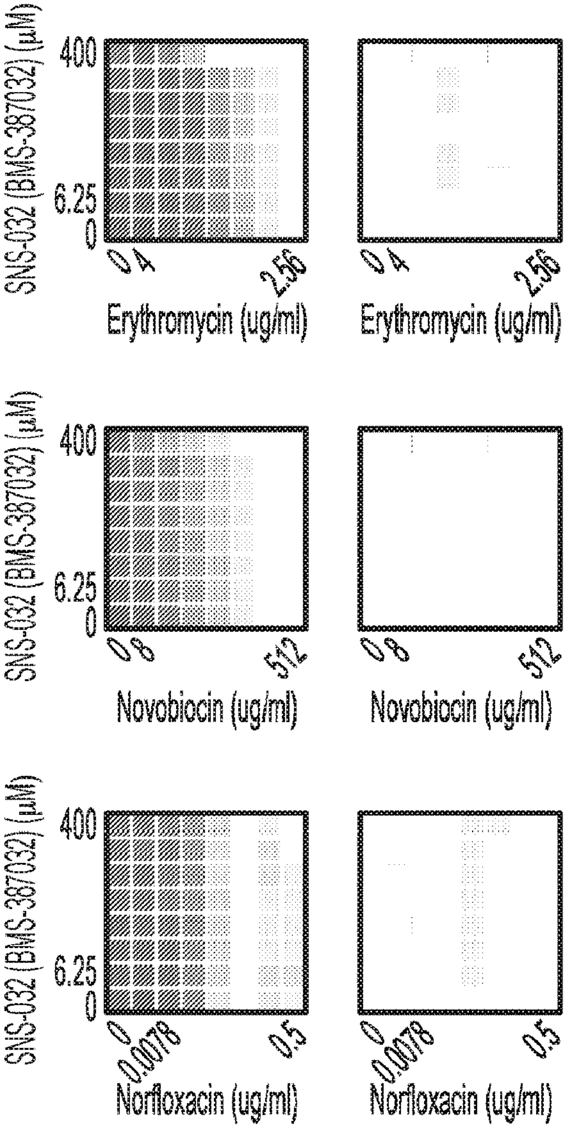
FIGS. 31A-31J show a series of checkerboard validation assays. Experiments selected 46 compound-antibiotic pairs to test the predictions of the primary screening data. For each pair checkerboard, the relative growth values (left panel), calculated Bliss scores for each well position (middle panel), and a table summarizing the primary screening data and checkerboard synergy scores (Bliss and FIC) are shown.
Figure 31A:
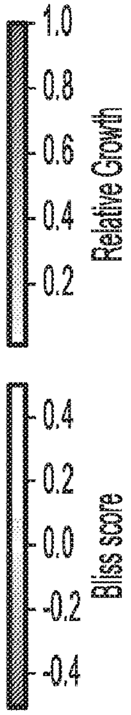
Figure 31A:
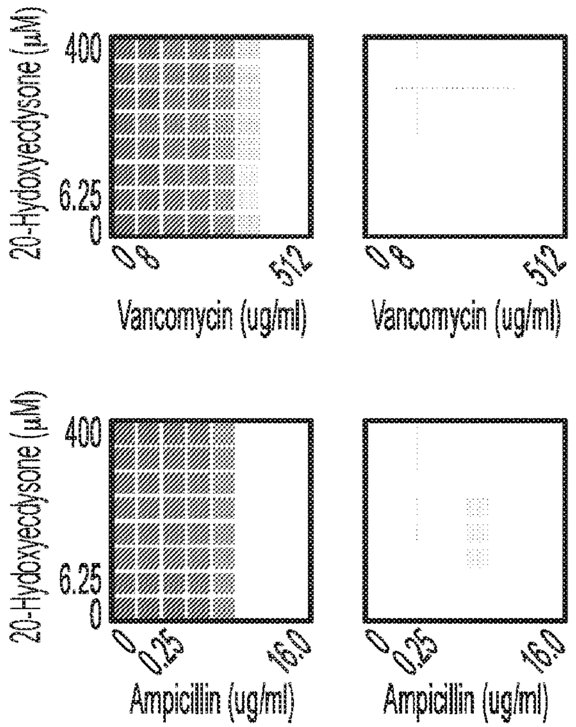
Figure 31A:
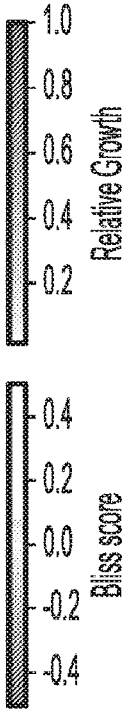
Figure 31B:
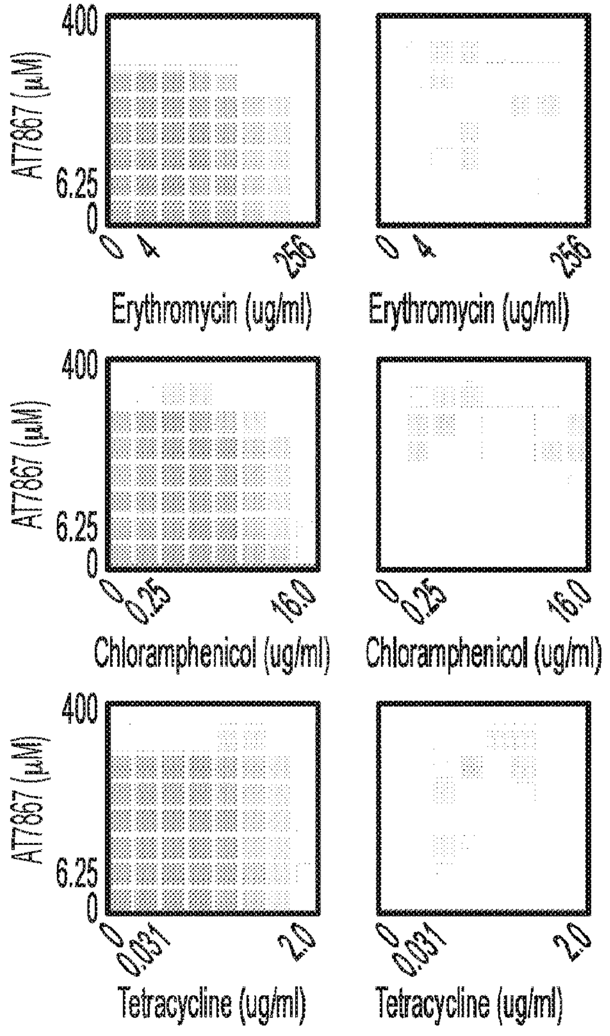
Figure 31B:
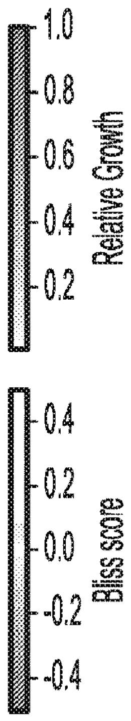
Figure 31B:
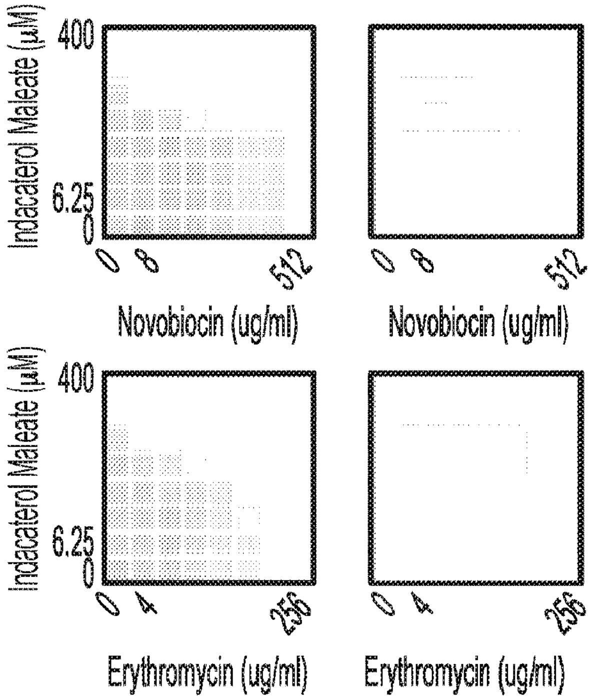
Figure 31B:
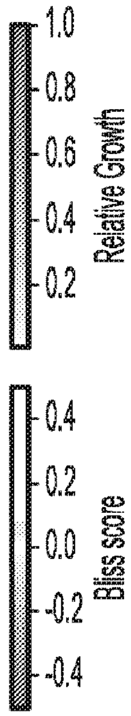
Figure 31C:
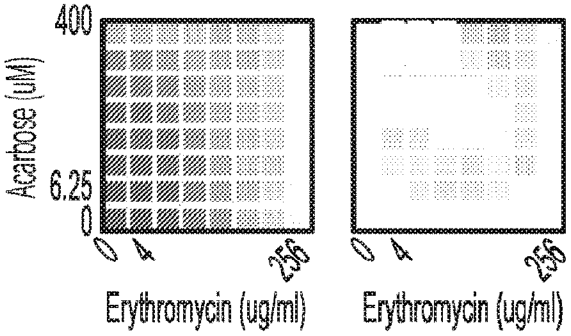
Figure 31C:
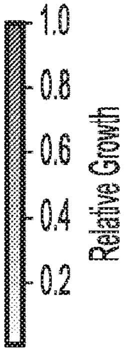
Figure 31C:
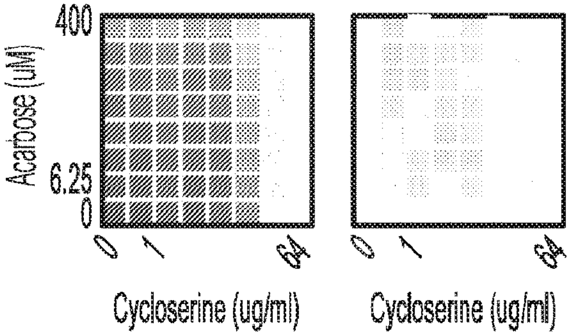
Figure 31C:
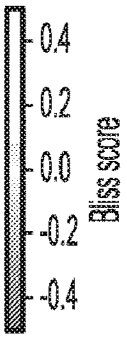
Figure 31D:
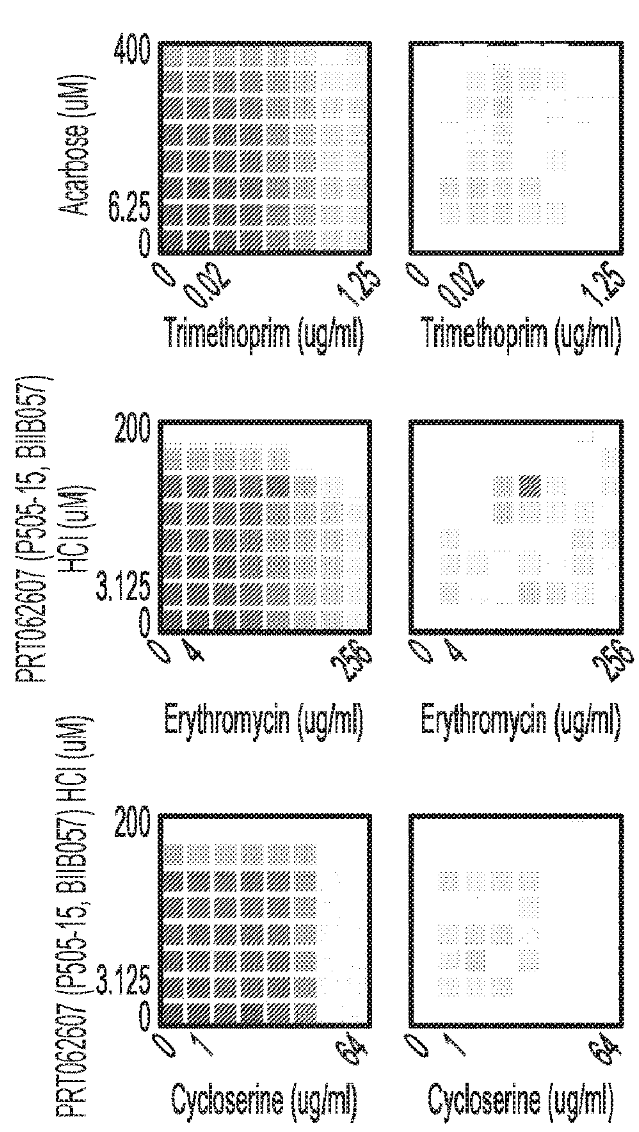
Figure 31D:
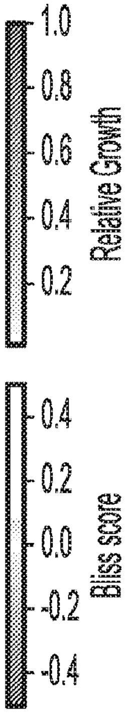
Figure 31D:
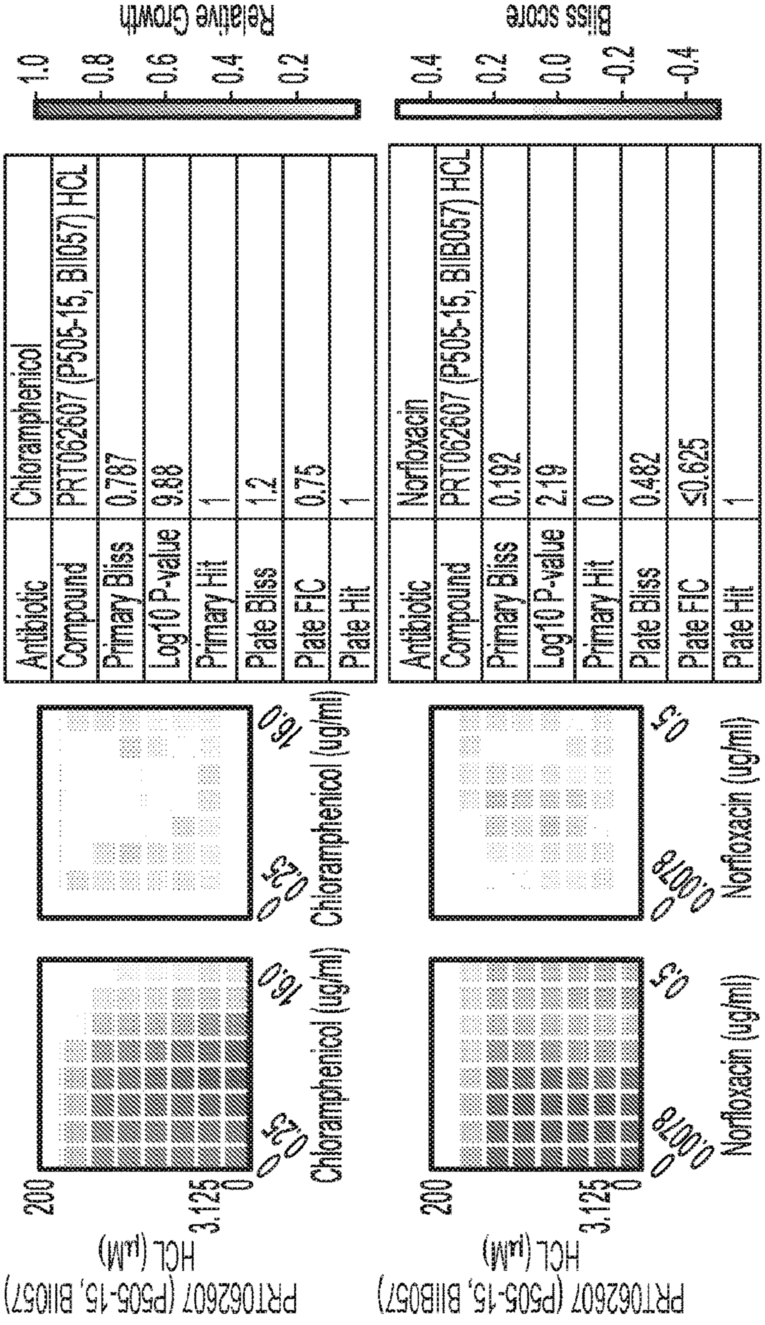
Figure 31E:
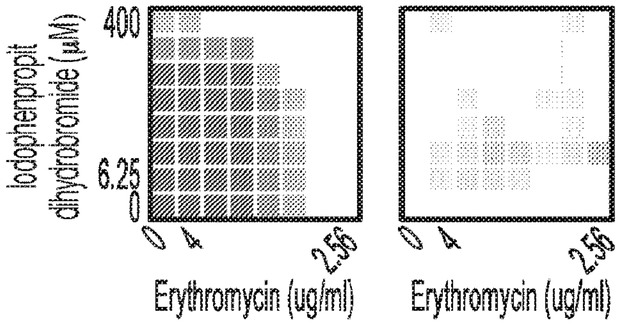
Figure 31E:
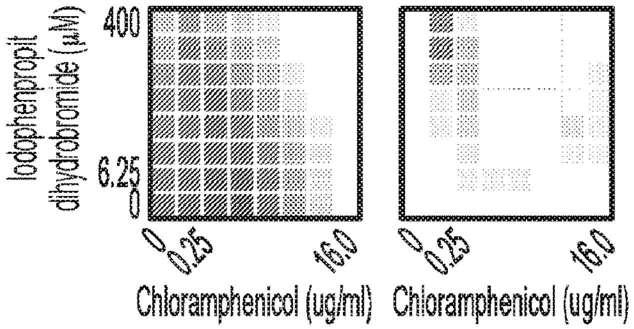
Figure 31E:
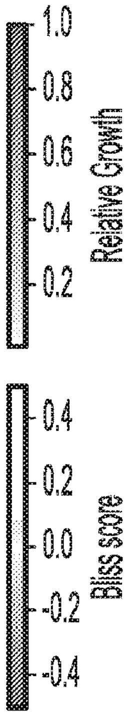
Figure 31F:
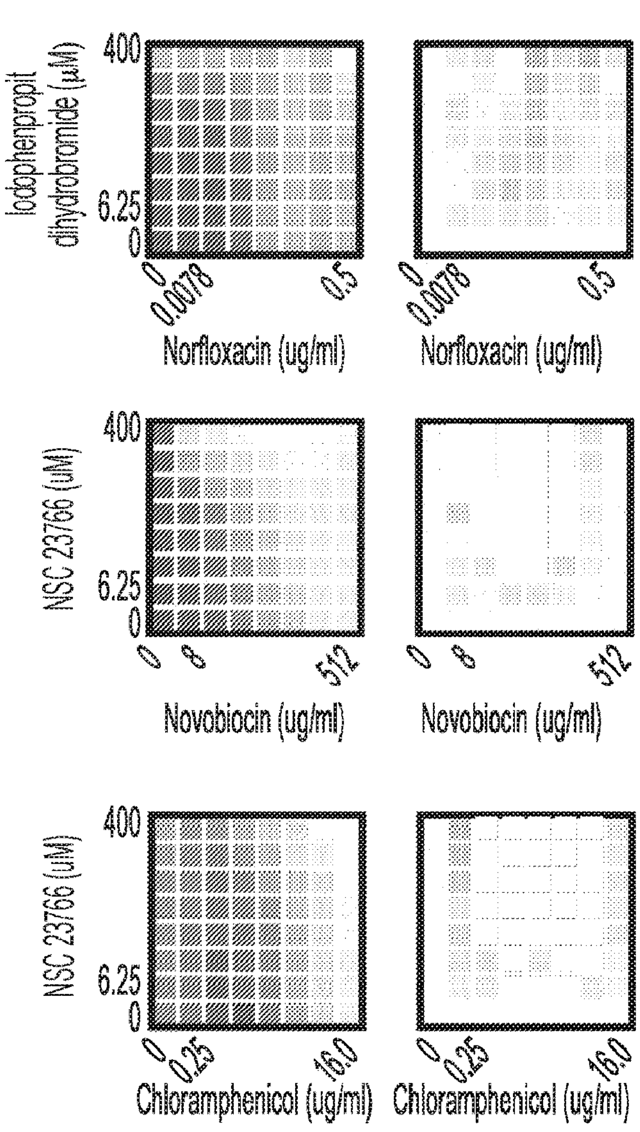
Figure 31F:
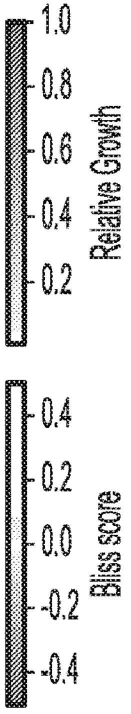
Figure 31F:
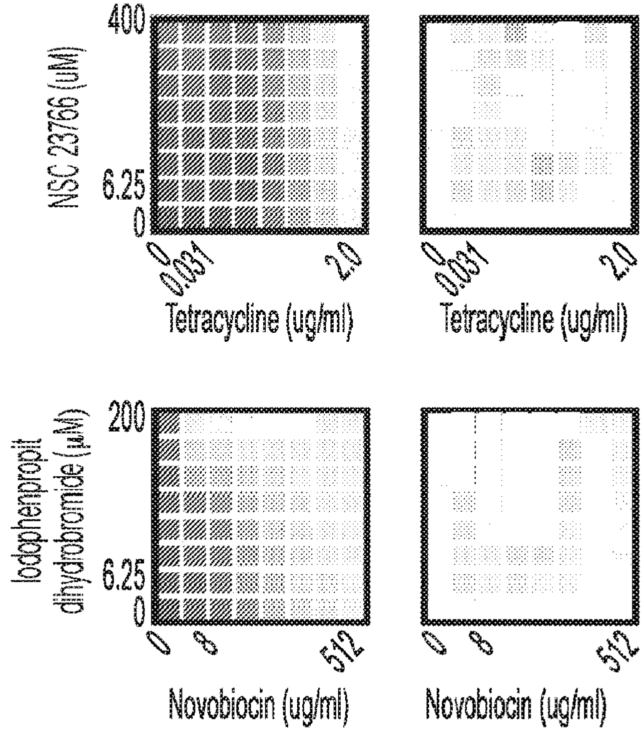
Figure 31F:
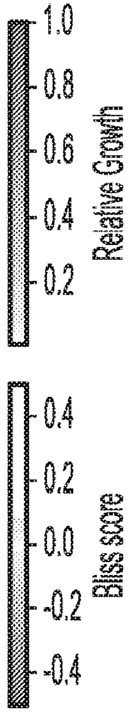
Figure 31G:
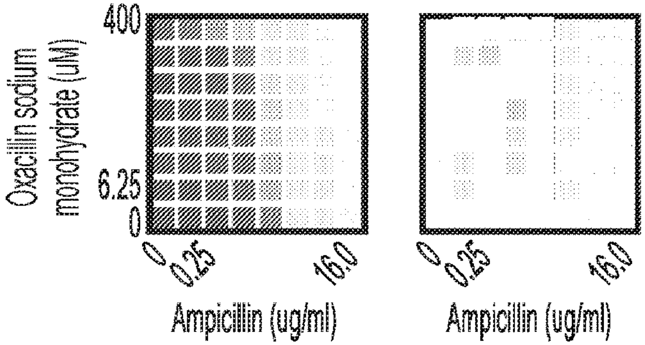
Figure 31G:
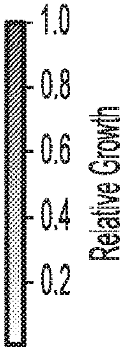
Figure 31G:
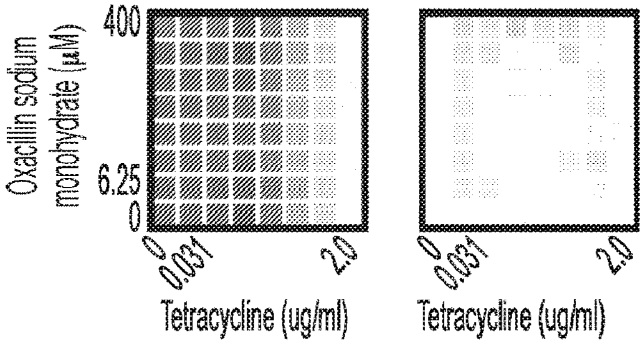
Figure 31G:
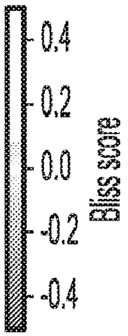
Figure 31H:
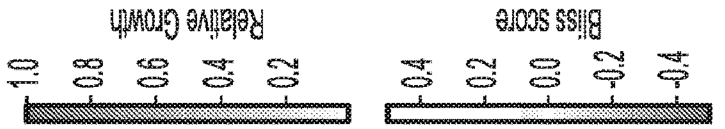
Figure 31H:
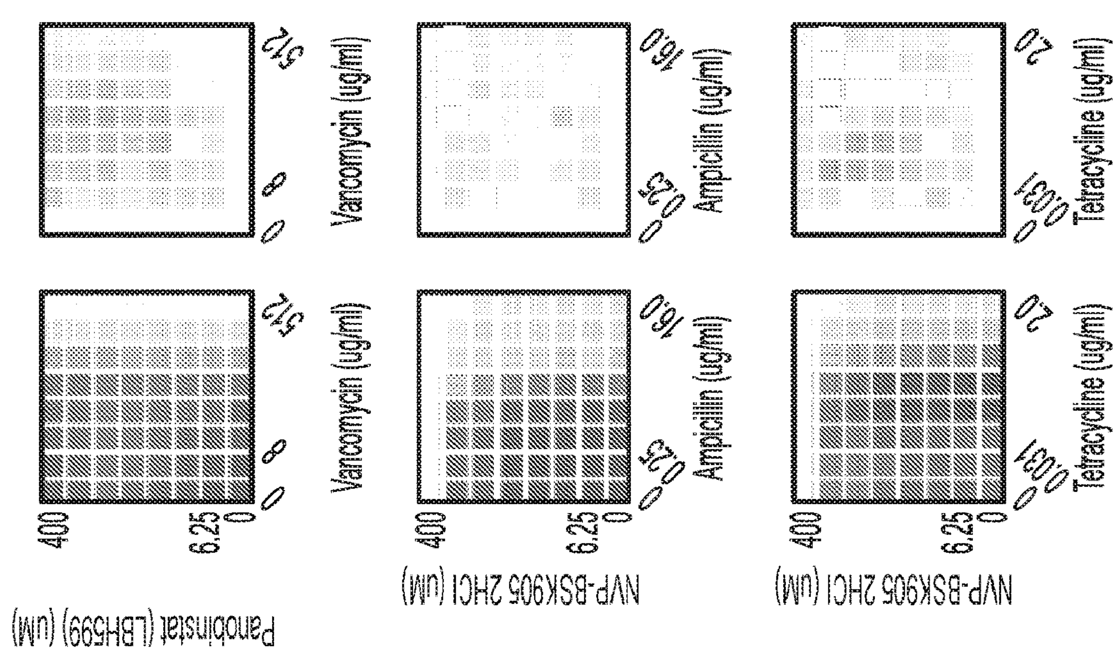
Figure 31H:
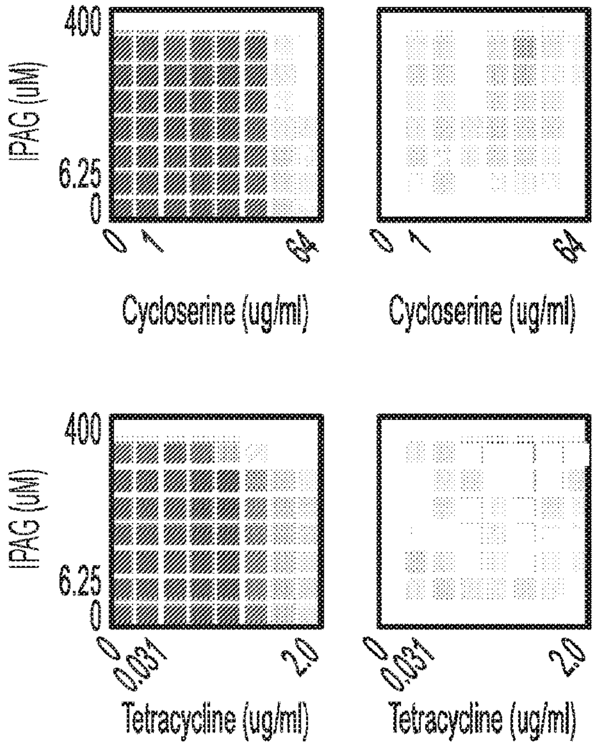
Figure 31H:
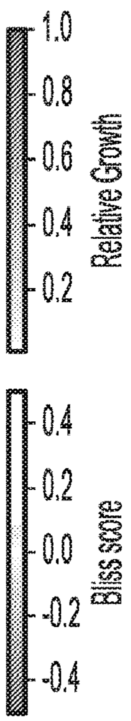
Figure 31I:
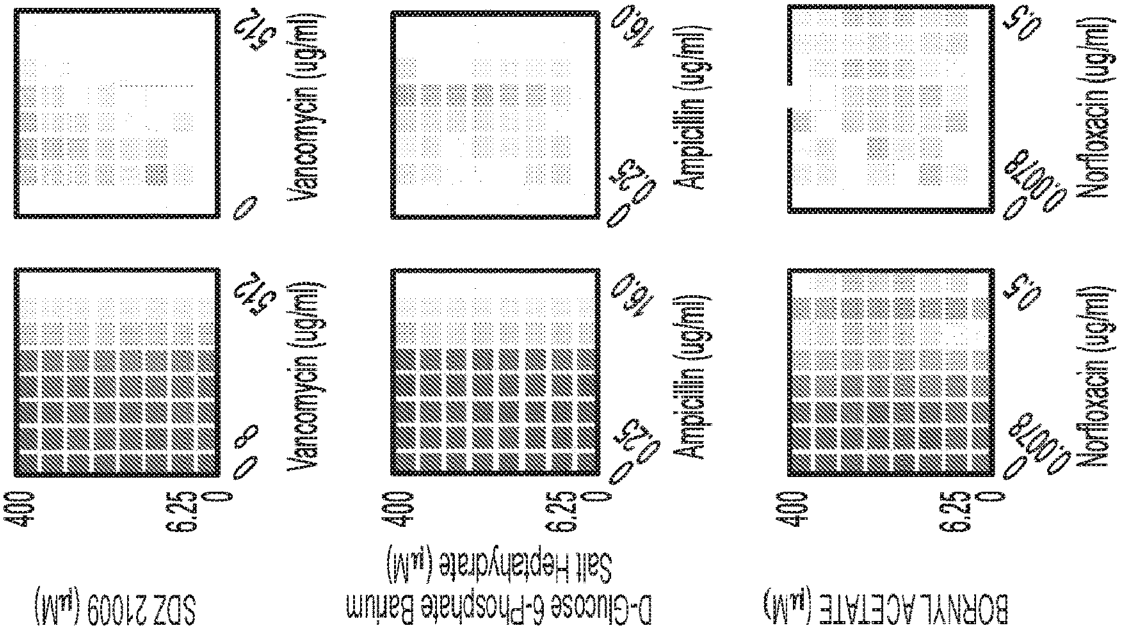
Figure 31I:
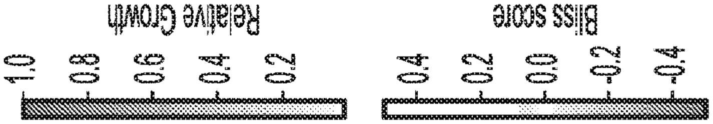
Figure 31I:
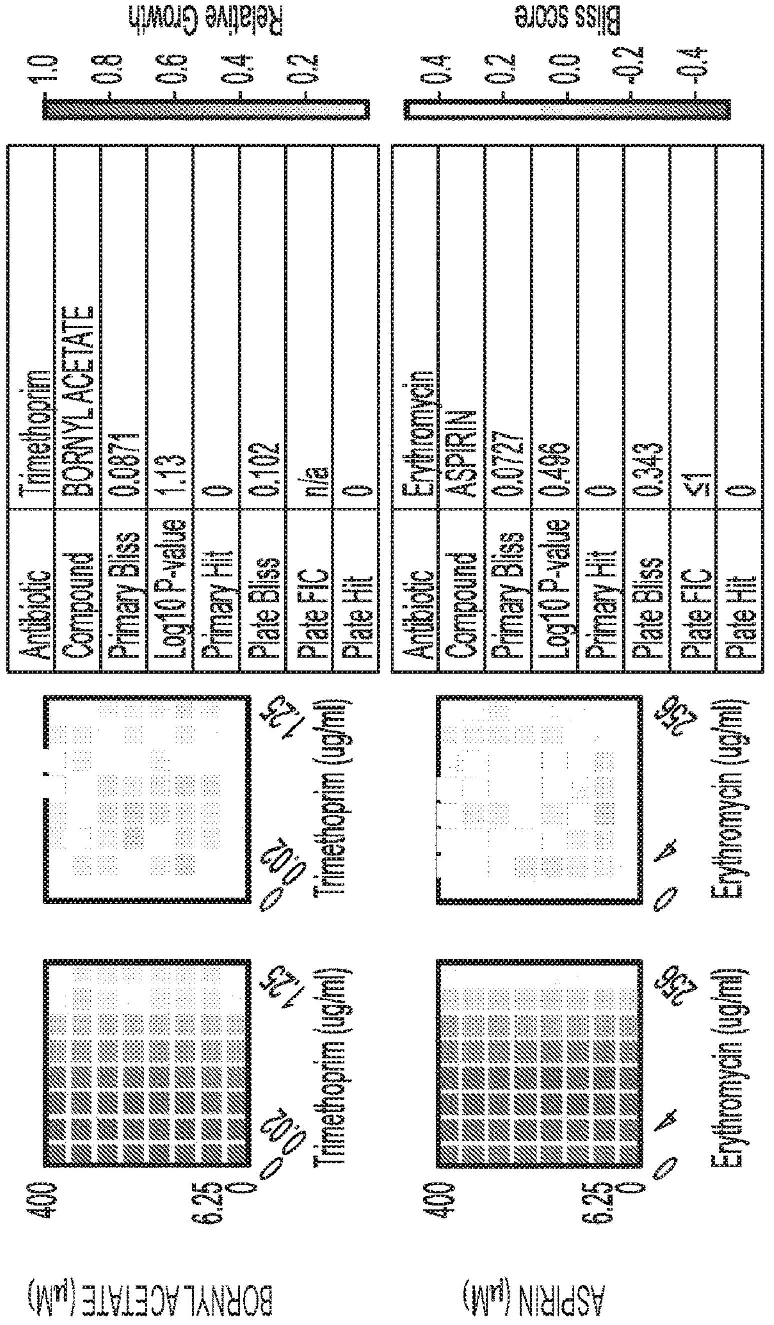
Figure 31J:
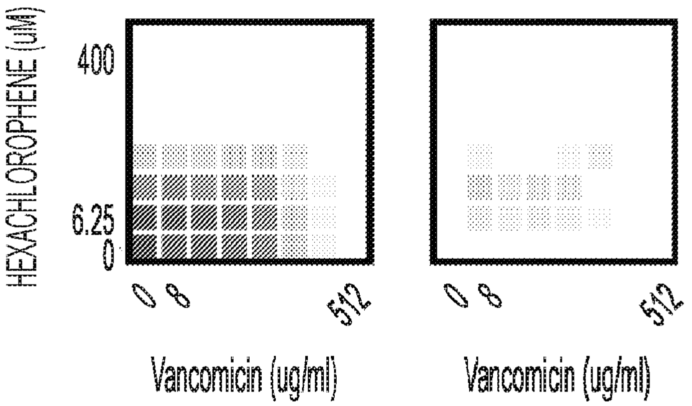

To assess data quality, each run was performed with a set of negative (blank media×all antibiotics) and positive (sulbactam×ampicillin; erythromycin×tetracycline) controls (FIG. 3A) to determine expected sensitivity and false positive rate of the screen (FIG. 3F, FIG. 3G). The Bliss score distribution of blank media×antibiotic pairs was well described by a T-distribution (FIG. 3C, FIG. 30A-FIG. 30B) from which p-values were calculated for each compound-antibiotic pair. To measure sensitivity, each run included one or both positive controls sulbactam×ampicillin (large effect size, expected Bliss score ~1) and erythromycin×tetracycline (small effect size, expected Bliss score ~0.5, FIG. 3G). In embodiments, expected Bliss scores were sulbactam (expected ampicillin bliss score ~1) and erythromycin (expected tetracycline bliss score ~0.5). At an expected false positive rate of 5e-4 (p-value threshold), 82.8% of sulbactam-ampicillin controls (n=70) and 65.7% of erythromycin-tetracycline (n=70) controls were recovered (FIG. 3C). To call hits from compound-antibiotic pairs, an effect size threshold was chosen (Bliss score >0.7) that separated weak positive control erythromycin×tetracycline, from our strong positive control, sulbactam×ampicillin (FIG. 3C). Using these thresholds to score hits yielded 28 hit compound-antibiotic combinations (0.098%) from 20 distinct compounds (0.70%, FIG. 3C). Seventeen hit combinations were selected from eleven distinct compounds for confirmation in 8-point "checkerboards" measured in conventional 96-well microplate assays (FIG. 4E, FIG. 31A-FIG. 31J). For comparison, an additional 29 combinations were measured (FIG. 4E, FIG. 4H, FIG. FIG. 31A-FIG. 31J). Of the hit combinations, 15 out of 17 scored as synergistic (88.2%, binomial p=5.8e-4 with 22 total positive for synergy out of 46 total tests, FIG. 4E, FIG. 31A-FIG. 31J).

Figure 4C:
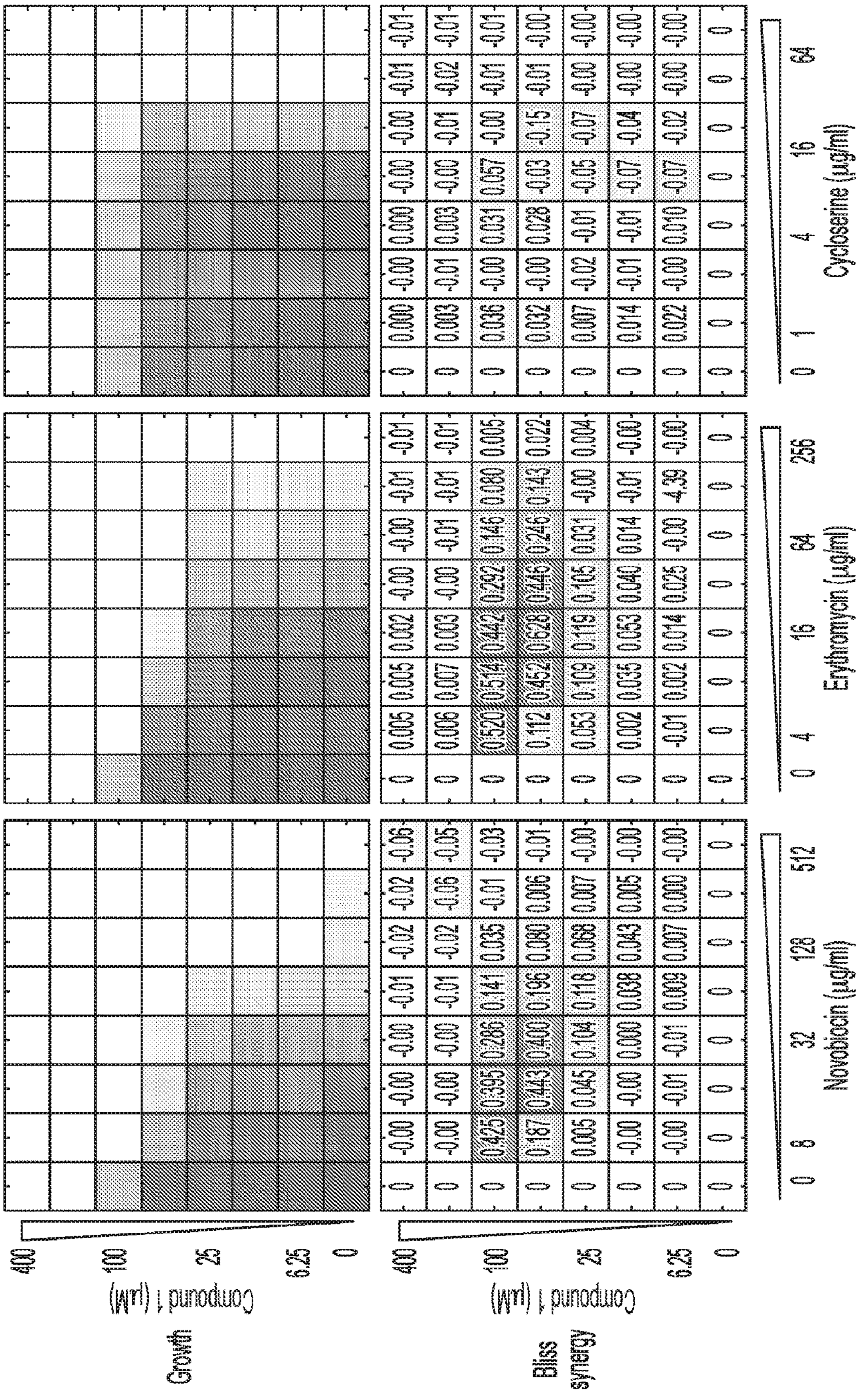
Figure 4D:
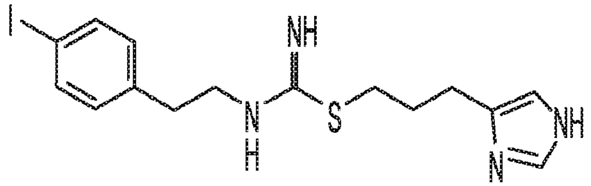
Figure 4D:
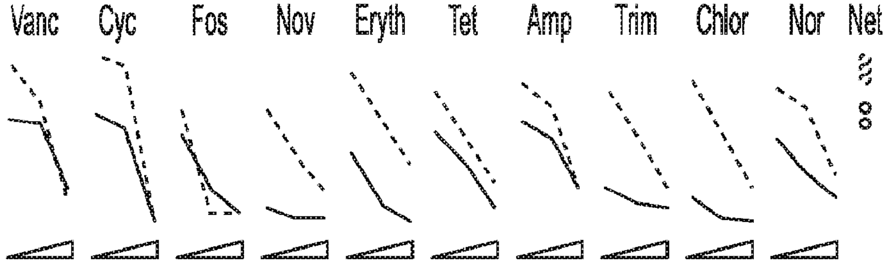
Figure 4D:
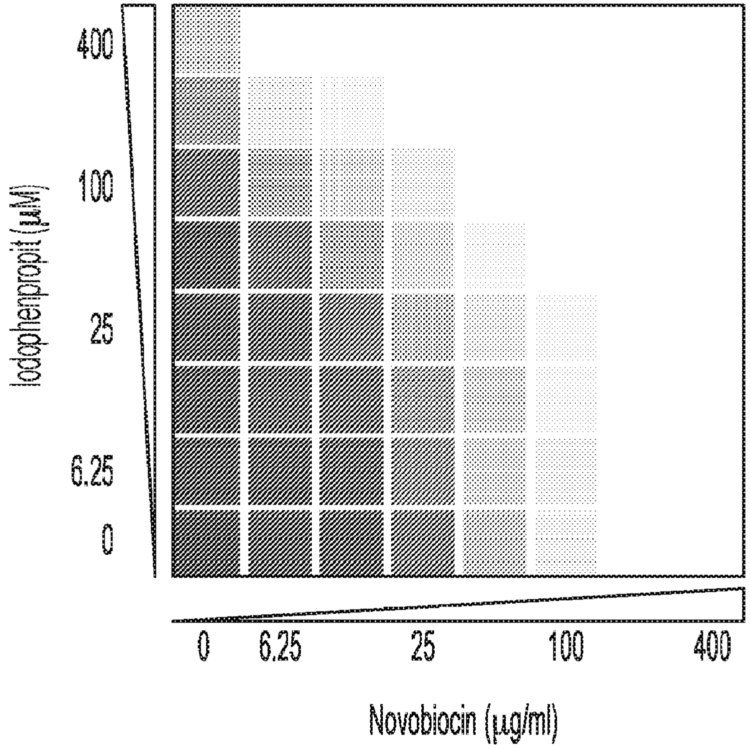
Figure 4E:
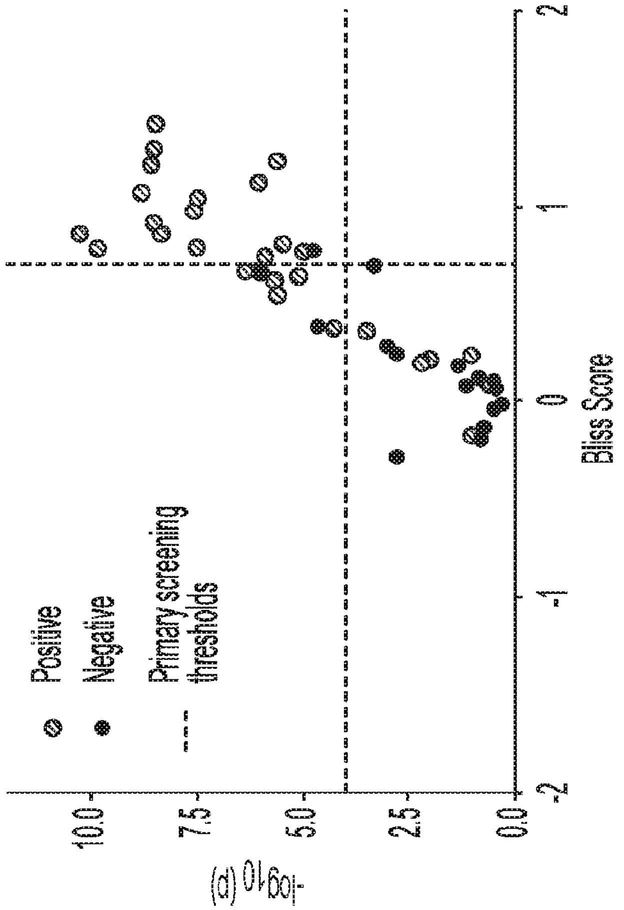
Figure 4G:
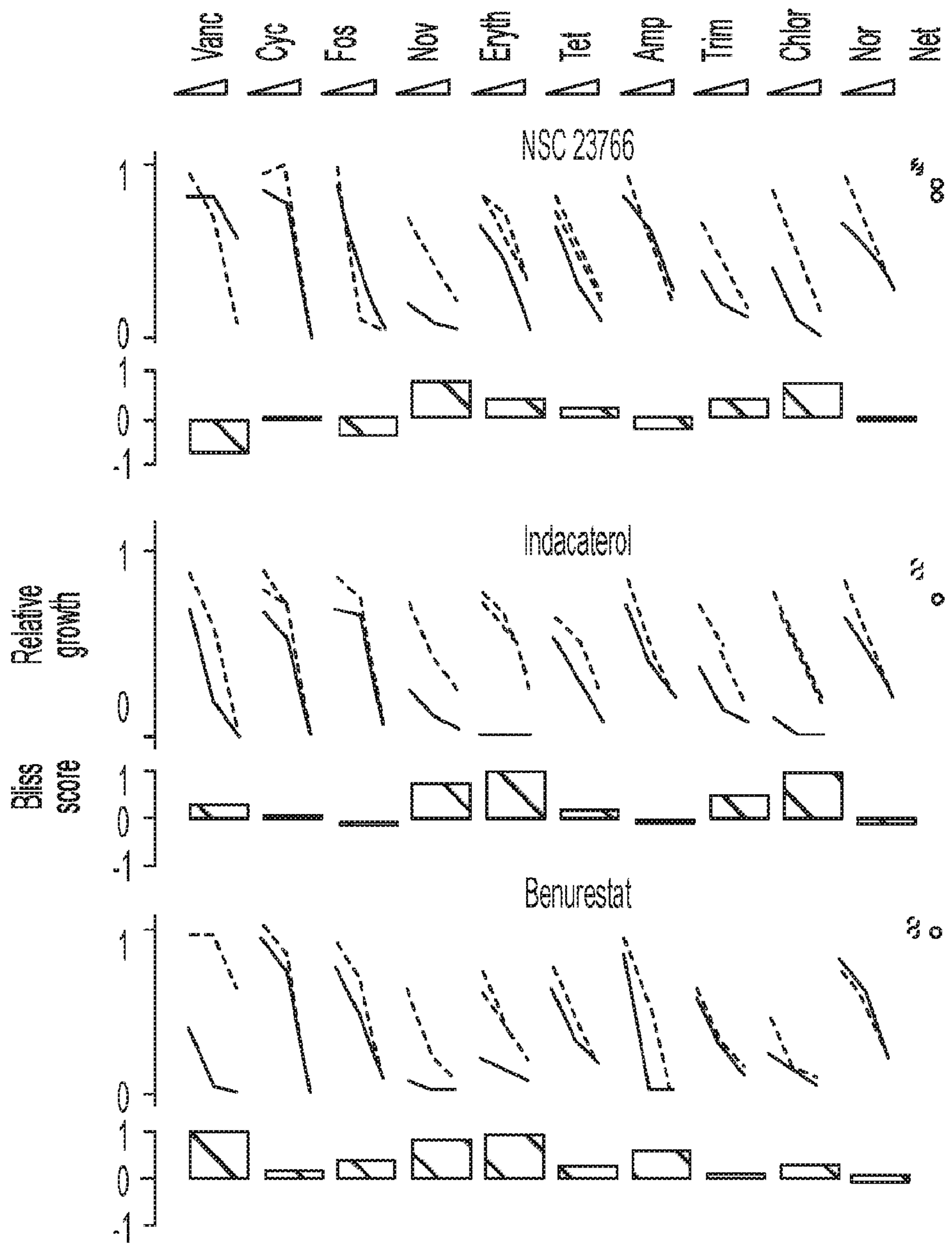
Figure 4H:
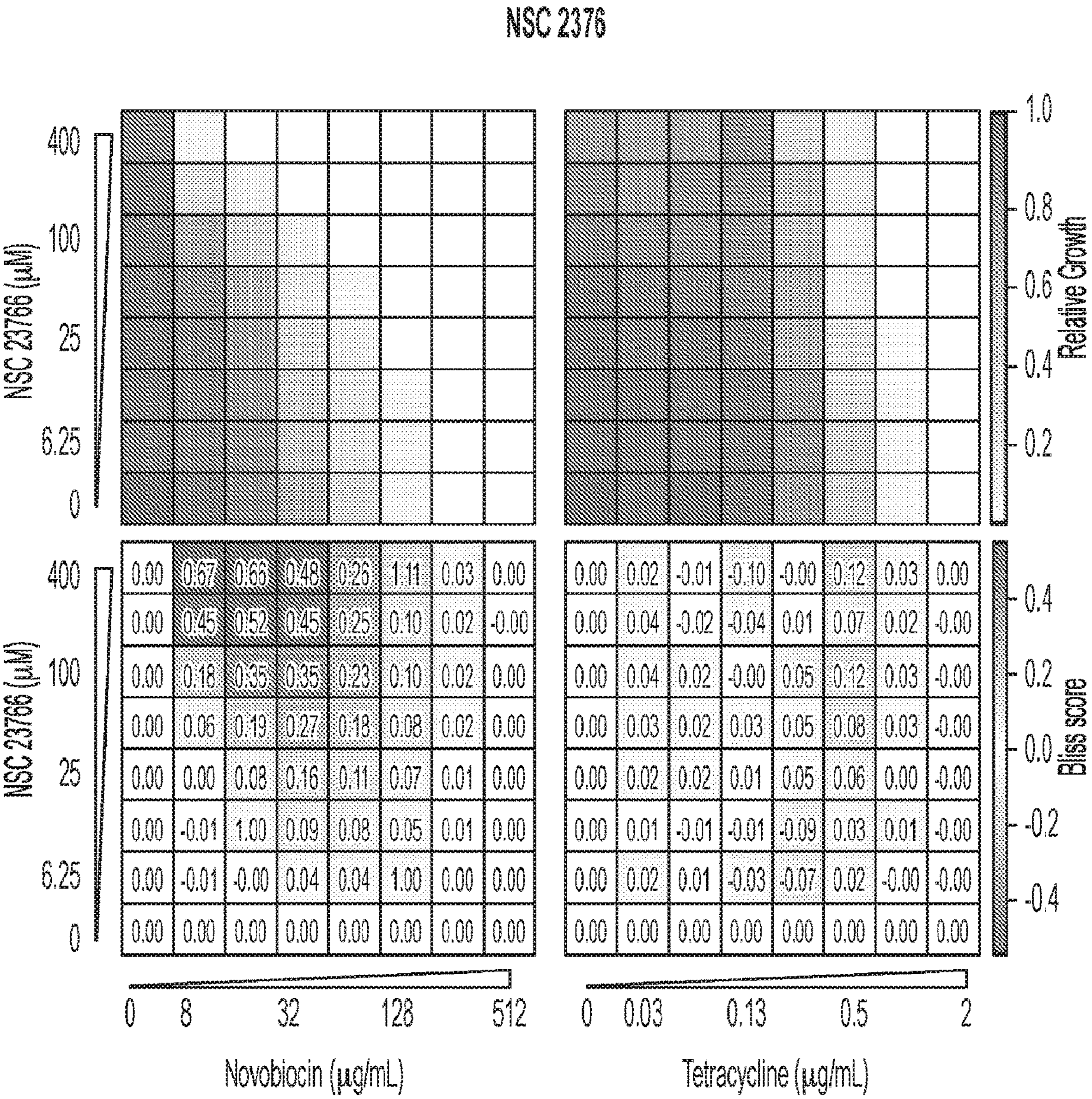
Figure 4I:
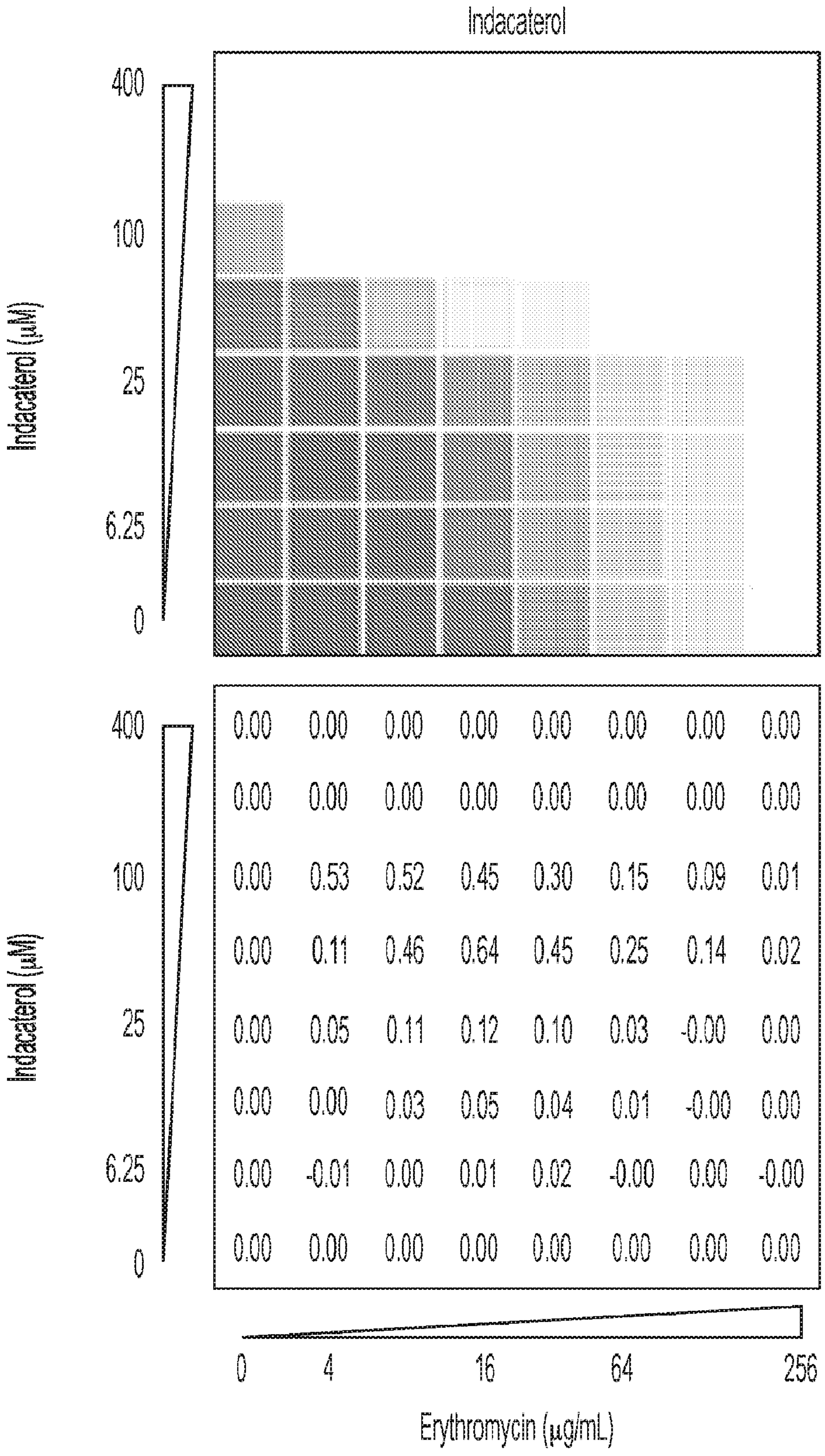
Figure 4J:
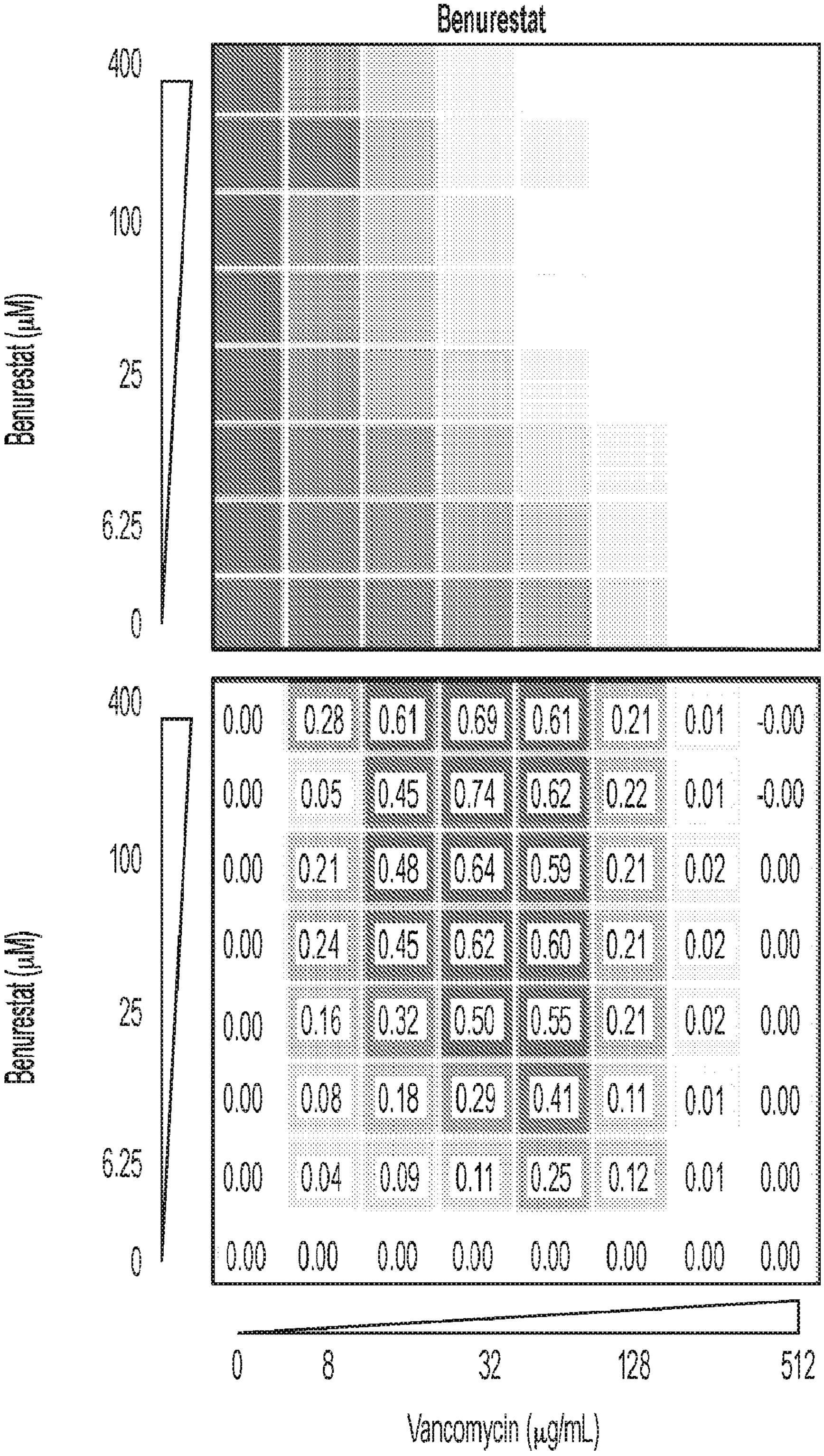
Figure 32:
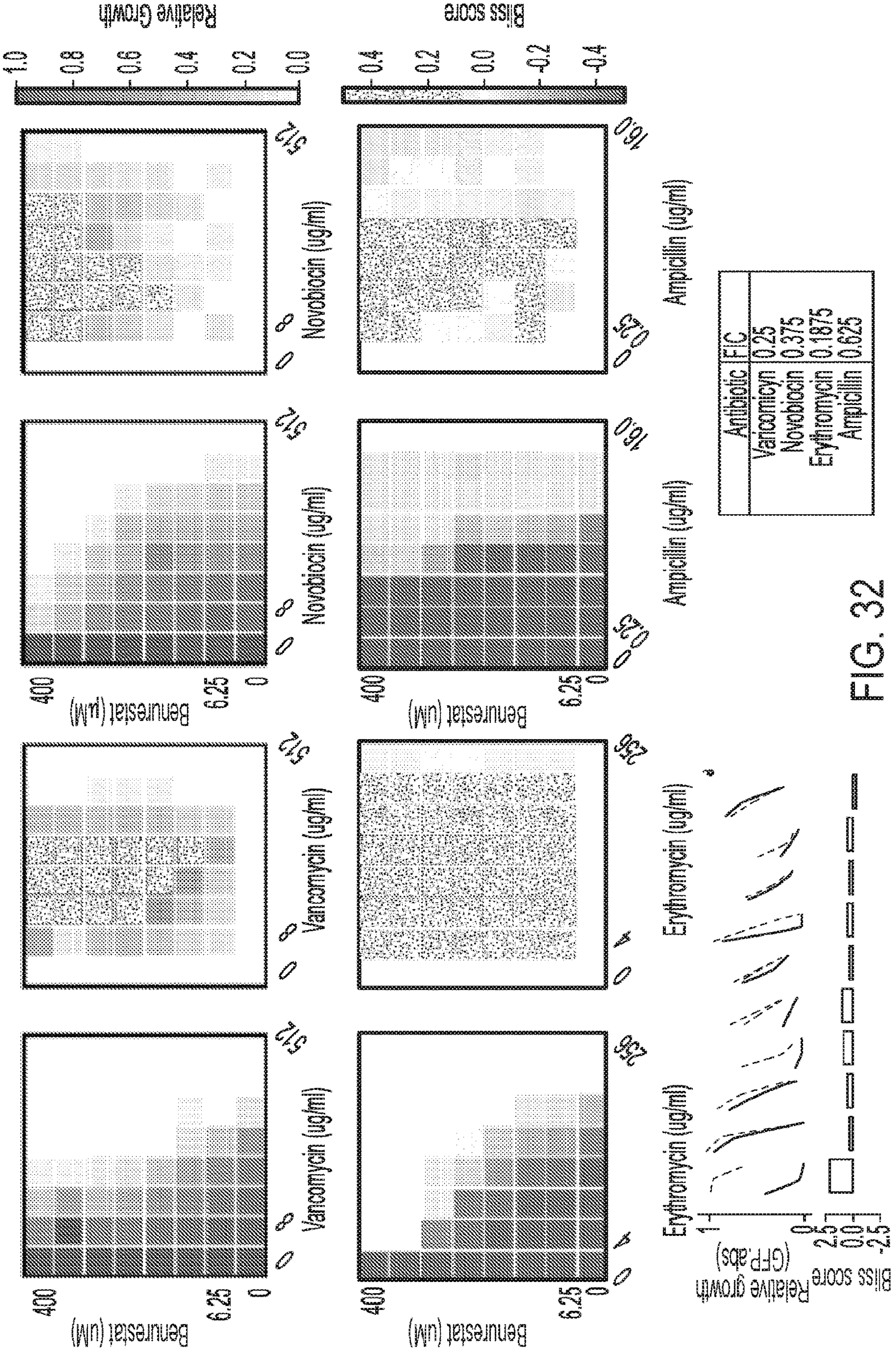
FIG. 32 shows checkerboard validation assays—Benurestat (pilot phase). Benurestat was a hit in our pilot phase, and is not included in checkerboard assays in FIG. 31A-FIG. 31J (limited to data from full-scale phase). Benurestat synergies were tested with 4 predicted antibiotics, measured by Bliss score and FIC.
Figure 33:
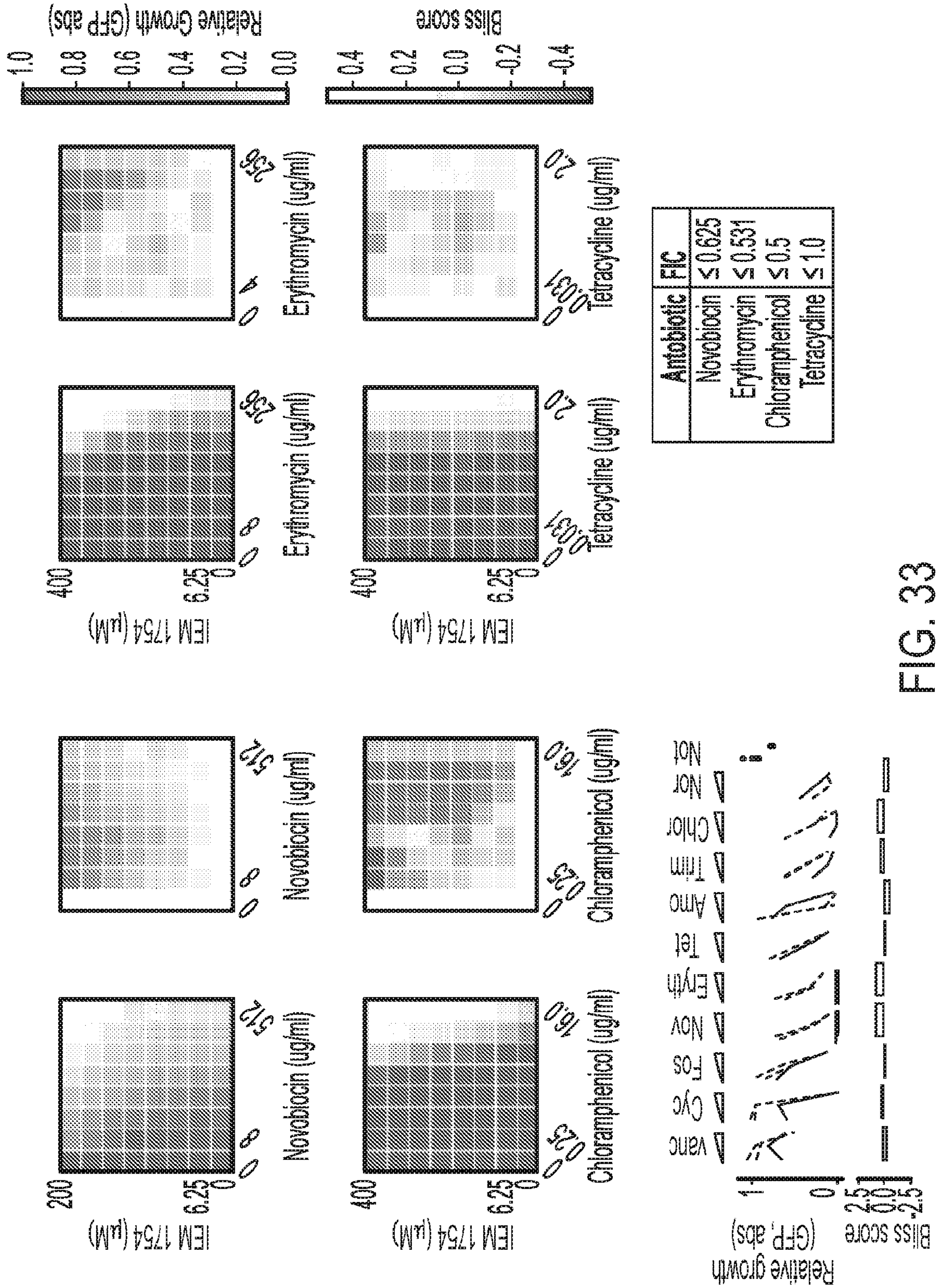
FIG. 33 shows checkerboard validation assays—IEM 1754 (pilot phase). IEM 1754 was a hit in the pilot phase, and is not included in checkerboard assays in FIG. 31A-FIG. 31J (limited to data from full-scale phase). IEM 1754 synergies were tested with 3 predicted antibiotics, and 1 antibiotic predicted neutral (tetracycline), measured by Bliss score and FIC.
Figure 34:
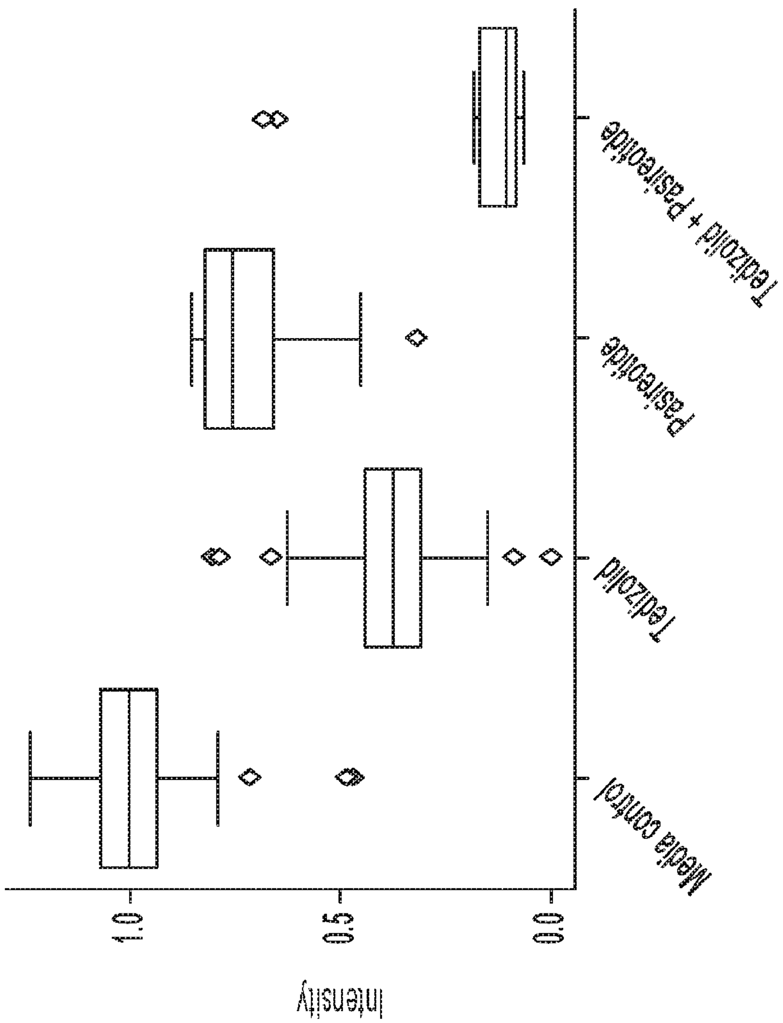
FIG. 34 is a box-plot depicting synergy between two compounds in antibiotic potentiation screen. Tedizolid and Pasireotide are two compounds from the repurposing library that were loaded on the same microwell array. As the array constructed compound-compound combinations in addition to compound-antibiotic combinations, we identified a synergistic interaction between these two compounds. Intensity reflects GFP measurements for each microwell, normalized to the median GFP value for microwells containing media (+ cells) and media (no cells). Tedizolid reflects relative GFP measurements for microwells with droplets carrying Tedizolid (100 μM; + cells) and media (no cells). Pasireotide reflects relative GFP measurements for microwells with droplets carrying Pasireotide (100 μM; + cells) and media (no cells). Tedizolid+Pasireotide reflects relative GFP measurements for microwells with droplets carrying Tedizolid (100 μM; + cells) and Pasireotide (100 μM; + cells).

After applying the more stringent synergy criterion of FIC<=0.5 to the hits, a set of six compounds were found that synergize with at least one antibiotic against *E. coli* (FIG. 4F, FIG. 32, FIG. 33). Notably, experiments found no previous indication of antibacterial activity for 5 of these 6 compounds which constitute a range of different chemical structures, characteristics, and biochemical targets (FIG. 4F). Comparing the primary screening data for each hit across the full panel of 10 antibiotics shows some commonalities and differences that may be indicative of the mechanism (FIG. 4G). For example, several hits shared common interactions with novobiocin and erythromycin (FIG. 4G, FIG. 4H, FIG. 4I), but divergent effects with vancomycin, ranging from strong synergy to strong antagonism (FIG. 4G, FIG. 4J).

Of all drug-antibiotic combinations tested, this statistical thresh holding yielded 280 drugs with significant effects against at least 1 antibiotic. Compounds were prioritized if they exceeded a bliss score of 0.7, the minimum score of statistically significant sulbactam/ampicillin controls, yielding 22 final drugs (0.77%) (FIG. 3D). Notably, each hit yields a signature of antibiotic potentiation, which can then be tested in conventional broth culture plates (FIG. 3E).

Eleven of the 22 hit drugs were selected for validation. Analysis was conducted to create 8-point checkerboards between each drug and antibiotics predicted to synergize from the primary screening data, as well as at least one antibiotic with no predicted synergy (FIG. 4A). In total, 100,800 drug-antibiotic combinations were tested, and 87% showed synergy as measured by Bliss score. Six of the validated hits satisfied the more stringent synergy criterion of FIC<=0.5 with at least one antibiotic (FIG. 4B). Notably, 5 of these 6 had no previous antibacterial indication, constitute a range of different chemical structures, and have been developed for a diversity of applications. As shown in FIG. 4C, a synergistic enhancement of the action of novobiocin, erythromycin, and cycloserine was observed for Compound 1 (Iodophenpropit) as determined by the overlay between effect on cell growth (top panels) and BLISS score (bottom panels). FIG. 4D shows synergistic enhancement of the action of novobiocin, erythromycin, and chloramphenicol with Iodophenpropit as determined by growth curves. The strongest observed synergy was with novobiocin, which showed a FIC score of 0.3125.

In summary, the techniques herein provide a combinatorial drug screening method in nanoliter droplets. Application of the droplet-based, nanoliter drug screening method enabled the discovery of many novel potentiators of antibiotics from a drug repurposing library, in particular, a set of five compounds with no previously noted anti-infective activity that may re-sensitize Gram-negative pathogens to Vancomycin, Erythromycin, and Novobiocin. The method resolves compound crosstalk between droplets to stabilize the compound library on the timescale of phenotypic assays. The platform and method is compatible with commercially available lab equipment already present in many academic and industrial life sciences research. The present platform supports a wide range of new organisms, cell lines, and assays. The techniques disclosed herein have also solved a key technical challenge in applying droplet microfluidics to drug screening.

The platform can be developed to support a wide range of new organisms, cell lines, and assays. Other groups have demonstrated successful droplet-based culture of a wide range of organisms and cell types, including adherent human cell lines. The present system uses conventional fluorescence microscopy and is also compatible with other optical assays and disease models such as phase microscopy, fluorescence gene expression reporters, etc. The conventional optical microscopy for assay readout promises extension to a wide variety of disease-specific models and optical assays including fluorescent gene expression reporters, high-resolution cell imaging, and more. The platform represents an important new tool to leverage drug-combinations for chemical biology and therapeutics discovery.

Materials and Methods

Figure 5E:
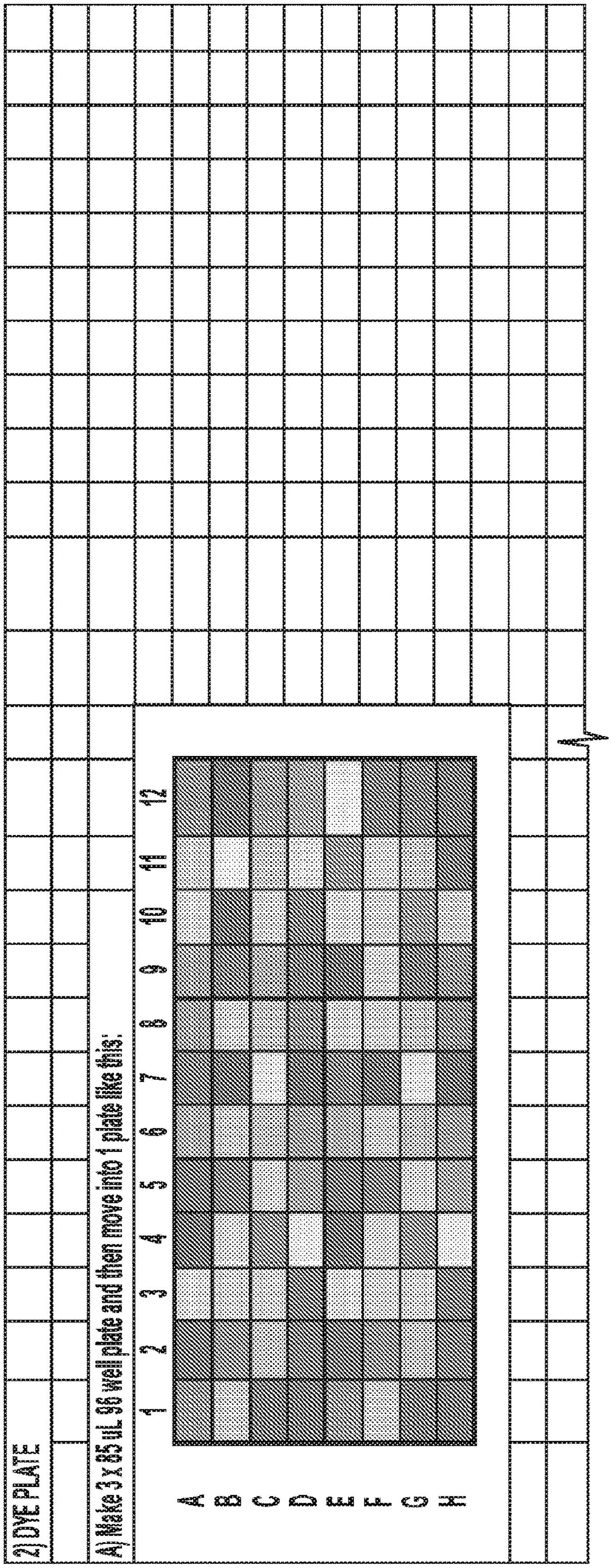
Figure 5E:
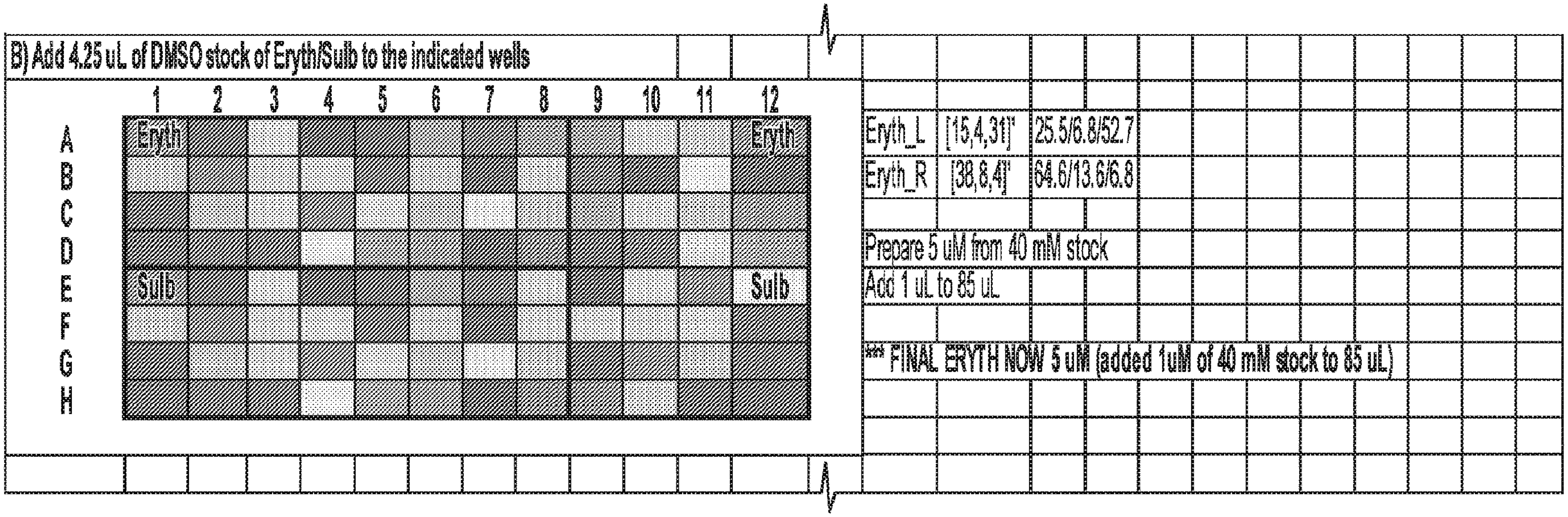
Figure 5E:
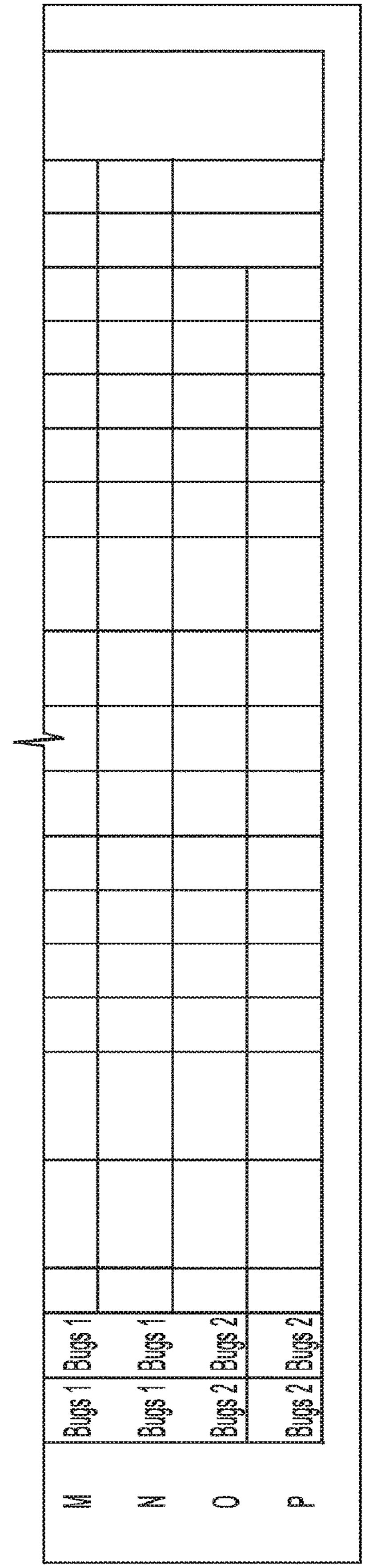

A two-step ARP process was used for processing. Compounds were stocked in 384 well plates (see e.g. FIG. 5A). In the first step compounds in each of four quadrants were echoed into 96-well plate ARPs (see e.g. FIG. 5B). In the second step a second plat of controls and dyes were added (see e.g. FIG. 5C). Construction of the source plate and controls is detailed in FIG. 5D. Outlines for dye plates and details on loading of wells is detailed in FIG. 5E. A map of a dye plate master plate is shown in FIG. 6A. An adjuvant plate set up is detailed in FIG. 6B.

Figure 7:
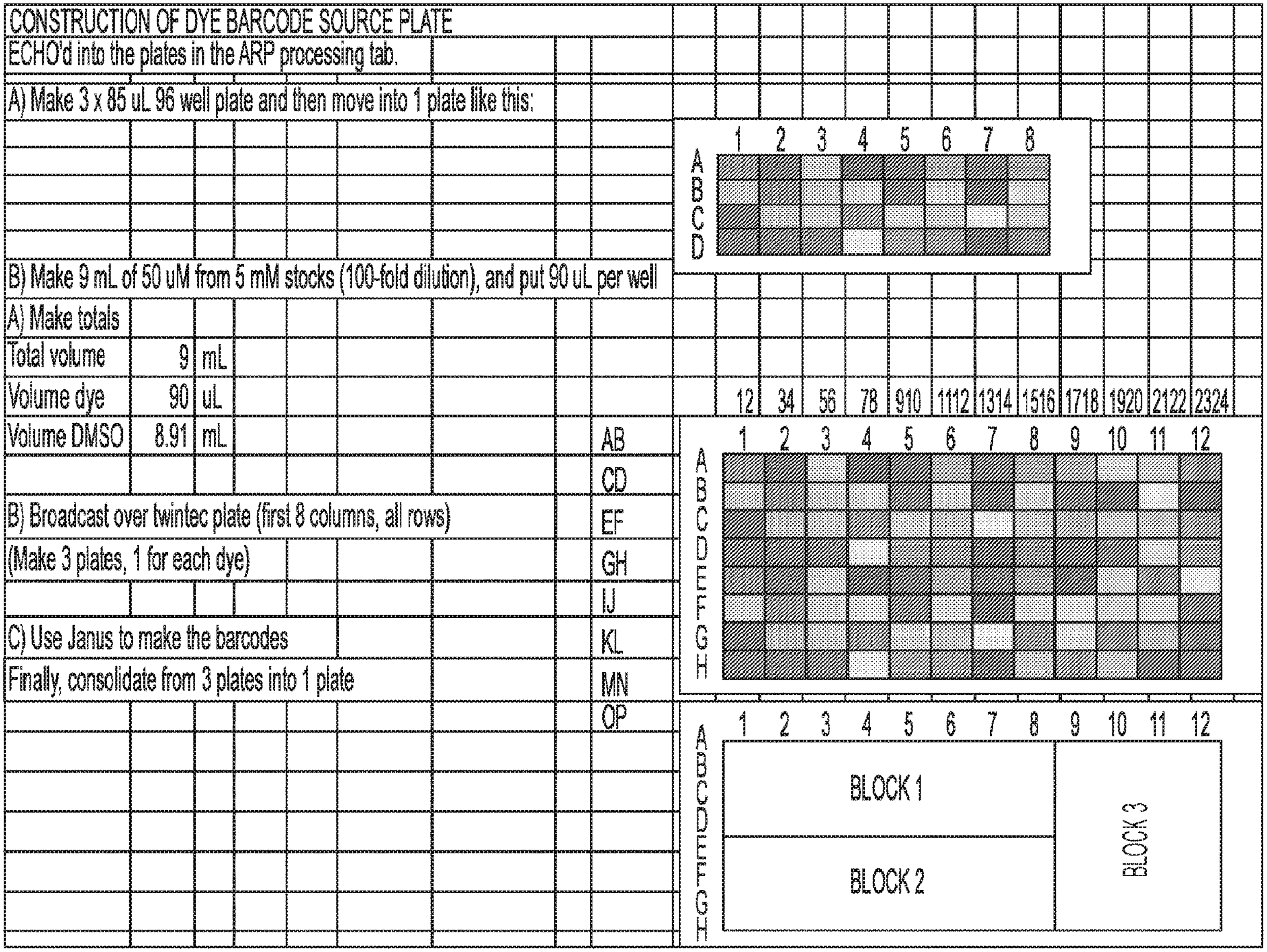
FIG. 7 is a schematic showing the construction of dye barcode source plates for adjuvants according to an exemplary embodiment of the disclosure. Janus may be used to make the barcodes, and dye barcode source plates may be echoed into the plates in the ARP processing tab.

Construction of dye barcode source plates for adjuvants is detailed in FIG. 7. Janus is used to make the barcodes. Dye barcode source plates are echoed into the plates in the ARP processing tab.

An example of a compound concentration model is given in FIG. 8. Methods for creating fluorescent Alexa dye stocks for Alexa 555, Alexa 594, and Alexa 647 are detailed in FIG. 9A and FIG. 9B. Nanodrop software was used for normalizing florescent Alexa concentrations.

Stock antibiotic concentration formulations for vancomycin, cycloserine, fosfomycin, novobiocin, erythromycin, tetracycline, ampicillin, trimethoprim, chloramphenicol, and norflaxacin are detailed in FIG. 10A. Standard curves for these antibiotics against *E. coli* were made (see e.g. FIG. 10B). An example of data from antibiotics at various concentrations before droplets were merged is given in FIG. 10C. Stock dilutions of 1×, 10×, and 100× concentrations were made (see e.g. FIG. 10D). Examples of plate maps for antibiotic concentrations were made (see e.g. FIG. 10E). Details regarding plate assembly with antibiotics is given in FIG. 10F.

Figure 11A:
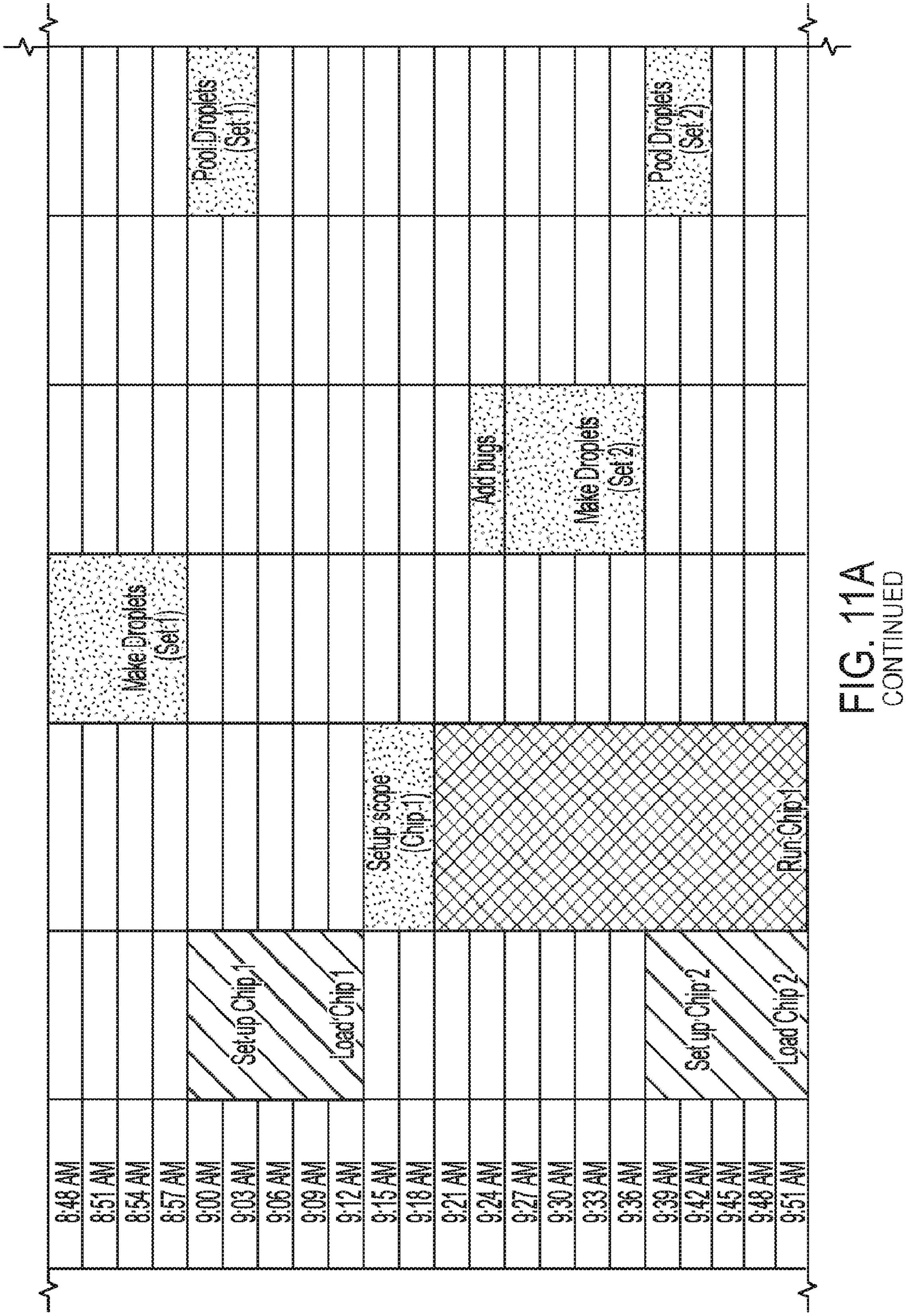
FIGS. 11A-11C provide an example overview of the workflow for the microdroplet platform. Workflow can be divided into shift 1 (FIG. 11A), shift 2 (FIG. 11B), and shift 3 (FIG. 11C).
Figure 11A:
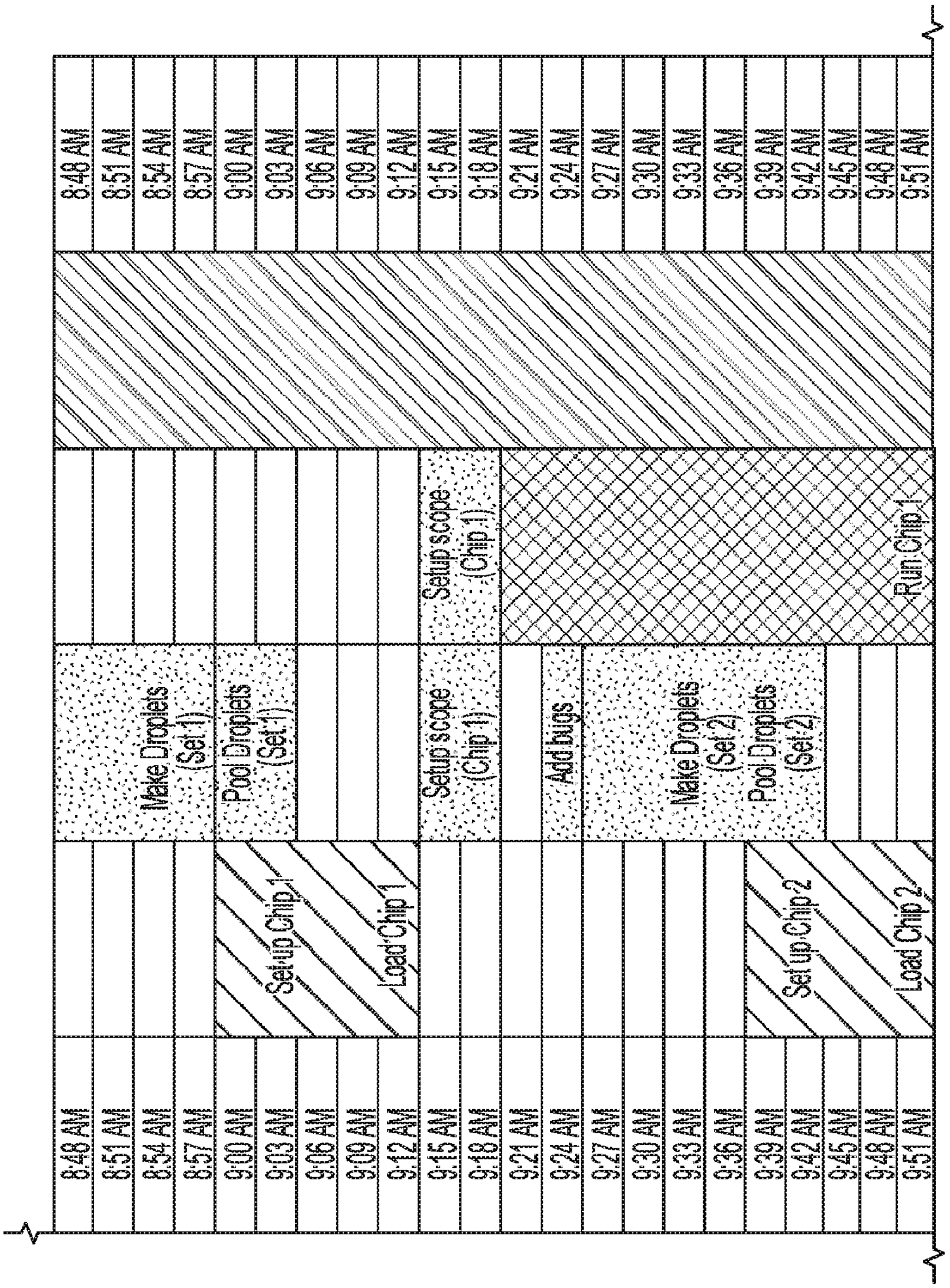
Figure 11A:
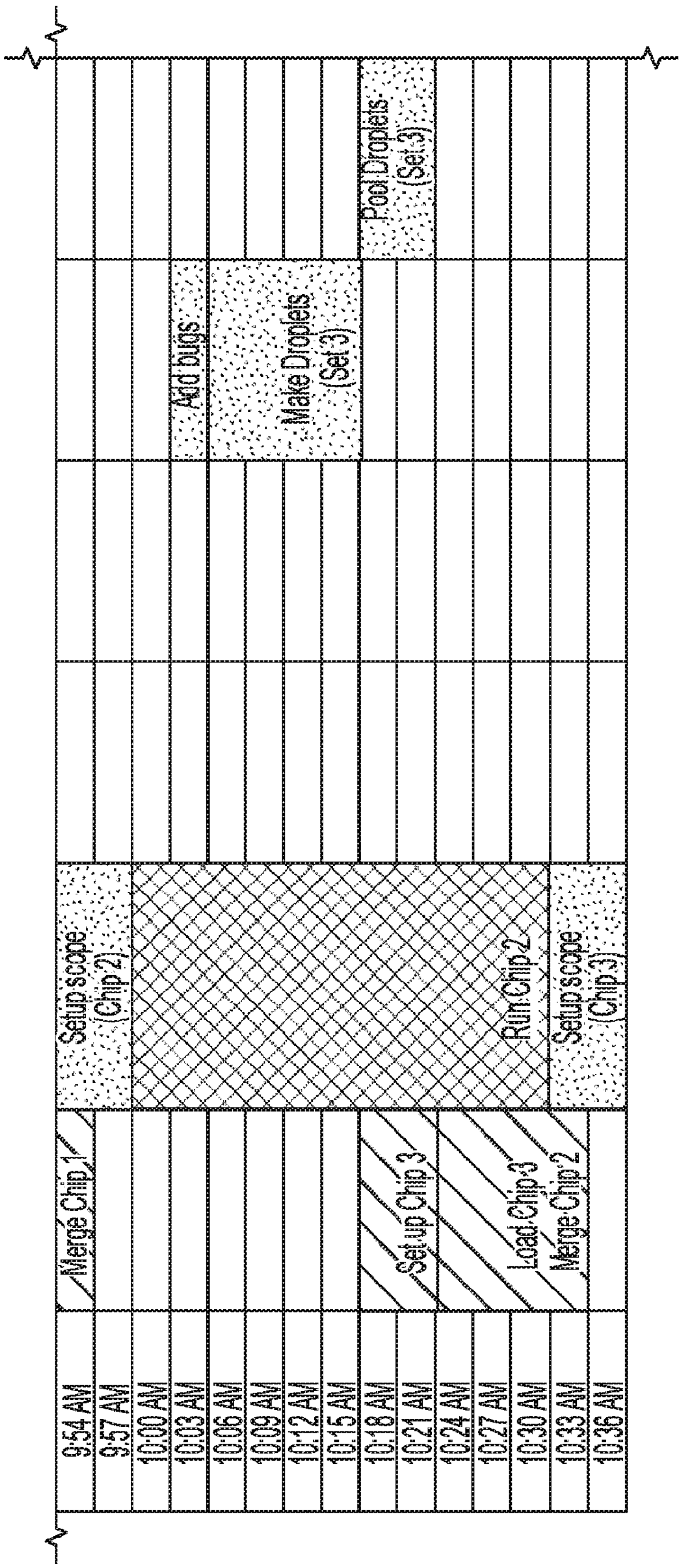
Figure 11A:
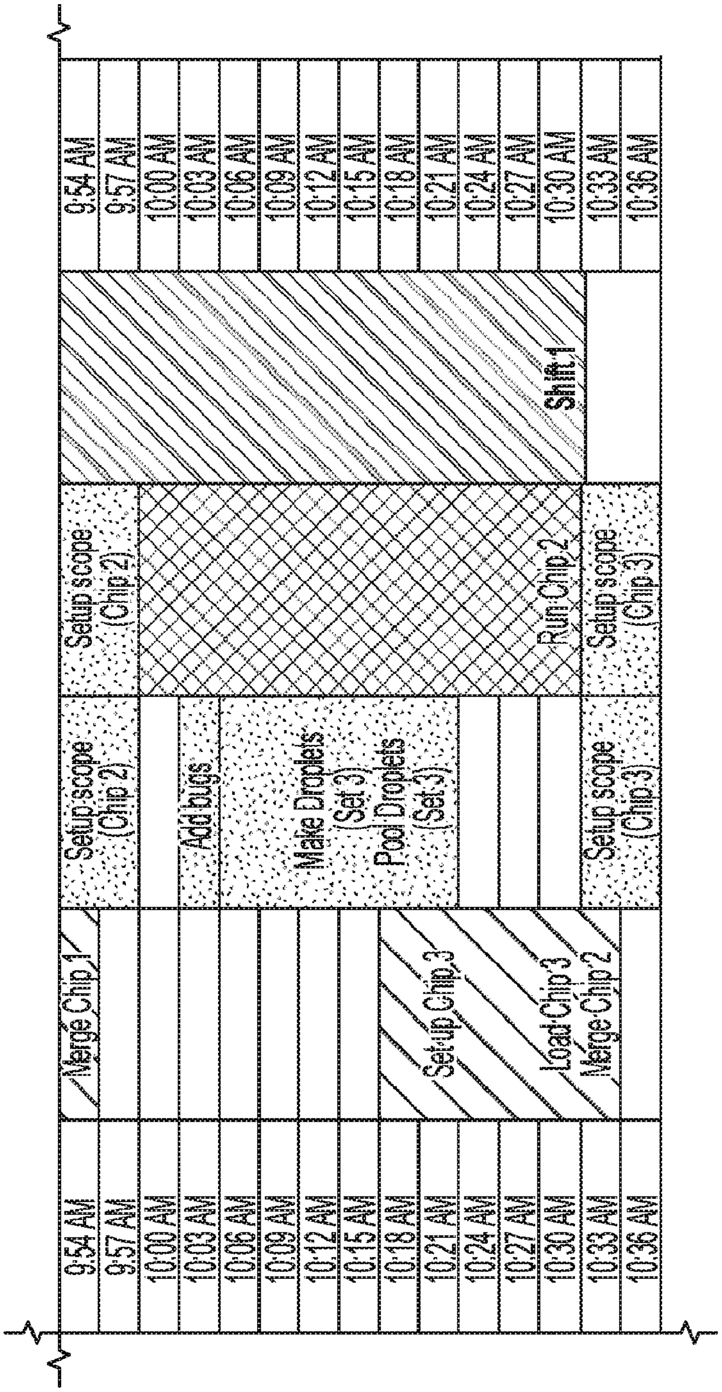
Figure 11B:
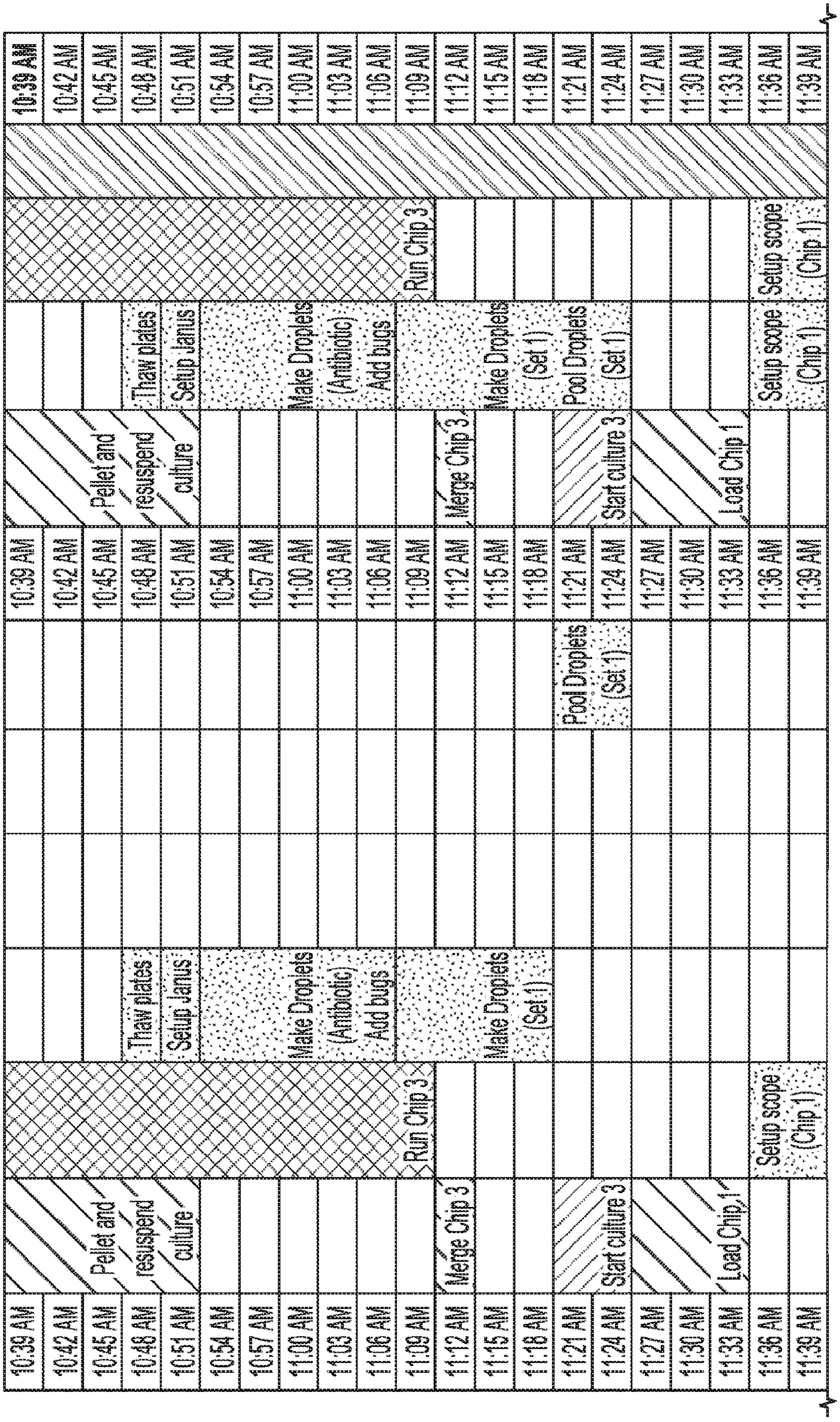
Figure 11B:
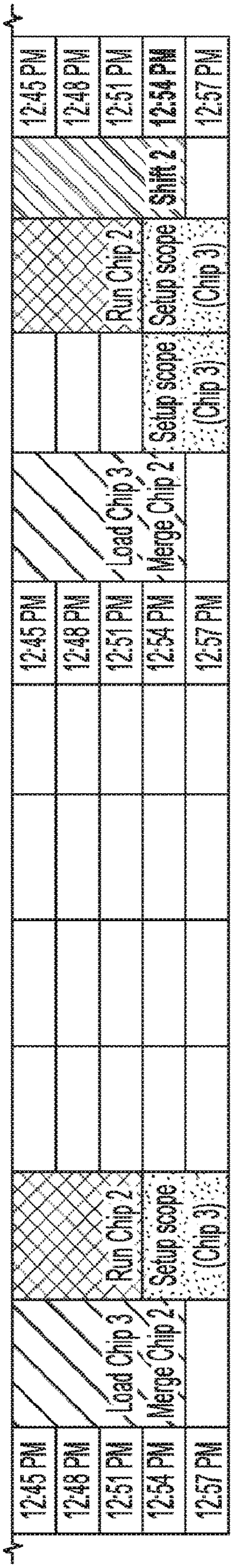
Figure 11C:
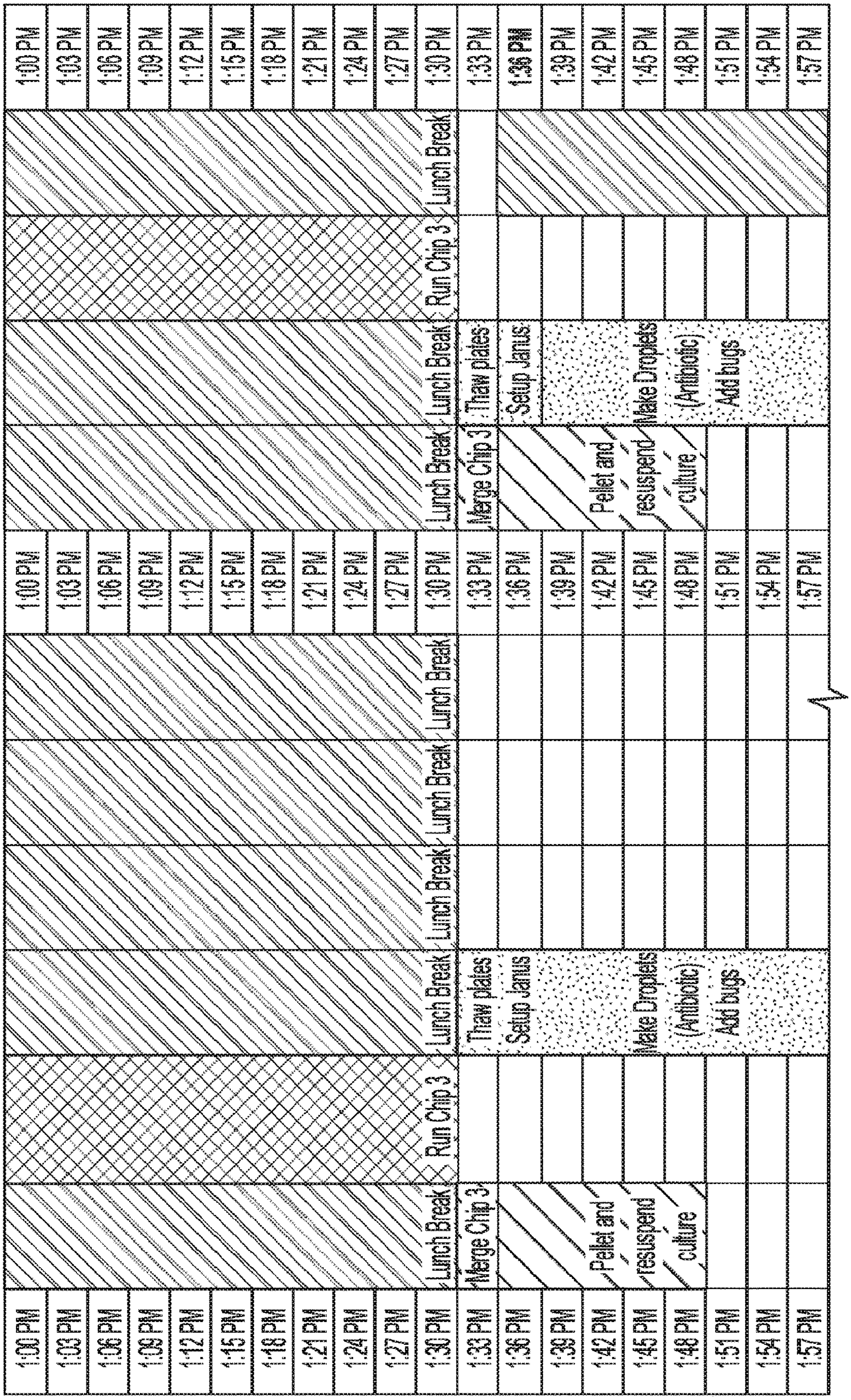
Figure 11C:
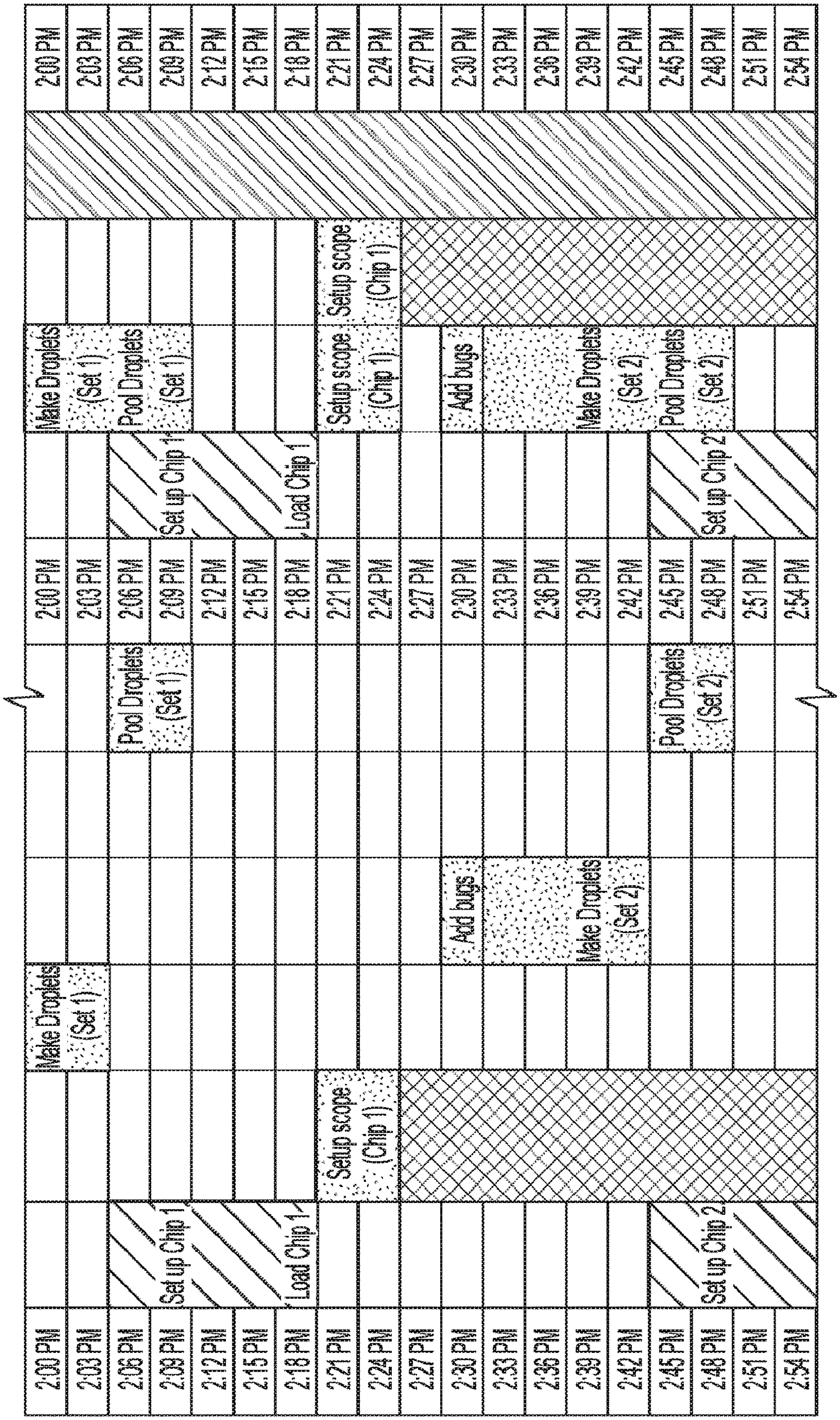
Figure 11C:
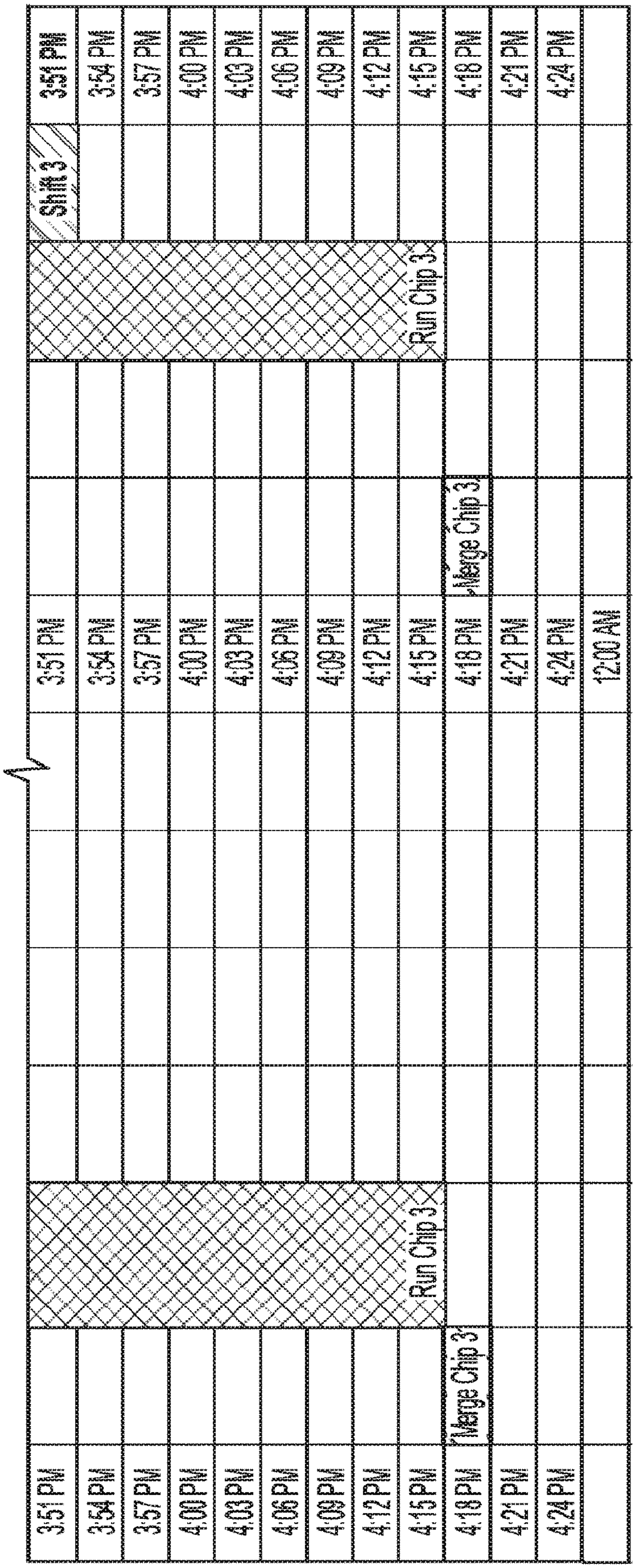

An example overview of the workflow for the microdroplet platform is given in FIG. 11A-FIG. 11C. Workflow can be divided into shift 1 (See e.g. FIG. 11A), shift 2 (see e.g. FIG. 11B), and shift 3 (see e.g. FIG. 11C).

Figure 12D:
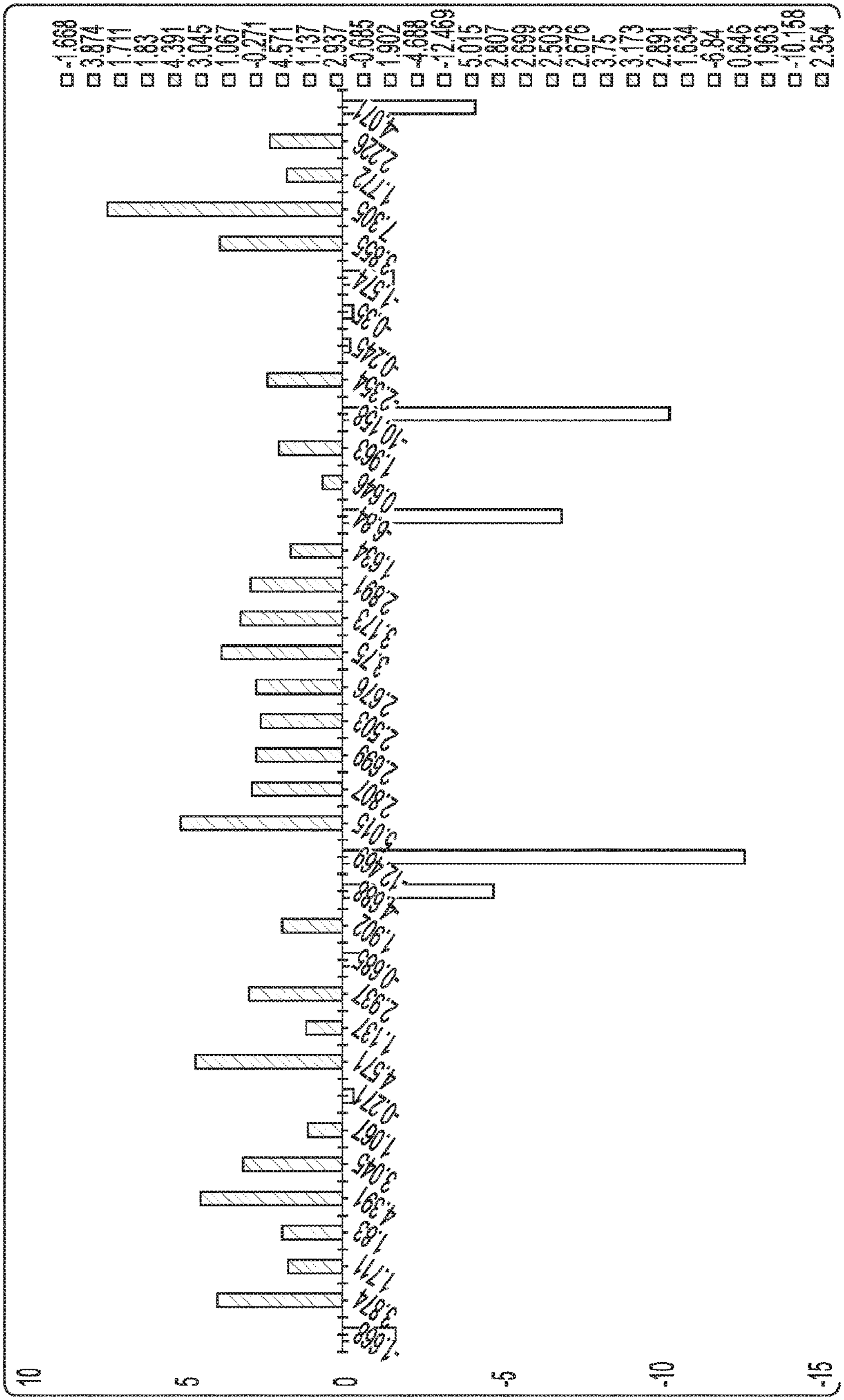

FIG. 12A-FIG. 12C depict three segments of a chart detailing primary hit information from a combination of antibiotics and adjuvants against bacterial models. FIG. 12D displays this hit data graphically.

Checkerboards of concentrations of antibiotics used for different screening runs were created (See e.g. FIG. 13A). Example concentrations of antibiotics used for screening against *E. coli* were made (See e.g. FIG. 13B). Barcode identifiers were made for each antibiotic (See e.g. FIG. 13C).

Checkerboard Adjuvant 14A-F Three batches of adjuvants were run during some screens (See e.g. FIG. 14A). Molar mass, mass, DMSO volume, plate volume, and DMSO solubility of the compounds were recorded for adjuvant compounds used during screens (See e.g. FIG. 14B). In some instances 800 microliter deep well plates were used for screening (See e.g. FIG. 14C). An exemplary plate map is shown in FIG. 14D. Exemplary antibiotic counts are listed in FIG. 14E. An exemplary annotated source plate is shown in FIG. 14F.

Checkerboards Model 15A-B. FIGS. 15A-B shows exemplary pipetting protocols for the adjuvant transfer (transfer 1), the antibiotic transfer (transfer 2), and the adjuvant stock.

Figure 16D:
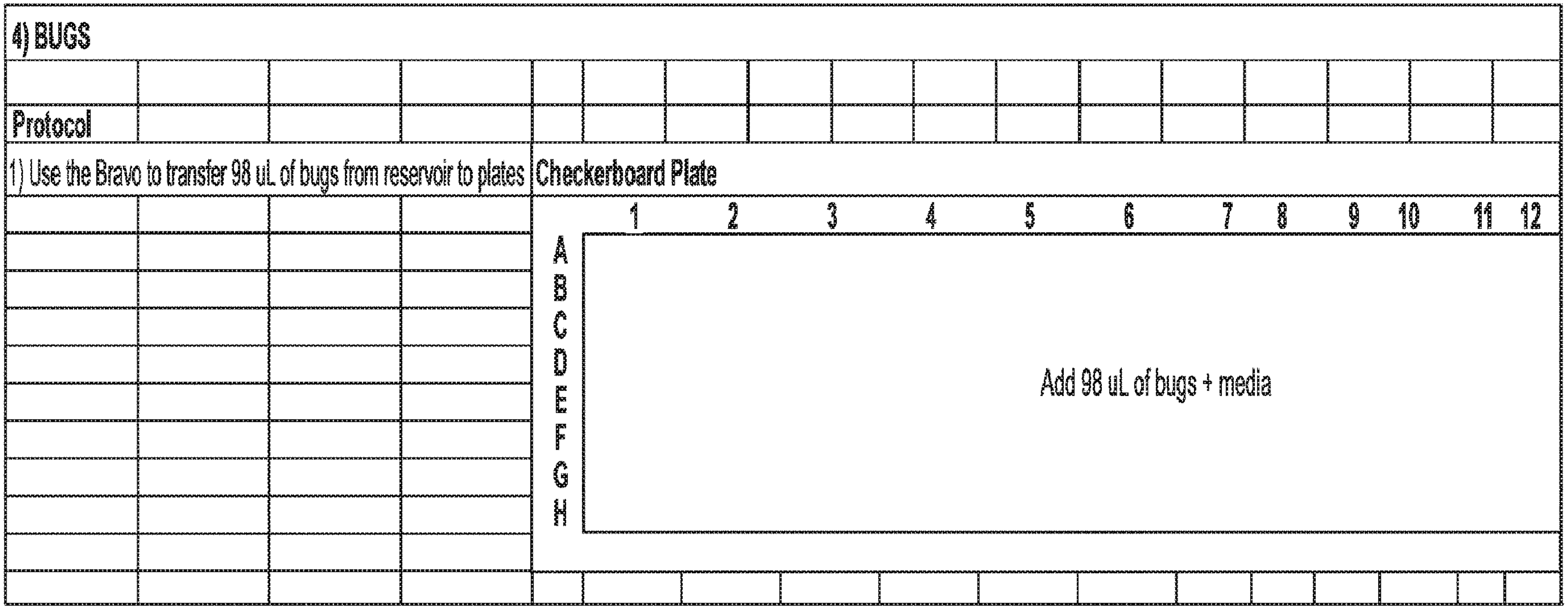

An exemplary checkerboards Workflow is depicted in FIGS. 16A-16D. FIG. 16A details a protocol for generating stock plates according to an exemplary embodiment of the invention. FIG. 16B details a protocol for generating source plates according to an exemplary embodiment of the invention. FIG. 16C details a protocol for generating checker board plates according to an exemplary embodiment of the invention. FIG. 16D details a protocol for adding bacteria to a checker board plate.

Primary hits identified by the techniques herein are summarized in FIGS. 17A-17C.

Exemplary checkerboard final barcodes are shown in FIGS. 18A-18E.

Bliss scores for antibiotic-compound combinations were determined (See FIG. 19A). The chart in FIG. 19A is zoomed in and split into two parts (See FIG. 19B and FIG. 19C).

Additionally, FIG. 20 is a table summarizing all raw screening data.

Chip Design and Microfabrication

Microwell chips were designed for two sizes in Autodesk AutoCAD as a normal format (6.2×7.2 cm, 49200 microwells) and a large format (7.4×10 cm, 97,194 microwells) array of microwells (two circles of 150 μm diameter set at 10% overlap) in a hexagonal lattice at 50 μm inter-well spacing (FIG. 20). All data in this work come from the normal format (6.2×7.2 cm). To create molds, we fabricated our designs to 100-120 μm feature height using photolithography on silicon wafers (Microchem SU8-2050), and chips were created using PDMS soft lithography (Dow Corning Sylgard). Chips were coated with 1.5 μm parylene C by vapor deposition (Paratronix) to inhibit evaporation, inhibit compound uptake, and stiffen the chip to prevent interior collapse during droplet loading.

Microwell Array Operation

Each compound was pre-mixed with a unique ratio of 3 fluorescent dyes (Alexa Fluor 555, 594, 647 from Thermo- Fisher Scientific, 1 μM final constant total concentration across all dye sets) (FIG. 1H, Section I; FIG. 21A). Starting from an overnight saturated culture, cells were diluted and grown to log-phase (106-107 cells/mL) as measured by optical density, resuspended in fresh media, and added to compounds and dye mixtures. Each mixture of compound, dye, and cells was emulsified into 20,000 1-nL droplets (continuous phase: fluorocarbon oil 3M Novec 7500 with 0.5-2% w/w RAN Biotech 008-FluoroSurfactant) using Bio-Rad QX200 cartridges and instrument, or a custom aluminum pressure manifold (FIG. 1H, Section I).

To prepare each microwell chip for droplet loading, the chip was suspended on a hydrophobic glass slide (Aquapel treated) with plastic spacers (height 250 μm), clamped from above and below by an acrylic housing with neodymium magnets (FIG. 20, Movie 1, FIG. 22A-FIG. 22C). Using 0% w/w surfactant oil, the gap between the chip and the glass created by the spacers was filled with oil. Droplets containing each input condition (total volume 200 μL, ~200,000 droplets) were pooled, and injected the pool into the chip, continuing to flow the droplets by injecting more oil and draining excess droplets (total time: 5 minutes pooling, 5 minutes loading) (FIG. 1H, Section II-III, Movie 1, Movie 2). After loading was complete, the chip was washed with oil (0% w/w surfactant) to purge free surfactant. The spacers were gently removed to seal microwells against the glass slide and bolted the clamp closed (FIG. 1H, Section II).

To decode the compounds present in each microwell, the chip was then imaged with an epifluorescence microscope (optical resolution 6.5 μm/pixel). The droplets were merged to mix the compounds in each microwell by applying an AC electric field (4.5 MHz, 10,000-45,000 volt source underneath glass slide supplied by corona treater). To allow cells to respond to the compounds present in each microwell, cells were incubated at 37° C. for 7 hours (static), and then assayed their growth by measuring constitutive GFP fluorescence using the epifluorescence microscope (FIG. 1H, Section IV).

Fluorescence Microscopy

All fluorescence microscopy was performed using a Nikon Ti-E inverted fluorescence microscope, with fluorescence excitation by a Lumencor Sola (100% power). Images were taken with 4 fluorescence channels for GFP (Semrock GFP-1828A) and 3 encoding dyes, Alexa Fluor 555, 594, 647 (Alexa Fluor 555: Semrock SpGold-B; Alexa 594: Semrock 3FF03-575/25-25+FF01-615/24-25; and Alexa 647: Semrock LF635-B). Images were collected by a Hamamatsu ORCA-Flash 4.0 CMOS camera (exposure times range 50 ms-500 ms) at 2× or 4× magnification (6.5 μm/pixel optical resolution).

Analysis of Microwell Array Data

To determine the effect of each pair of input conditions, (a) droplet pairs in each microwell must be identified; (b) each droplet must be assigned to an input condition using the 3 fluorescence colors; (c) the response assay signal at a later timepoint must be matched to each microwell and corresponding droplet pair; and (d) a statistic must be computed on all assay signals from all microwells containing the same pair of input conditions.

To detect each droplet in the image, we use a circular Hough Transform to detect circular fluorescent objects with 100-140 μm diameter. An inference was made for a pair of droplets sharing a microwell if the distance between their centroids is less than a given distance threshold.

Each droplet is assigned to an input condition barcode by determining the relative fluorescence of each of the three dyes. Barcodes are constructed such that the total dye concentration is constant (final 1 μM), only varying the ratios of the three component dyes. The 3-color dye fluorescence of each droplet can thus be projected onto a 2-dimensional plane, eliminating systematic effects from differences in illumination (FIG. 21A). The DBSCAN algorithm identifies the clusters of droplets corresponding to each input condition, with possible user input to correct errors. A quality score for each droplet can be computed based on the distance to the centroid of the assigned cluster (FIG. 21B-FIG. 21C). The Hungarian algorithm then maps each cluster to a priori known locations of each dye mixture barcode. If input conditions change the optical properties of each barcode dye mixture, the input-barcode mixture can be imaged prior to emulsification to predict the fluorescence of the resultant droplets.

Each microwell is matched with the later imaged response assay measurement (e.g. growth reported by constitutive GFP expression) (FIG. 1H, Section IV). All microwells with replicate pairs of input conditions comprise a sample from which a summary statistic was calculated, such as the median GFP signal. Additionally, standard errors are computed by bootstrapping from this sample.

Measurements of Compound Cross-Contamination

To construct source droplets, resorufin (10 μM) was emulsified in cation-adjusted Mueller Hinton broth (CAMHB) into 1-nL droplets in 2% w/w fluorosurfactant (RAN Biotech 008-FluoroSurfactant) in 3M Novec 7500 fluorocarbon oil. Sink droplets were made in a similar fashion, but with fluorescein (5 μM, CAMHB), as this dye shows negligible exchange on assay timescales. Droplets were pooled in 1:1 ratio (5 minutes), and then loaded into the microwell array chip (5 minutes total), such that microwells received either 2 sink droplets (sink-only wells), 2 source droplets (source-only wells), or 1 sink and 1 source droplet (mixed wells) (FIG. 2F). The chip was washed with oil containing either 2%, 0.5%, or 0% w/w surfactant, and then mechanically clamped the chip to the glass substrate (FIG. 20).

Resorufin fluorescence measurements of the sealed array were taken over 20 hours, with sink droplets indicated by fluorescein fluorescence and assay background subtracted from all measurements. To measure inter-well exchange, the mean resorufin fluorescence of source-only microwells and sink-only microwells were compared (normalized to their sum) (FIG. 2G). As a proxy for conventional droplet systems and predicting exchange during the pooling phase of the protocol, the mean resorufin fluorescence of source droplets and sink droplets in mixed wells was compared (normalized to their sum) (FIG. 2G, FIG. 22A).

To measure the relationship of exchange kinetics and flux surface area, we additionally created arrays with microwells sized to receive 7 droplets. The microwell chip was washed with 2% w/w surfactant, and all other experimental conditions were the same as above (FIG. 22B-FIG. 22C).

Comparison to Broth Culture Plates

Organisms used for comparison were *Pseudomonas aeruginosa* PAO1 (in cation-adjusted Mueller Hinton broth, CAMHB), *Staphylococcus aureus* (in LB media), and *Escherichia coli* K-12 MG1655 (in CAMHB), all with plasmid-mediated constitutive expression of GFP (FIG. 2H). To compare growth rates between conventional broth culture and the platform, saturated overnight cultures were diluted into fresh media, grew to log-phase (106-107 cells/mL) as measured by optical density, and resuspended in fresh media. Cultures were then split between (1) Erlenmeyer flasks (10% volume, 220 RPM, 37C) and (2) emulsions loaded into our microwell array platform (static, 37C).

Growth was monitored via accumulation of GFP fluorescence measured by (1) transferring to clear bottom 96-well plates and measuring by fluorescence plate reader (Molecular Devices SpectraMax), or (2) epifluorescence microscopy (Nikon Ti-E). For each organism, GFP measurements were transformed from the (1) 96-well plate reader to the same scale as the (2) microwell measurements by computing a least squares linear regression between measurements matched at each timepoint (FIG. 2H, data shown for (1) are transformed based on linear regression).

To compare antibiotic response curves, serial dilutions were created of 6 (for *P. aeruginosa*) or 12 (for *S. aureus, E. coli*) antibiotics in media in clear-bottom 96-well plates: Trimethoprim (Trim), Chloramphenicol (Chlor), Ceftriaxone (Ceft), Tetracycline (Tet), Kanamycin (Kan), Norfloxacin (Nor), Fosfomycin (Fos), Cycloserine (Cyc), Vancomycin (Vanc), Erythromycin (Eryth), Ampicillin (Amp), Novobiocin (Nov) (FIG. 2*f*). Cells cultured under same conditions as above were emulsified, and in parallel emulsified 5 points on each antibiotic dosage curve (no cells added). After pooling all emulsions, the emulsions were loaded in two technical replicate microwell arrays. Similarly, cells were added to the 96-well plates and split the cell-antibiotic mixtures across two technical replicate plates (clear bottom 96-well plates, with parafilm at edges to prevent edge effects, final volume 200 μL).

Using GFP fluorescence measurements similar to above, the median GFP value was compared from microwells that received 1 antibiotic droplet and 1 cells droplet, with equivalent dosage conditions in the 96-well plates (FIG. 23-FIG. 25). To compare dose responses, a non-linear least squares fit was obtained of the Hill curve for concentration C to data obtained from both 96-well plates and our platform using (3 local parameters: offset, magnitude, IC50; 1 global parameter for each antibiotic: Hill coefficient, h).

$$G = \text{offset} + \text{magnitude} * \frac{1}{1 + \frac{C^h}{IC_{50}^h}}$$

In comparing fit IC50's, we removed antibiotics with plasmid mediate resistance (*S. aureus*: Chlor; *E. coli*: Kan), or poor fit quality due to suboptimal dosage range (*S. aureus*: Ceft, Eryth, Nor, Tet; *E. coli*: Ceft).

As construction of droplet pairs in microwells is stochastic, each pair of droplets occurs a random number of replicate microwells. To compute how technical noise scales as a function of k replicate microwells, we resampled with replacement k microwells from each set of replicates and recomputed the median GFP across each sample (FIG. 2K).

Antibiotic Potentiation Screening Design and Analysis

To perform the antibiotic potentiation screen, each microwell chip received droplets containing a total of 64 input conditions, with 32 held constant across all chips, and 32 that vary on each chip (FIG. 3F). The first 32, held fixed, consisted of 30 antibiotic conditions (10 antibiotics×3 concentrations, no cells), and 2 media controls (no cells). The second 32 consisted of 1-2 positive controls (sulbactam 20 μM, + cells; or erythromycin 5 μM, + cells), 1-2 negative blank controls (+ cells), 2-4 media controls (+ cells), and 24-28 variable compounds (100 μM, + cells). All conditions were in cation-adjusted Mueller Hinton broth media, 2% DMSO (all concentrations reported are final concentrations).

This setup allowed the screen to be performed in a divide-and-conquer format. The repurposing compound library is composed of 4,160 compounds across 52 96-well plates (80 compounds per plate, with controls in column 1 and 12). Each 96-well plate was divided into 3 groups of 32, each run on a separate chip but pooled with the same set of antibiotics-carrying droplets.

*E. coli* K-12 MG1655 with plasmid-mediated constitutive expression of GFP was prepared as described above, and added to all conditions described as "+ cells" just prior to emulsification. After loading, imaging, and merging, microwell arrays were incubated at 37° C. (static), and then later imaged again to measure growth by GFP fluorescence.

All compounds and antibiotics were pre-mixed with barcoding dyes ahead of the screen. As the high concentration of compounds (200 μM prior to merging) can affect the encoding dye fluorescence, we imaged the mixtures ahead of time to predict the fluorescence of the droplets and aid their later classification.

To estimate synergy between compounds and antibiotics, the Bliss Independence metric was used. If treatment Antibiotic A results in 80% growth (1−fA), and Compound B results in 75% growth (1−fB), then assuming the antibiotic and compound act independently, it is expected that the combination of the antibiotic and compound results in 60% growth (1−fA)×(1−fB). To estimate antibiotic-compound synergy, we subtract the observed growth from the expected growth [(1−fA)×(1−fB)]−(1−fAB)=fAB−(fA+fB−fA fB).

The net growth inhibition for antibiotic A from microwells carrying an antibiotic A (no cells) droplet, and a media (+ cells) droplet were estimated. The net growth inhibition of a screening compound from microwells carrying compound B (+ cells) droplet, and a media (no cells) droplet were also estimated. All growth values were normalized to microwells containing a pair of media (+ cells) and media (no cells) droplets, and estimated synergy using the Bliss Independence metric. Since each antibiotic was present at 3 concentrations, a metric was summed for the compound across each of the 3 conditions to yield a final metric called "Bliss Score." Compounds with net growth inhibition exceeding 80% were removed from analysis.

To estimate the uncertainty in the Bliss Score measurement, all microwells in the array were bootstrap resampled (100 iterations) to the number of counted for each pair of inputs and recomputed Bliss Scores to estimate a sampling distribution and standard error. Bliss scores were divided by their corresponding standard errors to yield a test statistic modeled with a T-distribution fit to the blank negative controls (FIG. 30A-FIG. 30B) (density function $f_T$ fit with parameters: v=11.23, degrees of freedom; σ=0.922, scale parameter).

$$f_T = \frac{\Gamma\left(\frac{(\upsilon+1)}{2}\right)}{\sigma\sqrt{\pi\upsilon}\,\Gamma\left(\frac{\upsilon}{2}\right)}\left(1 + \frac{(x/\sigma)^2}{\upsilon}\right)^{-\frac{\upsilon+1}{2}}$$

Quality Scoring of Microwell Array Chips in Antibiotic Potentiation Screening

To quality score each microwell array chip in the antibiotic potentiation screen, we measured the difference between conditions representing the top and bottom of the assay dynamic range. The top of the dynamic range is given by microwells containing a media (+ cells) droplet, and a media (no cells) droplet. To represent the bottom of the dynamic range, we used microwells containing a media (+ cells) droplet and a droplet containing cycloserine 16 μg/mL (no cells).

The dynamic range on each microwell array was quantified by computing the Z-factor metric. The median GFP values were computed for each set of microwells (μ+, and μ−). To estimate a standard error, median GFP estimates were bootstrap resampled from each set (1000 iterations) to estimate a sampling distribution, and measured standard errors as the standard deviation of the sampling distribution (σ+, and σ−) (FIG. 28A-FIG. 28B). The Z-factor (Z') was computed as the following:

$$Z' = 1 - \frac{3(\sigma_+ + \sigma_-)}{|\mu_+ - \mu_-|}$$

Chips with Z-factors <0.21 were removed from analysis for low quality (FIG. 28B).

Quantification of Antibiotic Potentiation Assay Performance

For each antibiotic in our panel (FIG. 3F), the dynamic range of the potentiation assay is the difference between relative growth measured for the lowest concentration of the antibiotic tested and maximal growth inhibition. Cycloserine (16 μg/mL) was chosen to represent the assay lower limit to where growth inhibition (and therefore antibiotic potentiation) is maximized.

Figure 29:
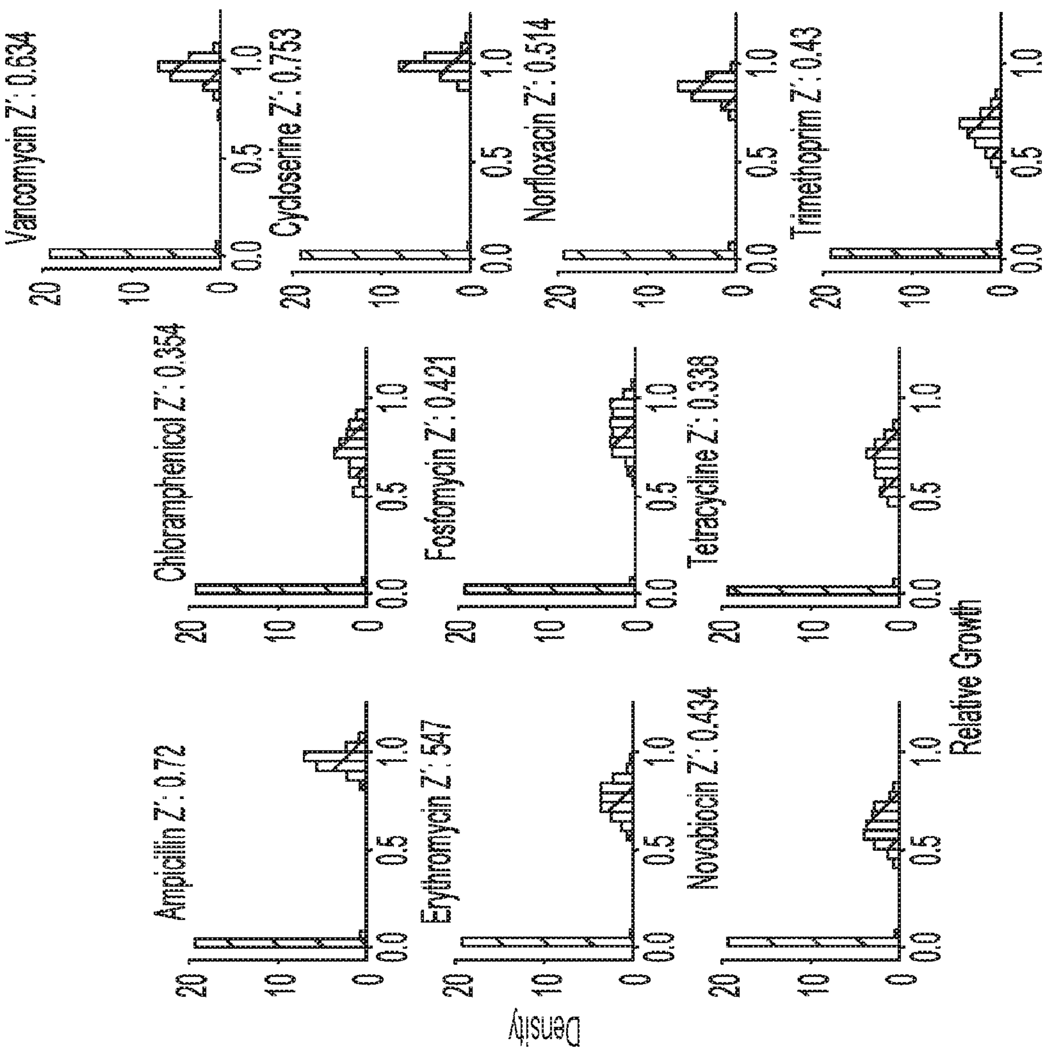
FIG. 29 shows screening assay performance for each antibiotic in panel. For each antibiotic in our panel, the dynamic range of the potentiation assay is the difference between the upper limit given by the relative growth values for the antibiotic at the lowest concentration tested (upper limit, red histogram), and the lower limit of detection (cycloserine 16 μg/mL, blue histogram), across all 108 chips analyzed. To quantify assay performance, the Z-factor (Z', displayed in title of each plot) was computed between these two distributions for each antibiotic.

To quantify assay performance for the overall screen, relative growth estimates (GFP) were compiled from all chips for each antibiotic and compared to cycloserine (16 μg/mL) (FIG. 29). This comparison was quantified by computing the Z-factor (Z') for each pair of distributions.

Checkerboard Validation Assays

Checkerboards were constructed from 2-fold serial dilutions of a compound and an antibiotic to create a 64-point matrix in 96-well v-bottom plates (Costar), 2% DMSO (final concentration). *E. coli* K-12 MG1655 were prepared as described above and added to the plates (final volume 100 μL; plate edges wrapped with parafilm to reduce edge effects). We incubated the plates at 37C, 220 RPM for 7 hours, and measured growth by GFP accumulation using a plate reader (Molecular Devices, SpectraMax) (FIG. 31A-FIG. 31J).

Bliss scores were calculated according to the formula above for each point in the dosage matrix, using the independent dosage response curves for each compound and antibiotic. To compare the plate data with primary screen data, The maximum of Bliss scores summed over 3 contiguous antibiotic doses (at the same compound dosage), for any of the top 4 compound doses tested, were taken. This variation in potency was allowed to account for (a) differences between the 96-well plate format and our microwell platform (b) day to day variation in culture conditions (c) all compounds were re-ordered and may not have the same potency as in primary screen.

A compound-antibiotic pair positive was considered for Bliss synergy if the maximum summed Bliss score ≥0.4. A validation rate was computed by computing the fraction of hit compound-antibiotic pairs in primary screening data (Bliss score >0.7 and p-value <1e-4) that scored positive in plates as well, and compared this to a binomial null model with probability equal to the fraction of positive pairs from all pairs tested.

The fractional inhibitory concentration (FIC) is a more stringent test, defining synergy as FIC ≤0.5. For a given antibiotic A and compound B, we measured the minimum inhibitory concentration (MIC) of each as the first well in the dosage series with <10% growth. If this was not observed in conditions tested, we assumed that the MIC was twice the highest tested dose. For a well in the matrix at dosage point (A: x, B: y) with <10% growth, FIC was calculated via the FIC=x/MICA+y/MICB (where MICA is the MIC measured for antibiotic A independently, and MICB is the MIC measured for compound B independently). The compound-antibiotic combination was classified as synergistic if the minimum FIC in the matrix ≤0.5.

Estimation of Compound Exchange Kinetics During Pooling Phase

Compartmentalization of droplets in the microwell array and depletion of free surfactant limits compound exchange between wells (FIG. 2F, FIG. 2G). However, limited quantities of compounds may still exchange between droplets via surfactant reverse-micelles in the continuous phase during the time that droplets are pooled prior to washing and sealing the array (FIG. 1H, Section I; 10 minutes). Reverse micelles in the bulk fluorous oil have a fluorous exterior and a PEG interior. It was hypothesized that exchange of small hydrophobic solutes occurs by partitioning of compounds from the aqueous droplet interior to the PEG phase of reverse micelles, the dynamic formation and fusion of reverse micelles with droplets, and the diffusion of compound-laden reverse micelles through the continuous oil phase.

The opportunity for exchange occurs in our workflow because droplets carrying different compounds are randomly dispersed in a 3-dimensionally packed bulk emulsion, possibly allowing transport to neighboring droplets. To estimate the transport kinetics, experiments (i) measured the exchange rate between neighboring droplets (FIG. 22A); (ii) measured the dependence on number of neighboring droplets (FIG. 22B-22C); and (iii) compared predictions to experimentally observed quantities (FIG. 22C).

As a baseline, the kinetics of resorufin exchange was measured between neighboring droplets in microwells containing one source and one sink droplet (FIG. 2F, FIG. 22A). We modeled exchange at early timepoints (<2 hours) by a single-exponential (FIG. 22A), from which we can fit a kinetic constant (k) as a function of surfactant concentration.

During droplet pooling, droplets are dispersed in a 3-dimensional bulk emulsion of packed spheres, so the compound exchange rate could be increased relative to the estimate from microwells containing only two droplets as each neighboring droplet in the bulk emulsion can participate in compound exchange. For example, a droplet carrying compound A may neighbor two droplets carrying compound B. To measure the relationship of neighboring droplet number and exchange kinetics, microwells were constructed that hold a total of 7 droplets each, with random loading of source (resorufin) or sink (fluorescein) droplets (FIG. 22B). A linear relationship was found between exchange rate (between source and sink droplets that shared the same microwell) and the number of source droplets in the microwell (and therefore, the interfacial surface area available for exchange) (FIG. 22B-FIG. 22C). To predict compound exchange in a bulk emulsion, the fit kinetic constants measured in FIG. 22A were linearly extrapolated by the number of neighboring droplets carrying a given compound (FIG. 22C).

As an experimental test of the prediction, the exchange between source and sink droplets was estimated during pooling in the experiment described in FIG. 2F and FIG. 2G. Since there was not detection of any increase in resorufin in microwells containing only sink droplets (FIG. 2G), the fraction of fluorescence detected at the first time point (0.096) must have occurred during the pooling step. Source and sink droplets were pooled in a 1:1 ratio, so it was expected that during pooling, for a given sink droplet, an average of 50% of the 8-12 neighboring droplets in the 3-dimensional sphere packing are source droplets (with the distribution as binomial). This measurement (0.096) is in good agreement with the predictions of exchange rate for 4 neighboring source droplets over the duration of the pooling step (FIG. 22C).

Under the conditions in the antibiotic potentiation screen, droplets carrying 64 distinct inputs for each chip were pooled, so the mixing ratio was much lower than 1:1 (1:64). Under these circumstances, it was rare that a given droplet neighbored more than one droplet carrying the same compound, so kinetics for exchange of any single compound are described by 1 neighbor (FIG. 22C, blue curve) and even more limited than in the above tests with resorufin (where pooling was in a 1:1 ratio).

However, while resorufin dye is a convenient model, exchange kinetics also depend on compound properties, specifically those that affect the relative affinity of a given compound for reverse-micelles. Empirically, more hydrophobic compounds exchange faster (fluorescein exchanges more slowly, and rhodamine more quickly resorufin) and Log D (log 10 of the octanol-buffer partition coefficient) is a useful predictor of exchange rate. The c Log P value (a calculated prediction of hydrophobicity) of resorufin is 1.77, which is of middling hydrophobicity compared with the compounds used in the screen.

There is ample evidence that the platform performs adequately despite the potential for false-negative from compound loss from an assay droplet, and false-positives by exchange among droplets during the initial pooling step. First, the antibiotic IC50s measured in the chip correspond closely to those measured in 96 well plates. Second, 108/124 chips without logistical failures passed stringent quality control assessments of the internal positive and control conditions. Finally, of the primary screening hits where validation was attempted, 88% (15/17 tests, p-value=0.00058 for a binomial null model across all pairs positive in plates; 10/11 distinct compounds) were successfully validated in conventional 96 well plate checkerboard assays (FIG. 4E, FIG. 32). Movies Movie 1 is a pool of emulsions loaded into a large-format (FIG. 20) microwell array using a P1000 micropipette. Movie 2 is a demonstration of microwell array chip loading and washing procedure on large-format array (FIG. 20).

INCORPORATION BY REFERENCE

All documents cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the disclosure.

EQUIVALENTS

It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

What is claimed is:

1. A composition comprising (i) a somatostatin receptor agonist and (ii) novobiocin.

2. The composition of claim 1, wherein the somatostatin receptor agonist is selected from the group consisting of Lanreotide, Pasireotide, and combination thereof.

3. The composition of claim 1, wherein the somatostatin receptor agonist is Pasireotide.

4. A method of treating a subject having a bacterial infection, the method comprising administering to the subject an effective amount of the composition of claim 1.

5. A method of treating a subject having a bacterial infection, the method comprising administering to the subject an effective amount of the composition of claim 3.

6. A method of treating a subject having a bacterial infection, the method comprising administering to the subject (i) an effective amount of an antibiotic selected from the group consisting of novobiocin, erythromycin, and combination thereof; and (ii) an effective amount of Lanreotide.

* * * * *